(12) United States Patent
Lieberman et al.

(10) Patent No.: US 11,180,762 B2
(45) Date of Patent: Nov. 23, 2021

(54) METHODS AND COMPOSITIONS FOR THE TREATMENT OF CANCER

(71) Applicant: CHILDREN'S MEDICAL CENTER CORPORATION, Boston, MA (US)

(72) Inventors: Judy Lieberman, Brookline, MA (US); Adi Gilboa-Geffen, Brookline, MA (US); Lee Adam Wheeler, Boston, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 268 days.

(21) Appl. No.: 16/409,081

(22) Filed: May 10, 2019

(65) Prior Publication Data

US 2019/0309297 A1 Oct. 10, 2019

Related U.S. Application Data

(62) Division of application No. 15/506,010, filed as application No. PCT/US2015/047449 on Aug. 28, 2015, now Pat. No. 10,385,343.

(60) Provisional application No. 62/043,803, filed on Aug. 29, 2014.

(51) Int. Cl.
| | |
|---|---|
| *C12N 15/11* | (2006.01) |
| *C12N 15/115* | (2010.01) |
| *C12N 15/113* | (2010.01) |
| *A61K 48/00* | (2006.01) |
| *C07H 21/00* | (2006.01) |
| *C07K 14/705* | (2006.01) |
| *A61K 39/00* | (2006.01) |

(52) U.S. Cl.
CPC ............ *C12N 15/115* (2013.01); *A61K 48/00* (2013.01); *C07H 21/00* (2013.01); *C07K 14/705* (2013.01); *C12N 15/113* (2013.01); *C12N 15/1137* (2013.01); *A61K 2039/5152* (2013.01); *C12N 2310/14* (2013.01); *C12N 2310/16* (2013.01); *C12N 2310/3519* (2013.01)

(58) Field of Classification Search
CPC ................ C12N 15/115; C12N 15/113; C12N 2310/14; C12N 2310/16
See application file for complete search history.

(56) References Cited

U.S. PATENT DOCUMENTS

| | | |
|---|---|---|
| 2005/0147593 A1 | 7/2005 | Kinch |
| 2012/0014875 A1 | 1/2012 | Giangrande et al. |

FOREIGN PATENT DOCUMENTS

| | | |
|---|---|---|
| CN | 101766817 A | 7/2010 |
| CN | 103977433 A | 8/2014 |
| WO | 2010/017319 A2 | 2/2010 |
| WO | 2010/019446 A1 | 2/2010 |
| WO | 2011/130458 A2 | 10/2011 |
| WO | 2011/142970 A2 | 11/2011 |
| WO | 2012/078637 A2 | 6/2012 |
| WO | 2013/025930 A1 | 2/2013 |
| WO | 2014/019025 A1 | 2/2014 |
| WO | 2014/068408 A2 | 5/2014 |
| WO | 2014/093698 A1 | 6/2014 |
| WO | 2014/126160 A1 | 8/2014 |
| WO | 2016/127216 A1 | 8/2016 |

OTHER PUBLICATIONS

Wang et al. "Intravenous Delivery of siRNA Targeting CD47 Effectively Inhibits Melanoma Tumor Growth and Lung Metastasis." Mol Ther 21 (10): 1919-1929 (2013).
Maire et al. "Polo-like kinase 1: a potential therapeutic option in combination with conventional chemotherapy for the management of patients with triple-negative breast cancer." Cancer Research 73(2): 813-823 (2013).
Takai et al. "Polo-like kinases (Plks) and cancer." Oncogene 24(2): 287-291 (2005).
Aliabadi et al., "Effective response of doxorubicin-sensitive and-resistant breast cancer cells to combinational siRNA therapy." Journal of Controlled Release 172(1):219-228 (2013).
Burnett et al., "RNA-based therapeutics: current progress and future prospects." Chemistry & Biology 19(1):60-71 (2012).
Dassie et al., "Systemic administration of optimized aptamer-siRNA chimeras promotes regression of PSMA-expressing tumors." Nature Biotechnology 27(9):839-849 (2009).
Fox et al., "Invasiveness of breast carcinoma cells and transcript profile: Eph receptors and ephrin ligands as molecular markers of potential diagnostic and prognostic application." Biochemical and Biophysical Research Communications 318(4):882-892 (2004).
Gilboa-Geffen et al., "Abstract CN01-02: Targeting basal-like TNBCs and epithelial tumor-initiating cells with aptamer-siRNA chimeras", Molecular Cancer Therapeutics 12(11 Suppl): (2013). (2 pages).
Gilboa-Geffen et al., "Gene knockdown by EpCAM aptamer-siRNA chimeras suppresses epithelial breast cancers and their tumor-initiating cells." Molecular Cancer Therapeutics 14(10):2279-2291 (2015).
Kim et al., "In Vitro Selection of RNA Aptamer and Specific Targeting of ErbB2 in Breast Cancer Cells." Nucleic Acid Therapeutics 21(3):173-178 (2011).
Machine translation of CN 101766817 A.
Mcnamara et al., "Cell type-specific delivery of siRNAs with aptamer-siRNA chimeras." Nature Biotechnology 24(8):1005-1015 (2006).
Mcnamara et al., "Multivalent 4-1BB binding aptamers costimulate CD8+ T cells and inhibit tumor growth in mice." The Journal of Clinical Investigation 118(1):376-386 (2008).
Neff et al., "An aptamer-siRNA chimera suppresses HIV-1 viral loads and protects from helper CD4+ T cell decline in humanized mice." Science Translational Medicine 3(66ra6):1-27 (2011).

(Continued)

*Primary Examiner* — Ekaterina Poliakova-Georgantas
(74) *Attorney, Agent, or Firm* — Nixon Peabody LLP; David S. Resnick; Nicole D. Kling

(57) ABSTRACT

Described herein are methods and compositions relating to the treatment of cancer, e.g., breast cancer, using, e.g., aptamer-siRNA chimera molecules.

9 Claims, 57 Drawing Sheets

Specification includes a Sequence Listing.

(56) References Cited

OTHER PUBLICATIONS

Pastor et al. "Targeting 4-1BB costimulation to disseminated tumor lesions with bi-specific oligonucleotide aptamers." Molecular Therapy 19(10):1878-1886 (2011).
Pastor et al., "Induction of tumour immunity by targeted inhibition of nonsense-mediated mRNA decay." Nature 465(7295):227-230 (2010).
Petrocca et al., "A genome-wide siRNA screen identifies proteasome addiction as a vulnerability of basal-like triple-negative breast cancer cells." Cancer Cell 24(2):182-196 (2013).
Rockey et al., "Rational Truncation of an RNA Aptamer to Prostate-Specific Membrane Antigen Using Computational Structural Modeling." Nucleic Acid Therapeutics 21(5):299-314 (2011).
Shigdar et al., "RNA aptamer against a cancer stem cell marker epithelial cell adhesion molecule." Cancer Science 102(5):991-998 (2011).
Subramanian et al., "EpCAM aptamer-siRNA chimera targets and regress epithelial cancer." PloS One 10(7) e0132407(2015).
Thiel et al., "Delivery of chemo-sensitizing siRNAs to HER2+- breast cancer cells using RNA aptamers." Nucleic Acids Research 40(13):6319-6337 (2012).
Wheeler et al., "Durable knockdown and protection from HIV transmission in humanized mice treated with gel-formulated CD4 aptamer-siRNA chimeras." Molecular Therapy 21(7):1378-1389 (2013).
Wheeler et al., "Inhibition of HIV transmission in human cervicovaginal explants and humanized mice using CD4 aptamer-siRNA chimeras." The Journal of Clinical Investigation 121(6):2401-2412 (2011).
Yang et al., "Wnt modulates MCL1 to control cell survival in triple negative breast cancer." BMC Cancer 14(124):1-13 (2014).
Zhang et al., "Synergistic effect of the γ-secretase inhibitor PF-03084014 and docetaxel in breast cancer models." Stem Cells Translational Medicine 2(3):233-242 (2013).
Zhou et al., "Aptamer-targeted cell-specific RNA interference." Silence 1(4): 1-10 (2010).
Zhou et al., "Cell-specific aptamer-mediated targeted drug delivery." Oligonucleotides 21(1): 1-10 (2011).
Zhou et al., "Cell-type-specific, aptamer-functionalized agents for targeted disease therapy." Molecular Therapy—Nucleic Acids 3(6):e169 (2014).
Zhou et al., "Novel dual inhibitory function aptamer-siRNA delivery system for HIV-1 therapy." Molecular Therapy 16(8):1481-1489 (2008).
Zhou et al., "Selection, characterization and application of new RNA HIV gp 120 aptamers for facile delivery of Dicer substrate siRNAs into HIV infected cells." Nucleic Acids Research 37(9):3094-3109 (2009).

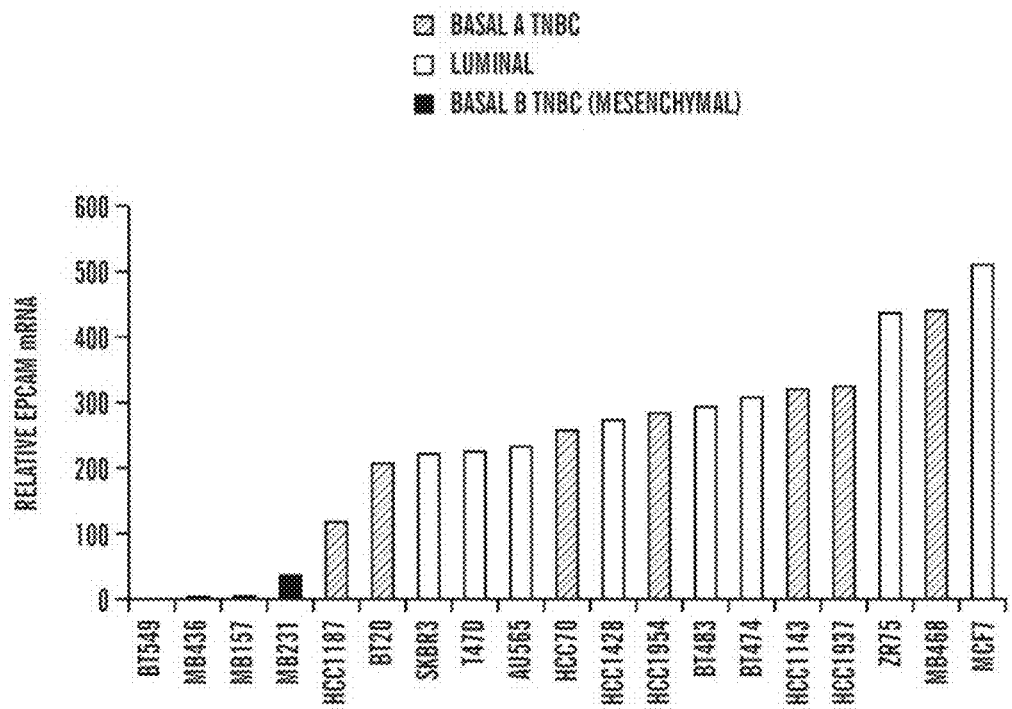
FIG. 1A
Fig. 1B
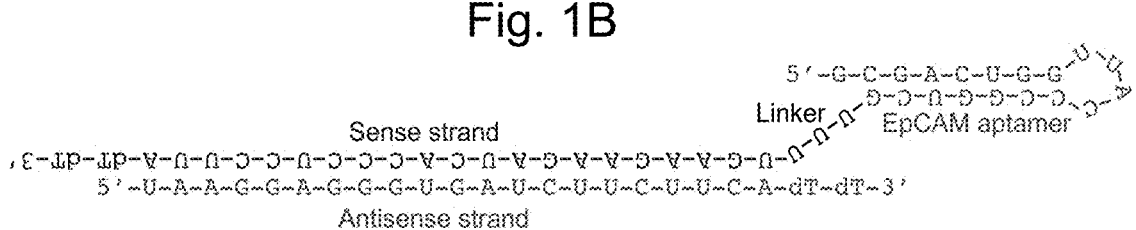
Fig. 1C

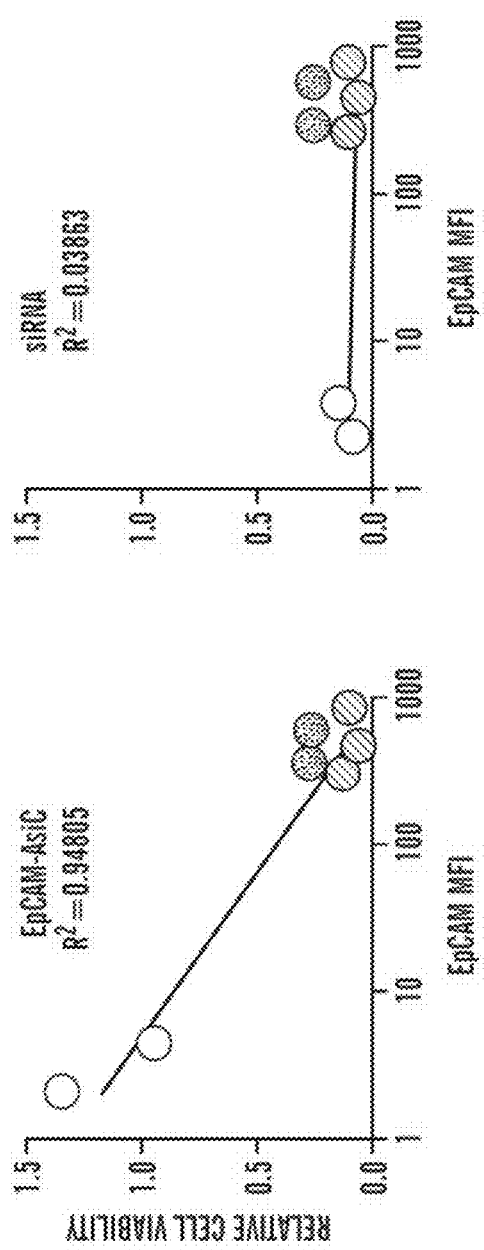
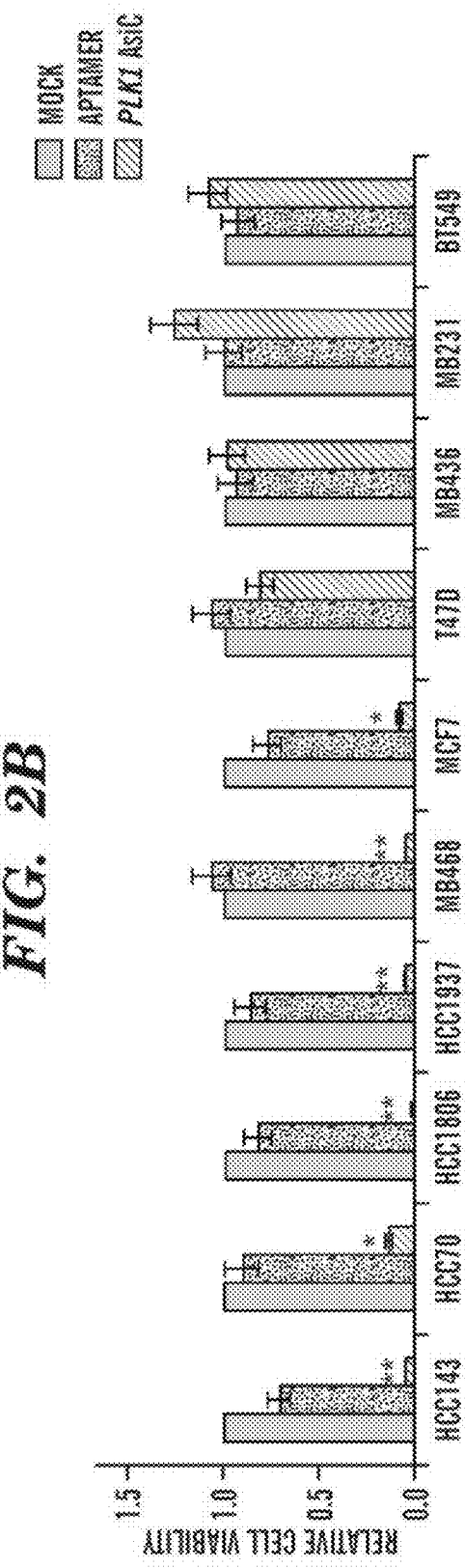
FIG. 2B
FIG. 2C

Figure 9. EpCAM-AsiC Sequences

| AsiC construct | Sequence |
|---|---|
| EpCAM PLK1 sense | GCG ACU GGU UAC CCG GUC GUU UUG AAG AAG AUC ACC CUC CUU AdTdT |
| EpCAM PLK1 anti-sense | UAA GGA GGG UGA UCU UCU UCA dTdT |
| EpCAM AKT1 sense | GCG ACU GGU UAC CCG GUC GUU GCU GGA GAA CCU CAU GCU GdTdT |
| EpCAM AKT1 anti-sense | CAG CAU GAG GUU CUC CAG CdTdT |
| EpCAM GFP sense | GCG ACU GGU UAC CCG GUC GUU UGG CUA CGU CCA GGA GCG CAdTdT |
| EpCAM GFP anti-sense | UGC GCU CCU GGA CGU AGC CdTdT |
| siGFP sense | UGG CUA CGU CCA GGA GCG |
| siGFP antisense | UGC GCU CCU GGA CGU AGC |
| siAKT1 sense | GCU GGA GAA CCU CAU GCU G |
| siAKT1 antisense | CAG CAU GAG GUU CUC CAG C |
| siPLK1 sense | UGA AGA AGA UCA CCC UCC UUA |
| siPLK1 antisense | UAA GGA GGG UGA UCU UCU UCA |

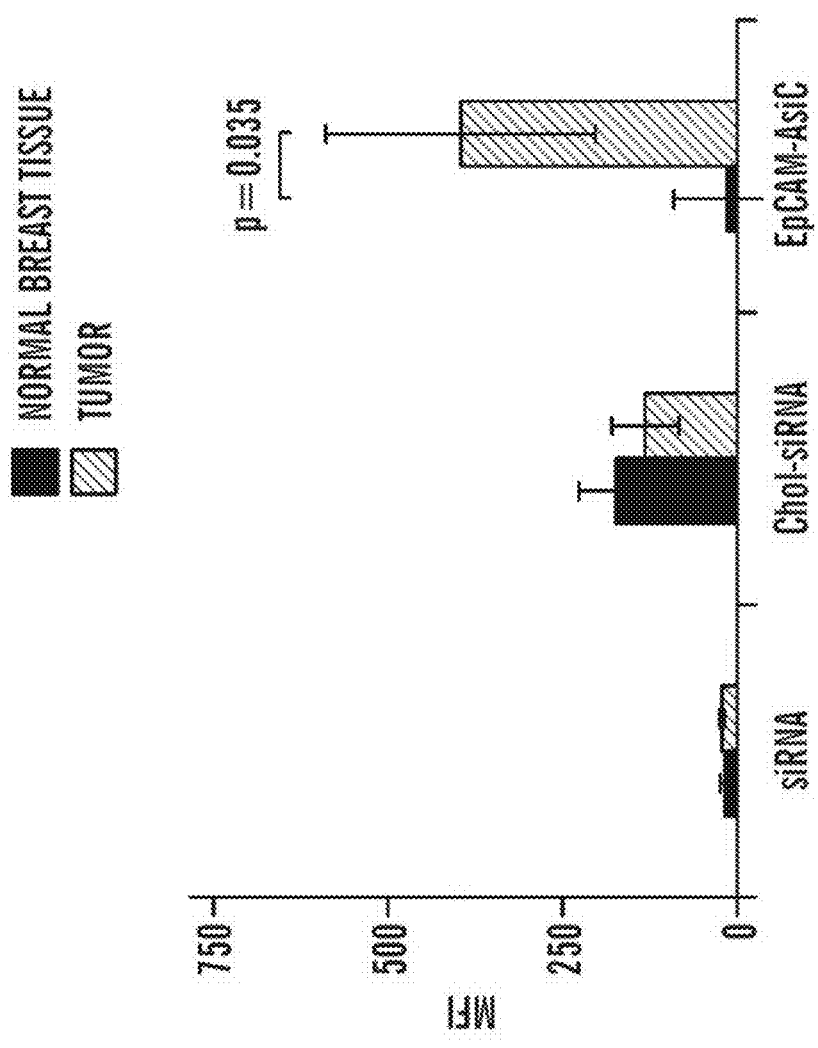
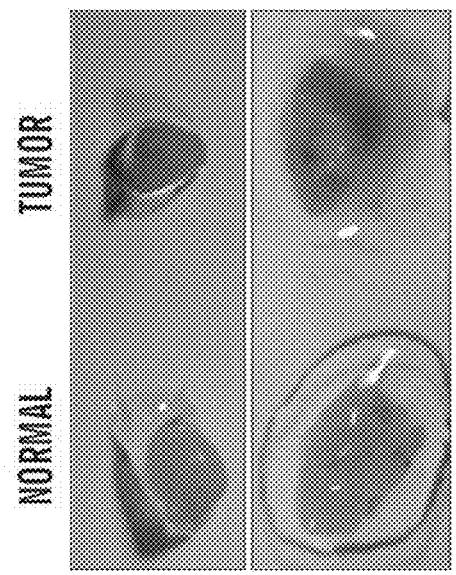
FIG. 14

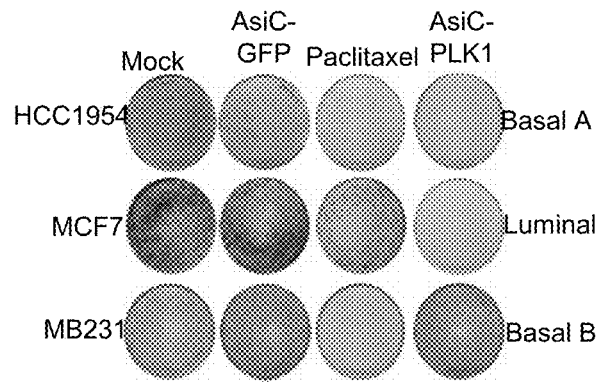
Fig. 29A
Fig. 29B
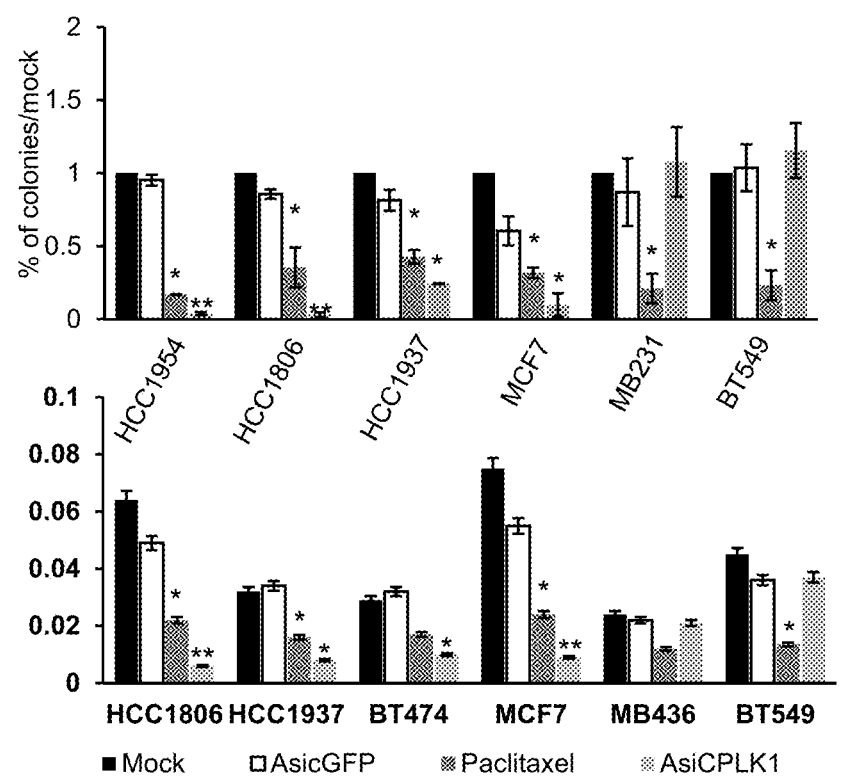
Fig. 29C

```
                        SEQUENCE LISTING

<160> NUMBER OF SEQ ID NOS: 33

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
gcgacugguu acccggucgu uuugaagaag aucacccucc uuatt            45

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
uaaggagggu gaucuucuuc att                                    23

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
gcgacugguu acccggucgu uuuaaggagg gugaucuucu ucatt            45

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttcaccacca tggagaaggc                                        20
```

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggcatggact gtggtcatga                                                  20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctggagcagc tgaatggaaa g                                                21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cttgaagtcc gccctgtagg t                                                21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgccttcatt tatcccttga a                                                21

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttactacatt cagccaaaaa gcac                                             24

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gctgccgtca ttttctgc                                                    18
```

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tctcactggc ccgtcatc                                                     18

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggaggttgca gtgccaacga ag                                                22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggaagggag gcagggcata ac                                                22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tttgcccaga ctcgagctcc tg                                                22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gggtgcaggt tcgggattca ac                                                22

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 16

Ala Ala Leu Glu Ala Leu Ala Glu Ala Leu Glu Ala Leu Ala Glu Ala
1               5                   10                  15

Leu Glu Ala Leu Ala Glu Ala Ala Ala Gly Gly Cys
            20                  25

<210> SEQ ID NO 17
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Gly Gly Cys
            20                  25                  30

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Leu Glu Ala Leu Ala Glu Ala Leu Glu Ala Leu Ala Glu Ala
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Val Ala Leu Leu Pro Ala Val Leu Leu Ala Leu Leu Ala Pro
1               5                   10                  15

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ala Leu Leu Pro Val Leu Leu Ala Ala Pro
1               5                   10

<210> SEQ ID NO 21
<211> LENGTH: 13
<212> TYPE: PRT
<213> ORGANISM: Human immunodeficiency virus

<400> SEQUENCE: 21

Gly Arg Lys Lys Arg Arg Gln Arg Arg Pro Pro Gln
1               5                   10
```

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Gln Ile Lys Ile Trp Phe Gln Asn Arg Arg Met Lys Trp Lys Lys
1               5                   10                  15

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
gcgacugguu acccggucgu ugcuggagaa ccucaugcug tt                          42

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
cagcaugagg uucuccagct t                                                 21

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
gcgacugguu acccggucgu uuggcuacgu ccaggagcgc att                         43

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
ugcgcuccug gacguagcct t                                                 21

```
<210> SEQ ID NO 27
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uggcuacguc caggagcg                                                 18

<210> SEQ ID NO 28
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ugcgcuccug gacguagc                                                 18

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gcuggagaac cucaugcug                                                19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cagcaugagg uucuccagc                                                19

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ugaagaagau cacccuccuu a                                             21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
uaaggagggu gaucuucuuc a                                             21
```

```
<210> SEQ ID NO 33
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
gcgacugguu acccggucgu uu                                           22
```

METHODS AND COMPOSITIONS FOR THE TREATMENT OF CANCER

CROSS-REFERENCE TO RELATED APPLICATIONS

This application is a divisional under 35 U.S.C. § 121 of co-pending U.S. application Ser. No. 15/506,010 filed Feb. 23, 2017, which is a 35 U.S.C. § 371 National Phase Entry Application of International Application No. PCT/US15/047449 filed Aug. 28, 2015, which designates the U.S. and claims benefit under 35 U.S.C. § 119(e) of U.S. Provisional Application No. 62/043,803 filed Aug. 29, 2014, the contents of which are incorporated herein by reference in their entireties.

GOVERNMENT SUPPORT

This invention was made with government support under grant number W81XWH-09-1-0058 awarded by the U.S. Department of the Army. The Government has certain rights in the invention.

SEQUENCE LISTING

The instant application contains a Sequence Listing which has been submitted electronically in ASCII format and is hereby incorporated by reference in its entirety. Said ASCII copy, created on Aug. 28, 2015, is named 701039-082401-PCT_SL.txt and is 8,984 bytes in size.

TECHNICAL FIELD

The technology described herein relates to chimeric molecules comprising an EpCAM binding-molecule and an inhibitory nucleic acid and methods of using such compositions for the treatment of cancer, e.g. epithelial cancer.

BACKGROUND

RNA interference (RNAi) has been explored for therapeutic use in reducing gene expression in the liver. However, the liver is unique in being easy to transfect with RNAi molecules. Delivery of small RNAs and resulting gene knockdown in other tissues continues to be inefficient and ultimately ineffective. In particular, the delivery roadblock is a major obstacle to harnessing RNAi to treat cancer.

SUMMARY

As described herein, the inventors have developed novel chimeric aptamer-siRNA molecules (AsiCs). These AsiC's target cancer cell markers to direct the siRNA specifically to the cancer cells, increasing delivery efficacy and therapeutic effectiveness while reducing the potential for side effects.

In one aspect, described herein is a chimeric molecule comprising a cancer marker-binding aptamer domain and an inhibitory nucleic acid domain. In some embodiments, the cancer marker is EpCAM or EphA2. In some embodiments, the inhibitory nucleic acid specifically binds to a gene product upregulated in a cancer cell. In some embodiments, the inhibitory nucleic acid inhibits the expression of a gene selected from the group consisting of: Plk1; MCL1; EphA2; PsmA2; MSI1; BMI1; XBP1; PRPF8; PFPF38A; RBM22; USP39; RAN; NUP205; and NDC80. In some embodiments, the cancer marker is EpCAM and the inhibitory nucleic acid domain inhibits the expression of Plk1.

In some embodiments, the molecule is an aptamer-siRNA chimera (AsiC). In some embodiments, the cancer marker-binding aptamer domain comprises the sequence of SEQ ID NO: 33. In some embodiments, the cancer marker-binding aptamer domain consists essentially of the sequence of SEQ ID NO: 33. In some embodiments, the inhibitory nucleic acid domain comprises the sequence of SEQ ID NO: 2. In some embodiments, the inhibitory nucleic acid domain consists essentially of the sequence of SEQ ID NO: 2. In some embodiments, the molecule comprises the sequence of one of SEQ ID NOs: 1-3. In some embodiments, the molecule consists essentially of the sequence of one of SEQ ID NOs: 1-3.

In some embodiments, the 3' end of the molecule comprises dTdT. In some embodiments, the molecule comprises at least one 2'-F pyrimidine.

In one aspect, described herein is a pharmaceutical composition comprising a chimeric molecule as described herein and a pharmaceutically acceptable carrier. In some embodiments, the composition comprises at least two chimeric molecules as described herein wherein the chimeric molecules have different aptamer domains and/or inhibitory nucleic acid domains. In some embodiments, the different aptamer or inhibitory nucleic acid domains recognize different targets. In some embodiments, the different aptamer or inhibitory nucleic acid domains have sequences and recognize the same target.

In one aspect, described herein is a method of treating cancer, the method comprising administering a chimeric molecule and/or composition as described herein. In some embodiments, the cancer is an epithelial cancer or breast cancer. In some embodiments, the breast cancer is triple-negative breast cancer. In some embodiments, the administration is subcutaneous. In some embodiments, the subject is further administered an additional cancer treatment. In some embodiments, the cancer treatment is paclitaxel.

BRIEF DESCRIPTION OF THE DRAWINGS

FIGS. 1A-1H demonstrate that EpCAM aptamer specifically targets Basal A breast cancer cells. Design of EpCAM-AsiC, containing an EpCAM aptamer and a PLK1 siRNA (sense strand disclosed as SEQ ID NO: 1 and antisense strand disclosed as SEQ ID NO: 2) (FIG. 1C). Epithelial breast cancer cell line (BPLER) over express EpCAM protein compared to normal breast epithelial cell line (BPE) (FIGS. 1A-1B). EpCAM-AsiC targeting GFP was Alexa647 or Cy3 labeled at the 3' end of the antisense siRNA strand and incubated with BPLER and BPE cells. Uptake was assessed 24 hours later by flow cytometry (FIG. 1D). Data are representative of 3 independent experiments. Cy3 and Alexa647-labeled EpCAM-AsiC was taken up by MB468 and BPLER (EpCAM+ cells) respectively and not by BPE (EpCAM-). MFI of each peak is shown. To test for gene silencing, BPLER and BPE were treated with EpCAM-AsiC targeting GFP (4 μM) and compared to Transfection controls using Dharmafect and GFP-siRNA (100 nM). Knockdown was assessed by flow cytometry 72 hours after incubation. Controls were mock and Dhrmafect only treatment (lipid). (n=4) (FIG. 1D). EpCAM-AsiC targeting AKT1 selectively knocks-down AKT1 mRNA (FIG. 1E) and protein (FIG. 1F) expression in basal A and luminal breast cancer cell lines and not in basal B or human fibroblasts (hFb). Transfection with siRNA targeting AKT1 induces gene knockdown in all cell lines, while treatment with EpCAM-AsiC targeting GFP doesn't effect AKT1 mRNA and protein levels (* p<0.05, p<0.01). Plots of AKT1 Protein and gene Knockdown comparing the effect of EpCAM-AsiC to siRNA transfection. EpCAM-AsiC induced knockdown correlates with EpCAM expression (FIG. 1E-H). (n=3; mean±SEM normalized to mock; *P<0.05, **P<0.01, 2-tailed t test).

FIGS. 2A-2E demonstrate that EpCAM AsiC targeting PLK1 specifically inhibits cell proliferation in Basal A breast cancer cells. The effect of EpCAM-AsiC targeting PLK1 on cell proliferation was tested on 10 breast cancer cell lines representative of basal A, B and luminal cell lines using cell-titer-glo assay (CTG). EpCAM-AsiC targeting PLK1 decreased cell proliferation in both basal A and luminal cell lines while having no effect on basal B cells (FIGS. 2A, 2C). A correlation was seen between EpCAM expression levels and cell viability (FIG. 2B). Basal A (EpCAM+GFP−) cell were co-cultured with BPE (EpCAM-GFP+) cells and treated with EpCAM-AsiC targeting PLK1 or untreated. Untreated co-culture displayed a similar ration of cells following EpCAM-AsiC targeting PLK1 treatment the ratio of EpCAM+ cells decreased and EpCAM− cells increased. A representative flow cytometry plot (FIG. 2D), the quantification of the experiment analyzed the ratio of GFP+/GFP− cells in 4 different cell lines (FIG. 2E). (n=4, * p<0.05, p<0.01).

FIG. 5A depicts the experimental setup; nude mice were injected with MB468-luc (left flank) and MB231-luc-mCherry (right flank) cells, 5 days post injection Alexa750 labeled EpCAM-AsiC targeting GFP (0.5 mg/kg) was injected s.c. in the neck area. The mice were imaged immediately after injection and again after 24, 48 hr and 5 days. The Alexa750 labeled EpCAM-AsiC targeting GFP was co-localized with the luciferase tumor in MB468-luc tumor (EpCAM+) and not the MB231-luc-mCherry (EpCAM−) tumor. Analysis of 7 mice indicates a significant increase of Alexa750 in MB468 (EpCAM+) tumors (FIG. 5B). FIG. 5C depicts a graph of Alexa750 uptake rates.

FIG. 6A depicts the experimental design. Nude mice injected with either MB231-luc-mCherry cells ($5\times10^5$) or MB468-luc cells ($5\times10^6$) were treated with 5 mg/Kg of either EpCAM AsiC targeting PLK1 or GFP every 72 h or left untreated. FIG. 6B: MB468-luc tumors treated with EpCAM-AsiC targeting PLK1 shrunk in size as early as 6 days post treatment and in many mice completely disappeared after 14 days, Untreated tumors both EpCAM+ and EpCAM-increased in size over the 14 days.

FIG. 8A: Serum samples, collected at baseline and 6 and 16 hr after treatment were assessed for IFNβ, IL-6 and IP-10 by multiplex immunoassay. * p<0.05.  p<0.01, * p<0.001, compared to baseline. FIG. 8B: mRNA expression of cytokine and IFN-induced genes, relative to gapdh was assayed by qRT-PCR in total splenocytes harvested 16 hr post treatment. ** p<0.01, compared to untreated (NT, n=3).

FIG. 9 depicts a table of sequences. (SEQ ID NOS 1-2 and 23-32, respectively, in order of appearance).

FIG. 10A depicts a diagram of the AsiC (aptamer covalently linked to one strand of an siRNA) specifically recognizing a cancer cell surface receptor, being endocytosed and then released to the cytosol, where it is processed like endogenous pre-miRNAs to knockdown a target gene. Bars indicate the 2 delivery hurdles—cell uptake and release from endosomes to the cytosol where Dicer and the RNA induced silencing complex (RISC) are located. FIG. 10B depicts the design of the EpCAM AsiC targeting PLK1. (sense strand disclosed as SEQ ID NO: 1 and antisense strand disclosed as SEQ ID NO: 2).

FIGS. 11A-11B: Representative experiment (FIG. 11A) and AKT1 knockdown comparing EpCAM-AsiC with lipid siRNA transfection (FIG. 11B). FIG. 11C: Anti-proliferative effect of EpCAM-AsiCs knocking down PLK1 only in EpCAM+ cell lines. D PLK1 EpCAM-AsiCs inhibit colony formation in luminal MCF and basal-A TNBC HCC1143, but not in mesenchymal basal-B MB231 cells.

FIG. 12B: EphA2+ breast cancer cells incubated for 2 h with EphA2apt (0 to 100 nM), but not control nonbinding aptamer (ctl), show reduced EphA2. Addition of Ephrin A was used as a positive control for EphA2 degradation.

FIG. 14. Normal breast tissue and basal-A TNBC tumor biopsies from the same subject were incubated with Cy3-labeled EpCAM-AsiC and single cell suspensions were analyzed 3 d later for uptake by flow cytometry. Naked siRNAs were not taken up by either, cholesterol-conjugated siRNAs were equally taken up, but EpCAM-AsiCs were specifically taken up by the tumor. Representative tissues are shown at left.

FIG. 17A depicts the experimental scheme. FIG. 17B depicts the concentration of EpCAM-AsiCs in excised tumors at sacrifice.

FIG. 18A depicts the experimental design. Imaging of luciferase activity of left and right flank tumors was performed sequentially over 2 wks. FIG. 18B depicts a graph of tumor size by luciferase activity. All the EpCAM+ tumors in mice treated with PLK1 AsiCs rapidly regressed, while the other tumors continued to grow.

FIG. 19A depicts cell viability, 3 d after knockdown, normalized to control siRNA. FIG. 19B depicts colony formation assessed by plating viable cells 2 d after knockdown. FIG. 19C depicts caspase activation 2 d after knockdown is specific for MB468 and does not occur in BPE cells.

FIG. 21A depicts the design of EpCAM-AsiC, containing an EpCAM aptamer and a PLK1 siRNA (sense strand disclosed as SEQ ID NO: 1 and antisense strand disclosed as SEQ ID NO: 2). FIG. 21B depicts graphs demonstrateing that epithelial breast cancer cell line (BPLER) over express EpCAM protein compared to normal breast epithelial cell line (BPE). EpCAM-AsiC targeting GFP was Alexa647 or Cy3 labeled at the 3' end of the antisense siRNA strand and incubated with BPLER and BPE cells. Uptake was assessed 24 hours later by flow cytometry (FIG. 21C). Data are representative of 3 independent experiments. Cy3 and Alexa647-labeled EpCAM-AsiC was taken up by MB468 and BPLER (EpCAM+ cells) respectively and not by BPE (EpCAM−). MFI of each peak is shown (mock, gray). FIG. 21D depicts graphs of experiments in which, to test for gene silencing, BPLER and BPE were treated with EpCAM-AsiC targeting GFP (4 µM) and compared to Transfection controls using Dharmafect and GFP-siRNA (100 nM). Knockdown was assessed by flow cytometry 72 hours after incubation. Controls were mock and Dhrmafect only treatment (lipid). (n=4).

FIG. 24F depicts the results of flow cytometry analysis.

FIG. 25A depicts the experimental design; Cy3-EpCAM-AsiC targeting GFP, Alexa647-siRNA-GFP or Alexa647-chol-siRNA-GFP (2 µM of each) were added to breast cancer and control explants and incubated for 24 h before tissue was digested with collagenase to a single cell suspension and analyzed by flow cytometry. FIG. 25B depicts graphs demonstrating that tumor biopsies over express EpCAM and cytokeratin, an epithelial cell marker. FIG. 25C depicts representative histograms from one of three independent experiments show that siRNA and chol-siRNA penetrated both tumor and healthy tissue with similar efficacy while EpCAM-AsiC was selectively uptaken by the tumor tissue biopsy and not by the healthy control tissue sample. The uptake experiment was repeated in tumors from three different patients, each biopsy received was tested 3 times for each treatment. FIG. 25D depicts representative tumors. A summary of all three patients is depicted in FIG. 25E. (n=3, *P<0.05, **P<0.005, t-test CD4-AsiC versus mock treatment).

FIG. 27C depicts representative flow cytometry plots, and FIG. 27D depicts a graph of the quantification of the experiment analyzed the ratio of GFP+/GFP− cells in 4 different cell lines. (n=4, * p<0.05, p<0.01).

FIGS. 29A-29C demonstrate that EpCAM AsiC targeting PLK1 specifically inhibits tumor initiation in Basal A breast cancer cells. Colony assays of breast cancer cell lines were treated with EpCAM-AsiC targeting PLK1 or GFP (4 uM) or paclitaxel (100 nM) for 24 hr and cultured for 8 days in drug-free medium. Treatment with paclitaxel decreased colony formation in all cells lines while treatment with EpCAM-AsiC targeting PLK1 only eliminated colony formation in luminal (MCF7) and basal A (HCC1954) cells, treatment with EpCAM-AsiC targeting GFP had no effect. FIG. 29A depicts images of the assay results. The assay was repeated in 3 more cells lines and results were reproducible, as demonstrated in the graph depicted in FIG. 29B. FIG. 29C depicts a graph demonstrating that sphere formation assay indicated similar results, EpCAM-AsiC targeting PLK1 decreased the number of spheres only in basal A and luminal cells and had no effect on basal B cells. MB468-luc cells were treated for 24 h with EpCAM-AsiC targeting either GFP or PLK1 and injected s.c. to the flank of nude mice. Mice were imaged every 5 days for 20 days. Untreated mice and mice treated with EpCAM-AsiC targeting GFP, displayed increase in tumor initiation while mice injected with cell pretreated with EpCAM-AsiC targeting PLK1 has no tumor initiation.

FIG. 30A depicts representative PAGE gels and FIG. 30B depicts graphs of the average intensity (+S.E.M.) of bands from two independent experiments analyzed by densitometry. Both the stabilized cholesterol-conjugated siRNA and the EpCAM-AsiC are stable over the 36 h of the experiment.

FIG. 31A depicts the experimental setup; nude mice were injected with MB468-luc (left flank) and MB231-luc-mCherry (right flank) cells, 5 days post injection Alexa750 labeled EpCAM-AsiC targeting GFP (0.5 mg/kg) was injected s.c. in the neck area. The mice were imaged immediately after injection and again after 24, 48 hr and 5 days. The Alexa750 labeled EpCAM-AsiC targeting GFP was co-localized with the luciferase tumor in MB468-luc tumor (EpCAM+) and not the MB231-luc-mCherry (EpCAM−) tumor. FIG. 31B depicts a graph of analysis of 7 mice indicating a significant increase of Alexa750 in MB468 (EpCAM+) tumors. At day 5 the tumors were removed and visualized to validate that the Alexa750 labeled EpCAM-AsiC targeting GFP indeed entered the tumors. Increased level of Alexa750 is negatively correlated with mCherry levels. (n=8, *P<0.05, t-test EpCAM+ versus EpCAM− cells).

FIG. 32A depicts the experimental setup; nude mice injected with either MB231-luc-mCherry cells ($5 \times 10^5$) or MB468-luc cells ($5 \times 10^6$) were treated with 5 mg/Kg of either EpCAM AsiC targeting PLK1 or GFP every 72 h or left untreated. Mice were imaged using the IVIS Spectra imaging system every 72 h for 14 days. FIG. 32B depicts a graph demonstrating that MB468-luc tumors treated with EpCAM-AsiC targeting PLK1 shrunk in size as early as 6 days post treatment and in many mice completely disappeared after 14 days, Untreated tumors both EpCAM+ and EpCAM− increased in size over the 14 days.

DETAILED DESCRIPTION

Figure 1D:
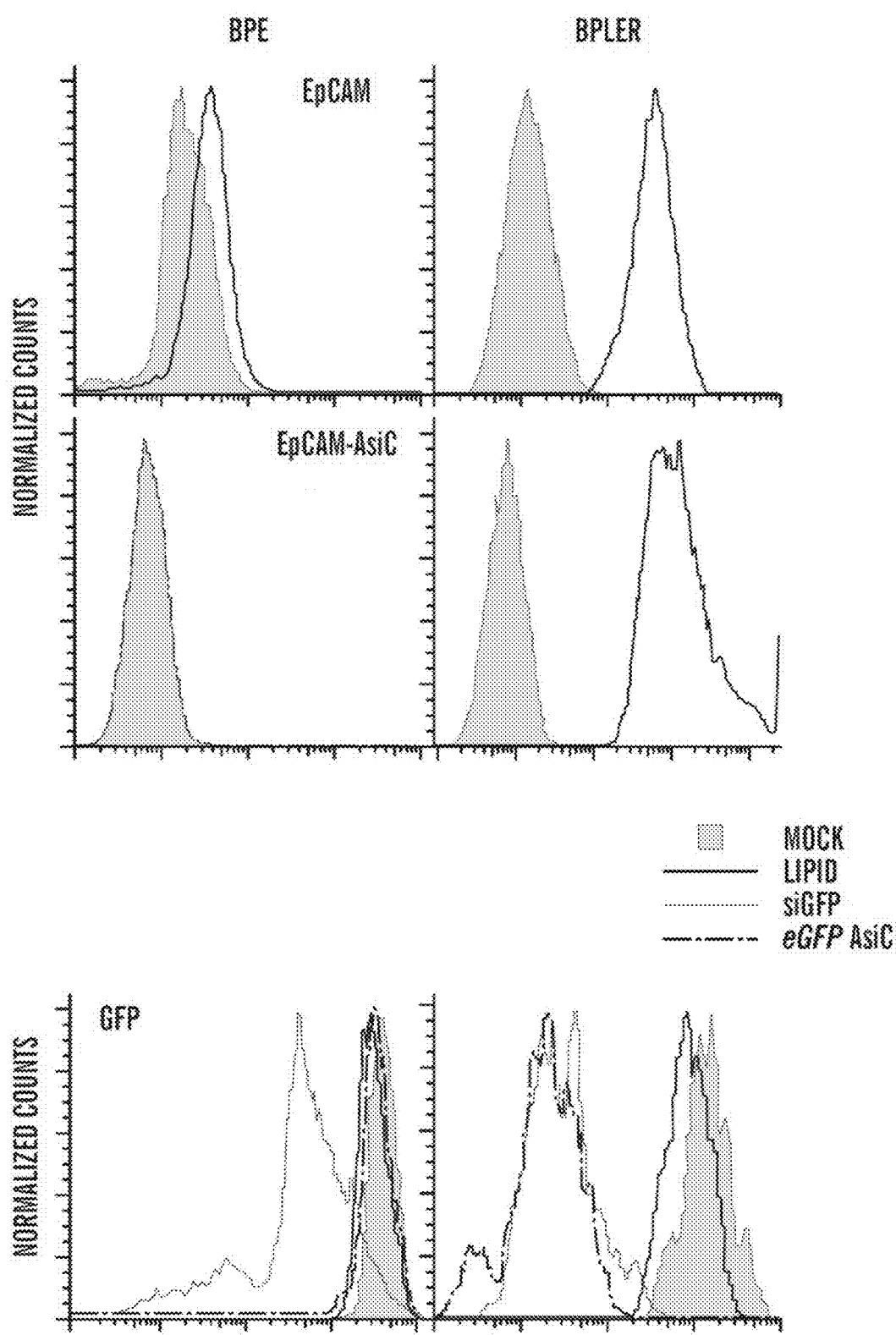

The inventors have demonstrated the suprising efficacy of AsiCs (aptamer-siRNA chimeric molecules) in treating cancer. The AsiC's described herein utilize an aptamer that targets the chimeric molecule specifically to cancer cells, providing effective and on-target suppression of the gene targeted by the siRNA.

In particular, the aptamers described herein, e.g. those targeting EpCAM and EphA2, permit the therapy to target tumor-initiating cells (also referred to as cancer stem cells). These cells are responsible not only for tumor initiation, replapse, and metastasis, but are also relatively resistant to conventional cytotoxic therapy. Thus, the compositions and methods described herein permit effective treatment of the underlying pathology in a way that existing therapies fail to do. The success of the AsiC's described herein is particularly suprising in that direct targeting of EpCAM with antibodies has been previously investigated and found to lack effectiveness.

Moreover, the AsiC's described herein are demonstrated to be surprisingly efficacious in the treatment of epithelial cancers, e.g. breast cancer (e.g. triple negative breast cancer (TNBC)). There are no current targeted therapies for TNBC and what treatments are available typically result in metastasis within 3 years, leading to death. The AsiC's described herein demonstrated effective gene knockdown specifically in luminal and basal-A TNBC cells as compared to healthy cells, suppressed colony and mammosphere formation in vitro and abrogated tumor initiation ex vivo. In vitro treatment with the AsiC's resulted in targeted delivery of the therapeutic and rapid tumor regression.

In one aspect, described herein is a chimeric molecule comprising a cancer marker-binding domain and an inhibitory nucleic acid domain. As used herein, "cancer marker-binding domain" refers to a domain and/or molecule that can bind specifically to a molecule more highly expressed on the surface of a cancer cell as compared to a healthy cell of the same type (a cancer marker). In some embodiments, the cancer marker can be a protein and/or polypeptide. In some embodiments, the cancer marker can be selected from EpCAM or EphA2. In some embodiments, the cancer marker-binding domain can be an aptamer.

As used herein, "EpCAM" or "epithelial cell adhesion molecule" refers to a transmembrane glycoprotein mediating Ca2+-independent homotypic cell-cell adhesion in epithelial cells. Sequences for EpCAM are known for a variety of species, e.g., human EpCAM (see, e.g., NCBI Gene ID:4072; protein sequence: NCBI Ref Seq: NP_002345.2).

As used herein, "EphA2" or "EPH receptor A2" refers to a ephirin type protein-tyrosine kinase receptor. EphA2 binding ephrin-A ligands and permits entry of Kaposi sarcoma-associated herpesvirus into host cells. Sequences for EphA2 are known for a variety of species, e.g., human EphA2 (see, e.g., NCBI Gene ID: 1969; protein sequence: NCBI Ref Seq: NP_004422.2).

As used herein, "inhibitory nucleic acid domain" refers to a domain comprising an inhibitory nucleic acid. In some embodiments, the inhibitory nucleic acid can be a siRNA. The inhibitory nucleic acid domain can inhibit, e.g., can target, the expression of a gene product that is upregulated in a cancer cell and/or the expression of a gene that is required for cell growth and/or survival. In some embodiments, the inhibitory nucleic acid domain can inhibit the expression of a gene selected from Plk1 (e.g. "polo-like kinase 1"; NCBI Gene ID: 5347); MCL1 (e.g. myeloid cell leukemia 1; NCBI Gene ID: 4170); EphA2 (NCBI Gene ID: 1969); PsmA2 (e.g. proteasome subunit alpha 2; NCBI Gene ID: 5683); MSI1 (e.g., musashi RNA-binding protein 1; NCBI Gene ID: 4440); BMI1 (e.g., B lymphoma Mo-MLV insertion 1, NCBI Gene ID: 648); XBP1 (X-boxn binding protein 1; NCBI Gene ID: 7494); PRPF8 (e.g., pre-mRNA processing factor 8; NCBI Gene ID:10594), PFPF38A (e.g., pre-mRNA processing factor 38A; NCBI Gene ID: 84950), RBM22 (e.g., RNA binding motif protein 22; NCBI Gene ID: 55696), USP39 (e.g., ubiquitin specific peptidase 39; NCBI Gene ID: 10713); RAN (e.g., ras-related nuclear protein; NCBI Gene ID: 5901); NUP205 (e.g., nucleoporin 205 kDa; NCBI Gene ID: 23165), and NDC80 (e.g., NDC80 kinetochore complex component; NCBI Gene ID: 10403). Sequences of these genes, e.g., the human mRNAs, are readily obtained from the NCBI database and can be used by one of skill in the art to design inhibitory nucleic acids. Furthermore, provided herein are exemplary inhibitory nucleic acid domains, e.g. a nucleic acid having the sequence of SEQ ID NO: 2.

In some embodiments, a composition as described herein can comprise a cancer marker-binding domain comprising an aptamer and an inhibitory nucleic acid domain comprising an siRNA, e.g. the composition can comprise an aptamer-siRNA chimera (AsiC).

In some embodiments, the methods described herein relate to treating a subject having or diagnosed as having cancer with a composition as described herein. Subjects having cancer can be identified by a physician using current methods of diagnosing cancer. Symptoms and/or complications of cancer which characterize these conditions and aid in diagnosis are well known in the art and include but are not limited to, for example, in the case of breast cancer a lump or mass in the breast tissue, swelling of all or part of a breast, skin irritation, dimpling of the breast, pain in the breast or nipple, nipple retraction, redness, scaliness, or irritation of the breast or nipple, and nipple discharge. Tests that may aid in a diagnosis of, e.g. breast cancer include, but are not limited to, mammograms, x-rays, MRI, ultrasound, ductogram, a biopsy, and ductal lavage. A family history of cancer or exposure to risk factors for cancer (e.g. smoke, radiation, pollutants, BRCA1 mutation, etc.) can also aid in determining if a subject is likely to have cancer or in making a diagnosis of cancer.

The terms "malignancy," "malignant condition," "cancer," or "tumor," as used herein, refer to an uncontrolled growth of cells which interferes with the normal functioning of the bodily organs and systems.

As used herein, the term "cancer" relates generally to a class of diseases or conditions in which abnormal cells divide without control and can invade nearby tissues. Cancer cells can also spread to other parts of the body through the blood and lymph systems.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. In some embodiments, the cancer can be epithelial cancer. In some embodiments, the cancer can be breast cancer. In some embodiments, the cancer can be triple negative breast cancer.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice. See, e.g., Freshney, CULTURE ANIMAL CELLS: MANUAL BASIC TECH. (3rd ed., 1994).

The compositions and methods described herein can be administered to a subject having or diagnosed as having cancer. In some embodiments, the methods described herein comprise administering an effective amount of compositions described herein, to a subject in order to alleviate a symptom of a cancer. As used herein, "alleviating a symptom of a cancer" is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic. In some embodiments, the administration is subcutaneous. In some embodiments, the administration of an AsiC as described herein is subcutaneous.

The term "effective amount" as used herein refers to the amount of of a composition needed to alleviate at least one or more symptom of the disease or disorder, and relates to a sufficient amount of pharmacological composition to provide the desired effect. The term "therapeutically effective amount" therefore refers to an amount that is sufficient to provide a particular anti-cancer effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a composition) which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for tumor size, among others. The dosage can be determined by a physician and adjusted, as necessary, to suit observed effects of the treatment.

In some embodiments, the technology described herein relates to a pharmaceutical composition as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. as described herein.

In some embodiments, the pharmaceutical composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008, 719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. Non-limiting examples of a second agent and/or treatment can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI11 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE™. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb™); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

In some embodiments of any of the aspects described herein, a chimeric molecule as described herein can be administered in combination with a taxane (e.g. docetaxel or paclitaxel). In some embodiments of any of the aspects described herein, a chimeric molecule as described herein can be administered in combination with paclitaxel. In some embodiments of any of the aspects described herein, an AsiC as described herein can be administered in combination with a taxane. In some embodiments of any of the aspects described herein, an AsiC as described herein can be administered in combination with paclitaxel.

In certain embodiments, an effective dose of a composition as described herein can be administered to a patient once. In certain embodiments, an effective dose of a composition can be administered to a patient repeatedly. For systemic administration, subjects can be administered a therapeutic amount of a composition comprising such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the composition. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

Inhibitors of the expression of a given gene can be an inhibitory nucleic acid or inhibitory oligonucleotide. In some embodiments, the inhibitory nucleic acid is an inhibitory RNA (iRNA). In some embodiments, the inhibitory nucleic acid is an inhibitory DNA (iDNA). Double-stranded RNA molecules (dsRNA) have been shown to block gene expression in a highly conserved regulatory mechanism known as RNA interference (RNAi). The inhibitory nucleic acids described herein can include an RNA or DNA strand (the antisense strand) having a region which is 30 nucleotides or less in length, i.e., 8-30 nucleotides in length, generally 19-24 nucleotides in length, which region is substantially complementary to at least part of a precursor or mature form of a target gene's transcript. The use of these inhibitory oligonucleotides enables the targeted degradation of the target gene, resulting in decreased expression and/or activity of the target gene.

As used herein, the term "inhibitory oligonucleotide," "inhibitory nucleic acid," or "antisense oligonucleotide" (ASO) refers to an agent that contains an oligonucleotide, e.g. a DNA or RNA molecule which mediates the targeted cleavage of an RNA transcript. In one embodiment, an inhibitory oligonucleotide as described herein effects inhibition of the expression and/or activity of a target gene. Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomirs, peptide nucleic acids (PNAs), and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

In certain embodiments, contacting a cell with the inhibitor (e.g. an inhibitory oligonucleotide) results in a decrease in the target RNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the inhibitory oligonucleotide.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of the target gene. In one aspect, an RNA interference agent includes a single stranded RNA that interacts with a target RNA sequence to direct the cleavage of the target RNA. Without wishing to be bound by theory, long double stranded RNA introduced into plants and invertebrate cells is broken down into siRNA by a Type III endonuclease known as Dicer (Sharp et al., Genes Dev. 2001, 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleaves the target to induce silencing (Elbashir, et al., (2001) Genes Dev. 15:188). Thus, in one aspect, an RNA interference agent relates to a double stranded RNA that promotes the formation of a RISC complex comprising a single strand of RNA that guides the complex for cleavage at the target region of a target transcript to effect silencing of the target gene.

In some embodiments, the inhibitory oligonucleotide can be a double-stranded nucleic acid (e.g. a dsRNA). A double-stranded nucleic acid includes two nucleic acid strands that are sufficiently complementary to hybridize to form a duplex structure under conditions in which the double-stranded nucleic acid will be used. One strand of a double-stranded nucleic acid (the antisense strand) includes a region of complementarity that is substantially complementary, and generally fully complementary, to a target sequence. The target sequence can be derived from the sequence of an mRNA and/or the mature miRNA formed during the expression of the target gene. The other strand (the sense strand) includes a region that is complementary to the antisense strand, such that the two strands hybridize and form a duplex structure when combined under suitable conditions. Generally, the duplex structure is between 8 and 30 inclusive, more generally between 18 and 25 inclusive, yet more generally between 19 and 24 inclusive, and most generally between 19 and 21 base pairs in length, inclusive. Similarly, the region of complementarity to the target sequence is between 8 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA and/or miRNA target is a contiguous sequence of an mRNA target of sufficient length to be a substrate for antisense-directed cleavage (e.g., cleavage through a RISC pathway). Double-stranded nucleic acids having duplexes as short as 8 base pairs can, under some circumstances, mediate antisense-directed RNA cleavage. Most often a target will be at least 15 nucleotides in length, preferably 15-30 nucleotides in length.

One of skill in the art will also recognize that the duplex region is a primary functional portion of a double-stranded inhibitory nucleic acid, e.g., a duplex region of 8 to 36, e.g., 15-30 base pairs. Thus, in one embodiment, to the extent that it becomes processed to a functional duplex of e.g., 15-30 base pairs that targets a desired RNA for cleavage, an inhibitory nucleic acid molecule or complex of inhibitory nucleic acid molecules having a duplex region greater than 30 base pairs is a double-stranded nucleic acid. Thus, an ordinarily skilled artisan will recognize that in one embodiment, then, a miRNA is a dsRNA. In another embodiment, a dsRNA is not a naturally occurring miRNA. In another embodiment, an inhibitory nucleic acid agent useful to target the target gene expression is not generated in the target cell by cleavage of a larger double-stranded nucleic acid molecule.

While a target sequence is generally 15-30 nucleotides in length, there is wide variation in the suitability of particular sequences in this range for directing cleavage of any given target RNA. When miRNAs are targeted, the target sequence can be as short as 8 nucleotides, including the "seed" region (e.g. nucleotides 2-8)). Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that may serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an inhibitory nucleic acid agent, mediate the best inhibition of target gene expression.

A double-stranded inhibitory nucleic acid as described herein can further include one or more single-stranded nucleotide overhangs. The double-stranded inhibitory nucleic acid can be synthesized by standard methods known in the art as further discussed below, e.g., by use of an automated DNA synthesizer, such as are commercially available from, for example, Biosearch, Applied Biosystems, Inc. In one embodiment, the antisense strand of a double-stranded inhibitory nucleic acid has a 1-10 nucleotide overhang at the 3' end and/or the 5' end. In one embodiment, the sense strand of a double-stranded inhibitory nucleic acid has a 1-10 nucleotide overhang at the 3' end and/or the 5' end. In one embodiment, at least one end of a double-stranded inhibitory nucleic acid has a single-stranded nucleotide overhang of 1 to 4, generally 1 or 2 nucleotides. Double-stranded inhibitory nucleic acids having at least one nucleotide overhang have unexpectedly superior inhibitory properties relative to their blunt-ended counterparts.

In another embodiment, one or more of the nucleotides in the overhang is replaced with a nucleoside thiophosphate.

As used herein, the term "nucleotide overhang" refers to at least one unpaired nucleotide that protrudes from the duplex structure of an inhibitory nucleic acid, e.g., a dsRNA. For example, when a 3'-end of one strand of a double-stranded inhibitory nucleic acid extends beyond the 5'-end of the other strand, or vice versa, there is a nucleotide overhang. A double-stranded inhibitory nucleic acid can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) may be on the sense strand, the antisense strand or any combination thereof. Furthermore, the nucleotide(s) of an overhang can be present on the 5' end, 3' end or both ends of either an antisense or sense strand of a double-stranded inhibitory nucleic acid.

The terms "blunt" or "blunt ended" as used herein in reference to a double-stranded inhibitory nucleic acid mean that there are no unpaired nucleotides or nucleotide analogs at a given terminal end of a dsRNA, i.e., no nucleotide overhang. One or both ends of a double-stranded inhibitory nucleic acid can be blunt. Where both ends of a double-stranded inhibitory nucleic acid are blunt, the double-stranded inhibitory nucleic acid is said to be blunt ended. To be clear, a "blunt ended" double-stranded inhibitory nucleic acid is a double-stranded inhibitory nucleic acid that is blunt at both ends, i.e., no nucleotide overhang at either end of the molecule. Most often such a molecule will be double-stranded over its entire length.

In this aspect, one of the two strands is complementary to the other of the two strands, with one of the strands being substantially complementary to a sequence of a the target gene precursor or mature miRNA. As such, in this aspect, a double-stranded inhibitory nucleic acid will include two oligonucleotides, where one oligonucleotide is described as the sense strand and the second oligonucleotide is described as the corresponding antisense strand of the sense strand. As described elsewhere herein and as known in the art, the complementary sequences of a double-stranded inhibitory nucleic acid can also be contained as self-complementary regions of a single nucleic acid molecule, as opposed to being on separate oligonucleotides.

The skilled person is well aware that inhibitory nucleic acid having a duplex structure of between 20 and 23, but specifically 21, base pairs have been hailed as particularly effective in inducing antisense-mediated inhibition (Elbashir et al., EMBO 2001, 20:6877-6888). However, others have found that shorter or longer inhibitory nucleic acids can be effective as well.

Further, it is contemplated that for any sequence identified, further optimization could be achieved by systematically either adding or removing nucleotides to generate longer or shorter sequences and testing those and sequences generated by walking a window of the longer or shorter size up or down the target RNA from that point. Again, coupling this approach to generating new candidate targets with testing for effectiveness of inhibitory nucleic acids based on those target sequences in an inhibition assay as known in the art or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes, etc.) as an expression inhibitor.

An inhibitory nucleic acid as described herein can contain one or more mismatches to the target sequence. In one embodiment, an inhibitory nucleic acid as described herein contains no more than 3 mismatches. If the antisense strand of the inhibitory nucleic acid contains mismatches to a target sequence, it is preferable that the area of mismatch not be located in the center of the region of complementarity. If the antisense strand of the inhibitory nucleic acid contains mismatches to the target sequence, it is preferable that the mismatch be restricted to be within the last 5 nucleotides from either the 5' or 3' end of the region of complementarity. For example, for a 23 nucleotide inhibitory nucleic acid agent strand which is complementary to a region of the target gene or a precursor thereof, the strand generally does not contain any mismatch within the central 13 nucleotides. The methods described herein or methods known in the art can be used to determine whether an inhibitory nucleic acid containing a mismatch to a target sequence is effective in inhibiting the expression of the target gene. Consideration of the efficacy of inhibitory nucleic acids with mismatches in inhibiting expression of the target gene is important, especially if the particular region of complementarity in the target gene is known to have polymorphic sequence variation within the population.

In yet another embodiment, the nucleic acid of an inhibitory nucleic acid, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of nucleic acid compounds useful in the embodiments described herein include, but are not limited to nucleic acids containing modified backbones or no natural internucleoside linkages. Nucleic acids having modified backbones include, among others, those that do not have a phosphorus atom in the backbone. For the purposes of this specification, and as sometimes referenced in the art, modified nucleic acids that do not have a phosphorus atom in their internucleoside backbone can also be considered to be oligonucleosides. In particular embodiments, the modified nucleic acid will have a phosphorus atom in its internucleoside backbone.

Modified backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference.

Modified backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other nucleic acid mimetics suitable or contemplated for use in inhibitory nucleic acids, both the sugar and the internucleoside linkage, i.e., the backbone, of the nucleotide units are replaced with novel groups. The base units are maintained for hybridization with an appropriate nucleic acid target compound. One such oligomeric compound, a nucleic acid mimetic that has been shown to have excellent hybridization properties, is referred to as a peptide nucleic acid (PNA). In PNA compounds, the sugar backbone of a nucleic acid is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include nucleic acids with phosphorothioate backbones and oligonucleosides with heteroatom backbones, and in particular —CH2-NH-CH2-, —CH2-N(CH3)-O—CH2-[known as a methylene (methylimino) or MMI backbone], —CH2-O—N(CH3)-CH2-, —CH2-N(CH3)-N(CH3)-CH2- and —N(CH3)-CH2-CH2-[wherein the native phosphodiester backbone is represented as —O—P—O—CH2-] of the above-referenced U.S. Pat. No. 5,489,677, and the amide backbones of the above-referenced U.S. Pat. No. 5,602,240. In some embodiments, the inhibitory nucleic acids featured herein have morpholino backbone structures of the above-referenced U.S. Pat. No. 5,034,506.

Modified nucleic acids can also contain one or more substituted sugar moieties. The inhibitory nucleic acids featured herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO] mCH3, O(CH2).nOCH3, O(CH2)nNH2, O(CH2) nCH3, O(CH2)nONH2, and O(CH2)nON[(CH2)nCH3)]2, where n and m are from 1 to about 10. In other embodiments, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an inhibitory nucleic acid, or a group for improving the pharmacodynamic properties of an inhibitory nucleic acid, and other substituents having similar properties. In some embodiments, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the nucleic acid of an inhibitory nucleic acid, particularly the 3' position of the sugar on the 3' terminal nucleotide or in 2'-5' linked dsRNAs and the 5' position of 5' terminal nucleotide. Inhibitory nucleic acids may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An inhibitory nucleic acid can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The nucleic acid of an inhibitory nucleic acid can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12):3185-3193).

Representative U.S. patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the nucleic acid of an inhibitory nucleic acid featured in the invention involves chemically linking to the nucleic acid one or more ligands, moieties or conjugates that enhance the activity, cellular distribution, pharmacokinetic properties, or cellular uptake of the inhibitory nucleic acid. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-

2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

In one embodiment, a ligand alters the distribution, targeting or lifetime of an inhibitory nucleic acid agent into which it is incorporated. In preferred embodiments a ligand provides an enhanced affinity for a selected target, e.g, molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid. Examples of polyamino acids include polylysine (PLL), poly L aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as an hepatopcyte or a macrophage, among others. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e,g, cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP Ligands can be proteins, e.g., glycoproteins, or peptides, e.g., molecules having a specific affinity for a co-ligand, or antibodies e.g., an antibody, that binds to a specified cell type such as a hepatocyte or macrophage. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose.

The ligand can be a substance, e.g, a drug, which can increase the uptake of the inhibitory nucleic acid agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an inhibitory nucleic acid as described herein acts as a pharmacokinetic (PK) modulator. As used herein, a "PK modulator" refers to a pharmacokinetic modulator. PK modulators include lipophiles, bile acids, steroids, phospholipid analogues, peptides, protein binding agents, PEG, vitamins etc. Examplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbaone are also amenable to the present invention as ligands (e.g. as PK modulating ligands). In addition, aptamers that bind serum components (e.g. serum proteins) are also suitable for use as PK modulating ligands in the embodiments described herein.

For macromolecular drugs and hydrophilic drug molecules, which cannot easily cross bilayer membranes, entrapment in endosomal/lysosomal compartments of the cell is thought to be the biggest hurdle for effective delivery to their site of action. A number of approaches and strategies have been devised to address this problem. For liposomal formulations, the use of fusogenic lipids in the formulation have been the most common approach (Singh, R. S., Goncalves, C. et al. (2004). On the Gene Delivery Efficacies of pH-Sensitive Cationic Lipids via Endosomal Protonation. A Chemical Biology Investigation. Chem. Biol. 11, 713-723. ). Other components, which exhibit pH-sensitive endosomolytic activity through protonation and/or pH-induced conformational changes, include charged polymers and peptides. Examples may be found in Hoffman, A. S., Stayton, P. S. et al. (2002). Design of "smart" polymers that can direct intracellular drug delivery. Polymers Adv. Technol. 13, 992-999; Kakudo, Chaki, T., S. et al. (2004). Transferrin-Modified Liposomes Equipped with a pH-Sensitive Fusogenic Peptide: An Artificial Viral-like Delivery System.

Biochemistry 436, 5618-5628; Yessine, M. A. and Leroux, J. C. (2004). Membrane-destabilizing polyanions: interaction with lipid bilayers and endosomal escape of biomacromolecules. Adv. Drug Deliv. Rev. 56, 999-1021; Oliveira, S., van Rooy, I. et al. (2007). Fusogenic peptides enhance endosomal escape improving inhibitory nucleic acid-induced silencing of oncogenes. Int. J. Pharm. 331, 211-4. They have generally been used in the context of drug delivery systems, such as liposomes or lipoplexes. For folate receptor-mediated delivery using liposomal formulations, for instance, a pH-sensitive fusogenic peptide has been incorporated into the liposomes and shown to enhance the activity through improving the unloading of drug during the uptake process (Turk, M. J., Reddy, J. A. et al. (2002). Characterization of a novel pH-sensitive peptide that enhances drug release from folate-targeted liposomes at endosomal pHs is described in Biochim. Biophys. Acta 1559, 56-68).

In certain embodiments, the endosomolytic components can be polyanionic peptides or peptidomimetics which show pH-dependent membrane activity and/or fusogenicity. A peptidomimetic can be a small protein-like chain designed to mimic a peptide. A peptidomimetic can arise from modification of an existing peptide in order to alter the molecule's properties, or the synthesis of a peptide-like molecule using unnatural amino acids or their analogs. In certain embodiments, they have improved stability and/or biological activity when compared to a peptide. In certain embodiments, the endosomolytic component assumes its active conformation at endosomal pH (e.g., pH 5-6). The "active" conformation is that conformation in which the endosomolytic component promotes lysis of the endosome and/or transport of the modular composition of the invention, or its any of its components (e.g., a nucleic acid), from the endosome to the cytoplasm of the cell.

Exemplary endosomolytic components include the GALA peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In certain embodiments, the endosomolytic component can contain a chemical group (e.g., an amino acid) which will undergo a change in charge or protonation in response to a change in pH. The endosomolytic component may be linear or branched. Exemplary primary sequences of endosomolytic components include H2N-(AALEALAEALEALAEALEA-LAEAAAAGGC)-CO2H (SEQ ID NO: 16); H2N-(AA-LAEALAEALAEALAEALAEALAAAAGGC)-CO2H (SEQ ID NO: 17); and H2N-(ALEALAEALEALAEA)-CONH2 (SEQ ID NO: 18).

In certain embodiments, more than one endosomolytic component can be incorporated into the inhibitory nucleic acid agent of the invention. In some embodiments, this will entail incorporating more than one of the same endosomolytic component into the inhibitory nucleic acid agent. In other embodiments, this will entail incorporating two or more different endosomolytic components into inhibitory nucleic acid agent.

These endosomolytic components can mediate endosomal escape by, for example, changing conformation at endosomal pH. In certain embodiments, the endosomolytic components can exist in a random coil conformation at neutral pH and rearrange to an amphipathic helix at endosomal pH. As a consequence of this conformational transition, peptides may insert into the lipid membrane of the endosome, causing leakage of the endosomal contents into the cytoplasm. Because the conformational transition is pH-dependent, the endosomolytic components can display little or no fusogenic activity while circulating in the blood (pH ~7.4). "Fusogenic activity," as used herein, is defined as that activity which results in disruption of a lipid membrane by the endosomolytic component. One example of fusogenic activity is the disruption of the endosomal membrane by the endosomolytic component, leading to endosomal lysis or leakage and transport of one or more components of the modular composition of the invention (e.g., the nucleic acid) from the endosome into the cytoplasm.

Suitable endosomolytic components can be tested and identified by a skilled artisan. For example, the ability of a compound to respond to, e.g., change charge depending on, the pH environment can be tested by routine methods, e.g., in a cellular assay. In certain embodiments, a test compound is combined with or contacted with a cell, and the cell is allowed to internalize the test compound, e.g., by endocytosis. An endosome preparation can then be made from the contacted cells and the endosome preparation compared to an endosome preparation from control cells. A change, e.g., a decrease, in the endosome fraction from the contacted cell vs. the control cell indicates that the test compound can function as a fusogenic agent. Alternatively, the contacted cell and control cell can be evaluated, e.g., by microscopy, e.g., by light or electron microscopy, to determine a difference in the endosome population in the cells. The test compound and/or the endosomes can labeled, e.g., to quantify endosomal leakage.

In another type of assay, an inhibitory nucleic acid agent described herein is constructed using one or more test or putative fusogenic agents. The inhibitory nucleic acid agent can be labeled for easy visulization. The ability of the endosomolytic component to promote endosomal escape, once the inhibitory nucleic acid agent is taken up by the cell, can be evaluated, e.g., by preparation of an endosome preparation, or by microscopy techniques, which enable visualization of the labeled inhibitory nucleic acid agent in the cytoplasm of the cell. In certain other embodiments, the inhibition of gene expression, or any other physiological parameter, may be used as a surrogate marker for endosomal escape.

In other embodiments, circular dichroism spectroscopy can be used to identify compounds that exhibit a pH-dependent structural transition. A two-step assay can also be performed, wherein a first assay evaluates the ability of a test compound alone to respond to changes in pH, and a second assay evaluates the ability of a modular composition that includes the test compound to respond to changes in pH.

In one embodiment of the aspects described herein, a ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

In another aspect, the ligand is a cell-permeation agent, preferably a helical cell-permeation agent. Preferably, such agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

Peptides suitable for use with the present invention can be a natural peptide, e.g., tat or antennopedia peptide, a synthetic peptide, or a peptidomimetic. Furthermore, the peptide can be a modified peptide, for example peptide can comprise non-peptide or pseudo-peptide linkages, and D-amino acids. A peptidomimetic (also referred to herein as an oligopeptidomimetic) is a molecule capable of folding into a defined three-dimensional structure similar to a natural peptide. The attachment of peptide and peptidomimetics to inhibitory nucleic acid agents can affect pharmacokinetic distribution of the inhibitory nucleic acid, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 19). An RFGF analogue (e.g., amino acid sequence AALLPVL-LAAP (SEQ ID NO: 20)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 21)) and the *Drosophila* Antennapedia protein (RQIKIWFQNRRMKWKK (SEQ ID NO: 22)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to a dsRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In some embodiments, the inhibitory nucleic acid oligonucleotides described herein further comprise carbohydrate conjugates. The carbohydrate conjugates are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include C5 and above (preferably C5-C8) sugars; di- and trisaccharides include sugars having two or three monosaccharide units (preferably C5-C8). In some embodiments, the carbohydrate conjugate further comprises other ligand such as, but not limited to, PK modulator, endosomolytic ligand, and cell permeation peptide.

In some embodiments, the conjugates described herein can be attached to the inhibitory nucleic acid oligonucleotide with various linkers that can be cleavable or non cleavable. The term "linker" or "linking group" means an organic moiety that connects two parts of a compound. Linkers typically comprise a direct bond or an atom such as oxygen or sulfur, a unit such as NR8, C(O), C(O)NH, SO, SO2, SO2NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), SO2, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between 1-24 atoms, preferably 4-24 atoms, preferably 6-18 atoms, more preferably 8-18 atoms, and most preferably 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. Further examples of cleavable linking groups include but are not limited to, redox-cleavable linking groups (e.g. a disulphide linking group (—S—S—)), phosphate-based cleavable linkage groups, ester-based cleavable linking groups, and peptide-based cleavable linking groups. Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; each of which is herein incorporated by reference.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

It is not necessary for all positions in a given compound to be uniformly modified, and in fact more than one of the aforementioned modifications can be incorporated in a single compound or even at a single nucleoside within an inhibitory nucleic acid. The present invention also includes inhibitory nucleic acid compounds that are chimeric compounds. "Chimeric" inhibitory nucleic acid compounds or "chimeras," in the context of this invention, are inhibitory nucleic acid compounds, e.g. dsRNAs, which contain two or more chemically distinct regions, each made up of at least one monomer unit, i.e., a nucleotide in the case of a dsRNA compound. These inhibitory nucleic acid typically contain at least one region wherein the nucleic acid is modified so as to confer upon the inhibitory nucleic acid increased resistance to nuclease degradation, increased cellular uptake, and/or increased binding affinity for the target nucleic acid. An additional region of the inhibitory nucleic acid may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibitory nucleic acid inhibition of gene expression. Consequently, comparable results can often be obtained with shorter inhibitory nucleic acids when chimeric inhibitory nucleic acids are used, compared to, e.g., phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the nucleic acid of an inhibitory nucleic acid can be modified by a non-ligand group. A number of non-ligand molecules have been conjugated to inhibitory nucleic acids in order to enhance the activity, cellular distribution or cellular uptake of the inhibitory nucleic acid, and procedures for performing such conjugations are available in the scientific literature. Such non-ligand moieties have included lipid moieties, such as cholesterol (Kubo, T. et al., Biochem. Biophys. Res. Comm., 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such nucleic acid conjugates have been listed above. Typical conjugation protocols involve the synthesis of an nucleic acid bearing an aminolinker at one or more positions of the sequence. The amino group is then reacted with the molecule being conjugated using appropriate coupling or activating reagents. The conjugation reaction may be performed either with the nucleic acid still bound to the solid support or following cleavage of the nucleic acid, in solution phase. Purification of the nucleic acid conjugate by HPLC typically affords the pure conjugate.

The term "aptamer" refers to a nucleic acid molecule that is capable of binding to a target molecule, such as a polypeptide. For example, an aptamer of the invention can specifically bind to a target molecule, or to a molecule in a signaling pathway that modulates the expression and/or activity of a target molecule. The generation and therapeutic use of aptamers are well established in the art. See, e.g., U.S. Pat. No. 5,475,096.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A chimeric molecule comprising a cancer marker-binding aptamer domain and an inhibitory nucleic acid domain.
2. The molecule of paragraph 1, wherein the cancer marker is EpCAM or EphA2.
3. The molecule of any of paragraphs 1-2, wherein the molecule is an aptamer-siRNA chimera (AsiC).
4. The molecule of any of paragraphs 1-3, wherein the inhibitory nucleic acid specifically binds to a gene product upregulated in a cancer cell.
5. The molecule of any of paragraphs 1-4, wherein the inhibitory nucleic acid inhibits the expression of a gene selected from the group consisting of: Plk1; MCL1; EphA2; PsmA2; MSI1; BMI1; XBP1; PRPF8; PFPF38A; RBM22; USP39; RAN; NUP205; and NDC80.
6. The molecule of any of paragraphs 1-5, wherein the cancer marker is EpCAM and the inhibitory nucleic acid domain inhibits the expression of Plk1.
7. The molecule of any of paragraphs 1-6, wherein the cancer marker-binding aptamer domain comprises the sequence of SEQ ID NO: 33.
8. The molecule of any of paragraphs 1-6, wherein the cancer marker-binding aptamer domain consists essentially of the sequence of SEQ ID NO: 33.
9. The molecule of any of paragraphs 1-8, wherein the inhibitory nucleic acid domain comprises the sequence of SEQ ID NO: 2.
10. The molecule of any of paragraphs 1-8, wherein the inhibitory nucleic acid domain consists essentially of the sequence of SEQ ID NO: 2.
11. The molecule of any of paragraphs 1-10, comprising the sequence of one of SEQ ID NOs: 1-3.
12. The molecule of any of paragraphs 1-11, consisting essentially of the sequence of one of SEQ ID NOs: 1-3.
13. The molecule of any of paragraphs 1-12, wherein the 3' end of the molecule comprises dTdT.
14. The molecule of any of paragraphs 1-13, wherein the molecule comprises at least one 2'-F pyrimidine.
15. A pharmaceutical composition comprising the molecule of any of paragraphs 1-14 and a pharmaceutically acceptable carrier.
16. The composition of paragraph 15, comprising at least two chimeric molecules of any of paragraphs 1-14, wherein the chimeric molecules have different aptamer domains or inhibitory nucleic acid domains.
17. The composition of paragraph 16, wherein different apatmer or inhibitory nucleic acid domains recognize different targets.
18. The composition of paragraph 16, wherein different apatmer or inhibitory nucleic acid domains have sequences and recognize the same target.
19. A method of treating cancer, the method comprising administering a molecule or composition of any of paragraphs 1-18.
20. The method of paragraph 19, wherein the cancer is an epithelial cancer or breast cancer
21. The method of paragraph 20, wherein the breast cancer is triple-negative breast cancer.
22. The method of any of paragraphs 19-21, wherein the administration is subcutaneous.
23. The method of any of paragraphs 19-22, wherein the subject is further administered an additional cancer treatment.
24. The method of paragraph 23, wherein the cancer treatment is paclitaxel.

EXAMPLES

Example 1: Gene Knockdown by EpCAM Aptamer-siRNA Chimeras Inhibits Basal-Like Triple Negative Breast Cancers and their Tumor-Initiating Cells Effective therapeutic strategies for in vivo siRNA delivery to knockdown genes in cells outside the liver are needed to harness RNA interference for treating cancer. EpCAM is a tumor-associated antigen highly expressed on common epithelial cancers and their tumor-initiating cells (T-IC, also known as cancer stem cells). It is demonstrated herein that aptamer-siRNA chimeras (AsiC, an EpCAM aptamer linked to an siRNA sense strand and annealed to the siRNA antisense strand) are selectively taken up and knockdown gene expression in EpCAM+ cancer cells in vitro and in human cancer biopsy tissues. PLK1 EpCAM-AsiCs inhibit colony and mammosphere formation (in vitro T-IC assays) and tumor initiation by EpCAM+ luminal and basal-A triple negative breast cancer (TNBC) cell lines, but not EpCAM– mesenchymal basal-B TNBCs, in nude mice. Subcutaneously administered EpCAM-AsiCs concentrate in EpCAM+ Her2+ and TNBC tumors and suppress their growth. Thus EpCAM-AsiCs provide an attractive approach for treating epithelial cancer.

Introduction

RNA interference (RNAi) offers the opportunity to treat disease by knocking down disease-causing genes.[1] Recent early phase clinical trials have shown vigorous (75-95%), sustained (lasting for several weeks or up to several months) and safe knockdown of a handful of gene targets in the liver using lipid nanoparticle-encapsulated or GalNAc-conjugated siRNAs.[2-5] The liver, the body's major filtering organ, traps particles and, hence, is relatively easy to transfect. The major obstacle to harnessing RNAi for treating most diseases however has yet to be solved—namely efficient delivery of small RNAs and gene knockdown in cells beyond the liver. In particular, the delivery roadblock is a major obstacle to harnessing RNAi to treat cancer.[6]

Triple negative breast cancers (TNBC), a heterogeneous group of poorly differentiated cancers defined by the lack of estrogen, progesterone and Her2 receptor expression, has the worst prognosis of any breast cancer subtype.[7-9] Most TNBCs have epithelial properties and are classified as basal-like or belong to the basal-A subtype, although a sizable minority are mesenchymal (basal-B subtype). TNBC afflicts younger women and is the subtype associated with BRCA1 genetic mutations. No targeted therapy is available. Although most TNBC patients respond to chemotherapy, within 3 years about a third develop metastases and eventually die. Thus new approaches are needed.

Described herein is a flexible, targeted platform for gene knockdown and treatment of basal-like TNBCs that might also be suitable for therapy against most of the common (epithelial) cancers. We deliver small interfering RNAs (siRNA) into epithelial cancer cells by linking them to an RNA aptamer that binds to EpCAM, the first described tumor antigen, a cell surface receptor over-expressed on epithelial cancers, including basal-like TNBCs. Aptamer-linked siRNAs, known as aptamer-siRNA chimeras (AsiC), have been used in small animal models to treat prostate cancer and prevent HIV infection.[10-18] We chose EpCAM for targeting basal-like TNBC because EpCAM is highly expressed on epithelial cancers. A high affinity EpCAM aptamer was previously identified. {Shigdar, 2011 #17903} EpCAM also marks tumor-initiating cells (T-ICs, also known as cancer stem cells).[20-27] These cells are thought responsible not only for initiating tumors, but are also relatively resistant to conventional cytotoxic therapy and are thought responsible for tumor relapse and metastasis. Devising therapies to eliminate T-ICs is an important unmet goal of cancer research.[28]

In normal epithelia, EpCAM is only weakly expressed on basolateral gap junctions, where it may not be accessible to drugs.[29] In epithelial cancers it is not only more abundant (by orders of magnitude), but is also distributed along the cell membrane. Ligation of EpCAM promotes adhesion and enhances cell proliferation and invasivity. Proteolytic cleavage of EpCAM releases an intracellular fragment that increases stem cell factor transcription.[30,31] EpCAM's oncogenic properties may make it difficult for tumor cells to develop resistance by down-modulating EpCAM. In one study about ⅔ of TNBCs, presumably the basal-A subtype, stained strongly for EpCAM.[25] The number of EpCAM+ circulating cells is linked to poor prognosis in breast cancer.[32-36] An EpCAM antibody has been evaluated clinically for epithelial cancers, but had limited effectiveness on its own.[37-39] EpCAM expression identifies circulating tumor cells in an FDA-approved method for monitoring metastatic breast, colon and prostate cancer treatment[32-36]. Moreover, about 97% of human breast cancers and virtually 100% of other common epithelial cancers, including lung, colon, pancreas and prostate, stain brightly for EpCAM, suggesting that the platform developed here could be adapted for RNAi-based therapy of common cancers.

It is demonstrated herein that all epithelial breast cancer cell lines tested stained brightly for EpCAM, while immortalized normal breast epithelial cells, fibroblasts and mesenchymal tumor cell lines did not. EpCAM-AsiCs caused targeted gene knockdown in luminal and basal-A TNBC cancer cells and human breast cancer tissues in vitro, but not in normal epithelial cells, mesenchymal tumor cells or normal human breast tissues. Knockdown was proportional to EpCAM expression. Moreover EpCAM-AsiC-mediated knockdown of PLK1, a gene required for mitosis, suppressed in vitro T-IC functional assays (colony and mammosphere formation) of epithelial breast cancer lines. Ex vivo treatment specifically abrogated tumor initiation. Subcutaneously injected PLK1 EpCAM-AsiCs were taken up specifically by EpCAM+ basal-A triple negative breast cancer (TNBC) orthotopic xenografts of poor prognosis basal-A and Her2 breast cancers and caused rapid tumor regression.

EpCAM is Highly Expressed on Epithelial Breast Cancer Cell Lines

First, EpCAM expression was examined in breast cancer cell lines. Based on gene expression data in the Cancer Cell Line Encyclopedia40,EpCAM mRNA is highly expressed in basal-A TNBC and luminal breast cancer cell lines, but poorly in basal-B (mesenchymal) TNBCs (FIG. 1A). Surface EpCAM staining, assessed by flow cytometry, was 2-3 logs brighter in all luminal and basal-like cell lines tested, than in normal epithelia immortalized with hTERT (BPE)[41], fibroblasts or mesenchymal TNBCs (FIG. 1B). Thus EpCAM is highly expressed in epithelial breast cancer cell lines compared to normal cells or mesenchymal tumors.

Figure 7:
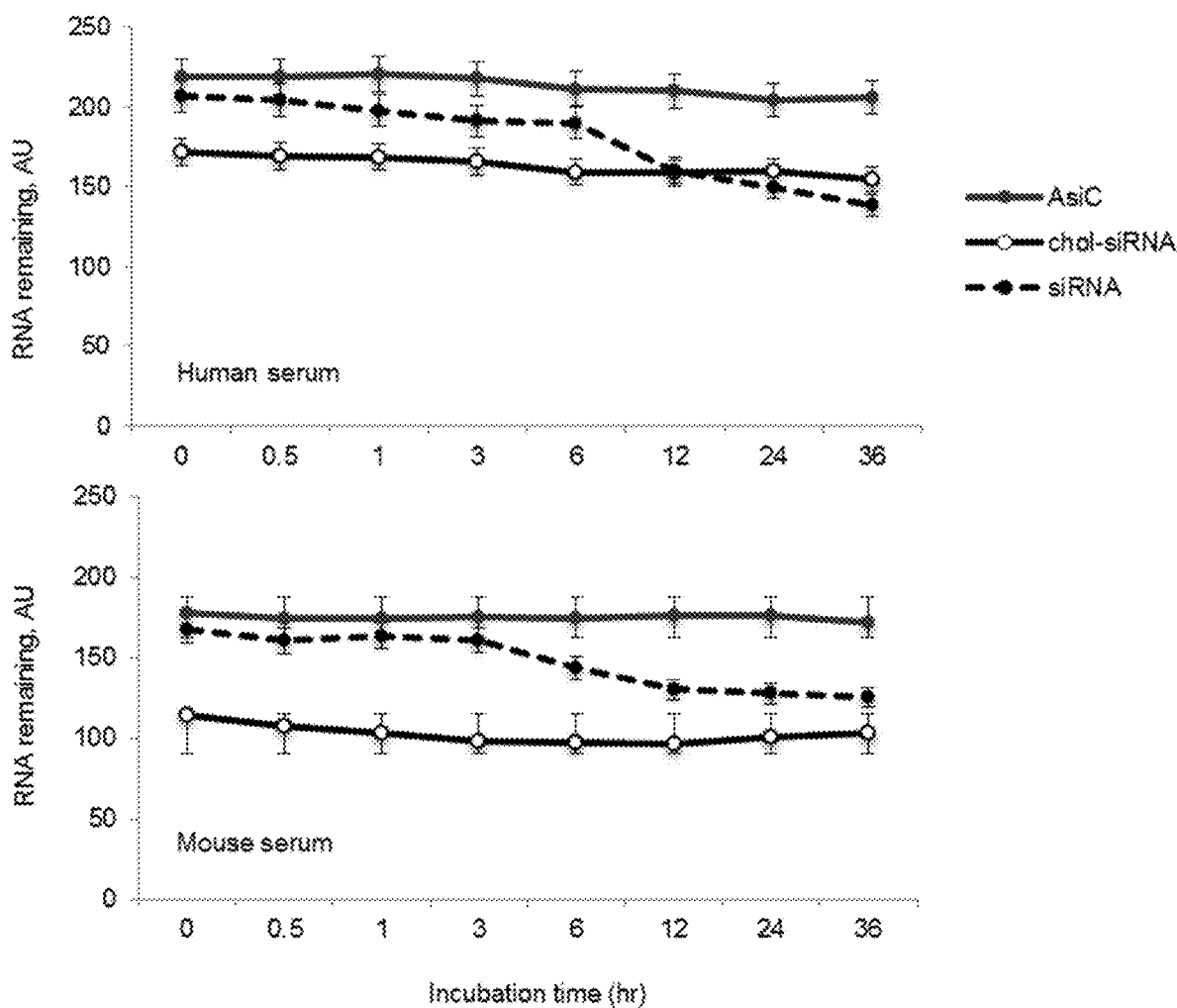
FIG. 7 demonstrates that EpCAM AsiCs are stable in human and mouse serum. eGFP EpCAM-AsiCs synthesized using 2'-fluoro-pyrimidines, chemically-stabilized cholesterol-conjugated eGFP siRNAs (chol-siRNA), or unmodified eGFP siRNAs were incubated with an equal volume of human or mouse serum. Aliquots were removed at regular intervals and resuspended in gel loading buffer and stored at −80° C. before electrophoresis on denaturing PAGE gels. The average intensity (+S.E.M.) of bands from 2 independent experiments quantified by densitometry after staining is shown.
Figure 8A:
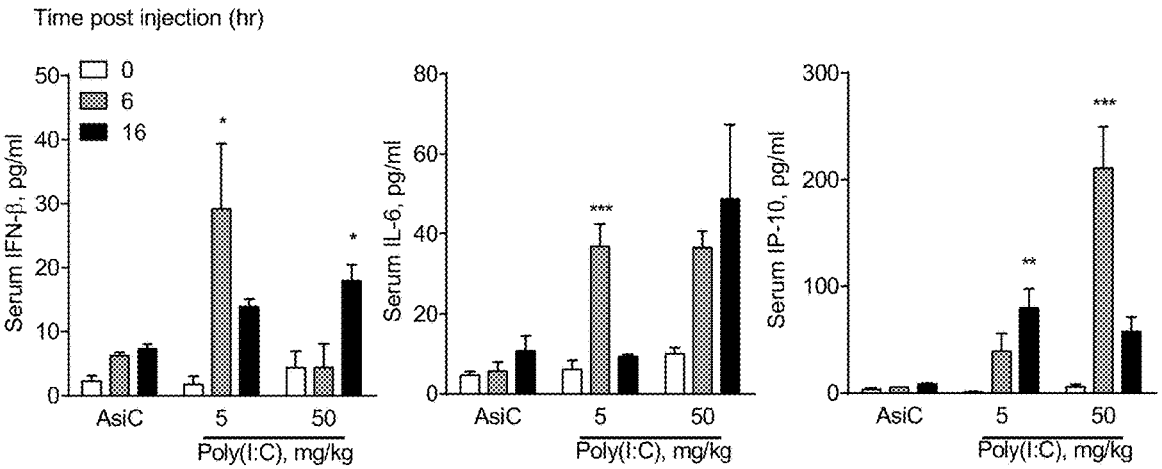
FIGS. 8A-8B demonstrate that injection of EpCAM AsiCs does not stimulate innate immunity in mice. Mice were injected sc with eGFP EpCAM-AsiCs (5 mg/kg, n=3) or ip with Poly(I:C) (5 or 50 mg/kg (n=2/dose).
Figure 8B:
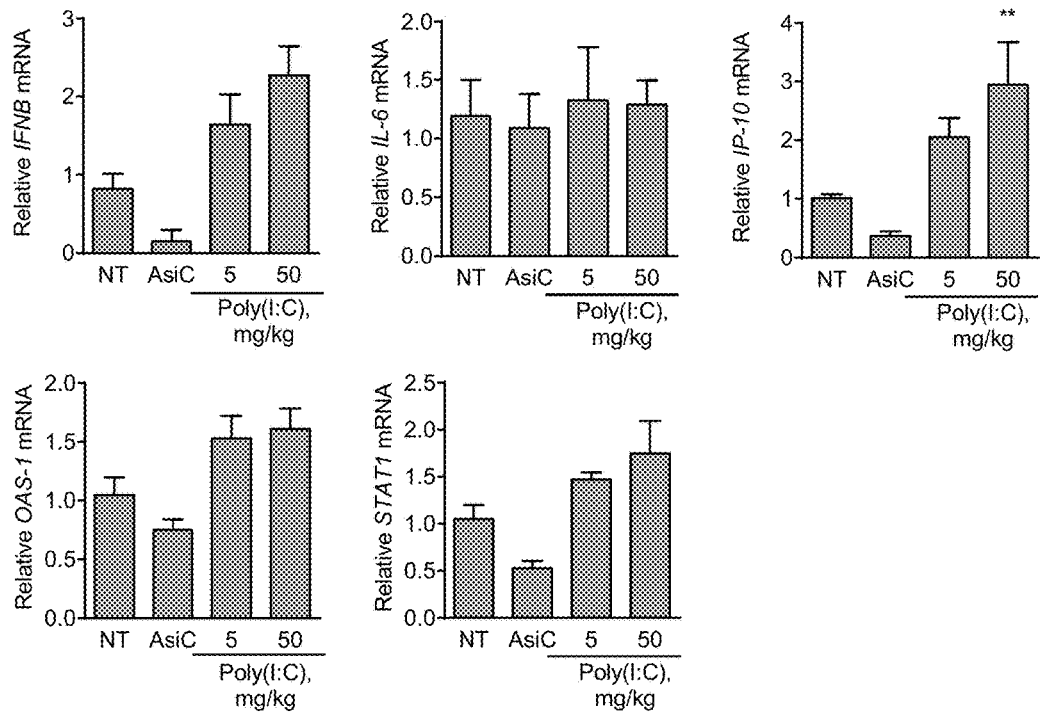

EpCAM-AsiCs Selectively Knock Down Gene Expression in EpCAM+ Breast Cancer Cells A 19 nucleotide (nt) aptamer that binds to human EpCAM with 12 nM affinity[19] was identified by SELEX.[42,43] It does not bind to mouse EpCAM (data not shown). A handful of EpCAM-AsiCs that linked either the sense or antisense strand of the siRNA to the 3'-end of the aptamer by several linkers were designed and synthesized with 2'-fluoropyrimidine substitutions and 3'-dTdT overhangs to enhance in vivo stability, avoid off-target knockdown of partially complementary genes bearing similar sequences, and limit innate immune receptor stimulation. To test RNA delivery, gene knockdown and anti-tumor effects, siRNAs were incorporated to knockdown eGFP (as a useful marker gene); AKT1, an endogenous gene expressed in all the cell lines studied, whose knockdown is not lethal; and PLK1, a kinase required for mitosis, whose knockdown is lethal (FIG. 9). The AsiC that performed best in dose response studies of gene knockdown joined the 19 nt EpCAM aptamer to the sense (inactive) strand of the siRNA via a U-U-U linker (FIG. 1C). The EpCAM-AsiC was produced by annealing the chemically synthesized ~42-44 nt long strand (19 nt aptamer+linker+ 20-22 nt siRNA sense strand) to a 20-22 nt antisense siRNA strand. Commercially synthesized with 2'-fluoropyrimidines {Jackson, 2003 #11353; Scacheri, 2004 #11912; Jackson, 2006 #13758; Wheeler, 2011 #17906}, these are RNase resistant and very stable in human serum ($T_{1/2}$>>36 hr, FIG. 7) and do not trigger innate immunity when injected in vivo into tumor-bearing mice (FIG. 7).

To verify selective uptake by EpCAM+ tumor cells, confocal fluorescence microscopy was used to compare internalization of the EpCAM aptamer, fluorescently labeled at the 5'-end with Cy3, in EpCAM+ MDA-MB-468 TNBC cells and BPE, $EpCAM^{dim}$ immortalized breast epithelial cells (data not shown). Without wishing to be bound by theory, because AsiCs contain only one aptamer, they do not crosslink the receptor they recognize. As a consequence, cellular internalization is slow since it likely occurs via receptor recycling, rather than the more rapid process of activation-induced endocytosis.

Figure 33:
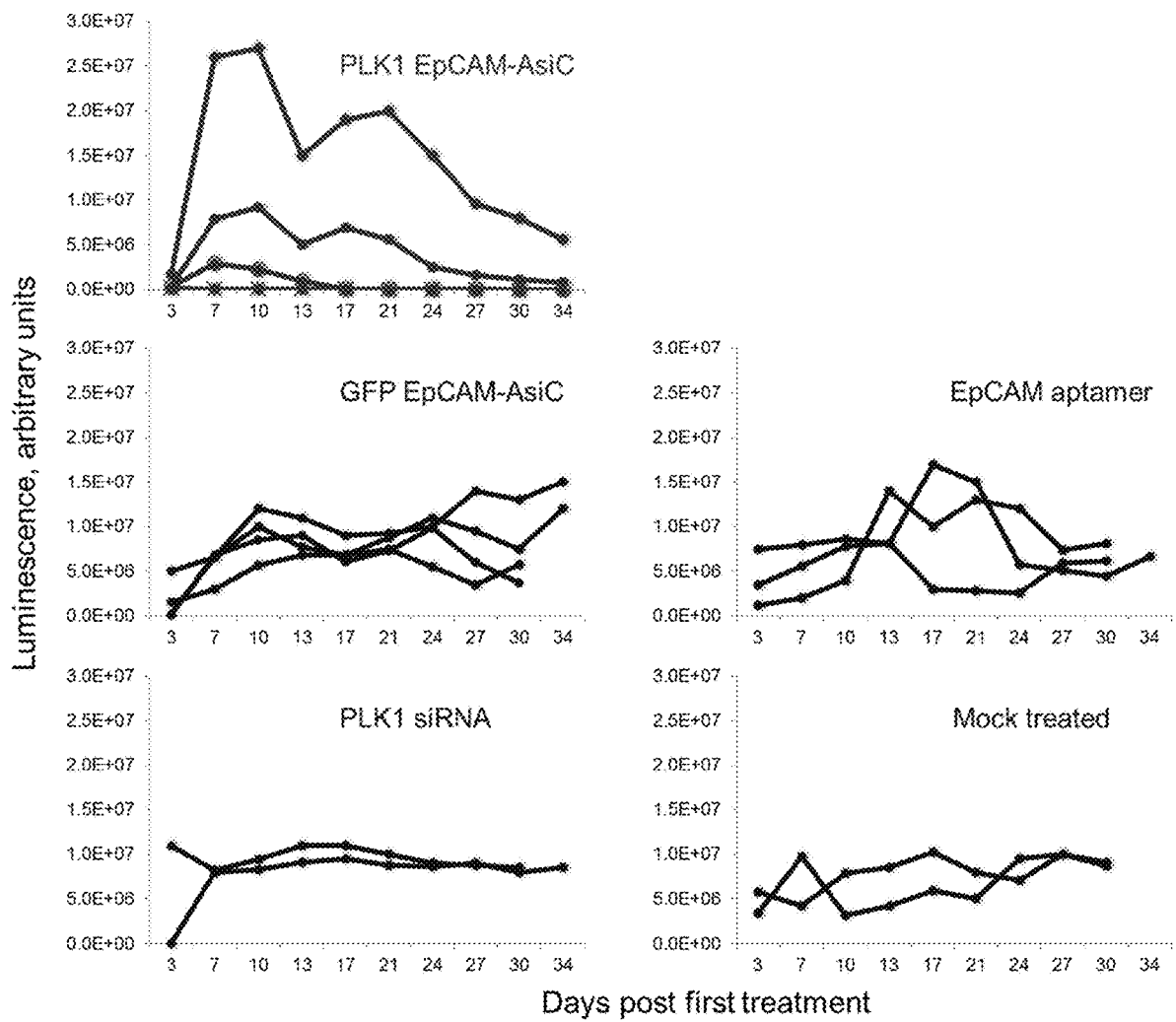
FIG. 33 depicts graphs of tumor growth demonstrating that MB468 tumors regress only after treatment with PLK1 EpCAM-AsiC. Mice with sc MB468 tumors were treated with 5 mg/kg RNA 2x/wk beginning when tumors became palpable. PLK1 EpCAM-AsiC, GFP SpCAM-AsiC, EpCAM aptamer, PLK1 siRNA, and mock treated samples were analyzed as indicated.
Figure 33:
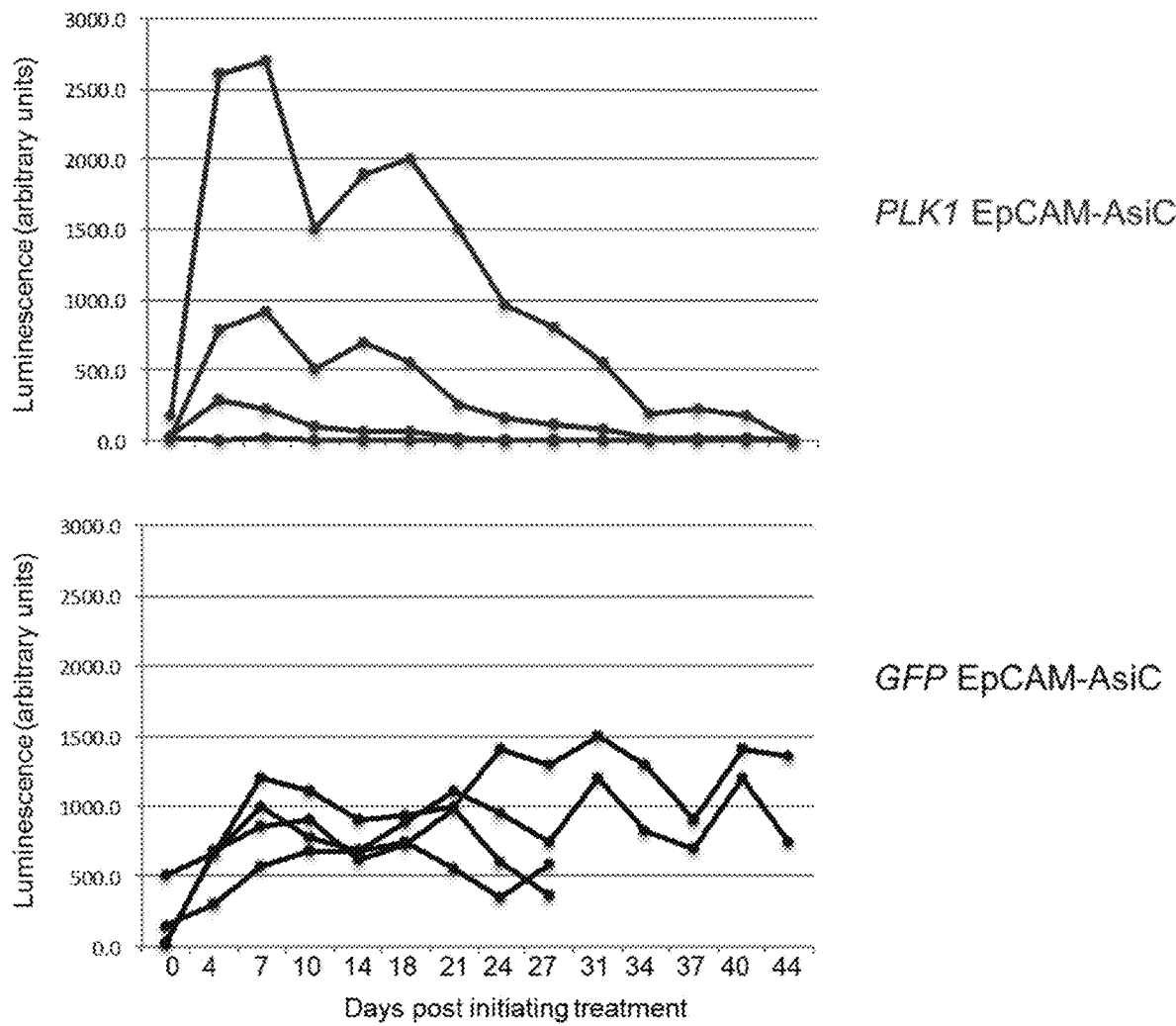
Figure 33:
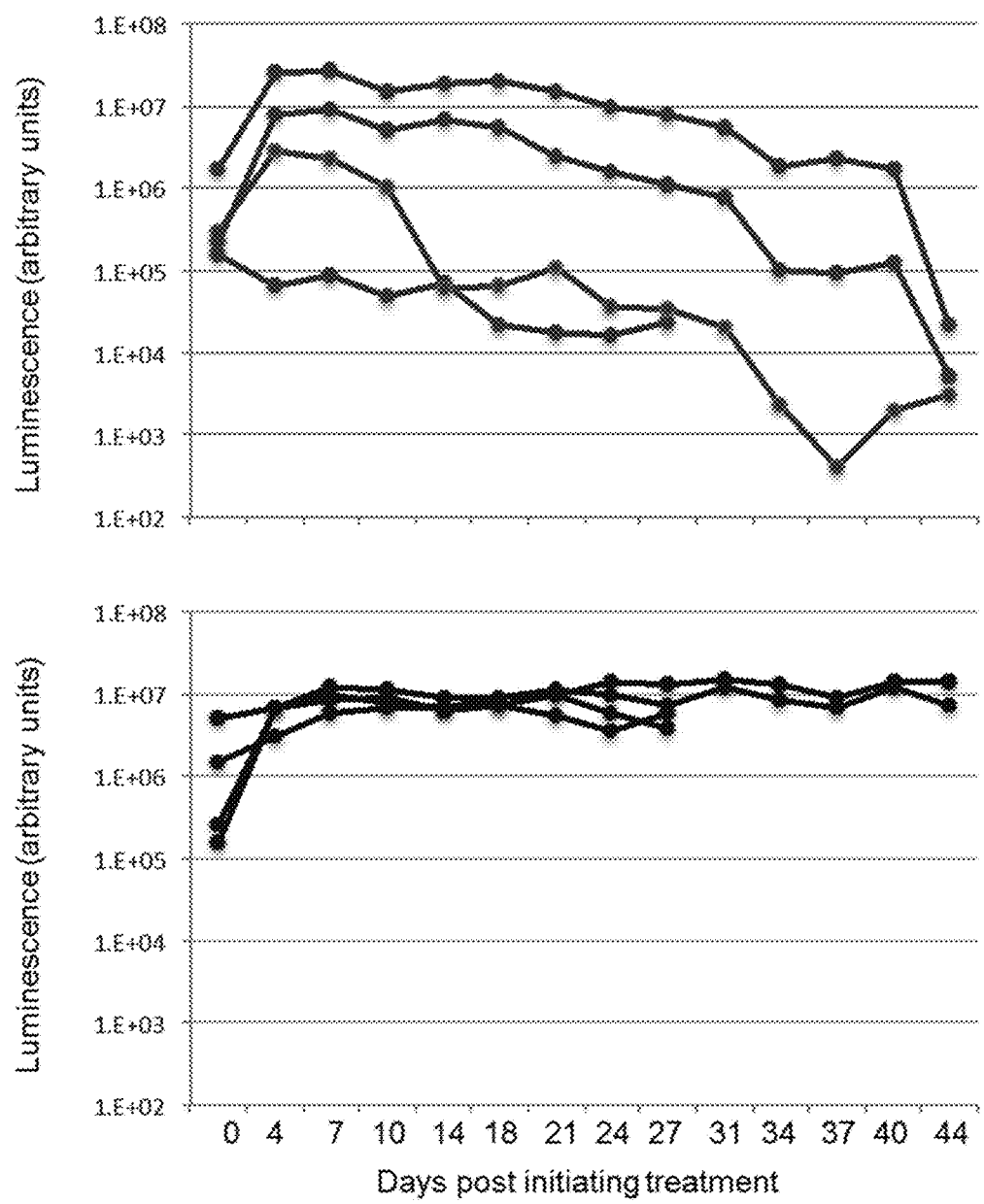

Only MDA-MB-468 cells took up the aptamer. Uptake was clearly detected at 22 hr, but increased greatly after 43 hr. To test whether EpCAM-AsiCs are specifically taken up by EpCAM bright cell lines, the 3' end of the antisense strand of the AsiC was fluorescently labeled. EpCAM+ BPLER, a basal-A TNBC cell line transformed from BPE by transfection with human TERT, SV40 early region and H-RASV12, took up Alexa-647 EpCAM-AsiCs when analyzed after a 24 hr incubation, but BPE cells did not (FIG. 1D). Previous studies have shown that AsiCs are processed within cells by Dicer to release the siRNA from the aptamer (10, 12, 15). To verify that the released siRNA was taken up by the RNA induced silencing complex (RISC), qRT-PCR was utilized to amplify that PLK1 siRNA immunoprecipitated with Ago when MDA-MB-468 cells were incubated with PLK1 EpCAM-AsiCs (FIG. 33). No PLK1 siRNA bound to Ago when the same cells were incubated with PLK1 siRNAs.

Figure 1E:
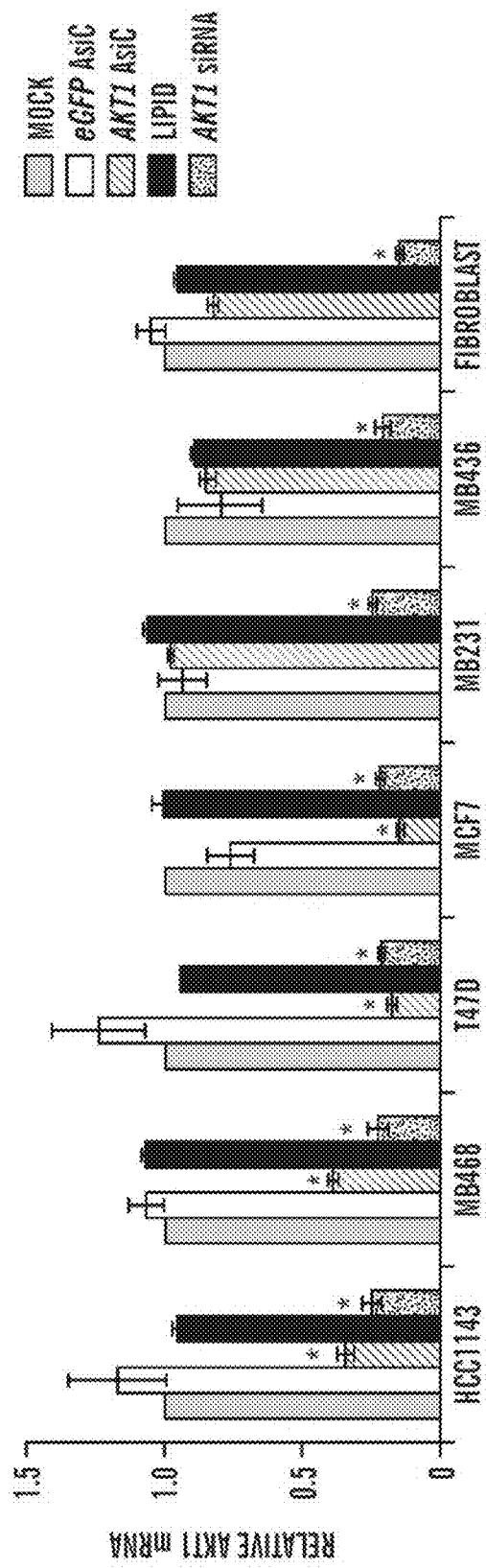
Figure 1F:
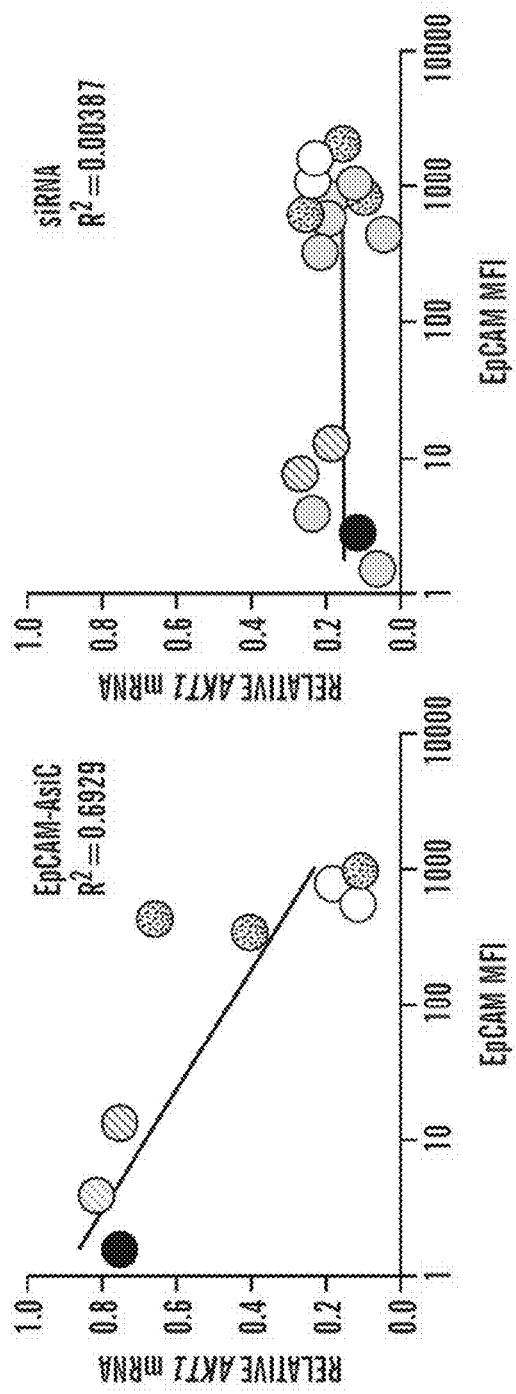
Figure 1G:
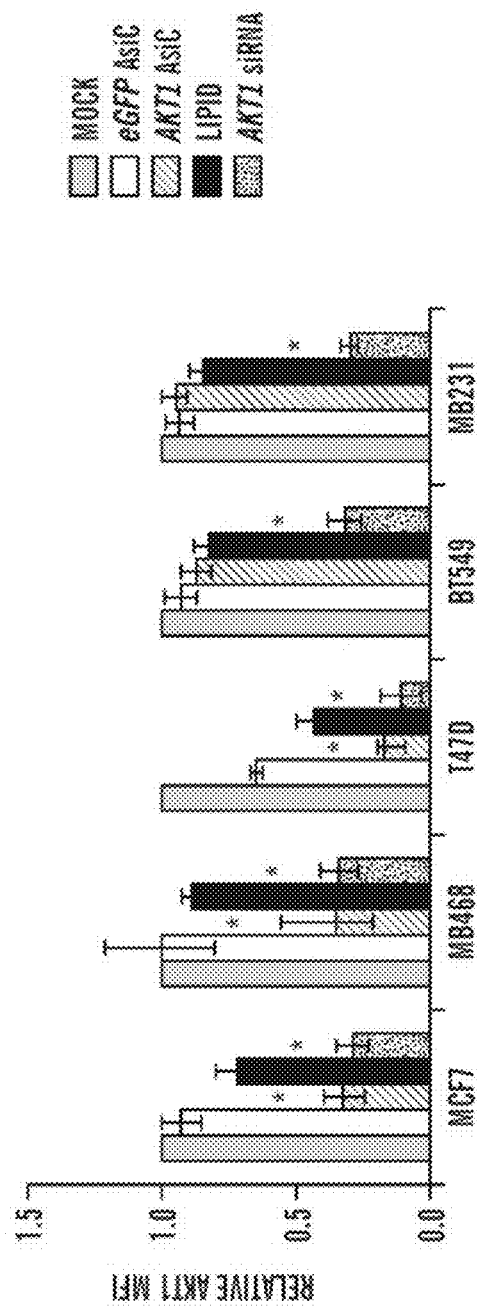
Figure 1H:
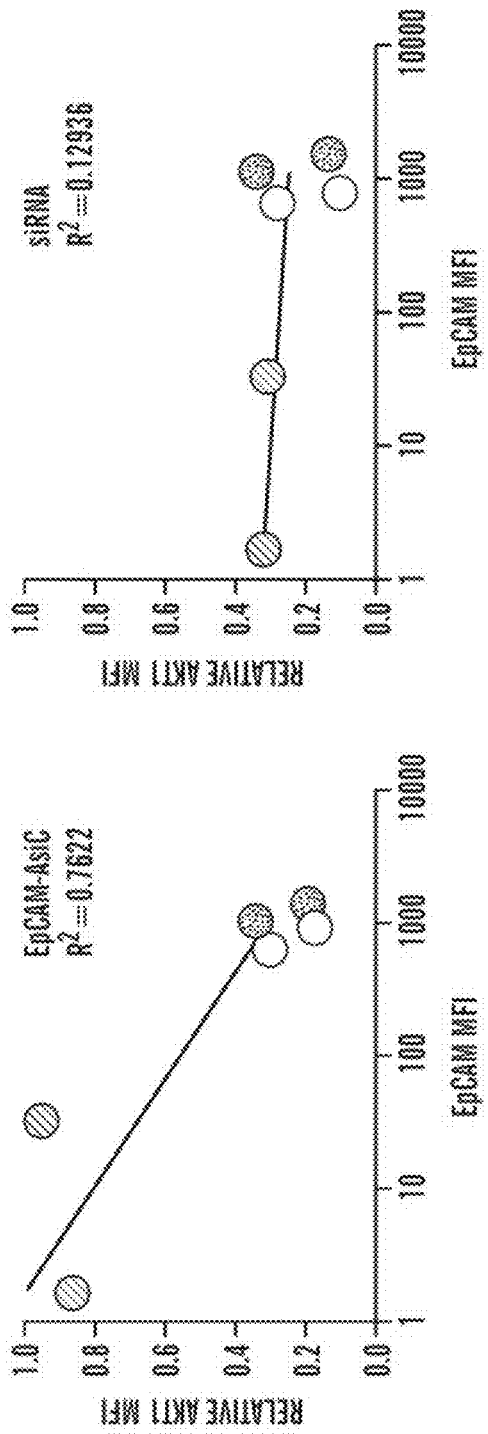

TNBC cells took up Alexa-467 EpCAM-AsiCs, but no uptake was detectable in BPE cells (FIG. 1E). Next to assess whether gene knockdown was specific to EpCAM+ tumors, eGFP knockdown was compared in these same cell lines, which stably express eGFP, by eGFP EpCAM-AsiCs and lipid transfection of eGFP siRNAs (FIG. 1D). Although transfection of eGFP siRNAs knocked down gene expression equivalently in BPE and BPLER, Incubation with EpCAM-AsiCs in the absence of any transfection lipid selectively knocked down expression only in BPLER. AsiC knockdown was uniform and comparable to that achieved with lipid transfection. Next we compared the specific knockdown of the endogenous AKT1 gene by AKT1 AsiCs and transfected AKT1 siRNAs in 6 breast cancer cell lines compared to normal human fibroblasts (FIG. 1E). AKT1 was selectively knocked down by EpCAM-AsiCs targeting AKT1 only in $EpCAM^{bright}$ luminal and basal-A TNBCs, but not in mesenchymal basal-B TNBCs, fibroblasts or BPE ells (data not shown). As expected, AsiCs targeting eGFP had no effect on AKT1 levels and transfection of AKT1 siRNAs comparably knocked down expression in all the cell lines studied. Moreover, EpCAM-AsiC knockdown of AKT1 strongly correlated with EpCAM expression (FIG. 1G). Similar results were obtained when AKT1 protein was analyzed by flow cytometry in stained transfected cells (FIG. 1G, 1H). Thus in vitro knockdown by EpCAM-AsiCs is effective and specific for $EpCAM^{bright}$ tumor cells.

PLK1 EpCAM-AsiCs Selectively Kill $EpCAM^{bright}$ Tumor Cells In Vitro

Figure 2A:
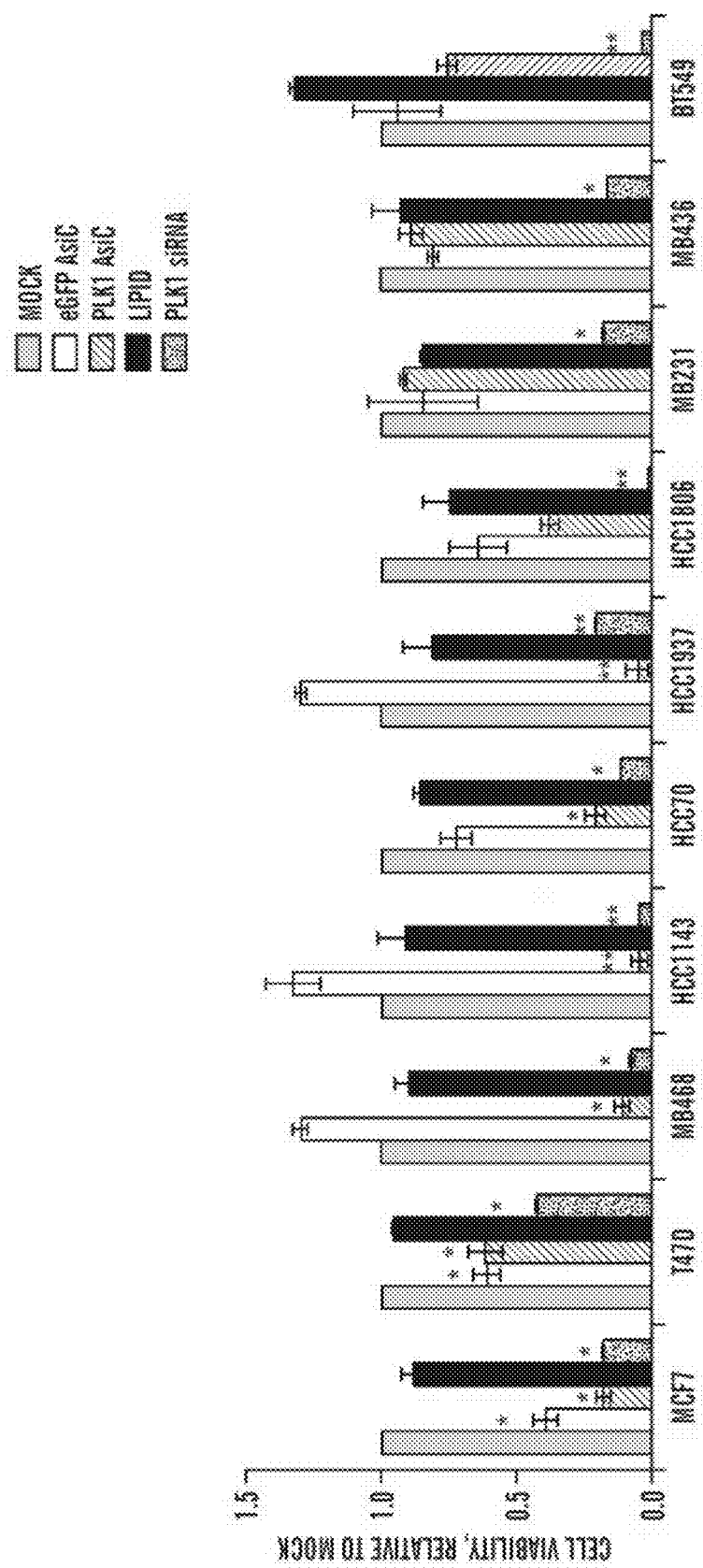

To explore whether EpCAM-AsiCs could be used as anti-tumor agents in breast cancer, we examined by CellTiterGlo assay the effect of AsiCs directed against PLK1, a kinase required for mitosis, on survival of 10 breast cancer cell lines that included 5 basal-A TNBCs, 2 luminal cell lines, and 3 basal-B TNBCs. EpCAM-AsiCs targeting PLK1, but not control AsiCs directed against eGFP, decreased cell proliferation in the basal-A and luminal cell lines, but did not inhibit basal-B cells (FIG. 2A). Lipid transfection of PLK1 siRNAs suppressed the growth of all the cell lines. The anti-proliferative effect strongly correlated with EpCAM expression (FIG. 2B). The reduction in viable EpCAM+ cells after knockdown was due to induction of apoptosis, assessed by annexin V-propidium iodide staining and caspase activation (data not shown). To determine whether ligation of the EpCAM aptamer contributed to the anti-proliferative effect of the EpCAM-AsiC, we compared survival of cells that were treated with the PLK1 EpCAM-AsiC with cells treated with the aptamer on its own (FIG. 2C). The aptamer by itself did not have a reproducible effect on survival of any breast cancer cell lines, possibly because as a monomeric agent it does not cross-link the EpCAM receptor to alter EpCAM signaling. Thus the PLK1 EpCAM-AsiC asserts its specific anti-tumor effect on EpCAM+ breast cancer cells by gene knockdown.

Figure 2D:
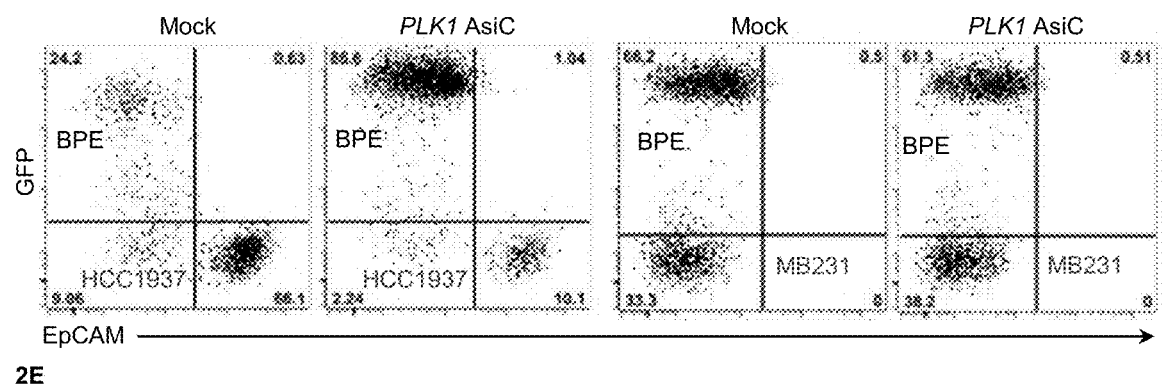
Figure 2E:
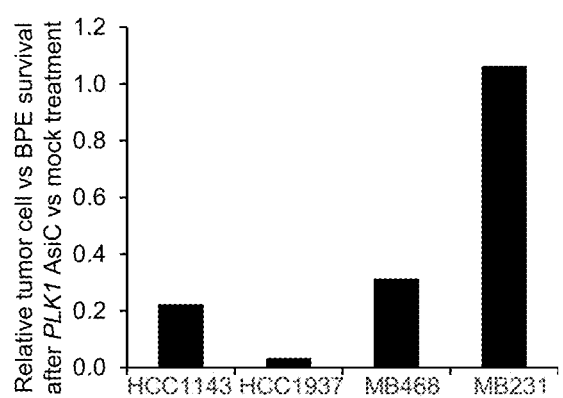

To determine whether EpCAM-AsiCs specifically target EpCAM+ cells when mixed with $EpCAM^{dim}$ non-transformed epithelial cells, we incubated co-cultures of GFP− TNBC cells and GFP+ BPE cells with PLK1 EpCAM-AsiCs or medium and used GFP fluorescence to measure their relative survival by flow cytometry 3 days later (FIG. 2D, 2E). EpCAM-AsiCs targeting PLK1 greatly reduced the proportion of surviving EpCAM+ basal-A tumor cells, but had no effect on survival of an EpCAM− basal-B cell line. Thus PLK1 EpCAM-AsiCs are selectively cytotoxic for EpCAM+ tumor cells when mixed with normal cells.

EpCAM-AsiCs Concentrate in EpCAM+ Breast Tumor Biopsy Specimens

Figure 3A:
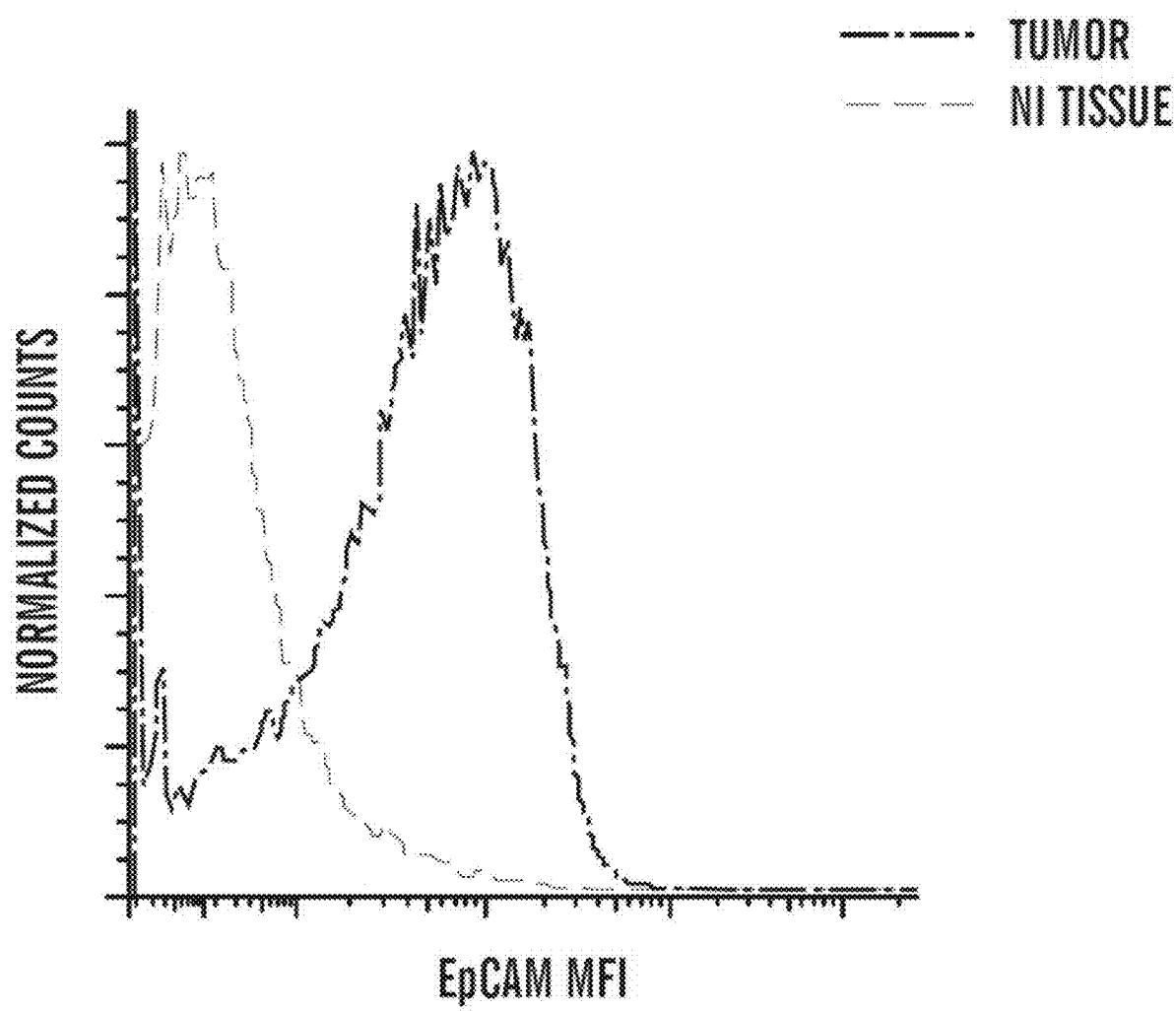
FIGS. 3A-3D demonstrate that human TNBC tissue specifically takes up Cy3-EpCAM aptamers. Experimental design; Cy3-EpCAM-AsiC targeting GFP, Alexa647-siRNA-GFP or Alexa647-chol-siRNA-GFP (2 µM of each) were added to breast cancer and control explants and incubated for 24 h before tissue was digested with collagenase to a single cell suspension and analyzed by flow cytometry (FIG. 3A). Tumor biopsies over express EpCAM and cytokeratin, an epithelial cell marker (FIG. 3B) Representative histograms from one of three independent experiments show that siRNA and chol-siRNA penetrated both tumor and healthy tissue with similar efficacy while EpCAM-AsiC was selectively uptaken by the tumor tissue biopsy and not by the healthy control tissue sample (FIG. 3C). The uptake experiment was repeated in tumors from three different patients, each biopsy receive was tested 3 times for each treatment. A summary of all three patients (FIG. 3D). (n=3, mock, gray EpCAM, red *P<0.05, **P<0.005, t-test CD4-AsiC versus mock treatment).
Figure 3B:
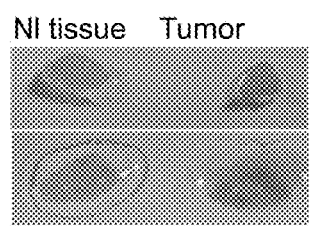

It was next examined whether EpCAM-AsiCs concentrate in human breast tumors relative to normal breast samples within intact tissues. Paired normal tissue and breast tumor biopsies from 3 breast cancer patients were cut into cubes with ~3 mm edges and placed in Petri dishes. The tumor sample cells were all $EpCAM^{bright}$ and the normal tissue cells were $EpCAM^{dim}$ (FIG. 3A). Fluorescently labeled Alexa647-siRNAs (not expected to be taken up by either normal tissue or tumor), Alexa647-cholesterol-conjugated siRNAs (chol-siRNAs, expected to be taken up by both), or Cy3-EpCAM-AsiCs were added to the culture medium and the tissues were incubated for 24 hr before harvest. The Cy3 signal of the AsiC, which could be visualized by the naked eye, concentrated only in the tumor specimens and was not detected in normal tissue (FIG. 3B). To quantify RNA uptake, flow cytometry analysis was performed on washed single cell suspensions of the tissue specimens (representative tumor-normal tissue pair (FIG. 3C), mean±SD of triplicate biospies from 3 $EpCAM^{bright}$ paired breast tumor-normal tissue samples (FIG. 3D)). The EpCAM-AsiC was significantly taken up by the tumor, but not normal tissue, while neither took up the unconjugated siRNA and both took up the chol-siRNA to some extent. Thus, within intact tissue, EpCAM-AsiCs are selectively delivered to $EpCAM^{bright}$ tumors relative to normal tissue.

PLK1 EpCAM-AsiCs Inhibit T-ICs of EpCAM+ Tumors

Figure 4A:
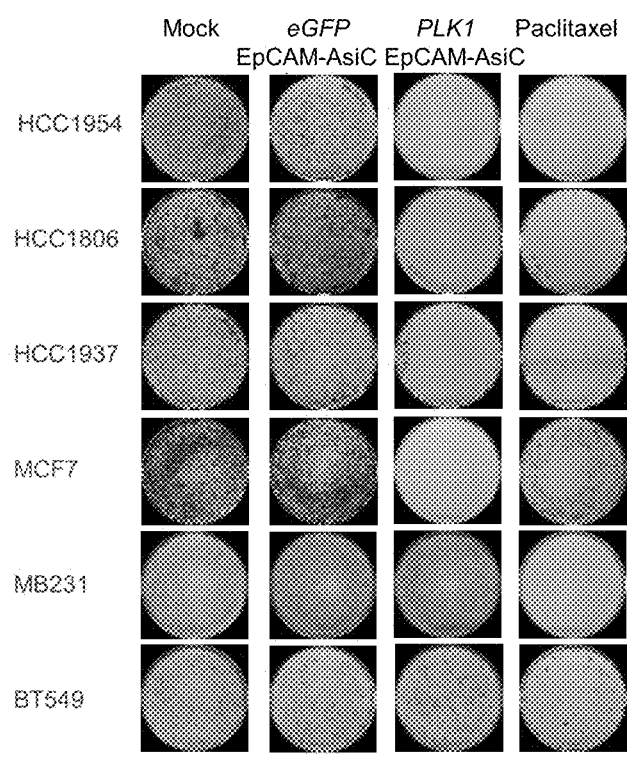
FIGS. 4A-4C demonstrate that EpCAM AsiC targeting PLK1 specifically inhibits tumor initiation in Basal A breast cancer cells. Colony assays of breast cancer cell lines were treated with EpCAM-AsiC targeting PLK1 or GFP (4 uM) or paclitaxel (100 nM) for 24 hr and cultured for 8 days in drug-free medium. Treatment with paclitaxel decreased colony formation in all cells lines while treatment with EpCAM-AsiC targeting PLK1 only eliminated colony formation in luminal (MCF7) and basal A (HCC1954) cells, treatment with EpCAM-AsiC targeting GFP had no effect (FIG. 4A). The assay was repeated in 3 more cells lines and results were reproducible (FIG. 4B). Sphere formation assay indicated similar results, EpCAM-AsiC targeting PLK1 decreased the number of spheres only in basal A and luminal cells and had no effect on basal B cells (FIG. 4C). MB468-luc cells were treated for 24 h with EpCAM-AsiC targeting either GFP or PLK1 and injected s.c. to the flank of nude mice. Mice were imaged every 5 days for 20 days. Untreated mice and mice treated with EpCAM-AsiC targeting GFP, displayed increase in tumor initiation while mice injected with cell pretreated with EpCAM-AsiC targeting PLK1 has no tumor initiation.
Figure 4B:
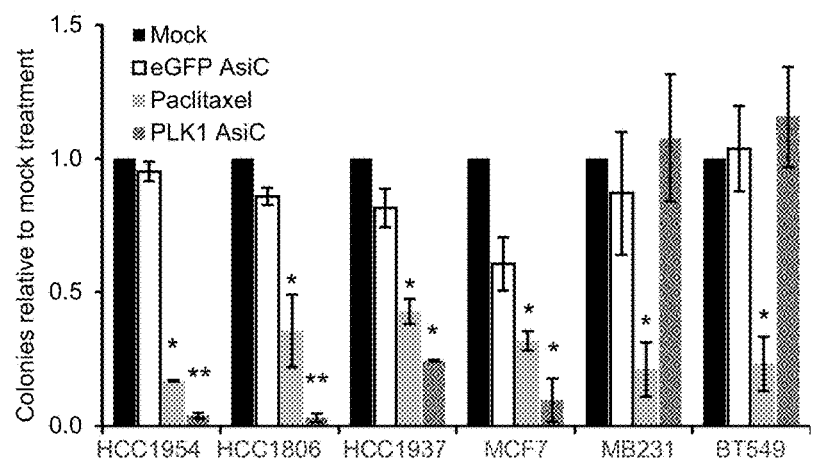
Figure 4C:
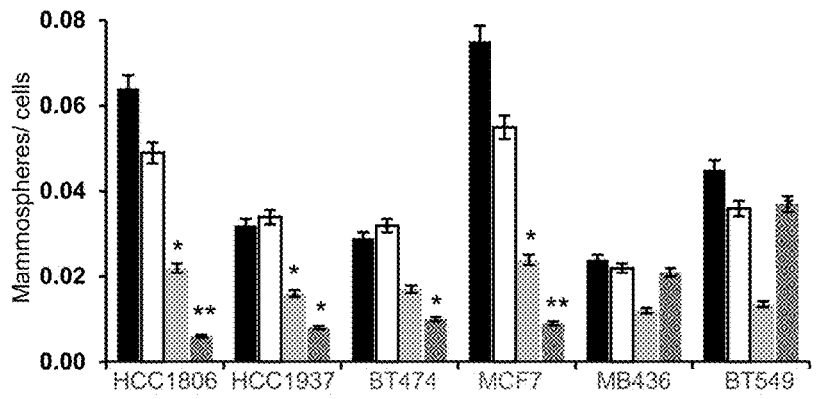

EpCAM was chosen for targeting in part because EpCAM marks T-ICs and metastasis-initiating cells (M-IC).[20,22,26,27,31] To investigate whether EpCAM-AsiCs inhibit T-ICs, we compared colony and mammosphere formation (T-IC functional surrogate assays) after mock treatment, treatment with paclitaxel or with EpCAM-AsiCs against eGFP or PLK1. PLK1 EpCAM-AsiCs more strongly inhibited colony and mammosphere formation of EpCAM+ basal-A TNBCs and luminal cell lines than paclitaxel, but were inactive against EpCAM− basal-B TNBCs (FIGS. 4A-C). T-IC inhibition was specific, since eGFP AsiCs had no effect. Incubation with PLK1 EpCAM-AsiCs, but not eGFP AsiCs, also reduced the proportion of cells with the phenotype of T-ICs, namely the numbers of CD44+ $CD24^{low/-}$ and ALDH+ cells specifically in basal-A and luminal breast cancer cell lines (data not shown). To evaluate the effect of EpCAM-AsiCs on tumor initiation, EpCAM+ MB468 cells stably expressing luciferase were treated overnight with medium or PLK1 or eGFP EpCAM-AsiCs and equal numbers of viable cells were then implanted sc in nude mice. PLK1 EpCAM-AsiCs completely blocked tumor formation assessed by in vivo tumor cell luminescence (data not shown). In contrast similar treatment of basal-B MB436 cells had no effect on tumor initiation (data not shown). Thus PLK1 EpCAM-AsiCs inhibit in vitro T-IC assays and tumor initiation selectively for EpCAM+ breast cancers.

Figure 5A:
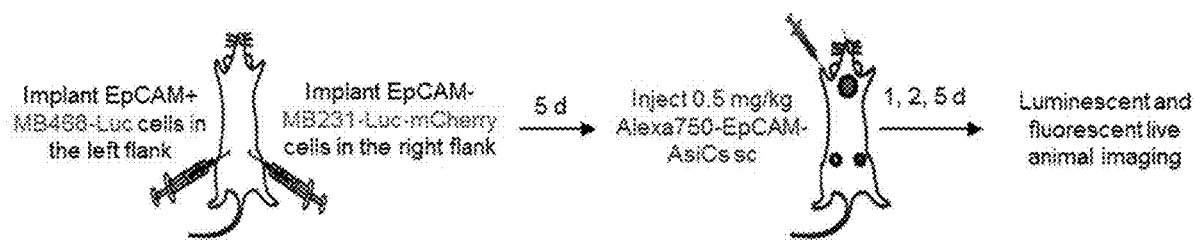
FIGS. 5A-5C demonstrate the selective uptake of Alexa750-EpCAM-AsiCs into EpCAM+ tumors.
Figure 5B:
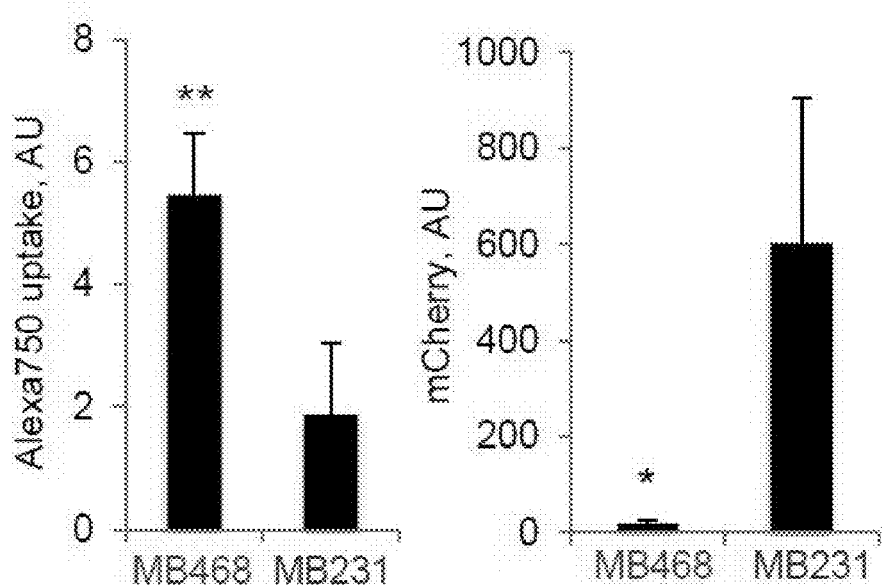
Figure 5C:
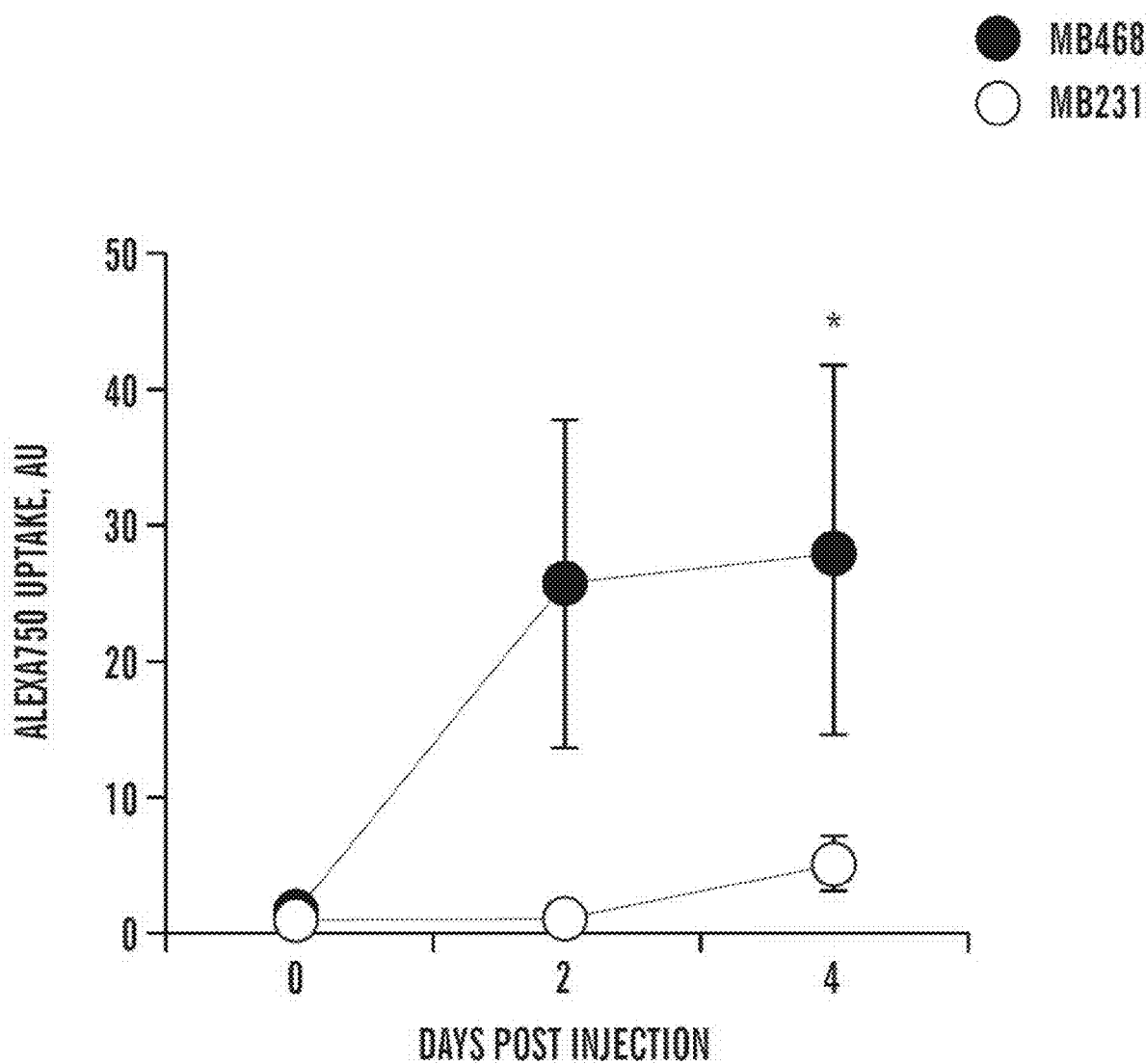

Subcutaneously Administered EpCAM-AsiCs are Selectively Taken Up by Distant EpCAM+ TNBCs To be clinically useful, EpCAM-AsiCs need to be taken up by disseminated tumor cells. Intravenous injection of fluorescent EpCAM-AsiCs in the tail vein of mice did not lead to significant AsiC accumulation within subcutaneous tumors implanted in the flanks of nude mice (data not shown), probably because their size (~25 kDa) is below the threshold for kidney filtration and they are rapidly excreted. Linkage to polyethylene glycol greatly enhanced the circulating half-life, tumor accumulation and antitumor therapeutic effect of PSMA-AsiCs in a mouse xenograft model of prostate cancer.[11] However, to see if this modification could be bypassed, we examined by live animal epifluorescence imaging whether sc injection of Alexa750-labeled eGFP EpCAM-AsiCs in the scruff of the neck of 7 mice led to accumulation in distant EpCAM+MB468 and EpCAM−MB231 TNBCs implanted sc in each flank (FIG. 5A, 5B). Within a day of injection, EpCAM-AsiCs concentrated only in the EpCAM+ tumor and persisted there for at least 4 days. The EpCAM-AsiCs were detected around the injection site on day 2, but were only found within the EpCAM+ tumor on day 4.

Figure 6A:
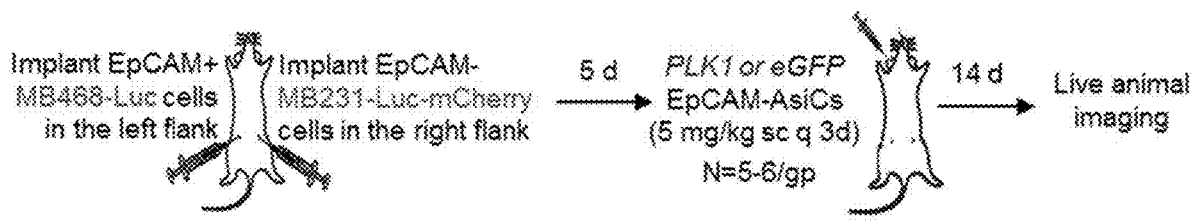
FIGS. 6A-6B demonstrate the EpCAM AsiC targeting PLK1 specifically inhibits tumor growth in Basal A breast cancer cells.
Figure 6B:
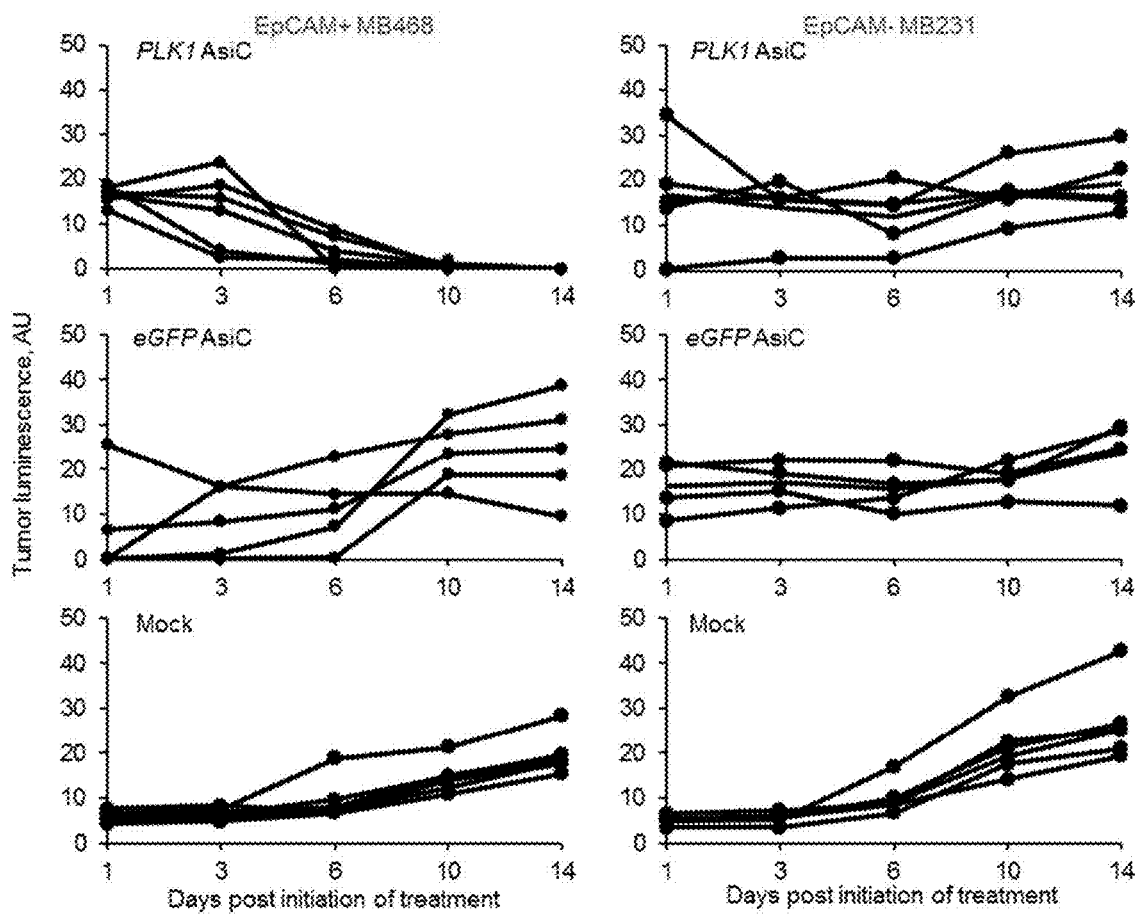
Figure 34:
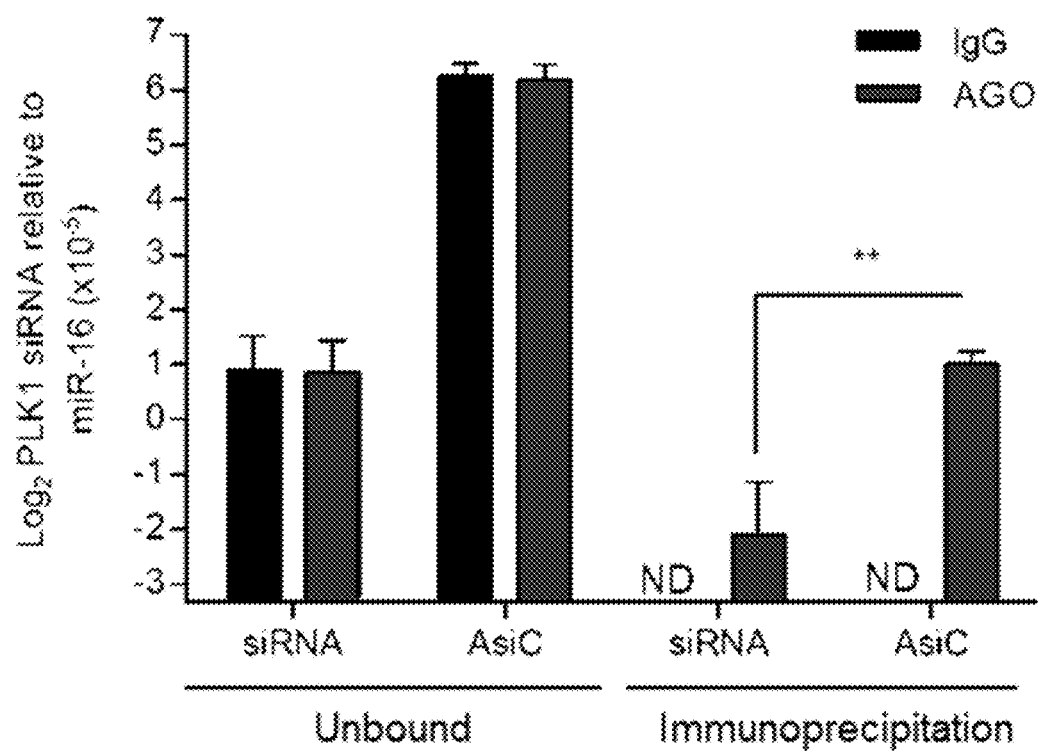
FIG. 34 demonstrates that PLK1 siRNA associates with Argonaute (AGO) in cells treated with PLK1 EpCAM-AsiCs. MB-468 cells, treated with PLK1 EPCAM-AsiC or siRNA for 2 days, were lysed, and cell lysates were immunoprecipitated with pan-AGO antibody or IgG isotype control. The amount of PLK1 siRNA in the immunoprecipitates was quantified by Taqman qRT-PCR, presented as $\log_2$ mean with SEM, relative to miR-16. **, P<0.01 by Student's t-test relative to siRNA-treated cells. ND, not detectable. PLK1 siRNA was found in the RISC after treatment with PLK1 EpCAM-AsiCs. However, the Ago immunoprecipitation did not significantly deplete PLK1 siRNAs from the supernatant. This is likely because most RNAs that are taken up by cells are not released from endosomes to the cytosol (A. Wittrup et al., Visualizing lipid-formulated siRNA release from endosomes and target gene knockdown. Nature Biotechnology 2015, in press).
Figure 35:
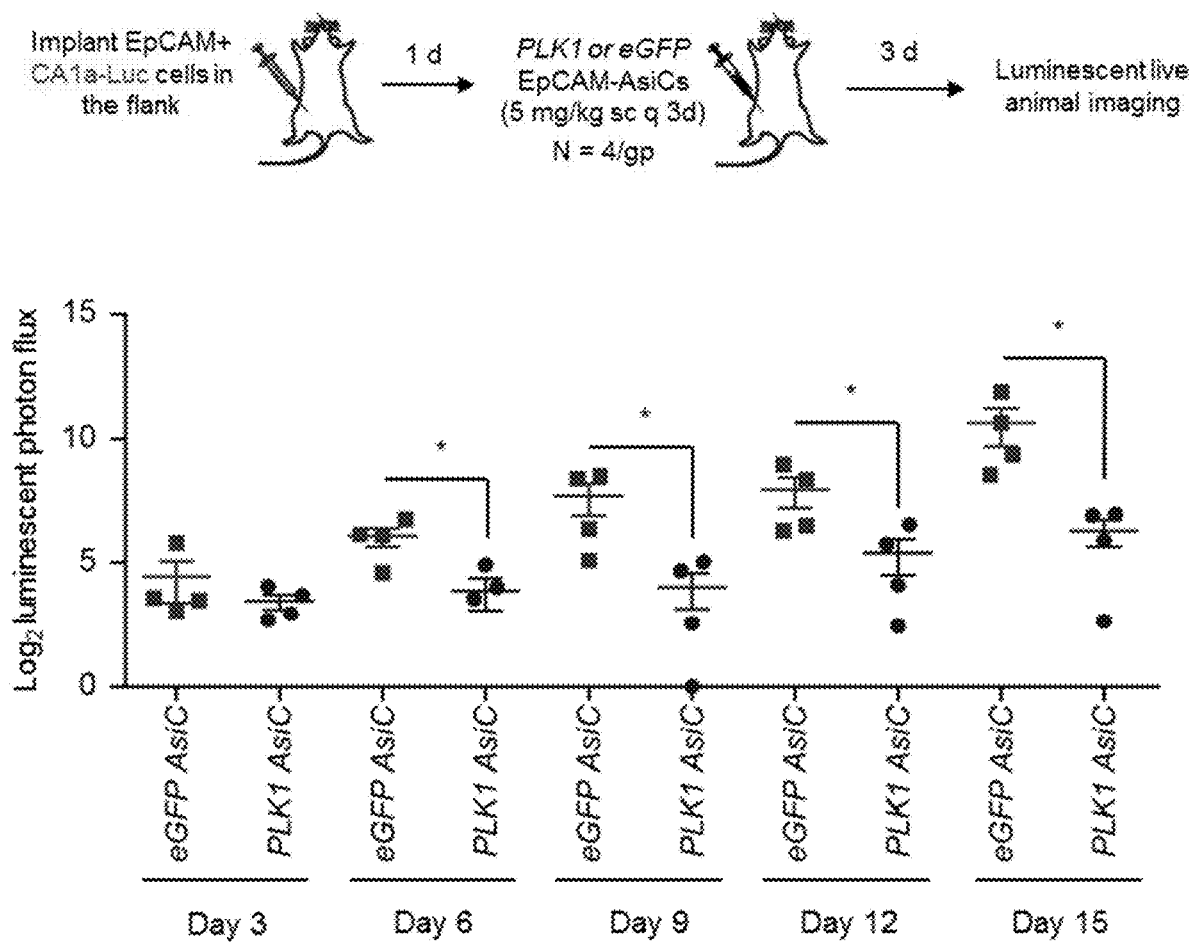
FIG. 35 demonstrates that PLK EpCAM AsiC suppresses MCF10CA1a (CA1a) tumor growth. The top panel depicts the experimental scheme. In this experiment the AsiCs were injected sc in the flank near the tumor, but not into the tumor. The bottom panel depicts a graph of $Log_2$ total luminescent photon flux of the tumors (N=4); *, P<0.05 by Student's t-test.

PLK1 EpCAM AsiCs Cause Regression of Basal-A TNBC and Her2 Breast Cancer Xenografts Because sc injected EpCAM-AsiCs concentrated in distant EpCAM+ tumors, we next looked at whether sc injection of PLK1 EpCAM-AsiCs could selectively inhibit the growth of an EpCAM+ TNBC xenografted tumor. EpCAM+ MB468-luc cells were implanted in Matrigel in one flank of a nude mouse and EpCAM− MB231-luc-mCherry cells were implanted on the opposite flank. Once the luciferase signal of both tumors was clearly detected above background, groups of 5-6 mice were mock treated or injected sc with 5 mg/kg of EpCAM-AsiCs targeting PLK1 or eGFP every 3 d for 2 wks. Tumor growth was followed by luminescence. All the EpCAM+ tumors rapidly completely regressed only in mice that received the PLK1-targeting AsiCs (FIG. 6A, 6B). The EpCAM+ tumors in mice treated with eGFP-targeting AsiCs and all the EpCAM− tumors continued to grow. This experiment was repeated with similar results after injection of PLK1 AsiCs. Tumors also continued to grow without significant change in additional groups of control mice treated with just the EpCAM aptamer or the PLK1 siRNA (data not shown) and into mice bearing Her2+ MCF10A-CA1a (FIG. 34). Thus sc injected PLK1 EpCAM-AsiCs show specific antitumor activity against basal-A TNBCs and EpCAM+ human xenografts.

Discussion

Targeted therapy so far has relied on using tumor-specific antibodies or inhibitors to oncogenic kinases. No one before has shown that an unconjugated AsiC can have potent antitumor effects or that AsiCs could be administered sc. There is currently no targeted therapy for TNBC or for T-ICs. Developing targeted therapy for TNBC and developing ways of eliminating T-ICs are important unmet goals of cancer research.

It is demonstrated herein that EpCAM-AsiCs can be used to knockdown genes selectively in epithelial breast cancer cells and their stem cells, sparing normal epithelial cells and stroma, to cause tumor regression and suppress tumor initiation. In one very aggressive TNBC xenograft model, the EpCAM-AsiCs caused complete tumor regression after only 3 injections. This is a flexible platform for targeted therapy, potentially for all the common epithelial cancers, which uniformly express high levels of EpCAM.

Although EpCAM-AsiCs targeting PLK1 was used herein, the siRNA can be varied to knockdown any tumor dependency gene that would be customized to the tumor subtype or the molecular characteristics of an individual patient's tumor. AsiC cocktails targeting more than one gene would be ideal for cancer therapeutics to lessen the chances of developing drug resistance. Targeted cancer therapy so far has relied on using tumor-specific antibodies or small molecule inhibitors to oncogenic kinases. Using EpCAM as an AsiC ligand and developing RNAi therapy to target cancer stem cells is novel. No one before has shown that an unconjugated AsiC can have potent antitumor effects or that AsiCs could be administered sc. Moreover, preliminary studies of sc administered CD4-AsiCs in humanized mice showed strong knockdown in CD4 cells in the spleen and distant lymph nodes, suggesting that AsiCs targeting receptors on cells located elsewhere in the body could also be administered sc. There is currently no targeted therapy for TNBC or for T-ICs. Targeted delivery has the advantage of reduced dosing and reduced toxicity to bystander cells.

The major obstacle to harnessing RNAi for cancer is delivering small RNAs into disseminated cells. Described herein is the use of AsiCs to overcome this obstacle. Described herein is a new class of potent anticancer drugs. AsiCs are a flexible platform that can target different cell surface receptors and knockdown any gene or combination of genes. {Burnett, 2012 #18447; Zhou, 2011 #18448; Thiel, 2010 #18445} By changing the aptamer, the AsiC platform can tackle the delivery roadblock that has thwarted the application of RNAi-based therapy to most diseases. This approach is ideal for personalized cancer therapy, since the choice of genes to target can be adjusted depending on a tumor's molecular characteristics. Moreover RNA cocktails can knockdown multiple genes at once to anticipate and overcome drug resistance. AsiCs are the most attractive method for gene knockdown outside the liver. They are better than complicated liposomal, nanoparticle or conjugated methods of delivering RNAs because they are a single chemical entity that is stable in the blood, easy to manufacture, nonimmunogenic, able to readily penetrate tissues and are not trapped in the filtering organs.

An important cancer research goal is to eliminate T-ICs (cancer stem cells). T-ICs are relatively resistant to chemotherapy and are thought responsible for tumor relapse and metastasis. {Federici, 2011 #19371} The AsiCs described herein target (epithelial) T-ICs with high efficiency. As such they may eliminate this aggressive subpopulation within tumors at risk for progressive disease (see FIG. 6A, 6B).

The small size of the EpCAM aptamer used here is ideal for an AsiC drug, since RNAs <60 nt can be efficiently synthesized.

In addition to their potential therapeutic use, EpCAM-AsiCs are also a powerful in vivo research tool for identifying the dependency genes of tumors and T-ICs to define novel drug targets. In principle, aptamer chimeras could be designed to deliver not only siRNAs but also miRNA mimics or antagomirs, antisense oligonucleotides that function by other mechanisms besides RNAi, or even longer mRNAs or noncoding RNAs (50, 51). They could also be designed to incorporate more than one aptamer, multiple siRNAs, or even toxins or small molecule anticancer drugs.

Its small size is ideal for an AsiC drug, since RNAs <60 nt can be efficiently synthesized. Not only is the siRNA targeted to the tumor, but the drug targets can also be chosen to attack the tumor's Achilles' heels by knocking down tumor dependency genes. This flexibility can be used for personalized cancer therapy that targets the molecular vulnerabilities of an individual patient's cancer.

Material and Methods

Cell culture. Human BPE and BPLER cells were grown in WIT medium (Stemgent). MB468 were transduced with a luciferase reporter. All other human cell lines were obtained from ATCC and grown in MEM (MCF7, BT474), McCoy's 5A (SKBR3), RPMI1640 (HCC1806, HCC1143, HCC1937, HCC1954, HCC1187, MB468, T47D) or DMEM (MB231, BT549, MB436) all supplemented with 10% FBS, 1 mM L-glutamine and penicillin/streptomycin (Gibco) unless otherwise indicated. 4T1 mouse breast cancer cells were grown in 10% FBS DMEM. For in vivo imaging, MB468 cells stably expressing Firefly luciferase (MB468-luc) were used and MB231 cells stably expressing Firefly luciferase and mCherry (MB231-luc-mCherry) were selected after infection with pLV-Fluc-mCherry-Puro lentivirus (provided by Andrew Kung, Columbia University). MB231 Cells were selected with puromycin.

For uptake and silencing treatment, cells were plated at low density (10,000 cells/well in 96-well plates) and treated immediately. All AsiC and siRNA treatments were performed in either OptiMEM or WIT medium. Cell viability was assessed by CellTiter-Glo (Promega) or by Trypan-Blue staining in 96-well plates.

For colony formation assay, 1,000 viable cells were treated for 6 h in round bottom 96-well plates and then transferred to 10-cm plates in serum-containing medium. Medium was replaced every 3 d. After 8-14 d, cells were fixed in methanol (−20 C) and stained with crystal violet. For sphere formation assay, 1,000/ml viable cells were treated for 6 h in round bottom 96-well plates and then cultured in suspension in serum-free DMEM/F12 1:1 (Invitrogen), supplemented with EGF (20 ng/ml, BD Biosciences), B27 (1:50, Invitrogen), 0.4% bovine serum albumin (Sigma) and 4 µg/ml insulin (Sigma). Spheres were counted after 1 or 2 weeks.

siRNA Transfection.

Cells were transfected with Dharmafect I per the manufacturer's protocol. See FIG. 9 for all siRNA sequences.

Flow Cytometry.

For flow cytometry, cells were stained as previously described (Yu, F. et al (2007). let-7 Regulates Self Renewal and Tumorigenicity of Breast Cancer Cells. Cell 131, 1109-1123. ), briefly, direct immunostaining of EpCAM and AKT1 was performed using 1:50 dilutions of hAb for 30-60 minutes at 4° C. (BioLegend/BD). Cells were stained in PBS containing 0.5% FCS, 1 mM EDTA, and 25 mM HEPES. Samples were washed twice in the same buffer. Data was acquired using FACS-Canto II (BD Biosciences). Analyses were performed in triplicate and 10,000 gated events/sample were counted. All data analysis was performed using FlowJo (Treestar Inc.).

RNA Analysis.

qRT-PCR analysis was performed as described (Petrocca, F., et al. (2008). E2F1-regulated microRNAs impair TGF-beta-dependent cell-cycle arrest and apoptosis in gastric cancer. Cancer Cell 13, 272-286). Briefly, total RNA was extracted with Trizol (Invitrogen) and cDNA prepared from 1000 ng total RNA using Thermoscript RT kit (Invitrogen) as per the manufacturer's SYBR Green Master Mix (Applied Biosystems) and a BioRad C1000 Thermal Cycler (Biorad). Relative CT values were normalized to GAPDH and converted to a linear scale.

Collagenase Digestion of Human Breast Tissue.

Fresh breast or colon cancer and control biopsies were received from the UMASS Tissue Bank, samples were cut into 3×3×3 mm samples and placed in a 96 well plate with 100 ul RPMI. Samples were treated with either Alexa647-siRNA-GFP, Alexa647-chol-siRNA-GFP or Cy3-AsiC-GFP for 24 hr. Samples were photographed and digested. Three samples from each treatment were pooled and put in 10 ml RPMI containing 1 mg/ml collagenase II (Sigma-Aldrich) for 30 minutes at 37° C. with shaking. Samples were disrupted in a gentleMACS dissociator (Miltenyi) using the spleen program for 30 minutes at 37° C. both before and after collagenase digestion. Cell suspensions were passed through a 70-µm cell strainer (BD Falcon), washed with 30 ml RPMI, and stained for flow cytometry.

Animal Experiments.

All animal procedures were performed with Harvard Medical School and Boston Children's Hospital Animal Care and Use Committee approval. Nude mice were purchased from the Jackson Laboratory.

In Vivo Experiments.

For tumor initiation studies 8-week old female Nu/J mice (Stock #002019, Jackson Laboratories) were injected subcutaneously with MB468-luc ($5 \times 10^6$) cells pretreated for 24 h with EpCAM-AsiC-GFP, EpCAM-AsiC-PLK1 or untreated. Cells were trypsinized with Tryple Express (Invitrogen), resuspended in WIT media and injected subcutaneously in the flank. Following intraperitoneal injection of 150 mg/kg D-luciferin (Caliper Life Sciences) luminescent images of the whole body were taken every 5 days for a total of 20 days using the IVIS Spectra system (Caliper Life Sciences).

For AsiC uptake experiments MB468-luc ($5 \times 10^6$) and MB231-luc-mCherry ($5 \times 10^5$) cells trypsinized with Tryple Express (Invitrogen), were resuspended in a 1:1 WIT-Matrigel solution and injected subcutaneously in the flank of 8-week old female Nu/J mice (Stock #002019, Jackson Laboratories). Tumors size was analyzed daily using the IVIS Spectra system (Caliper Life Sciences). After 5 days tumors were clearly visible and mice were injected subcutaneously in the neck area with Alexa750-EpCAM-AsiC-GFP (0.5 mg/kg). Localization of the AsiC compared to the tumor was tested every 48 h for 7 days.

For tumor inhibition studies, MB468-luc (5×10⁶) and MB231-luc-mCherry (5×10⁵) cells trypsinized with Tryple Express (Invitrogen), resuspended in a 1:1 WIT-Matrigel solution and injected subcutaneously in the flank of 8-week old female Nu/J mice (Stock #002019, Jackson Laboratories). Tumors size was analyzed daily using the IVIS Spectra, after 5 days tumors were clearly visible. Mice bearing tumors of comparable size were randomized into 5 groups and treated with 5 mg/kg of EpCAM-AsiC-PLK1, EpCAM-AsiC-GFP, EpCAM-Aptamer, siRNA-PLK1 or untreated. Mice were treated every 72 h for 14 days.

All Images were analyzed using Living Image® software (Caliper Life Sciences).

Statistical Analysis.

Student's t-tests, computed using Microsoft Excel, were used to analyze the significance between the treated samples and the controls where the test type was set to one-tail distribution and two-sample equal variance. To assess innate immune stimulation, one-way analysis of variance (ANOVA) with Bonferroni's Multiple comparison test was performed using GraphPad Prizm 4 software (GraphPad Software, San Diego, Calif.). $P<0.05$ was considered significant.

Measurement of Innate Immune Stimulation.

Mice were injected sc with eGFP EpCAM-AsiCs (5 mg/kg) or ip with Poly(I:C) (5 or 50 mg/kg). Serum samples, collected at baseline and 6 and 16 hr after treatment were stored at −80° C. before measuring IFNβ, IL-6 and IP-10 using the ProcartaPlex Multiplex Immunoassay (Affymetrix/eBioscience, San Diego, Calif.). Spleens, harvested at sacrifice 16 hr post treatment, were stored in RNAlater (Qiagen) before extracting RNA using TRIZOL (Invitrogen) with the gentleMACS Dissociator (MACS Miltenyi Biotec, San Diego, Calif.). cDNA was synthesized using Superscript III and random hexamers (Invitrogen) and PCR was performed using SsoFast EvaGreen Supermix and a Bio-Rad CFX96 Real-Time PCR System (Bio-Rad Laboratories, Hercules, Calif.) using the following primers:

```
Gapdh forward:
                                        (SEQ ID NO: 4)
5'-TTCACCACCATGGAGAAGGC-3', Gapdh reverse:
                                        (SEQ ID NO: 5)
5'-GGCATGGACTGTGGTCATGA-3', ifnb forward:
                                        (SEQ ID NO: 6)
5'-CTGGAGCAGCTGAATGGAAAG-3', ifnb reverse:
                                        (SEQ ID NO: 7)
5'-CTTGAAGTCCGCCCTGTAGGT-3', il-6 forward:
                                        (SEQ ID NO: 8)
5'-TGCCTTCATTTATCCCTTGAA-3', il-6 reverse:
                                        (SEQ ID NO: 9)
5'-TTACTACATTCAGCCAAAAGCAC-3', ip-10 forward:
                                        (SEQ ID NO: 10)
5'-GCTGCCGTCA1TTTCTGC-3', ip-10 reverse:
                                        (SEQ ID NO: 11)
5'-TCTCACTGGCCCGTCATC-3', oas-1 forward:
                                        (SEQ ID NO: 12)
5'-GGAGGTTGCAGTGCCAACGAAG-3', oas-1 reverse:
                                        (SEQ ID NO: 13)
5'-TGGAAGGGAGGCAGGGCATAAC-3', stat1 forward:
                                        (SEQ ID NO: 14)
5'-TTTGCCCAGACTCGAGCTCCTG-3', stat1 reverse:
                                        (SEQ ID NO: 15)
5'-GGGTGCAGGTTCGGGATTCAAC-3'.
```

| | | |
|---|---|---|
| EpCAM PLK1 sense | GCG ACU GGU UAC CCG GUC GUU UUG AAG AAG AUC ACC CUC CUU AdTdT | SEQ ID NO: 1 |
| EpCAM PLK1 anti-sense | UAA GGA GGG UGA UCU UCU UCA dTdT | SEQ ID NO: 2 |
| EpCAM PLK1 anti-sense | GCG ACU GGU UAC CCG GUC GUU UUAA GGA GGG UGA UCU UCU UCA dTdT | SEQ ID NO: 3 |
| EpCAM aptamer | GCG ACU GGU UAC CCG GUC GUU U | SEQ ID NO: 33 |

EpCAM is over expressed in basal A and luminal but not basal B breast cancer cell lines (data not shown). FACS was performed with 8 different breast cancer cell lines, testing EpCAM expression levels by flow cytometery using a hEpCAM Antibody. EpCAM is over expressed in all basal A and luminal cells lines and not in basal B.

Specific decrease in cell viability in Basal A breast cancer cell lines is PLK1 dependent. Ten different breast cancer cell lines representing basal A, B and luminal cells were treated with either EpCAM-AsiC targeting PLK1 or just the EpCAM-aptamer and compared to untreated controls. None of the cell lines treated with EpCAM-aptamer displayed decrease in cell viability, while basal A and luminal cell lines displayed a decrease in cell viability following treatment with EpCAM-AsiC targeting PLK1 (data not shown).

EpCAM-AsiC is taken up by both healthy and colon cancer biopsies. Cy3-EpCAM-AsiC targeting GFP, Alexa647-siRNA-GFP or Alexa647-chol-siRNA-GFP (2 µM of each) were added to colon cancer and control explants and incubated for 24 h before tissues were digested with collagenase to a single cell suspension and analyzed by flow cytometry. EpCAM-AsiC, siRNA and chol-siRNA penetrated both tumor and healthy tissue with similar efficacy. At day 5 the tumors were removed and visualized to validate that the Alexa750 labeled EpCAM-AsiC targeting GFP indeed entered the tumors. Increased level of Alexa750 is negatively correlated with mCherry levels (n=8, *P<0.05, t-test EpCAM+ versus EpCAM− cells) (data not shown).

REFERENCES 1. de Fougerolles A, Vornlocher H P, Maraganore J, Lieberman J. Interfering with disease: a progress report on siRNA-based therapeutics. Nat Rev Drug Discov 2007; 6:443-453.
2. Tabernero J, Shapiro G I, LoRusso P M, Cervantes A, Schwartz G K, Weiss G J et al. First-in-humans trial of an RNA interference therapeutic targeting VEGF and KSP in cancer patients with liver involvement. Cancer Discov 2013; 3:406-417.
3. Adams D, Coehlo T, Suhr O, Conceicao I, Waddington-Cruz M, Schmidt H et al. Interim Results for Phase II Trial of ALN-TTR02, a Novel RNAi Therapeutic for the Treatment of Familial Amyloidotic Polyneuropathy. Biennial Meeting of the Peripheral Nerve Society, St Malo, France 2013. Avilable from: alnylam.com/capella/presentations/aln-ttr02phiidata/.
4. Fitzgerald K, Frank-Kamenetsky M, Shulga-Morskaya S, Liebow A, Bettencourt B R, Sutherland J E et al. Effect of an RNA interference drug on the synthesis of proprotein convertase subtilisin/kexin type 9 (PCSK9) and the concentration of serum LDL cholesterol in healthy volunteers: a randomised, single-blind, placebo-controlled, phase 1 trial. Lancet 2014; 383:60-68.
5. Sorensen B, Mant T, Georgiev P, Rangarajan S, Pasi K J, Creagh D et al. A Subcutaneously Administered Investigational RNAi Therapeutic (ALN-AT3) Targeting Antithrombin for Treatment of Hemophilia: Phase 1 Study Results in Subjects with Hemophilia A or B. International Society of Thrombosis and Hemostasis, Toronto, Canada. 2015. Available from: alnylam.com/capella/presentations/aln-at3-isth-june2015/.
6. Petrocca F, Lieberman J. Promise and challenge of RNA interference-based therapy for cancer. J Clin Oncol 2011; 29:747-754.
7. Foulkes W D, Smith I E, Reis-Filho J S. Triple-negative breast cancer. N Engl J Med 2010; 363:1938-1948.
8. Lehmann B D, Bauer J A, Chen X, Sanders M E, Chakravarthy A B, Shyr Y et al. Identification of human triple-negative breast cancer subtypes and preclinical models for selection of targeted therapies. J Clin Invest 2011; 121:2750-2767.
9. Metzger-Filho O, Tutt A, de Azambuja E, Saini K S, Viale G, Loi S et al. Dissecting the heterogeneity of triple-negative breast cancer. J Clin Oncol 2012; 30:1879-1887.
10. McNamara J O, 2nd, Andrechek E R, Wang Y, Viles K D, Rempel R E, Gilboa E et al. Cell type-specific delivery of siRNAs with aptamer-siRNA chimeras. Nat Biotechnol 2006; 24:1005-1015.
11. Dassie J P, Liu X Y, Thomas G S, Whitaker R M, Thiel K W, Stockdale K R et al. Systemic administration of optimized aptamer-siRNA chimeras promotes regression of PSMA-expressing tumors. Nat Biotechnol 2009; 27:839-849.
12. Zhou J, Li H, Li S, Zaia J, Rossi J J. Novel dual inhibitory function aptamer-siRNA delivery system for HIV-1 therapy. Mol Ther 2008; 16:1481-1489.
13. Neff C P, Zhou J, Remling L, Kuruvilla J, Zhang J, Li H et al. An aptamer-siRNA chimera suppresses HIV-1 viral loads and protects from helper CD4(+) T cell decline in humanized mice. Sci Transl Med 2011; 3:66ra66.
14. Kim M Y, Jeong S. In vitro selection of RNA aptamer and specific targeting of ErbB2 in breast cancer cells. Nucleic Acid Ther 2011; 21:173-178.
15. Wheeler L A, Trifonova R, Vrbanac V, Basar E, McKernan S, Xu Z et al. Inhibition of HIV transmission in human cervicovaginal explants and humanized mice using CD4 aptamer-siRNA chimeras. J Clin Invest 2011; 121:2401-2412.
16. Thiel K W, Hernandez L I, Dassie J P, Thiel W H, Liu X, Stockdale K R et al. Delivery of chemo-sensitizing siRNAs to HER2+-breast cancer cells using RNA aptamers. Nucleic Acids Res 2012; 40:6319-6337.
17. Pastor F, Kolonias D, Giangrande P H, Gilboa E. Induction of tumour immunity by targeted inhibition of nonsense-mediated mRNA decay. Nature 2010; 465:227-230.
18. Wheeler L A, Vrbanac V, Trifonova R, Brehm M A, Gilboa-Geffen A, Tanno S et al. Durable knockdown and protection from HIV transmission in humanized mice treated with gel-formulated CD4 aptamer-siRNA chimeras. Mol Ther 2013; 21:1378-1389.
19. Shigdar S, Lin J, Yu Y, Pastuovic M, Wei M, Duan W. RNA aptamer against a cancer stem cell marker epithelial cell adhesion molecule. Cancer Sci 2011; 102:991-998.
20. Stingl J, Eaves C J, Zandieh I, Emerman J T. Characterization of bipotent mammary epithelial progenitor cells in normal adult human breast tissue. Breast Cancer Res Treat 2001; 67:93-109.
21. Osta W A, Chen Y, Mikhitarian K, Mitas M, Salem M, Hannun Y A et al. EpCAM is overexpressed in breast cancer and is a potential target for breast cancer gene therapy. Cancer Res 2004; 64:5818-5824.
22. Marhaba R, Klingbeil P, Nuebel T, Nazarenko I, Buechler M W, Zoeller M. CD44 and EpCAM: cancer-initiating cell markers. Curr Mol Med 2008; 8:784-804.
23. Spizzo G, Fong D, Wurm M, Ensinger C, Obrist P, Hofer C et al. EpCAM expression in primary tumour tissues and metastases: an immunohistochemical analysis. J Clin Pathol 2011; 64:415-420.
24. Sarrio D, Franklin C K, Mackay A, Reis-Filho J S, Isacke C M. Epithelial and mesenchymal subpopulations within normal basal breast cell lines exhibit distinct stem cell/progenitor properties. Stem Cells 2012; 30:292-303.
25. Soysal S D, Muenst S, Barbie T, Fleming T, Gao F, Spizzo G et al. EpCAM expression varies significantly and is differentially associated with prognosis in the luminal B HER2(+), basal-like, and HER2 intrinsic subtypes of breast cancer. Br J Cancer 2013; 108:1480-1487.
26. Imrich S, Hachmeister M, Gires O. EpCAM and its potential role in tumor-initiating cells. Cell Adh Migr 2012; 6:30-38.
27. Munz M, Baeuerle P A, Gires O. The emerging role of EpCAM in cancer and stem cell signaling. Cancer Res 2009; 69:5627-5629.
28. Federici G, Espina V, Liotta L, Edmiston K H. Breast cancer stem cells: a new target for therapy. Oncology 2011; 25:25-28, 30.
29. Ladwein M, Pape U F, Schmidt D S, Schnolzer M, Fiedler S, Langbein L et al. The cell-cell adhesion molecule EpCAM interacts directly with the tight junction protein claudin-7. Exp Cell Res 2005; 309:345-357.
30. Gonzalez B, Denzel S, Mack B, Conrad M, Gires O. EpCAM is involved in maintenance of the murine embryonic stem cell phenotype. Stem Cells 2009; 27:1782-1791.
31. Lu T Y, Lu R M, Liao M Y, Yu J, Chung C H, Kao C F et al. Epithelial cell adhesion molecule regulation is associated with the maintenance of the undifferentiated phenotype of human embryonic stem cells. J Biol Chem 2010; 285:8719-8732.
32. Schulze K, Gasch C, Staufer K, Nashan B, Lohse A W, Pantel K et al. Presence of EpCAM-positive circulating tumor cells as biomarker for systemic disease strongly correlates to survival in patients with hepatocellular carcinoma. Int J Cancer 2013.
33. Konigsberg R, Obermayr E, Bises G, Pfeiler G, Gneist M, Wrba F et al. Detection of EpCAM positive and negative circulating tumor cells in metastatic breast cancer patients. Acta Oncol 2011; 50:700-710.
34. Weissenstein U, Schumann A, ReifM, Link S, Toffol-Schmidt U D, Heusser P. Detection of circulating tumor cells in blood of metastatic breast cancer patients using a combination of cytokeratin and EpCAM antibodies. BMC Cancer 2012; 12:206.
35. Zhao S, Yang H, Zhang M, Zhang D, Liu Y, Song Y et al. Circulating tumor cells (CTCs) detected by triple-marker EpCAM, CK19, and hMAM R T-PCR and their relation to clinical outcome in metastatic breast cancer patients. Cell Biochem Biophys 2013; 65:263-273.
36. Chen Q, Ge F, Cui W, Wang F, Yang Z, Guo Y et al. Lung cancer circulating tumor cells isolated by the EpCAM-independent enrichment strategy correlate with Cytokeratin 19-derived CYFRA21-1 and pathological staging. Clin Chim Acta 2013; 419:57-61.
37. Schmidt M, Scheulen M E, Dittrich C, Obrist P, Marschner N, Dirix L et al. An openlabel, randomized phase II study of adecatumumab, a fully human anti-EpCAM antibody, as monotherapy in patients with metastatic breast cancer. Ann Oncol 2010; 21:275-282.
38. Marschner N, Ruttinger D, Zugmaier G, Nemere G, Lehmann J, Obrist P et al. Phase II study of the human anti-epithelial cell adhesion molecule antibody adecatumumab in prostate cancer patients with increasing serum levels of prostatespecific antigen after radical prostatectomy. Urol Int 2010; 85:386-395.
39. Schmidt M, Ruttinger D, Sebastian M, Hanusch C A, Marschner N, Baeuerle P A et al. Phase I B study of the EpCAM antibody adecatumumab combined with docetaxel in patients with EpCAM-positive relapsed or refractory advanced-stage breast cancer. Ann Oncol 2012; 23:2306-2313.
40. Barretina J, Caponigro G, Stransky N, Venkatesan K, Margolin A A, Kim S, et al. The Cancer Cell Line Encyclopedia enables predictive modelling of anticancer drug sensitivity. Nature 2012; 483:603-607.
41. Ince T A, Richardson A L, Bell G W, Saitoh M, Godar S, Karnoub A E et al. Transformation of different human breast epithelial cell types leads to distinct tumor phenotypes. Cancer Cell 2007; 12:160-170.
42. Daniels D A, Chen H, Hicke B J, Swiderek K M, Gold L. A tenascin-C aptamer identified by tumor cell SELEX: systematic evolution of ligands by exponential enrichment. Proc Natl Acad Sci USA 2003; 100:15416-15421.
43. Huang Z, Szostak J W. Evolution of aptamers with a new specificity and new secondary structures from an ATP aptamer. RNA 2003; 9:1456-1463.
44. Gold L, Janjic N, Jarvis T, Schneider D, Walker J J, Wilcox S K et al. Aptamers and the RNA world, past and present. Cold Spring Harbor perspectives in biology 2012; 4.
45. Zimmermann B, Gesell T, Chen D, Lorenz C, Schroeder R. Monitoring genomic sequences during SELEX using high-throughput sequencing: neutral SELEX. PLoS One 2010; 5:e9169.
46. Burnett J C, Rossi J J. RNA-based therapeutics: current progress and future prospects. Chem Biol 2012; 19:60-71.
47. Dassie J P, Giangrande P H. Current progress on aptamer-targeted oligonucleotide therapeutics. Ther Deliv 2013; 4:1527-1546.
48. Keefe A D, Pai S, Ellington A. Aptamers as therapeutics. Nat Rev Drug Discov 2010; 9:537-550.
49. Sundaram P, Kurniawan H, Byrne M E, Wower J. Therapeutic RNA aptamers in clinical trials. Eur J Pharm Sci 2013; 48:259-271.
50. Kotula J W, Pratico E D, Ming X, Nakagawa O, Juliano R L, Sullenger B A. Aptamermediated delivery of splice-switching oligonucleotides to the nuclei of cancer cells. Nucleic Acid Ther 2012; 22:187-195.
51. Esposito C L, Cerchia L, Catuogno S, De Vita G, Dassie J P, Santamaria G et al. Multifunctional aptamer-miRNA conjugates for targeted cancer therapy. Mol Ther 2014; 22:1151-1163.

Example 2

Described herein is the development of targeted siRNA delivery (aptamer-siRNA chimeras (AsiC)) that use chimeric RNAs composed of a structured RNA, called an aptamer, selected for high affinity binding to a cell surface protein, that is covalently linked to an siRNA. These AsiCs are taken up by cells expressing a receptor that the aptamer recognizes and are processed within cells to release the active siRNA. This is a flexible platform that can be modified to target different cells by targeting specific cell surface receptors and can be designed to knockdown any gene or combination of genes.

The aptamer, was selected for high affinity binding to human EpCAM (CD326 or ESA) which is expressed on all epithelial cells, but is much more highly expressed on epithelial cancers including poorly differentiated breast cancers, such as basal-like TNBC. All the common cancers (lung, pancrease, prostate, breast and colon) have high EpCAM expression and can potentially be targeted.

It is demonstrated herein that epithelial breast cancer cells, but not mesenchymal or normal epithelial cells, selectively take up EpCAM-AsiCs and undergo gene knockdown in vitro. Moreover, the extent of knockdown strongly correlates with EpCAM levels. Knockdown of PLK1, a gene needed for mitosis, using EpCAM-AsiCs eliminates cancer cell line growth and stem cell properties including colony and mammosphere formation and tumor initiation in xenografts. This platform can be used to eliminate cancer cells and the malignant cancer stem cells within epithelial tumors.

EpCAM AsiCs can be delivered specifically to basal-like tumors and inhibit tumor growth. These AsiCs can also be a powerful research tool for identifying the genes that T-IC cells depend on, which could be good targets for either conventional drugs or RNAi-based drugs.

Example 3

A ubiquitous mechanism for regulating gene expression is called RNA interference. It uses small RNAs bearing a short complementary sequence to block the translation of genetic information into proteins. Harnessing this endogenous process offers the exciting possibility to treat disease by knocking down expression of disease-causing genes. The major obstacle is delivering small RNAs into cells, where the RNA interference machinery lies. In the past year, preliminary clinical studies have shown very promising results without significant toxicity in a few diseases caused by aberrant gene expression in the liver. However, delivery to the liver, an organ that traps particles in the blood, is easier to accomplish than delivering drugs to metastatic tumor cells. Described herein is a strategy for targeting RNAs into epithelial cancer cells that is especially good at targeting the most aggressive type of breast cancer, triple negative breast cancer (TNBC). Moreover, it also targets the most malignant subpopulation in most breast cancers, which are called cancer stem cells. These cells are resistant to chemotherapy drugs and are thought responsible for tumor recurrence and metastasis. An important goal of current cancer research is to replace cytotoxic chemotherapy drugs that are toxic for both cancer cells and normally dividing cells (such as the blood forming cells and cells lining the gut) with agents that have selective activity against the tumor, especially against the cancer stem cells within the tumor.

Targeted therapy for one type of breast cancer (Her2+) has revolutionized treatment and significantly improved survival. There is currently no targeted therapy for TNBC or for breast cancer stem cells.

Described herein in are data demonstrating that RNAs that link an interfering RNA to a structured RNA (aptamer) that recognizes a cell surface protein can knockdown gene expression in aggressive breast cancer cells. Aptamers that bind to proteins highly expressed on breast cancer stem cells and most TNBC cells can knock down proteins required for cancer cell division or survival specifically in the most common subtype of TNBC. These RNAs can be tested, e.g., in both tissue culture and in mouse models of TNBC. Described herein is a platform for harnessing RNA-based drugs to treat poor prognosis breast cancer and demonstration in a mouse model of its efficacy.

Ultimate applicability for treating breast cancer (which patients, how will it help them, clinical applications/benefits/risks, projected time to patient-related outcome) The proteins that this therapy can target are expressed on all epithelial cancer cells, but are more strongly expressed on the least differentiated, and hence most malignant, cancer cells. This approach could be used to treat not only most epithelial breast cancers (and most breast cancer cells are epithelial), but also has the potential to treat the common cancers, including colon, lung, pancreas, and prostate. Our focus is on the most aggressive and poorest prognosis breast cancer, TNBC, which preferentially strikes down young women and women from minority populations. This approach permits a new platform for breast cancer therapy. Any cancer-causing or promoting gene, or combinations of genes, could be knocked down, making this strategy ideal for the coming era of personalized cancer therapy in which each patient's therapy will be customized according to the molecular characteristics of her individual tumor.

Moreover, if a tumor is nonresponsive or becomes resistant, the cocktail of target genes could be nimbly adjusted. Because normal epithelial cells express low levels of the proteins used for targeting, there may be some uptake and toxicity to normal epithelial cells, which is evaluated herein. However, the platform is flexible so that the therapeutic siRNA cargo can be chosen to kill tumor cells with minimal toxicity to normal cells.

Described herein are the design and testing in mouse TNBC models of several molecules capable of causing tumor-specific gene knockdown and tumor suppression.

There is no targeted therapy for TNBC or for highly malignant tumor-initiating cell subpopulations within breast cancers.

Triple negative breast cancer (TNBC) has the worst breast cancer prognosis. 1-4 There is no targeted therapy, and TNBCs often relapse. Described herein is the development of small RNA-based drugs that knockdown tumor dependency genes in basal-like (or basal-A) TNBCs. In principle RNA interference (RNAi) can be harnessed to knockdown disease-causing genes to treat any disease. 5-9 However, converting small RNAs into drugs is challenging. Recent Phase I and II clinical trials have shown dramatic and durable gene knockdown in the liver (~80-95%, lasting for almost a month after a single injection) with no significant toxicity. 10-16 Realizing the potential of gene knockdown for treating cancer, however, requires a robust method to deliver RNAs into disseminated cancer cells, which the liver-targeting RNAs are unable to do. 7 An ideal therapy would selectively knockdown genes in cancer cells, sparing normal cells to minimize toxicity. 17

Figure 10A:
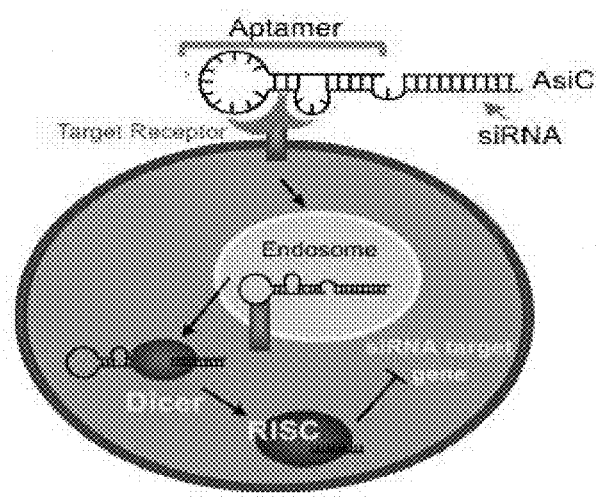
FIGS. 10A-10B depict aptamers-siRNA chimera (AsiC).
Figure 10B:
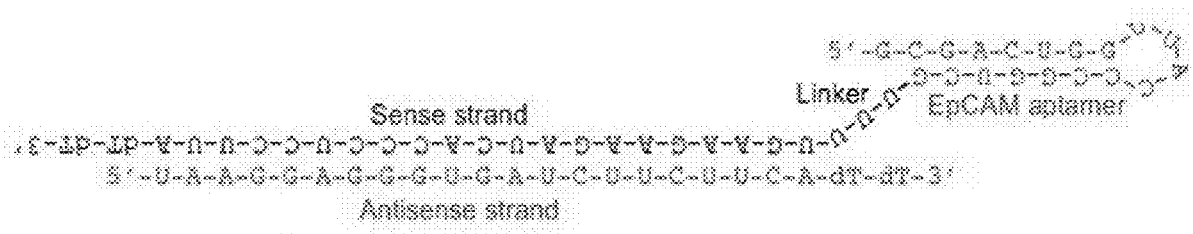

AsiCs are composed of an RNA aptamer (a structured RNA with high affinity for a receptor)18,19 covalently linked to an siRNA (FIGS. 10A-10B).

Described herein is the use of an AsiC to knockdown genes in epithelial cancers using an EpCAM aptamer. 37 EpCAM, the first described tumor antigen, is highly expressed on all common epithelial cancers. 38-45 On epithelial breast cancers, EpCAM is ~400-fold more abundant than on normal breast tissue. 46 EpCAM39,45,47-53 is also highly expressed on most epithelial cancer tumor-initiating cells (T-IC, also known as cancer stem cells). 39,45,47-53

The EpCAM aptamer has high affinity (12 nM) and is short (19 nt), which is ideal for an AsiC drug, since RNAs <60 nt can be cheaply and efficiently synthesized. The EpCAM-AsiCs consist of a long 42-44 nt strand (19 nt aptamer+3 nt linker+20-22 nt siRNA sense strand) annealed to a 20-22 nt antisense (active) siRNA strand (FIG. 10B). They are commercially synthesized with 2'-fluoropyrimidines, which enhance serum stability (T1/2>3d) and block innate immune recognition. 28,54-56

Figure 3C:
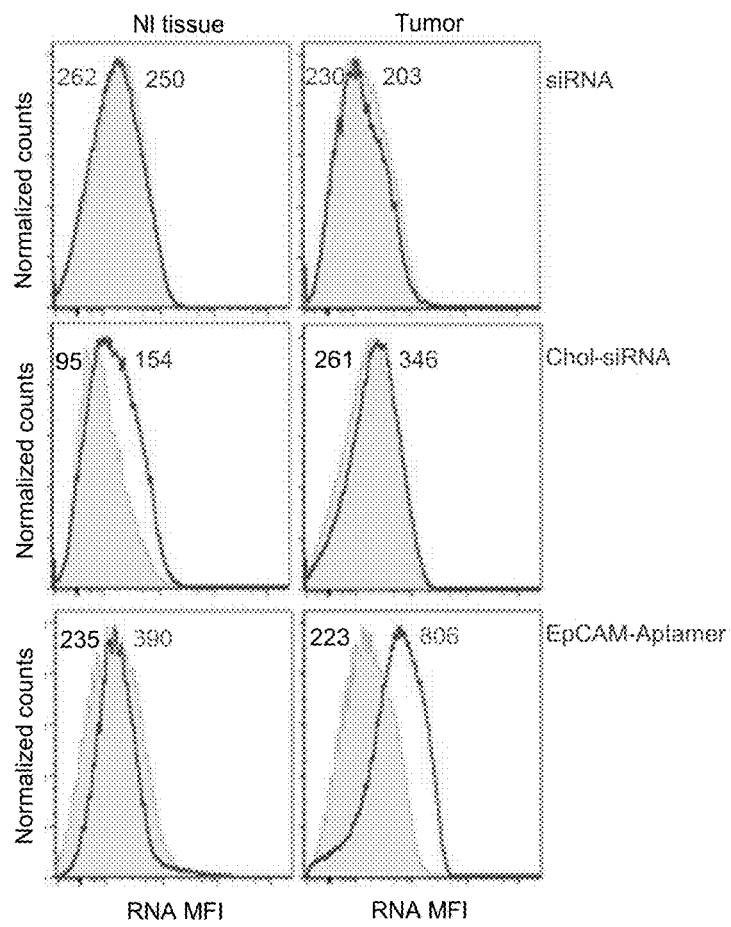
Figure 3D:
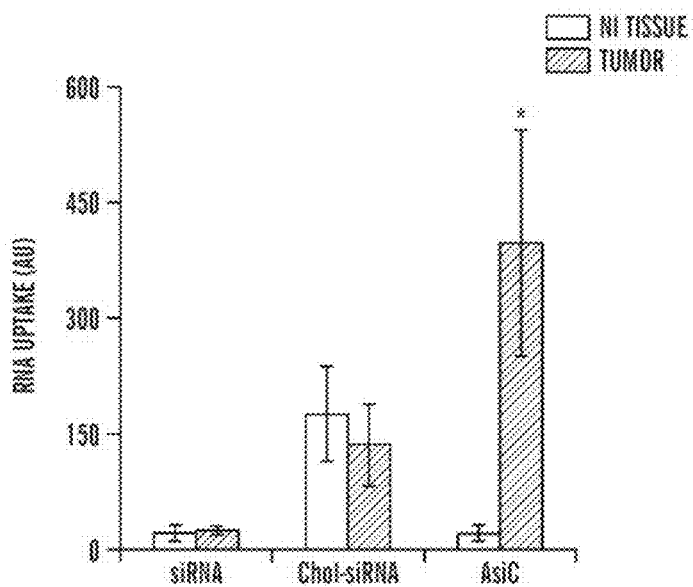

EpCAM targeting can cause selective gene knockdown in basal-like TNBCs, relative to normal epithelia. Selective knockdown will reduce both the drug dose and normal tissue toxicity. In normal epithelia, EpCAM is only expressed on basolateral gap junctions, where it may not be accessible. In epithelial cancers, it's both more abundant and distributed along the whole cell membrane. EpCAM promotes adhesion, and also enhances proliferation and invasiveness. Proteolytic cleavage of EpCAM releases an intracellular fragment that increases transcription of stem cell factors. The oncogenic properties of EpCAM may make it difficult for tumor cells to develop resistance by down-modulating EpCAM. The number of EpCAM+ circulating cells is linked to poor prognosis in breast cancer. In fact, enumerating circulating EpCAM+ cells is the basis of an FDA-approved method for monitoring metastatic breast, colon and prostate cancer treatment. In our studies, 9 of 9 basal-A TNBC and luminal breast cancer cell lines were strongly EpCAM+, while a normal breast cancer epithelial line and mesenchymal TNBCs had close to background levels (FIG. 1B). Thus most basal-like TNBCs and luminal breast cancers will likely be targeted by EpCAM-AsiCs. In preliminary data, EpCAM-AsiCs selectively knocked down expression in EpCAM+ breast and colon cancer cell lines but not in normal epithelial cells or mesenchymal tumor cells; knockdown was uniform and comparable to lipid transfection, but lipid transfection uniformly knocked down gene expression in all the lines. (FIG. 3A-3C)

AKT1 knockdown and inhibition of cell proliferation by EpCAM-AsiCs against PLK1, a kinase required for mitosis, correlated with EpCAM levels. When normal transformed epithelial cells (BPE) 57 were mixed with epithelial TNBC cell lines, EpCAM- AsiCs caused PLK1-sensitive cell death only in the tumor cells, sparing BPE cells (not shown). Moreover when tumor biopsies and normal tissue biopsies were coincubated with fluorescent AsiCs, only the tumors took up the AsiCs and fluoresced (not shown). These results suggest that EpCAM-AsiCs are specific for epithelial tumor cells compared to normal epithelia.

Figure 11A:
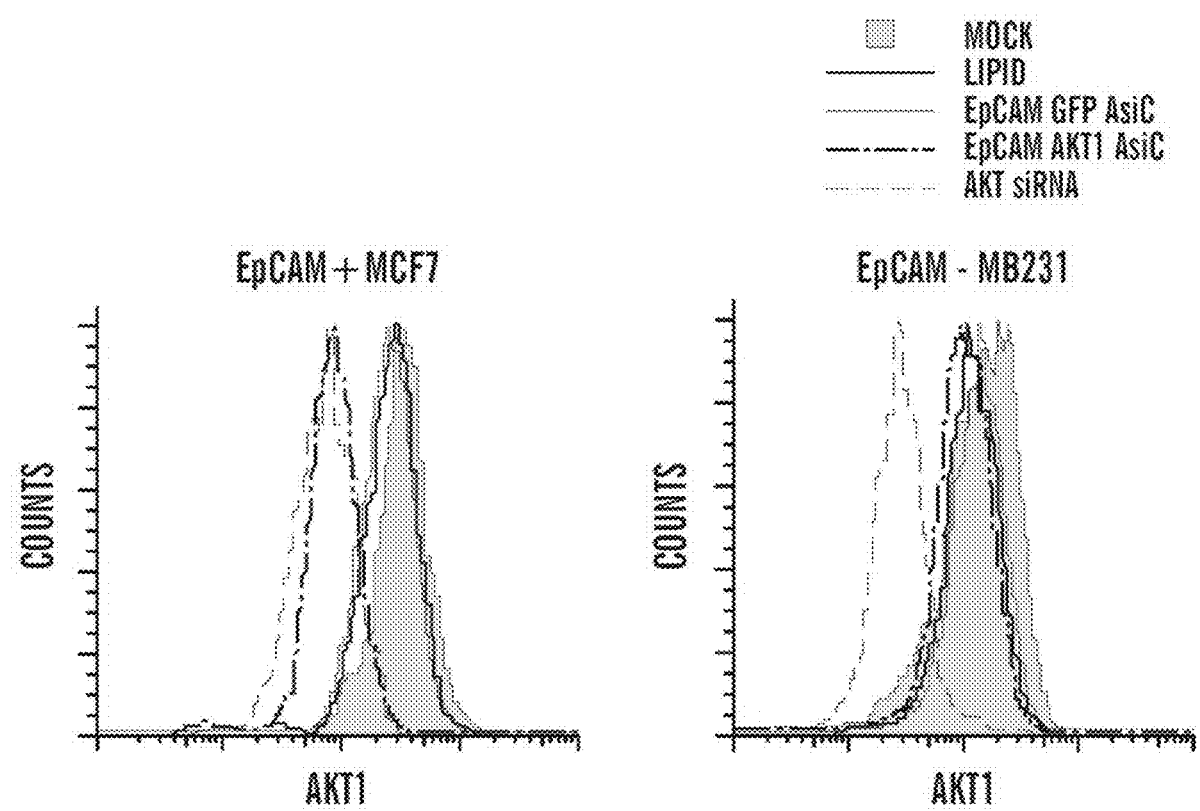
FIGS. 11A-11D demonstrate that EpCAM-AsiC knockdown and antitumor effect correlates with EpCAM levels and inhibits epithelial breast tumor T-ICs.
Figure 11B:
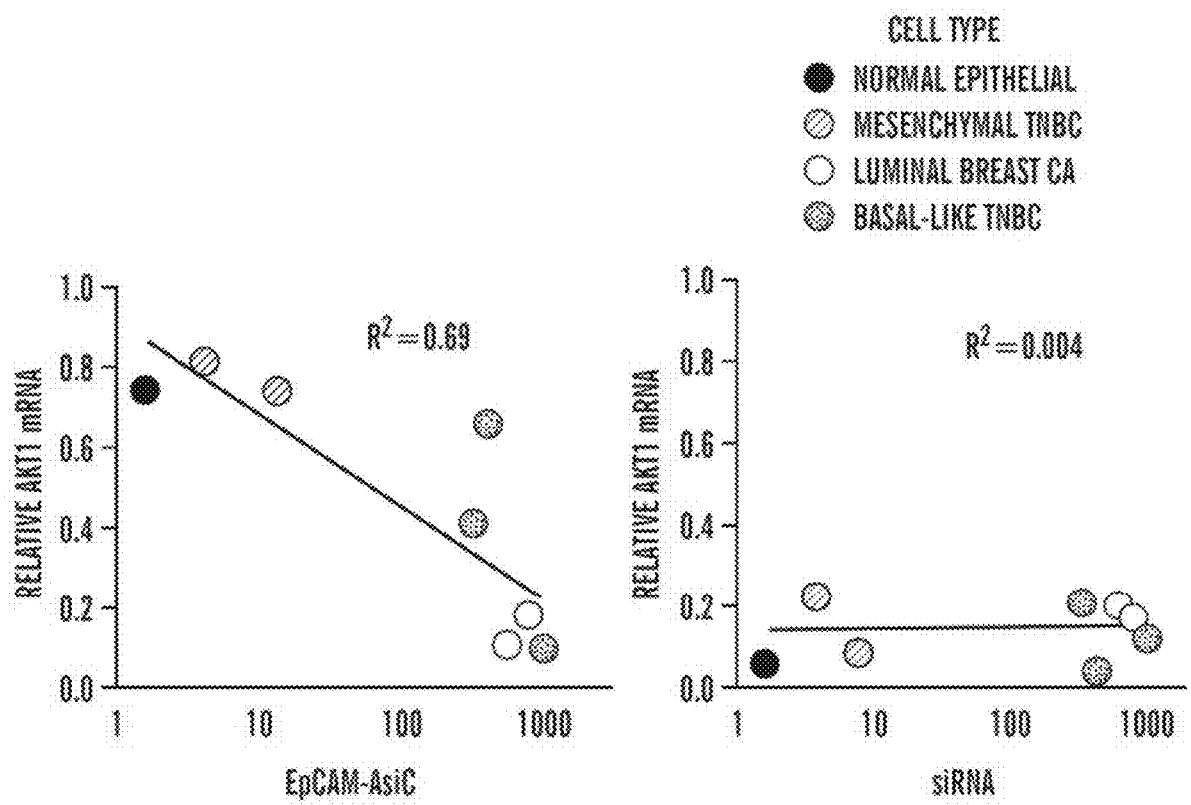
Figure 11C:
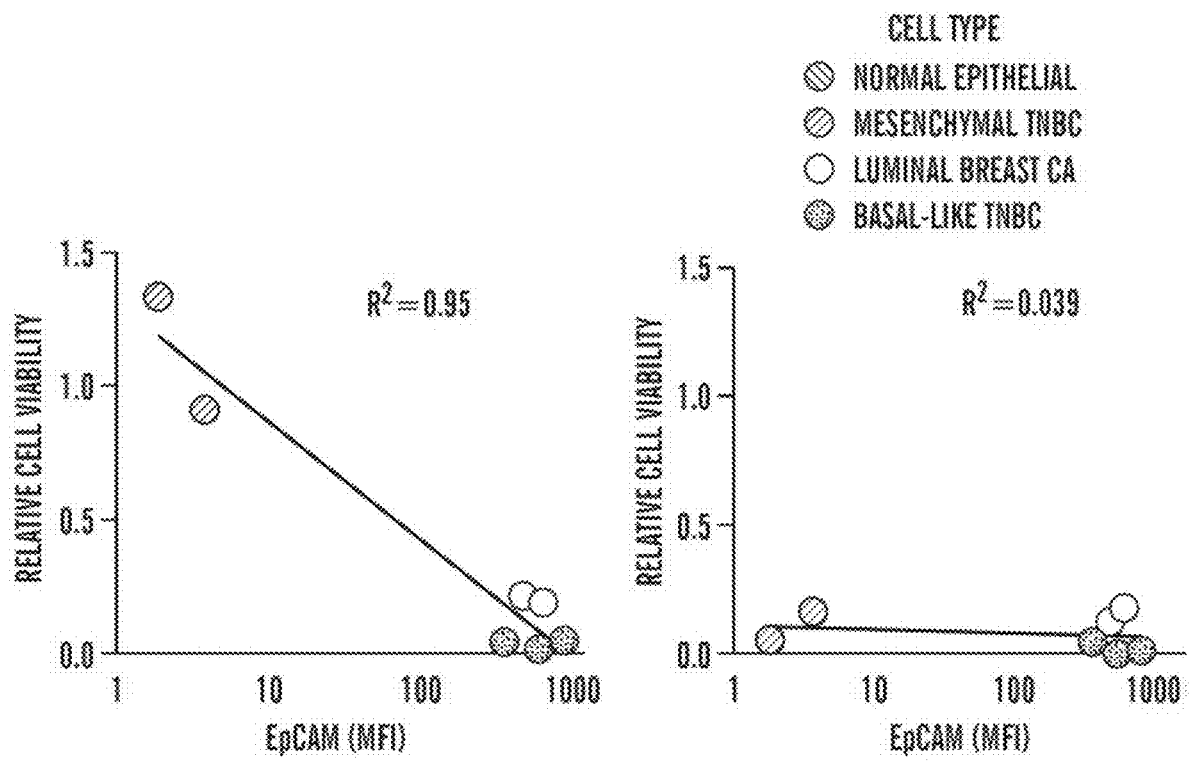
Figure 11D:
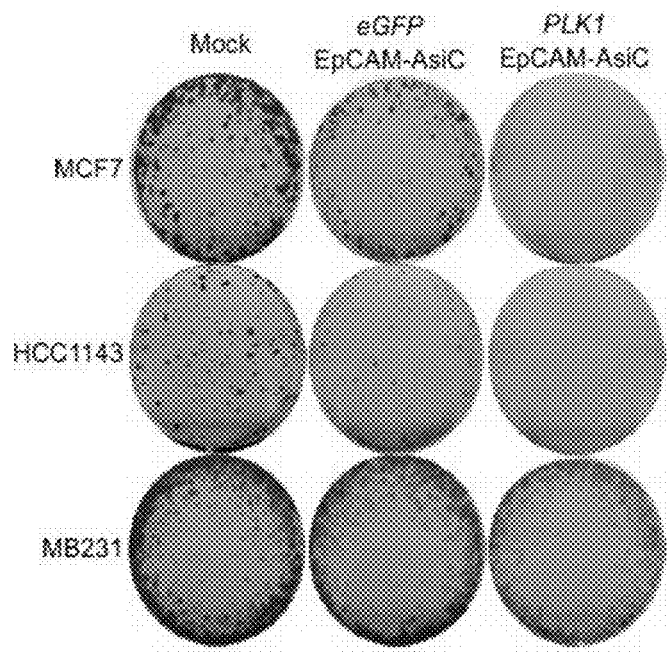
Figure 12A:
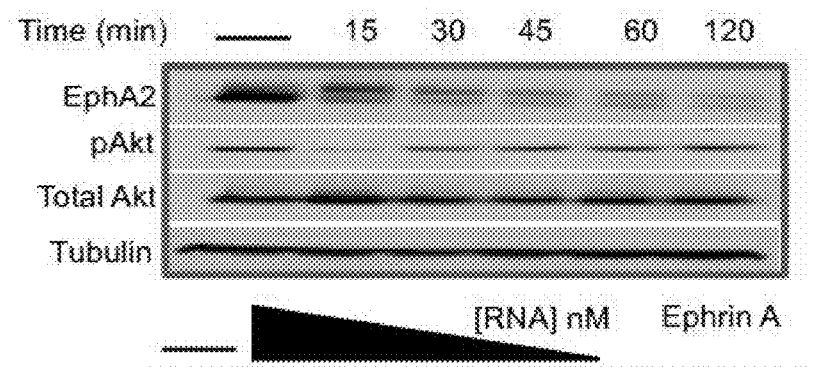
FIGS. 12A-12B demonstrate the identification of a functional EphA2 aptamer FIG. 12A:Incubation of EphA2+ basal-B MB231 cells with EphA2 aptamer (EphA2apt) leads to EphA2 degradation and a transient decrease in active Akt (pAkt).
Figure 12B:

EpCAM also marks T-ICs. 40,45,58 An important goal of cancer research is to develop a way to target T-ICs. Although the stem cell hypothesis is controversial and may not apply to all cancers, there is good evidence that breast cancers contain a T-IC subpopulation. 59-82 T-Ics are relatively resistant to chemotherapy and are also thought responsible for tumor relapse and metastasis. The AsiCs described herein are designed to target (epithelial) T-ICs with high efficiency. As such they may be suitable for eliminating this aggressive subpopulation within patients at risk for relapse. To investigate whether EpCAM-AsiCs inhibit TNBC T-ICs, we compared mammosphere and colony formation (in vitro surrogates of T-IC function) of breast tumor cells that were mocktreated or treated with EpCAM-AsiCs against eGFP or PLK1. PLK1 EpCAM-AsiCs, but not control GFP AsiCs, eliminated mammosphere and colony formation of breast luminal and basal-like TNBC cell lines (FIG. 11D). PLK1 EpCAM-AsiCs also reduced CD44+CD24low and Aldefluor+ cells (not shown). Importantly, treatment with PLK1 EpCAM-AsiCs eliminated tumor initiation by basal-like TNBCs, but, as expected, had no effect on basal-B TNBC tumor initiation (data not shown). Luciferase-expressing cell lines were mock-treated or treated overnight with AsiCs before orthotopic implantation in the mammary fatpad.

AsiCs targeting EphA2, important in EGF receptor signaling. 83-92 are also contemplated herein. EphA2 is expressed on epithelial and mesenchymal (basal-A and basal-B, respectively) TNBC cell lines, including their T-ICs, but less than EpCAM and only weakly on other breast cancers. Inhibiting EphA2 reduces tumor growth and angiogenesis in multiple cancer models. Furthermore, EphA2 is selectively accessible on cancer cells, but not normal cells.

Also contemplated herein are mouse-human cross-reactive AsiCs, which will be valuable for future drug development, since they will enable us to evaluate toxicity and effectiveness in spontaneous mouse tumor models.

AsiCs targeting EphA2 can produce dual functioning RNAs that both inhibit EphA2 signaling and cell proliferation and knockdown genes.

AsiCs are ideal for personalized cancer therapy, since the genes targeted for knockdown can be adjusted to the molecular characteristics of a tumor. Moreover cocktails of RNAs can be assembled to knockdown multiple genes at once for combinatorial therapy to anticipate and overcome drug resistance. AsiCs not only target the drug to the tumor, but the siRNAs can also be chosen to attack the specific Achilles' heels of the tumor. siRNAs also provide a unique opportunity to target "undruggable" genes. AsiCs that knock down tumor dependency genes, required for tumor, but not normal cell, survival, should have reduced toxicity. To identify genetic dependencies of basal-like TNBCs that we could knockdown, we performed a genomewide siRNA lethality screen comparing 2 TNBC cell lines—basal-like BPLER and myoepithelial HMLER cells, human 10 breast epithelial cells transformed with the same oncogenes in different media. 57,93

Although essentially isogenic, BPLER are highly malignant and enriched for T-ICs, forming tumors in nude mice with only 50 cells, while HMLER require >105 cells to initiate tumors. The screen identified 154 genes on which BPLER, but not HMLER, depended. Proteasome genes were highly enriched (P<10-14). BPLER dependency gene expression correlated with poor prognosis in breast, but not lung or colon, cancer. Because TNBCs are heterogeneous 1,3,4,94, to identify shared dependencies in basal-like TNBCs, we did another screen to test 17 breast cancer cell lines for their dependency on the 154 BPLER dependency genes (unpublished). Although many of the BPLER dependencies were shared with only a subset of basal-like TNBC cell lines, the proteasome, MCL1, some splicing genes, and a few other novel genes stood out because virtually all (at least 8 of 9) basal-like TNBC lines were dependent on these genes, but normal cells were not. As the screen predicted, the proteasome inhibitor bortezomib both killed basal-A TNBCs and also blocked T-IC function, assessed by colony and mammosphere formation, again mostly selectively in basal-like TNBCs. Brief exposure to bortezomib also inhibited colony formation and tumor inhibition of a mouse epithelial TNBC line. Bortezomib strongly inhibited tumor growth of multiple human basal-A lines and primary TNBCs that arose spontaneously in Tp53+/− mice, but not basal-B or luminal cell lines. Bortezomib also blocked metastatic lung colonization of IV-injected TNBC cells. However, bortezomib does not penetrate well into solid tumors. The maximum tolerated dose was needed to inhibit proteasome activity and suppress tumors. Although tumor penetration may improve with proteasome inhibitors in development, proteasome gene knockdown might provide more sustained and efficient proteasome inhibition.

EpCAM- and EphA2-AsiCs can be used for targeted gene knockdown to treat basal-like TNBC cancers, sparing normal cells, and eliminate the T-Ics within them. There may be some uptake in normal epithelial cells that weakly express EpCAM or EphA2, but gene knockdown will be concentrated in aptamer ligandbright tumor cells.

It can be determined which breast cancer subtypes EpCAM- and EphA2-AsiCs target and determine how aptamer ligand level affects gene silencing. uptake/knockdown in cancer tissues vs normal epithelium can also be evaluated. EpCAM-AsiCs can be compared with EphA2-AsiCs for effectiveness in causing knockdown in basal-like TNBCs. It can be determined whether EpCAM-AsiCs and EphA2-AsiCs can target T-ICs to inhibit tumor initiation.

Pharmacokinetics (PK)/pharmacodynamics (PD) studies of EpCAM- and EphA2-AsiCs can be performed using live animal imaging of orthotopic TNBC xenografted mice. Treated tissue samples and animals can be examined for toxicity and innate immune activation, and AsiCs will be chemically modified if needed to improve PK/PD or reduce toxicity. As proof of principle, the antitumor effect of knockdown of PLK1 will be assessed. Suppression of recently identified basal-A TNBC dependency genes, such as MCL1 and proteasome genes can be accomplished according to the methods described herein.

Contemplated herein are:
cross-species reactive aptamers that recognize EpCAM and EphA2 and are internalized selectively into basal-A TNBCs vs normal epithelial cells
verification of selective uptake, gene silencing and cytotoxic effect in vitro of TNBC-targeting AsiCs in breast cancer cell lines vs normal epithelial cells, determination of the subtypes of breast cancer cell lines they transfect and evaluation of their potential to transfect and eliminate breast T-Ics
Evaluation of systemic delivery and tumor concentration in vivo, definition of PK and PD and maximally tolerated dose of TNBC-targeting AsiCs, and evaluation of the antitumor effect of optimized TNBC-targeting AsiCs that knockdown PLK1 and dependency genes of basal-like TNBC in human TNBC cell line models of primary and metastatic cancer in mice Selection of TNBC-targeting aptamers. Aptamers that bind to a chosen target are identified by iterative screening of combinatorial nucleic acid sequence libraries of vast complexity (typically 1012-1014 distinct sequences) by a process termed SELEX (Systematic Evolution of Ligands by Exponential enrichment). 95,96 In the classic method, the RNA library is incubated with the protein target and the RNAs that bind are separated and amplified to generate a pool of binding RNAs. These are again applied in multiple cycles to generate increasingly enriched high affinity RNA pools. Identification of the sequences that emerge after multiple rounds of SELEX was previously accomplished by cloning and sequencing <100 individual sequences.

While this often provided a sufficient number of winning sequences to identify aptamers, the number of sequences that were analyzed was quite small in comparison with the sequence complexity of evolved oligonucleotide pools. With many selection cycles, some effective aptamer sequences that are not efficiently amplified may be depleted and lost. Next generation deep sequencing methods and bioinformatics can permit evaluation of more sequences within early cycle SELEX sequence pools to identify winning aptamer sequences at earlier selection rounds, thus reducing the time and resources needed to complete identification of high affinity aptamers. 30,97-104

An important property of aptamers useful for incorporation into AsiCs is efficient internalization into cells. Some ligands of cell-surface proteins are efficiently internalized after binding their cell surface protein targets, while others are not. Another strategy ("toggle SELEX") selects for cross-reactive aptamers that recognize the same ligand from different species, a useful attribute for preclinical development. By toggling cycles between selection with orthologous protein ligands (e.g., mouse and human forms), it is possible to enrich for cross-species reactive aptamers. 105

These SELEX techniques can permit identification of high affinity cross-species reactive aptamers for EpCAM and EphA2 that are internalized into human (and mouse) basal-like TNBCs, but not into a normal immortalized epithelial cell line. To select additional EpCAM and EphA2 aptamers that have antagonistic activity and/or cross-recognize the corresponding mouse antigen (the published EpCAM aptamer does not recognize mouse EpCAM (data not shown)), we can toggle between commercially available mouse and human purified, recombinant target proteins, starting with a library of 1012 RNA sequences containing 2'-fluoropyrimidines. This library of 51 nt long oligonucleotides is designed with a random region of 20 nucleotides flanked by constant regions of known sequence for PCR amplification at each selection round. Previously described methods will be used to select for high affinity RNAs that bind to immobilized C-terminal tagged proteins. 37 (This leaves the N-terminal region exposed to facilitate selection of aptamers that recognize the extracellular domain.) A tagged control protein can be used to pre-clear the RNA aptamer library to remove non-specific binders. 7-10 iterative rounds of SELEX can be performed to enrich for specific aptamers. Enrichment after each round can be monitored by Surface Plasmon Resonance. Enriched pools that show specific binding can be sequenced using high-throughput sequencing. Sequences can be chosen for experimental validation using bioinformatics analysis of the enriched library sequences as described. 97,98,106

The top 10-15 sequences from the high throughput sequencing and bioinformatics analysis can be evaluated by Surface Plasmon Resonance to assess relative binding affinities as described, 99,106 using the previously characterized human aptamers for comparison.

An alternative approach to dentify high affinity cross-reactive aptamers, is cellinternalization SELEX, positively selecting on 293T cells transfected to expression human or mouse EpCAM and preclearing on cells expressing a control protein. The ability of the 5 highest affinity aptamers to be internalized into EpCAM/EphA2+ cells will be compared to the previously selected aptamers by qRT-PCR and flow cytometry (using fluorescently tagged aptamers) as previously described. 37

These aptamers can also be evaluated for their ability to inhibit tumor cell line proliferation specifically. Aptamers with this property may be receptor antagonists, which will be verified by examining their effect on cell signaling. Given the high homology between the human and mouse EphA2 extracellular domains (>90% identity; >90% structural homology), identifying aptamers that cross-react with human and mouse EphA2 can be as simple as testing the already selected aptamers for cross-reactivity against mouse. The existing set of 20 human EphA2 aptamers can therefore first be evaluated for the ability to bind mouse EphA2. Alternatively, the approach described above can be followed. For a few of the top aptamers, truncated sequences (lacking either or both of the library adapter sequences) can be synthesized to define the minimal sequence required for binding.

Aptamers of ~20-35 nt in length can be identified for each ligand, which can be designed into AsiCs amenable for chemical synthesis.

In vitro assessment of TNBC-targeting AsiCs and their activity against T-Ics. It can be defined which breast cancer subtypes are efficiently transfected with TNBC-targeting AsiCs and evaluated whether tumor knockdown is specific relative to normal tissue cells, first in cell lines and then in 10 tumor specimens to verify that the results for cell lines translate to 10 tissues. We can also evaluate the potential of TNBC-targeting AsiCs to transfect and target breast T-ICs.

AsiC design and initial testing The most attractive aptamers identified above (prioritized based on considerations of affinity, selectivity of binding and expression in poor prognosis cancer vs normal cells, truncation to shorter length, the importance of the ligand in oncogenesis and stem cell behavior, receptor antagonism and cross-species reactivity) can be designed into AsiCs by linkage to siRNAs targeting eGFP, AKT1 and PLK1 (vs control scrambled siRNAs) that have been used for the initial EpCAM-AsiCs as described above herein.

Basal-like NBC cell lines stably expressing destabilized (dl)EGFP (protein T1/2 of −1 hr) were previously generated using lentiviruses. GFP expression can be readily quantified by flow and imaging, and its knockdown has no biological consequences. The short T1/2 allows for rapid and sensitive detection of knockdown. AKT1, which is expressed in all cells, is a good endogenous gene to study, since its knockdown does not much affect cell viability.

PLK1 is used for its antitumor effect because its knockdown is cytotoxic to dividing cells. Described herein is robust and reproducible gene knockdown with EpCAM-AsiCs targeting each of these genes. AsiCs will be chemically synthesized with 2'-fluoropyrimidines for stability and inhibition of innate immune recognition and dT residues at their 3'-ends to protect against exonuclease digestion. The 2 strands will be annealed to generate the final RNA (FIG. 10A-10B). These AsiCs can be evaluated and compared to the original EpCAM-AsiC (as positive control) and CD4- or PSMA-AsiCs (as negative control) in in vitro dose response experiments for AsiC uptake (using fluorophores such as AF-647 (which doesn't affect AsiC activity) conjugated to the 3'end of the short strand), gene knockdown and reduced tumor cell line growth and survival. Selective uptake, gene knockdown and antitumor effect in a few human basal-A TNBC cell lines (MB468, HCC1937, BPLER vs immortalized epithelial cells) can be quantified by flow cytometry; flow cytometry and qRT-PCR; and Cell-TiterGlo and annexin-PI staining, respectively. These experiments can permit the selection of a handful of the best performing AsiCs that recognize EpCAM and EphA2.

Types of breast cancer responsive to TNBC-targeting AsiCs. It can be determined which types of breast cancer can be transfected with the selected AsiCs and how specific gene knockdown is in tumors relative to normal epithelial cells. In vitro knockdown by the selected AsiCs in 20 human breast cancer cell lines that represent the common breast cancer subtypes, but are weighted towards TNBC (14 TNBC lines, plus a sampling of luminal and Her2+ cell lines) can be evaluated. 93 Aptamer ligand expression, uptake of fluorescent-labeled AsiC and gene silencing can be compared to BPE57 and fibroblast lines as negative controls. This large panel of cell lines can permit evaluation of how cell surface EpCAM and EphA2 levels influence RNA uptake and gene silencing and whether there is an expression threshold needed for efficient knockdown. A dose response experiment can permit verification that the high affinity of the aptamers is preserved in the AsiC. Specificity of uptake (versus nonspecific "sticking") will be verified by using acid washing to remove loosely adhered aptamers and showing that binding is competed by unlabeled aptamers and eliminated when cells are trypsinized prior to treatment. AsiC-mediated transfection will be compared to lipid transfection as positive control and to naked siRNA as negative control. Knockdown will be assessed by flow cytometry and qRT-PCR after 5 d, the optimal time for AsiC-mediated knockdown. It is expected that uptake and gene silencing will correlate with aptamer ligand levels. To verify that specificity for tumor cells is maintained in mixtures of ligand+ and liganddim/- untransformed breast epithelial cells, we can compare fluorescent AsiC uptake, gene knockdown and survival when PLK1 is the gene target in mixtures of tumor cells expressing different aptamer ligand levels with different numbers of GFP+ BPE cells.

Do epithelial primary breast cancer cells preferentially take up TNBC-targeting AsiCs and show knockdown relative to normal epithelial cells in tissue explants? To assess primary tumor uptake and knockdown and anticipate potential toxicity to normal tissue cells, we can next assess in situ transfection and gene knockdown in explants of 10 luminal, Her2+ and TNBC breast cancers and surrounding normal tissue. We can analyze samples from ~25 tumors to provide a comprehensive look at common tumor subtypes. Tumor typing can be confirmed by histology and immunohistochemistry (IHC) staining for ER, PR, Her2 and E-cadherin. If the aptamer recognizes the mouse ligand, we can also assess potential toxicity to normal epithelia using mouse tumor/normal tissues. We can compare normal tissues that have no large competing source of tumor cells to tissues that contain tumor cells. This might be important for anticipating toxicity in situations where AsiCs are given to patients with low/undetectable tumor burden following therapy or surgery. These experiments can also permit assessment of whether knockdown by 10 tumors is comparable to that in cell lines, whether tissue architecture affects uptake/knockdown in tumor cells and how well different tumor subtypes are transfected. It is contemplated herein that epithelial breast cancers will undergo efficient gene knockdown, but normal epithelial cells will not.

Biopsies, cut into ~3×3×3 mm3 pieces, can be transfected in microtiter wells, which should mimic in vivo uptake after SQ or IV infusion. Lipofectamine encapsulated siRNAs and cholesterol-conjugated siRNAs are both effective at gene knockdown of normal epithelial cells in polarized columnar and squamous genital tract mucosa108,109, while naked siRNAs are not taken up. Similar results are expected with these controls in normal breast epithelial tissue. In parallel we can analyze knockdown of collagenase-digested 10 cells to compare knockdown with what is achieved in tissue and with cancer cell lines. We can first verify these controls using siRNAs to target epithelial genes, which we have previously knocked down (such as E-cadherin, cytokeratin (CK)-5 (a good marker of basal cells) and 14, and nectin-1) 93,108,109, whose expression can be readily followed by IHC, fluorescence microscopy (FM) or flow cytometry of isolated cells. Staining of the target gene can be correlated with staining for phenotypic markers and fluorescently labeled siRNAs to determine which cell types are targeted. Pan-CK antibody can distinguish epithelial cells (normal and tumor) from stroma. Of particular interest is delivery and CK5 knockdown in rare basal tissue stem cells, since EpCAM-AsiCs can target these cells and potentially lead to depletion of normal tissue stem cells. Tissue toxicity and inflammation will be assessed by H&E staining of tissue sections and qRT-PCR assays for Type I interferons and inflammatory cytokines (IL-1, IL-6, TNF-!). Additional chemical modifications of the RNA sequence (besides 2'-fluoropryrimidines) will be introduced to eliminate potentially harmful inflammation if it's detected.

Can TNBC-targeting AsiCs target breast tumor-initiating cells? We chose EpCAM and EphA2 as aptamer targets partly because of their potential to transfect T-ICs. Breast T-ICs are not uniquely defined by phenotypic markers (and they may in fact be heterogeneous93,110-113), making experiments challenging, since T-ICs are defined functionally by their ability to initiate tumors in small numbers that can be serially transplanted. Staining for CD44, CD24, EpCAM, CD133, CD49f or ALDH1 in different combinations enriches for T-ICs. 59,72,78,114-121 Different protocols define overlapping, but not identical, subsets of potential T-ICs. Without wishing to be bound by theory, it is contemplated herein that EpCAM- and EphA2-AsiCs will be taken up by and cause gene silencing in T-ICs and can be used for targeted therapy to eliminate or cripple T-IC capability within tumors.

To analyze AsiC uptake and gene silencing in T-IC subpopulations, multicolor flow cytometry of EpCAM, EphA2, CD44 and CD24 in a panel of breast cancer lines (luminal, Her2+, basal-A and B TNBCs) can be used to identify which breast cell lines have putative T-IC populations that contain cells that stain brightly for EpCAM and/or EphA2. We can also examine EpCAM/EphA2 staining of mammospheres and Aldefluor+ cells121,123-125 generated from these cell lines. We can select ~4-5 lines with the brightest/most uniform EpCAM/EphA2 expression within T-ICs as the most attractive cell lines to study in this subaim and can produce stable (dl)GFP-expressing variants. These cell lines, as well as their mammospheres and Aldefluor+ subpopulation, can be incubated with AF647-labeled AsiCs (and as a negative control, nontargeting PSMA-AsiCs) bearing GFP siRNAs. AsiC uptake will be assessed by AF-647 fluorescence together with EpCAM or EphA2, CD44 and CD24 and Aldefluor staining. AsiCs can be taken up by EpCAM+ or EphA2+CD44+CD24-/dim Aldefluor+ cells. To assess gene knockdown in T-IC phenotype cells, we can monitor GFP expression in the T-IC population and remaining cells by flow cytometry and qRT-PCR after treatment with eGFP or control siRNA-bearing AsiCs. We can also assess knockdown of endogenous PLK1 and AKT1.

These experiments can indicate whether T-Ics in different subtypes of breast cancer are targeted by EpCAM/EphA2-AsiCs. In subsequent experiments we will focus on the cell lines in which we have >80% knockdown in T-IC-enriched populations. If knockdown is inefficient, we can modify the transfection conditions (amount of AsiC, number of cells, volume, etc). Next, we can assess whether AsiCs inhibit mammosphere and colony formation, reduce CD44 and ALDH1-expressing subpopulations, and the size of the side population. In addition to knocking down PLK1, we can design and evaluate AsiCs against a few additional genes that breast T-ICs depend on for self-renewal or maintaining multipotency. Basal-like TNBC T-ICs are selectively sensitive to proteasome inhibition. 93

We can therefore evaluate knockdown of a proteasome component (PSMA2) and potentially other selective T-IC dependency genes (such as MSI1 (Musashi), an RNA binding protein in breast T-ICs that regulates Wnt and Notch signaling126-130 or BMI1, a polycomb component required for stem cell self-renewal131-134). After verifying that these genes are expressed and knocked down in mammosphere cells, we can treat both adherent cells and mammospheres with AsiCs targeting PLK1, MSI1, BMI1 or PSMA2 or with AsiCs targeting eGFP as a negative control and measure the size of T-IC subpopulations after 5-7 d by staining with CD44, CD24, EpCAM, CD133, CD49f and ALDH1. We can also measure the proportion of cells that efflux small molecule dyes (the "side population"). These experiments can be complemented by functional assays quantifying the frequency of colony forming cells and mammospheres. Serial replating can assess whether the ability to continuously propagate T-ICs as spheres is inhibited. It is contemplated herein that knocking down PLK1, MSI1, BMI1 or PSMA2 can reduce T-IC numbers, proliferation and function in the T-ICs from some cell lines, but different genes may be more active for different breast cell lines. For example proteasome inhibition eliminated T-ICs in basal-like TNBCs, but only in 1 of 3 mesenchymal TNBC cell lines and not in more differentiated non-TNBC tumors. 93

The knockdown approaches that suppress T-IC can be further investigated by experiments using chemical inhibitors where available (such as bortezomib) or by examining whether knocking down other genes in the same pathway (such as NOTCH1, 3-catenin or WNT1 for MSI1) also has anti-T-IC activity. Next, we can determine whether short-term ex vivo exposure of basal-like TNBC lines to AsiCs inhibits TNBC tumor initiation as the ultimate measure of inhibition of T-IC capacity, using AsiCs that look promising in vitro. Cell lines, treated overnight with the chosen AsiCs (and as negative controls AsiCs that use PSMA aptamer or contain eGFP siRNA), will be assessed for viability. After verifying that short-term siRNA exposure does not affect viability, ex vivo treated cells will be injected in a range of cell numbers orthotopically into NOD/scid/"c-/- (NSG) mice (these mice have the highest take for tumor implantation). Bortezomib treatment for 24 hr (at this time ~40% of cells are still viable) can serve as a positive control.

In vivo evaluation of TNBC-targeting AsiCs

A few of the AsiCs that perform best can next be evaluated in vivo using nude mice bearing mammary fatpad xenografts of an aptamer ligand+ basal-A TNBC line, such as MB468 or HCC1187, on one side compared to ligand-breast cancer cell line, such as basal-B MB231, on the other (~5-8 mice/gp to obtain reproducible statistics based on our experience with these models). For in vivo imaging, we have already made stable luminescent/fluorescent cell lines by infection with luciferase- and mCherry-expressing lentivirus.

Systemic delivery and knockdown in tumor cells Because unmodified AsiCs are small (~30 kDa), when injected IV or IP they are rapidly eliminated by kidney filtration. 20 kDa polyethylene glycol (PEG) can be attached to the 5'-end of the inactive (passenger) strand of the siRNA. 21 IV injected PEGylated PSMA-AsiCs concentrated in subcutaneous tumors; PEGylation extended the circulating T1/2 of Ipinjected AsiCs from <35 min to >>30 hr, increased the durability of gene silencing to ~5 d and reduced the effective tumor-inhibitory dose 8-fold to 250 pmol×5 injections. We have also found (not shown) that SQ injection of 5 mg/kg unmodified CD4-AsiCs caused systemic specific knockdown in CD4+ cells in the spleen and proximal and distal lymph nodes of humanized mice. Therefore we can compare AsiC levels after IV and SQ administration of the original AsiC constructs and PEG-AsiCs by in vivo imaging using AF-790-coupled AsiCs and the IVIS Spectrum and by Taqman assay of the active strand in blood, urine, liver and tumor samples. Samples can be analyzed over 5 d with frequent sample collection the first day. Tissue sections can be assessed for tissue damage and the blood can be analyzed for hematological, liver and kidney toxicity by blood counts and serum chemistries. Toxicity associated with induction of innate immunity or inflammation can be assessed by ELISA assays of serum interferons and inflammatory cytokines. The circulating T1/2 and proportion of the injected drug that localizes to the EpCAM+ tumor can be calculated. Based on our preliminary experiments with SQ and IV administration of the CD4-AsiCs and in vivo experience with the PSMA-AsiC9,21,25, it is contemplated herein, without wishing to be bound by theory, that unPEGylated AsiCs will be rapidly excreted after IV administration, but that SQ EpCAM-AsiC and IV PEG-AsiCs will have more favorable localization to tumor xenografts.

Knockdown of mCherry and PLK1 following a single AsiC injection in a range of concentrations can be assessed by in vivo imaging and by flow cytometry, FM, and qRT-PCR of tumor specimens harvested 4, 7 and 12 d post-treatment. These experiments can provide estimates of the effective dose required for peak tumor gene knockdown of 50, 75 and 90% (ED50, ED75, ED90) and for the durability of knockdown in the tumor (quantified as T-KD50=time for tumor expression to return halfway to control from the peak knockdown). These parameters can be determined for each construct. We can also determine the maximally tolerated dose (MTD) for the PLK1 constructs. Inadequate PK/PD or signs of innate immune stimulation will lead us to adjust chemical modifications (adding 2'-OMe riboses to some residues) or add longer PEG polymers to improve these parameters using straightforward.

Antitumor effect. It can be tested by in vivo imaging how effective the best TNBC-targeting AsiCs are against basal-A tumors implanted in the mammary fat pads or injected IV (as a metastasis model) in nude mice. We can begin by targeting PLK1 as proof of principle. 21,107 PLK1-AsiCs can be injected SQ and/or IV in groups of 8 mice (group size chosen for statistical significance based on previous experiments) bearing a basal-A TNBC fatpad tumor using dosing schedules chosen based on the PK/PD results. Mice can be treated as soon as tumors become palpable. Effects on a representative ligand+ and ligand- tumor will be compared. Control mice can be treated with PBS or naked siRNAs, AsiCs bearing a scrambled siRNA and PLK1 PSMA-AsiCs. Tumor size can be quantified by imaging and calipers. If the antitumor effect is suboptimal, the dosing regimen can be adjusted to the maximally tolerated regimen.

We can also compare the effect of PLK1 knockdown and standard-of-care chemotherapy, administered on their own and in combination to anticipate potential clinical studies. If there is complete tumor regression, we can evaluate decreased doses. Effective regimens can also be evaluated in mice implanted with a few other basal-A TNBC lines to verify the generality of the antitumor response. We can also evaluate AsiC treatment after tumor cells are injected IV to determine effectiveness against distal metastases. At the time of sacrifice, mice can be sacrificed and mammary fatpads can be inspected for residual microscopic or macroscopic tumor by FM, H&E and IHC. Residual tumor cells can also be assessed for EpCAM/EphA2 expression to determine whether tumor resistance may have developed as a consequence of down-regulating the aptamers ligand. Treated mice can also be observed for clinical signs of toxicity and at time of sacrifice can be carefully examined for gut and bone marrow toxicity, by blood counts and pathological examination of gut, bone marrow and spleen. AsiCs designed with the cross-reacting aptamers can be used to evaluate normal epithelial toxicity. Using our best AsiC design, we can next begin to compare PLK1 knockdown with knockdown of TNBC dependency genes (such as PSMA2 or MCL1) identified in our siRNA screen93 tested alone or in combination with PLK1.

REFERENCES CITED

1. Foulkes W D, Smith I E, Reis-Filho J S. Triple-negative breast cancer. N Engl J Med. 2010. 363: 1938-1948
2. Gusterson B. Do 'basal-like' breast cancers really exist? Nat Rev Cancer. 2009. 9: 128-134.
3. Metzger-Filho O, Tutt A, de Azambuja E, Saini K S, Viale G, Loi S, Bradbury I, Bliss J M, Azim H A, Jr., EllisP, Di Leo A, Baselga J, Sotiriou C, Piccart-Gebhart M. Dissecting the heterogeneity of triple-negative breast cancer. J Clin Oncol. 2012. 30: 1879-1887.
4. Shah S P, Roth A, Goya R, Oloumi A, Ha G, Zhao Y, Turashvili G, Ding J, Tse K, Haffari G, Bashashati A, Prentice L M, Khattra J, Burleigh A, Yap D, Bernard V, McPherson A, Shumansky K, Crisan A, Giuliany R, Heravi-Moussavi A, Rosner J, Lai D, Birol I, Varhol R, Tam A, Dhalla N, Zeng T, Ma K, Chan S K, Griffith M, Moradian A, Cheng S W, Morin G B, Watson P, Gelmon K, Chia S, Chin S F, Curtis C, Rueda O M, Pharoah P D, Damaraju S, Mackey J, Hoon K, Harkins T, Tadigotla V, Sigaroudinia M, Gascard P, Tlsty T, Costello J F, Meyer I M, Eaves C J, Wasserman W W, Jones S, Huntsman D, Hirst M, Caldas C, Marra M A, Aparicio S. The clonal and mutational evolution spectrum of primary triple-negative breast cancers. Nature. 2012. 486: 395-399.
5. Dykxhoorn D M, Lieberman J. Knocking down disease with siRNAs. Cell. 2006. 126: 231-235.
6. de Fougerolles A, Vornlocher H P, Maraganore J, Lieberman J. Interfering with disease: a progress report on siRNA-based therapeutics. Nat Rev Drug Discov. 2007. 6: 443-453.
7. Petrocca F, Lieberman J. Promise and challenge of RNA interference-based therapy for cancer. J Clin Oncol. 2011. 29: 747-754.
8. Watts J K, Corey D R. Silencing disease genes in the laboratory and the clinic. J Pathol. 2012. 226: 365-379.
9. Burnett J C, Rossi J J. RNA-based therapeutics: current progress and future prospects. Chem Biol. 2012. 19:60-71.
10. Tabernero J, Shapiro G I, LoRusso P M, Cervantes A, Schwartz G K, Weiss G J, Paz-Ares L, Cho D C, Infante J R, Alsina M, Gounder M M, Falzone R, Harrop J, White A C, Toudjarska I, Bumcrot D, Meyers R E, Hinkle G, Svrzikapa N, Hutabarat R M, Clausen V A, Cehelsky J, Nochur S V, Gamba-Vitalo C, Vaishnaw A K, Sah D W, Gollob J A, Burris H A, 3rd. First-in-humans trial of an RNA interference therapeutic targeting VEGF and KSP in cancer patients with liver involvement. Cancer Discov. 2013. 3: 406-417.
11. Janssen H L, Reesink H W, Lawitz E J, Zeuzem S, Rodriguez-Torres M, Patel K, van der Meer A J, Patick A K, Chen A, Zhou Y, Persson R, King B D, Kauppinen S, Levin A A, Hodges M R. Treatment of HCV infection by targeting microRNA. N Engl J Med. 2013. 368: 1685-1694.
12. Sehgal A, Vaishnaw A, Fitzgerald K. Liver as a target for oligonucleotide therapeutics. J Hepatol. 2013.
13. Coelho T, Adams D, Silva A, Lozeron P, Hawkins P N, Mant T, Perez J, Chiesa J, Warrington S, Tranter E, Munisamy M, Falzone R, Harrop J, Cehelsky J, Bettencourt B R, Geissler M, Butler J S, Sehgal A, Meyers R E, Chen Q, Borland T, Hutabarat R M, Clausen V A, Alvarez R, Fitzgerald K, Gamba-Vitalo C, Nochur S V, Vaishnaw A K, Sah D W, Gollob J A, Suhr O B. Safety and efficacy of RNAi therapy for transthyretin amyloidosis. N Engl J Med. 2013. 369: 819-829.
14. Alnylam. Interim Results for Phase II Trial of ALN-TTR02: A Novel RNAi Therapeutic for the Treatment of Familial Amyloidotic Polyneuropathy. Biennial Meeting of the Peripheral Nerve Society, St Malo, France. 2013.
15. Lieberman J, Sarnow P. Micromanaging hepatitis C virus. N Engl J Med. 2013. 368: 1741-1743.
16. Fitzgerald K, Frank-Kamenetsky M, Shulga-Morskaya S, Liebow A, Bettencourt B R, Sutherland J E, Hutabarat R M, Clausen V A, Karsten V, Cehelsky J, Nochur S V, Kotelianski V, Horton J, Mant T, Chiesa J, Ritter J, Munisamy M, Vaishnaw A K, Gollob J A, Simon A. Effect of an RNA interference drug on the synthesis of proprotein convertase subtilisin/kexin type 9 (PCSK9) and the concentration of serum LDL cholesterol in healthy volunteers: a randomised, single-blind, placebo-controlled, phase 1 trial. Lancet. 2013.
17. Peer D, Lieberman J. Special delivery: targeted therapy with small RNAs. Gene Ther. 2011. 18: 1127-1133.
18. Daniels D A, Chen H, Hicke B J, Swiderek K M, Gold L. A tenascin-C aptamer identified by tumor cell SELEX: systematic evolution of ligands by exponential enrichment. Proc Natl Acad Sci USA. 2003. 100: 15416-15421.
19. Huang Z, Szostak J W. Evolution of aptamers with a new specificity and new secondary structures from an ATP aptamer. RNA. 2003. 9: 1456-1463.
20. McNamara J O, 2nd, Andrechek E R, Wang Y, Viles K D, Rempel R E, Gilboa E, Sullenger B A, Giangrande P H. Cell type-specific delivery of siRNAs with aptamer-siRNA chimeras. Nat Biotechnol. 2006. 24: 1005-1015.
21. Dassie J P, Liu X Y, Thomas G S, Whitaker R M, Thiel K W, Stockdale K R, Meyerholz D K, McCaffrey A P, McNamara J O, 2nd, Giangrande P H. Systemic administration of optimized aptamer-siRNA chimeras promotes regression of PSMA-expressing tumors. Nat Biotechnol. 2009. 27: 839-849.
22. Zhou J, Li H, Li S, Zaia J, Rossi J J. Novel dual inhibitory function aptamer-siRNA delivery system for HIV1 therapy. Mol Ther. 2008. 16: 1481-1489.
23. Zhou J, Rossi J J. Aptamer-targeted cell-specific RNA interference. Silence. 2010. 1: 4.
24. Zhou J, Swiderski P, Li H, Zhang J, Neff C P, Akkina R, Rossi J J. Selection, characterization and application of new RNA HIV gp 120 aptamers for facile delivery of Dicer substrate siRNAs into HIV infected cells. Nucleic Acids Res. 2009. 37: 3094-3109.
25. Neff C P, Zhou J, Remling L, Kuruvilla J, Zhang J, Li H, Smith D D, Swiderski P, Rossi J J, Akkina R. An aptamer-siRNA chimera suppresses HIV-1 viral loads and protects from helper CD4(+) T cell decline in humanized mice. Sci Transl Med. 2011. 3: 66ra66.
26. McNamara J O, Kolonias D, Pastor F, Mittler R S, Chen L, Giangrande P H, Sullenger B, Gilboa E. Multivalent 4-1BB binding aptamers costimulate CD8+ T cells and inhibit tumor growth in mice. J Clin Invest. 2008. 118: 376-386.
27. Kim M Y, Jeong S. In vitro selection of RNA aptamer and specific targeting of ErbB2 in breast cancer cells. Nucleic Acid Ther. 2011. 21: 173-178.
28. Wheeler L A, Trifonova R, Vrbanac V, Basar E, McKernan S, Xu Z, Seung E, Deruaz M, Dudek T, Einarsson J I, Yang L, Allen™, Luster A D, Tager A M, Dykxhoorn D M, Lieberman J. Inhibition of HIV transmission in human cervicovaginal explants and humanized mice using CD4 aptamer-siRNA chimeras. J Clin Invest. 2011. 121: 2401-2412.
29. Rockey W M, Hernandez F J, Huang S Y, Cao S, Howell C A, Thomas G S, Liu X Y, Lapteva N, Spencer D M, McNamara J O, Zou X, Chen S J, Giangrande P H. Rational truncation of an RNA aptamer to prostate-specific membrane antigen using computational structural modeling. Nucleic Acid Ther. 2011. 21: 299-314.
30. Thiel K W, Hernandez L I, Dassie J P, Thiel W H, Liu X, Stockdale K R, Rothman A M, Hernandez F J, McNamara J O, 2nd, Giangrande P H. Delivery of chemosensitizing siRNAs to HER2+-breast cancer cells using RNA aptamers. Nucleic Acids Res. 2012. 40: 6319-6337.
31. Pastor F, Kolonias D, Giangrande P H, Gilboa E. Induction of tumour immunity by targeted inhibition of nonsense-mediated mRNA decay. Nature. 2010. 465: 227-230.
32. Zhou J, Rossi J J. Cell-specific aptamer-mediated targeted drug delivery. Oligonucleotides. 2011. 21: 1-10.
33. Pastor F, Kolonias D, McNamara J O, 2nd, Gilboa E. Targeting 4-1BB costimulation to disseminated tumor lesions with bi-specific oligonucleotide aptamers. Mol Ther. 2011. 19: 1878-1886.
34. Wheeler L A, Vrbanac V, Trifonova R, Brehm M A, Gilboa-Geffen A, Tanno S, Greiner D L, Luster A D, Tager A M, Lieberman J. Durable knockdown and protection from HIV transmission in humanized mice treated with gel-formulated CD4 aptamer-siRNA chimeras. Mol Ther. 2013. 21: 1378-1389.
35. Keefe A D, Pai S, Ellington A. Aptamers as therapeutics. Nat Rev Drug Discov. 2010. 9: 537-550.
36. Sundaram P, Kurniawan H, Byrne M E, Wower J. Therapeutic RNA aptamers in clinical trials. Eur J Pharm Sci. 2013. 48: 259-271.
37. Shigdar S, Lin J, Yu Y, Pastuovic M, Wei M, Duan W. RNA aptamer against a cancer stem cell marker epithelial cell adhesion molecule. Cancer Sci. 2011. 102: 991-998.
38. Stingl J, Eaves C J, Zandieh I, Emerman J T. Characterization of bipotent mammary epithelial progenitor cells in normal adult human breast tissue. Breast Cancer Res Treat. 2001. 67: 93-109.
39. Trzpis M, Popa E R, McLaughlin P M, van Goor H, Timmer A, Bosman G W, de Leij L M, Harmsen M C. Spatial and temporal expression patterns of the epithelial cell adhesion molecule (EpCAM/EGP-2) in developing and adult kidneys. Nephron Exp Nephrol. 2007. 107: e119-131.
40. Marhaba R, Klingbeil P, Nuebel T, Nazarenko I, Buechler M W, Zoeller M. CD44 and EpCAM: cancer-initiating cell markers. Curr Mol Med. 2008. 8: 784-804.
41. Gonzalez B, Denzel S, Mack B, Conrad M, Gires O. EpCAM is involved in maintenance of the murine embryonic stem cell phenotype. Stem Cells. 2009. 27: 1782-1791.
42. Lu T Y, Lu R M, Liao M Y, Yu J, Chung C H, Kao C F, Wu H C. Epithelial cell adhesion molecule regulation is associated with the maintenance of the undifferentiated phenotype of human embryonic stem cells. J Biol Chem. 2010. 285: 8719-8732.
43. Martin-Killias P, Stefan N, Rothschild S, Pluckthun A, Zangemeister-Wittke U. A novel fusion toxin derived from an EpCAM-specific designed ankyrin repeat protein has potent antitumor activity. Clin Cancer Res. 2011. 17: 100-110.
44. Spizzo G, Fong D, Wurm M, Ensinger C, Obrist P, Hofer C, Mazzoleni G, Gastl G, Went P. EpCAM expression in primary tumour tissues and metastases: an immunohistochemical analysis. J Clin Pathol. 2011. 64: 415-420.
45. Keller P J, Arendt L M, Skibinski A, Logvinenko T, Klebba I, Dong S, Smith A E, Prat A, Perou C M, Gilmore H, Schnitt S, Naber S P, Garlick J A, Kuperwasser C. Defining the cellular precursors to human breast cancer. Proc Natl Acad Sci USA. 2012. 109: 2772-2777.
46. Osta W A, Chen Y, Mikhitarian K, Mitas M, Salem M, Hannun Y A, Cole D J, Gillanders W E. EpCAM is overexpressed in breast cancer and is a potential target for breast cancer gene therapy. Cancer Res. 2004. 64:5818-5824.
47. Baeuerle P A, Gires O. EpCAM (CD326) finding its role in cancer. Br J Cancer. 2007. 96: 417-423.
48. Carpenter G, Red Brewer M. EpCAM: another surface-to-nucleus missile. Cancer Cell. 2009. 15: 165-166.
49. Maetzel D, Denzel S, Mack B, Canis M, Went P, Benk M, Kieu C, Papior P, Baeuerle P A, Munz M, Gires O. Nuclear signalling by tumour-associated antigen EpCAM. Nat Cell Biol. 2009. 11: 162-171.
50. Schulze K, Gasch C, Staufer K, Nashan B, Lohse A W, Pantel K, Riethdorf S, Wege H. Presence of EpCAMpositive circulating tumor cells as biomarker for systemic disease strongly correlates to survival in patients with hepatocellular carcinoma. Int J Cancer. 2013.
51. Konigsberg R, Obermayr E, Bises G, Pfeiler G, Gneist M, Wrba F, de Santis M, Zeillinger R, Hudec M, Dittrich C. Detection of EpCAM positive and negative circulating tumor cells in metastatic breast cancer patients. Acta Oncol. 2011. 50: 700-710.
52. Weissenstein U, Schumann A, Reif M, Link S, Toffol-Schmidt U D, Heusser P. Detection of circulating tumor cells in blood of metastatic breast cancer patients using a combination of cytokeratin and EpCAM antibodies. BMC Cancer. 2012. 12: 206.
53. Zhao S, Yang H, Zhang M, Zhang D, Liu Y, Song Y, Zhang X, Li H, Ma W, Zhang Q. Circulating tumor cells (CTCs) detected by triple-marker EpCAM, CK19, and hMAM R T-PCR and their relation to clinical outcome in metastatic breast cancer patients. Cell Biochem Biophys. 2013. 65: 263-273.
54. Jackson A L, Bartz S R, Schelter J, Kobayashi S V, Burchard J, Mao M, Li B, Cavet G, Linsley P S. Expression profiling reveals off-target gene regulation by RNAi. Nat Biotechnol. 2003. 21: 635-637.
55. Scacheri P C, Rozenblatt-Rosen O, Caplen N J, Wolfsberg T G, Umayam L, Lee J C, Hughes C M, Shanmugam K S, Bhattacharjee A, Meyerson M, Collins F S. Short interfering RNAs can induce unexpected and divergent changes in the levels of untargeted proteins in mammalian cells. Proc Natl Acad Sci USA. 2004. 101: 1892-1897.
56. Jackson A L, Burchard J, Leake D, Reynolds A, Schelter J, Guo J, Johnson J M, Lim L, Karpilow J, Nichols K, Marshall W, Khvorova A, Linsley P S. Position-specific chemical modification of siRNAs reduces "offtarget" transcript silencing. RNA. 2006. 12: 1197-1205.
57. Ince T A, Richardson A L, Bell G W, Saitoh M, Godar S, Karnoub A E, Iglehart J D, Weinberg R A. Transformation of different human breast epithelial cell types leads to distinct tumor phenotypes. Cancer Cell. 2007. 12: 160-170.
58. Imrich S, Hachmeister M, Gires O. EpCAM and its potential role in tumor-initiating cells. Cell Adh Migr. 2012. 6: 30-38.
59. Al-Hajj M, Wicha M S, Benito-Hernandez A, Morrison S J, Clarke M F. Prospective identification of tumorigenic breast cancer cells. Proc Natl Acad Sci USA. 2003. 100: 3983-3988.
60. Dick J E. Breast cancer stem cells revealed. Proc Natl Acad Sci USA. 2003. 100: 3547-3549.
61. Hirschmann-Jax C, Foster A E, Wulf G G, Nuchtern J G, Jax T W, Gobel U, Goodell M A, Brenner M K. A distinct "side population" of cells with high drug efflux capacity in human tumor cells. Proc Natl Acad Sci USA. 2004. 101: 14228-14233.
62. Dean M, Fojo T, Bates S. Tumour stem cells and drug resistance. Nat Rev Cancer. 2005. 5: 275-284.
63. Bao S, Wu Q, McLendon R E, Hao Y, Shi Q, Hjelmeland A B, Dewhirst M W, Bigner D D, Rich J N. Glioma stem cells promote radioresistance by preferential activation of the DNA damage response. Nature. 2006. 444:756-760.
64. Clarke M F, Dick J E, Dirks P B, Eaves C J, Jamieson CHM, Jones D L, Visvader J, Weissman I L, Wahl G M (2006). Cancer stem cells-perspectives on current status and future directions: AACR Workshop on cancer stem cells. In Cancer Res, pp. 9339-9344.
65. Jordan C T, Guzman M L, Noble M. Cancer stem cells. N Engl J Med. 2006. 355: 1253-1261.
66. Phillips™, McBride W H, Pajonk F. The response of CD24(~/low)/CD44+ breast cancer-initiating cells to radiation. J Natl Cancer Inst. 2006. 98: 1777-1785.
67. Polyak K, Hahn W C. Roots and stems: stem cells in cancer. Nat Med. 2006. 12: 296-300.
68. Sheridan C, Kishimoto H, Fuchs R K, Mehrotra S, Bhat-Nakshatri P, Turner C H, Goulet R, Jr., Badve S, Nakshatri H. CD44+/CD24-breast cancer cells exhibit enhanced invasive properties: an early step necessary for metastasis. Breast Cancer Res. 2006. 8: R59.
69. Wicha M S. Cancer stem cells and metastasis: lethal seeds. Clin Cancer Res. 2006. 12: 5606-5607.
70. Cho R W, Wang X, Diehn M, Shedden K, Chen G Y, Sherlock G, Gurney A, Lewicki J, Clarke M F. Isolation and Molecular Characterization of Cancer Stem Cells in MMTV-Wnt-1Murine Breast Tumors. Stem Cells (Dayton, Ohio). 2008. 26: 364-371.
71. Dalerba P, Clarke M. Cancer Stem Cells and Tumor Metastasis: First Steps into Uncharted Territory. Cell Stem Cell. 2007. 1: 241-242.
72. Fillmore C, Kuperwasser C. Human breast cancer stem cell markers CD44 and CD24: enriching for cells with functional properties in mice or in man? Breast Cancer Res. 2007. 9: 303.
73. Kelly P N, Dakic A, Adams J M, Nutt S L, Strasser A. Tumor growth need not be driven by rare cancer stem cells. Science. 2007. 317: 337.
74. O'Brien C A, Pollett A, Gallinger S, Dick J E. A human colon cancer cell capable of initiating tumour growth in immunodeficient mice. Nature. 2007. 445: 106-110.
75. Shafee N, Smith C R, Wei S, Kim Y, Mills G B, Hortobagyi G N, Stanbridge E J, Lee E Y-H P. Cancer stem cells contribute to cisplatin resistance in Brca1/p53-mediated mouse mammary tumors. Cancer Res. 2008. 68: 3243-3250.
76. Charafe-Jauffret E, Ginestier C, Iovino F, Wicinski J, Cervera N, Finetti P, Hur M-H, Diebel M E, Monville F, Dutcher J, Brown M, Viens P, Xerri L, Bertucci F, Stassi G, Dontu G, Bimbaum D, Wicha M S. Breast Cancer Cell Lines Contain Functional Cancer Stem Cells with Metastatic Capacity and a Distinct Molecular Signature. Cancer Res. 2009. 69: 1302-1313.
77. Rosen J M, Jordan C T. The Increasing Complexity of the Cancer Stem Cell Paradigm. Science (New York,N Y). 2009. 324: 1670-1673.
78. Liu H, Patel M R, Prescher J A, Patsialou A, Qian D, Lin J, Wen S, Chang Y F, Bachmann M H, Shimono Y, Dalerba P, Adorno M, Lobo N, Bueno J, Dirbas F M, Goswami S, Somlo G, Condeelis J, Contag C H, Gambhir S S, Clarke M F. Cancer stem cells from human breast tumors are involved in spontaneous metastases in orthotopic mouse models. Proc Natl Acad Sci USA. 2010. 107: 18115-18120.
79. McDermott S P, Wicha M S. Targeting breast cancer stem cells. Mol Oncol. 2010. 4: 404-419.
80. Federici G, Espina V, Liotta L, Edmiston K H. Breast cancer stem cells: a new target for therapy. Oncology. 2011. 25: 25-28, 30.
81. Castano Z, Fillmore C M, Kim C F, McAllister S S. The bed and the bugs: interactions between the tumor microenvironment and cancer stem cells. Semin Cancer Biol. 2012. 22: 462-470.
82. Valent P, Bonnet D, De Maria R, Lapidot T, Copland M, Melo J V, Chomienne C, Ishikawa F, Schuringa J J, Stassi G, Huntly B, Herrmann H, Soulier J, Roesch A, Schuurhuis G J, Wohrer S, Arock M, Zuber J, Cerny-Reiterer S, Johnsen H E, Andreeff M, Eaves C. Cancer stem cell definitions and terminology: the devil is in the details. Nat Rev Cancer. 2012. 12: 767-775.
83. Hiramoto-Yamaki N, Takeuchi S, Ueda S, Harada K, Fujimoto S, Negishi M, Katoh H. Ephexin4 and EphA2 mediate cell migration through a RhoG-dependent mechanism. J Cell Biol. 2010. 190: 461-477.
84. Wykosky J, Palma E, Gibo D M, Ringler S, Turner C P, Debinski W. Soluble monomeric EphrinA1 is released from tumor cells and is a functional ligand for the EphA2 receptor. Oncogene. 2008. 27: 7260-7273.

85. Brantley-Sieders D M, Zhuang G, Hicks D, Fang W B, Hwang Y, Cates J M, Coffman K, Jackson D, Bruckheimer E, Muraoka-Cook R S, Chen J. The receptor tyrosine kinase EphA2 promotes mammary adenocarcinoma tumorigenesis and metastatic progression in mice by amplifying ErbB2 signaling. J Clin Invest. 2008. 118: 64-78.

86. Fang W B, Brantley-Sieders D M, Parker M A, Reith A D, Chen J. A kinase-dependent role for EphA2 receptor in promoting tumor growth and metastasis. Oncogene. 2005. 24: 7859-7868.

87. Macrae M, Neve R M, Rodriguez-Viciana P, Haqq C, Yeh J, Chen C, Gray J W, McCormick F. A conditional feedback loop regulates Ras activity through EphA2. Cancer Cell. 2005. 8: 111-118.

88. Ireton R C, Chen J. EphA2 receptor tyrosine kinase as a promising target for cancer therapeutics. Curr Cancer Drug Targets. 2005. 5: 149-157.

89. Coffman K T, Hu M, Carles-Kinch K, Tice D, Donacki N, Munyon K, Kifle G, Woods R, Langermann S, Kiener P A, Kinch M S. Differential EphA2 epitope display on normal versus malignant cells. Cancer Res. 2003. 63: 7907-7912.

90. Carles-Kinch K, Kilpatrick K E, Stewart J C, Kinch M S. Antibody targeting of the EphA2 tyrosine kinase inhibits malignant cell behavior. Cancer Res. 2002. 62: 2840-2847.

91. Zelinski D P, Zantek N D, Stewart J C, Irizarry A R, Kinch M S. EphA2 overexpression causes tumorigenesis of mammary epithelial cells. Cancer Res. 2001. 61: 2301-2306.

92. Zhuang G, Brantley-Sieders D M, Vaught D, Yu J, Xie L, Wells S, Jackson D, Muraoka-Cook R, Arteaga C, Chen J. Elevation of receptor tyrosine kinase EphA2 mediates resistance to trastuzumab therapy. Cancer Res. 2010. 70: 299-308.

93. Petrocca F, Altschuler G, Tan S M, Mendillo M L, Yan H, Jerry D J, Kung A L, Hide W, Ince T A, Lieberman J. A Genome-wide siRNA Screen Identifies Proteasome Addiction as a Vulnerability of Basal-like Triple-Negative Breast Cancer Cells. Cancer Cell. 2013. 24: 182-196.

94. Lehmann B D, Bauer J A, Chen X, Sanders M E, Chakravarthy A B, Shyr Y, Pietenpol J A. Identification of human triple-negative breast cancer subtypes and preclinical models for selection of targeted therapies. J Clin Invest. 2011. 121: 2750-2767.

95. Ellington A D, Szostak J W. In vitro selection of RNA molecules that bind specific ligands. Nature. 1990. 346: 818-822.

96. Tuerk C, Gold L. Systematic evolution of ligands by exponential enrichment: RNA ligands to bacteriophage T4 DNA polymerase. Science. 1990. 249: 505-510.

97. Thiel W H, Bair T, Peek A S, Liu X, Dassie J, Stockdale K R, Behlke M A, Miller F J, Jr., Giangrande P H. Rapid identification of cell-specific, internalizing RNA aptamers with bioinformatics analyses of a cell-based aptamer selection. PLoS One. 2012. 7: e43836.

98. Thiel W H, Bair T, Wyatt Thiel K, Dassie J P, Rockey W M, Howell C A, Liu X Y, Dupuy A J, Huang L, Owczarzy R, Behlke M A, McNamara J O, Giangrande P H. Nucleotide bias observed with a short SELEX RNA aptamer library. Nucleic Acid Ther. 2011. 21: 253-263.

99. Huang Y Z, Hernandez F J, Gu B, Stockdale K R, Nanpaneni K, Scheetz T E, Behlke M A, Peek A S, Bair T, Giangrande P H, McNamara J O. RNA Aptamer-based Functional Ligands of the Neurotrophin Receptor, TrkB. Mol Pharmacol. 2012.

100. Meyer S, Maufort J P, Nie J, Stewart R, McIntosh B E, Conti L R, Ahmad K M, Soh H T, Thomson J A. Development of an efficient targeted cell-SELEX procedure for DNA aptamer reagents. PLoS One. 2013. 8:e71798.

101. Reiss D J, Howard F M, Mobley H L. A novel approach for transcription factor analysis using SELEX with high-throughput sequencing (TFAST). PLoS One. 2012. 7: e42761.

102. Zimmermann B, Gesell T, Chen D, Lorenz C, Schroeder R. Monitoring genomic sequences during SELEX using high-throughput sequencing: neutral SELEX. PLoS One. 2010. 5: e9169.

103. Jagannathan V, Roulet E, Delorenzi M, Bucher P. HTPSELEX-a database of high-throughput SELEX libraries for transcription factor binding sites. Nucleic Acids Res. 2006. 34: D90-94.

104. Roulet E, Busso S, Camargo A A, Simpson A J, Mermod N, Bucher P. High-throughput SELEX SAGE method for quantitative modeling of transcription-factor binding sites. Nat Biotechnol. 2002. 20: 831-835.

105. White R, Rusconi C, Scardino E, Wolberg A, Lawson J, Hoffman M, Sullenger B. Generation of speciescross-reactive aptamers using "toggle" SELEX. Mol Ther. 2001. 4: 567-573.

106. Berezhnoy A, Stewart C A, McNamara Ii J O, Thiel W, Giangrande P, Trinchieri G, Gilboa E. Isolation and Optimization of Murine IL-10 Receptor Blocking Oligonucleotide Aptamers Using High-throughput Sequencing. Mol Ther. 2012. 20: 1242-1250.

107. Yao Y D, Sun™, Huang S Y, Dou S, Lin L, Chen J N, Ruan J B, Mao C Q, Yu F Y, Zeng M S, Zang J Y, Liu Q, Su F X, Zhang P, Lieberman J, Wang J, Song E. Targeted delivery of PLK1-siRNA by ScFv suppresses Her2+ breast cancer growth and metastasis. Sci Transl Med. 2012. 4: 130ra148.

108. Palliser D, Chowdhury D, Wang Q Y, Lee S J, Bronson R T, Knipe D M, Lieberman J. An siRNA-based microbicide protects mice from lethal herpes simplex virus 2 infection. Nature. 2006. 439: 89-94.

109. Wu Y, Navarro F, Lal A, Basar E, Pandey R K, Manoharan M, Feng Y, Lee S J, Lieberman J, Palliser D. Durable protection from Herpes Simplex Virus-2 transmission following intravaginal application of siRNAs targeting both a viral and host gene. Cell Host Microbe. 2009. 5: 84-94.

110. Sarrio D, Franklin C K, Mackay A, Reis-Filho J S, Isacke C M. Epithelial and mesenchymal subpopulations within normal basal breast cell lines exhibit distinct stem cell/progenitor properties. Stem Cells. 2012. 30: 292-303.

111. Polyak K, Weinberg R A. Transitions between epithelial and mesenchymal states: acquisition of malignant and stem cell traits. Nat Rev Cancer. 2009. 9: 265-273.

112. Biddle A, Liang X, Gammon L, Fazil B, Harper L J, Emich H, Costea D E, Mackenzie I C. Cancer Stem Cells in Squamous Cell Carcinoma Switch between Two Distinct Phenotypes That Are Preferentially Migratory or Proliferative. Cancer Res. 2011. 71: 5317-5326.

113. Scheel C, Eaton E N, Li S H-J, Chaffer C L, Reinhardt F, Kah K-J, Bell G, Guo W, Rubin J, Richardson A L, Weinberg R A. Paracrine and Autocrine Signals Induce and Maintain Mesenchymal and Stem Cell States in the Breast. Cell. 2011. 145: 926-940.

114. Dontu G, Abdallah W M, Foley J M, Jackson K W, Clarke M F, Kawamura M J, Wicha M S. In vitro propagation and transcriptional profiling of human mammary stem/progenitor cells. Genes Dev. 2003. 17:1253-1270.

115. Ponti D, Costa A, Zaffaroni N, Pratesi G, Petrangolini G, Coradini D, Pilotti S, Pierotti M A, Daidone M G. Isolation and in vitro propagation of tumorigenic breast cancer cells with stem/progenitor cell properties. Cancer Res. 2005. 65: 5506-5511.
116. Honeth G, Bendahl P O, Ringner M, Saal L H, Gruvberger-Saal S K, Lovgren K, Grabau D, Ferno M, Borg A, Hegardt C. The CD44+/CD24-phenotype is enriched in basal-like breast tumors. Breast Cancer Res. 2008. 10: R53.
117. Giatromanolaki A, Sividris E, Fiska A, Koukourakis M I. The CD44+/CD24-phenotype relates to 'triplenegative' state and unfavorable prognosis in breast cancer patients. Med Oncol. 2010.
118. Park S Y, Lee H E, Li H, Shipitsin M, Gelman R, Polyak K. Heterogeneity for stem cell-related markers according to tumor subtype and histologic stage in breast cancer. Clin Cancer Res. 2010. 16: 876-887.
119. Leth-Larsen R, Terp M G, Christensen A G, Elias D, Kuhlwein T, Jensen O N, Petersen O W, Ditzel H J. Functional heterogeneity within the CD44 high human breast cancer stem cell-like compartment reveals a gene signature predictive of distant metastasis. Mol Med. 2012. 18: 1109-1121.
120. Ginestier C, Wicha M S. Mammary stem cell number as a determinate of breast cancer risk. Breast Cancer Res. 2007. 9: 109.
121. Ricardo S, Vieira A F, Gerhard R, Leitao D, Pinto R, Cameselle-Teijeiro J F, Milanezi F, Schmitt F, Paredes J. Breast cancer stem cell markers CD44, CD24 and ALDH1: expression distribution within intrinsic molecular subtype. J Clin Pathol. 2011. 64: 937-946.
122. Yu F, Yao H, Zhu P, Zhang X, Pan Q, Gong C, Huang Y, Hu X, Su F, Lieberman J, Song E. let-7 Regulates Self Renewal and Tumorigenicity of Breast Cancer Cells. Cell. 2007. 131: 1109-1123.
123. Douville J, Beaulieu R, Balicki D. ALDH1 as a functional marker of cancer stem and progenitor cells. Stem cells and development. 2009. 18: 17-25.
124. Wright M H, Calcagno A M, Salcido C D, Carlson M D, Ambudkar S V, Varticovski L. Brca1 breast tumors contain distinct CD44+/CD24- and C D 133+ cells with cancer stem cell characteristics. Breast Cancer Res. 2008. 10: R10.
125. Seigel G M, Campbell L M, Narayan M, Gonzalez-Fernandez F. Cancer stem cell characteristics in retinoblastoma. Mol Vis. 2005. 11: 729-737.
126. Clarke R B. Isolation and characterization of human mammary stem cells. Cell Prolif. 2005. 38: 375-386.
127. Clarke R B, Anderson E, Howell A, Potten C S. Regulation of human breast epithelial stem cells. Cell Prolif. 2003. 36 Suppl 1: 45-58.
128. Clarke R B, Spence K, Anderson E, Howell A, Okano H, Potten C S. A putative human breast stem cell population is enriched for steroid receptor-positive cells. Dev Biol. 2005. 277: 443-456.
129. Kagara N, Huynh K T, Kuo C, Okano H, Sim M S, Elashoff D, Chong K, Giuliano A E, Hoon D S. Epigenetic regulation of cancer stem cell genes in triple-negative breast cancer. Am J Pathol. 2012. 181: 257-267.
130. Wang X Y, Penalva L O, Yuan H, Linnoila R I, Lu J, Okano H, Glazer R I. Musashi1 regulates breast tumor cell proliferation and is a prognostic indicator of poor survival. Mol Cancer. 2010. 9: 221.
131. Liu S. Hedgehog Signaling and Bmi-1 Regulate Self-renewal of Normal and Malignant Human Mammary Stem Cells. Cancer Res. 2006. 66: 6063-6071.
132. Polytarchou C, Iliopoulos D, Struhl K. An integrated transcriptional regulatory circuit that reinforces the breast cancer stem cell state. Proc Natl Acad Sci USA. 2012. 109: 14470-14475.
133. Pietersen A, Evers B, Prasad A, Tanger E, Cornelissensteijger P, Jonkers J, Vanlohuizen M. Bmi1 Regulates Stem Cells and Proliferation and Differentiation of Committed Cells in Mammary Epithelium. Curr Biol. 2008. 18: 1094-1099.
134. Hoenerhoff M J, Chu I, Barkan D, Liu Z-y, Datta S, Dimri G P, Green J E. BMI1 cooperates with H-RAS to induce an aggressive breast cancer phenotype with brain metastases. Oncogene. 2009. 28: 3022-3032.

Example 4

RNA interference (RNAi) offers the exciting opportunity to treat disease by knocking down disease-causing genes. Recent early phase clinical trials have shown promising and sustained gene knockdown and/or clinical benefit in a handful of diseases caused by aberrant gene expression in the liver. The major obstacle to harnessing RNAi for cancer treatment is delivery of small RNAs to disseminated cancer cells. Most epithelial cancer cells and the tumor-initiating cells (T-IC) within them highly express EpCAM, the first described tumor antigen. All epithelial breast cancer cell lines we tested stain brightly for EpCAM, while immortalized normal breast epithelial cells and fibroblasts do not. Targeted gene knockdown in epithelial cancer cells in vitro can be achieved using chimeric RNAs composed of a structured RNA, called an aptamer, selected for high affinity binding to EpCAM, that is covalently linked to an siRNA. These EpCAM aptamer-siRNA chimeras (AsiC) are taken up by EpCAM+ cells and selectively cause gene knockdown in epithelial breast cancer cells, but not normal epithelial cells. Moreover knockdown of PLK1 with EpCAM-AsiCs suppresses colony and mammosphere formation of epithelial breast cancer lines, in vitro assays of tumor-initiating potential, and tumor initiation.

Subcutaneously injected PLK1 EpCAM-AsiCs are taken up specifically by EpCAM+ basal-A triple negative breast cancer (TNBC) orthotopic xenografts and cause rapid tumor regression. TNBC has the worst prognosis of any breast cancer and there is no targeted therapy for it. It is specifically contemplated herei that EpCAM-AsiCs can be used for targeted gene knockdown to treat epithelial (basal-like) TNBC cancers, sparing normal cells, and eliminate the T-ICs within them. It can be defined which breast cancer subtypes can be targeted by EpCAM-AsiCs and determine how EpCAM level affects uptake and gene silencing. Relative uptake/knockdown in cancer cells expressing EpCAM and normal epithelium can be evaluated in human breast cancer tissue explants. It can also be determined whether EpCAM-AsiCs can target breast T-ICs to disrupt tumor initiation.

The drug-like features of EpCAM-AsiCs can be optimized. EpCAM-AsiCs can be optimized for cell uptake, endosomal release, systemic delivery and in vivo gene knockdown. Pharmacokinetics (PK) and pharmacodynamics (PD) of EpCAM-AsiC uptake and gene silencing and tumor suppression can be evaluated using live animal imaging in TNBC cell line xenograft models. As proof of principle, the antitumor effect of knockdown of PLK1, which is needed for cell proliferation can be evaluated. In addition knockdown of novel gene targets identified in a genome-wide siRNA screen for TNBC genetic dependencies will be evaluated in mouse xenograft models. An optimized EpCAM-AsiC and knowledge of its PK, PD and possible toxicity, can be used in experiments for further toxicity and other preclinical studies.

Described herein is the development of EpCAM aptamer-siRNA chimeras as a method for targeted gene knockdown in basal-like triple negative breast cancer and other epithelial cancers and the tumor-initiating cells within them. There is currently no targeted therapy for triple negative breast cancers, which frequently relapse, or for highly malignant tumor-initiating cell subpopulations within breast cancers, which may be responsible for some cases of drug resistance and relapse. These RNAs provide a versatile and flexible platform for RNA-based drugs to treat poor prognosis breast cancers.

Example 5

Figure 18A:
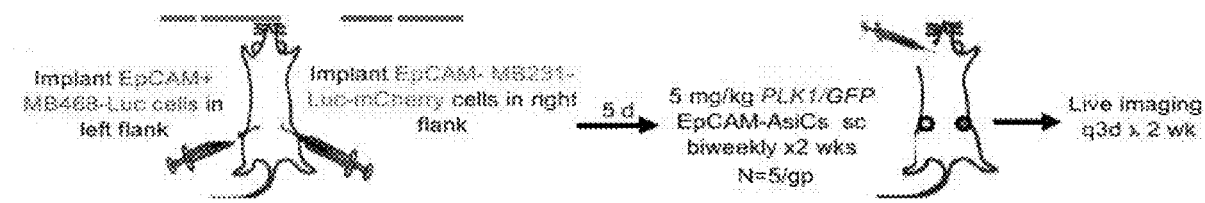
FIG. 18A-18B demonstrate that PLK1 EpCAM-AsiCs caused complete tumor regression of EpCAM+ TNBC xenografts, but had no effect on EpCAM− basal-B xenografts.
Figure 18B:
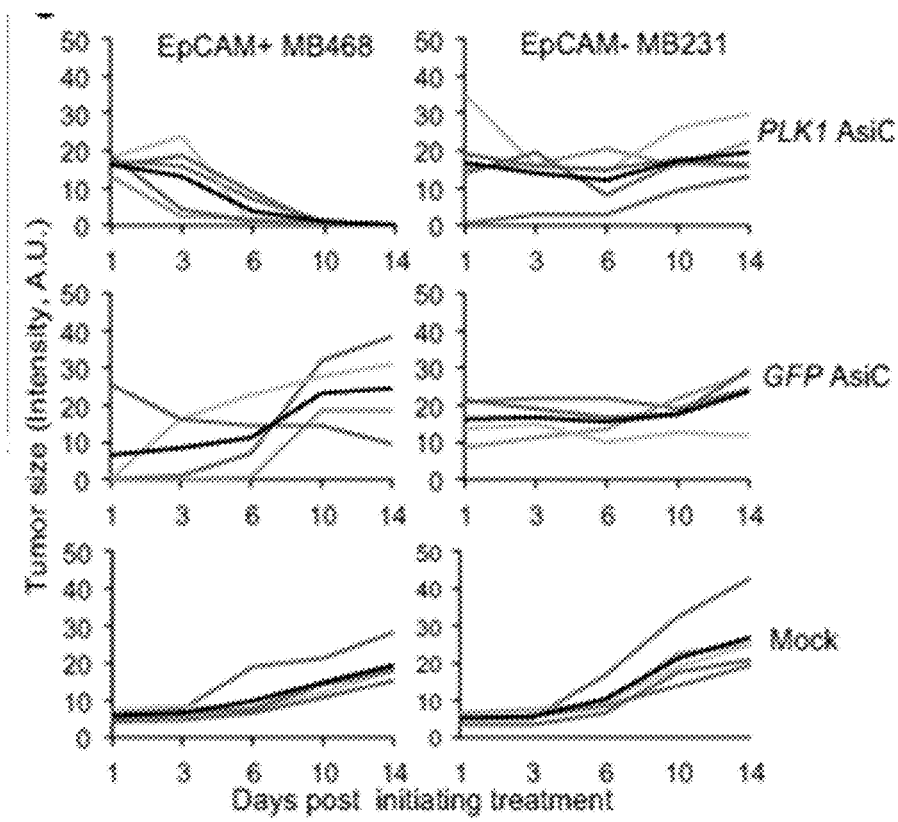
Figure 19A:
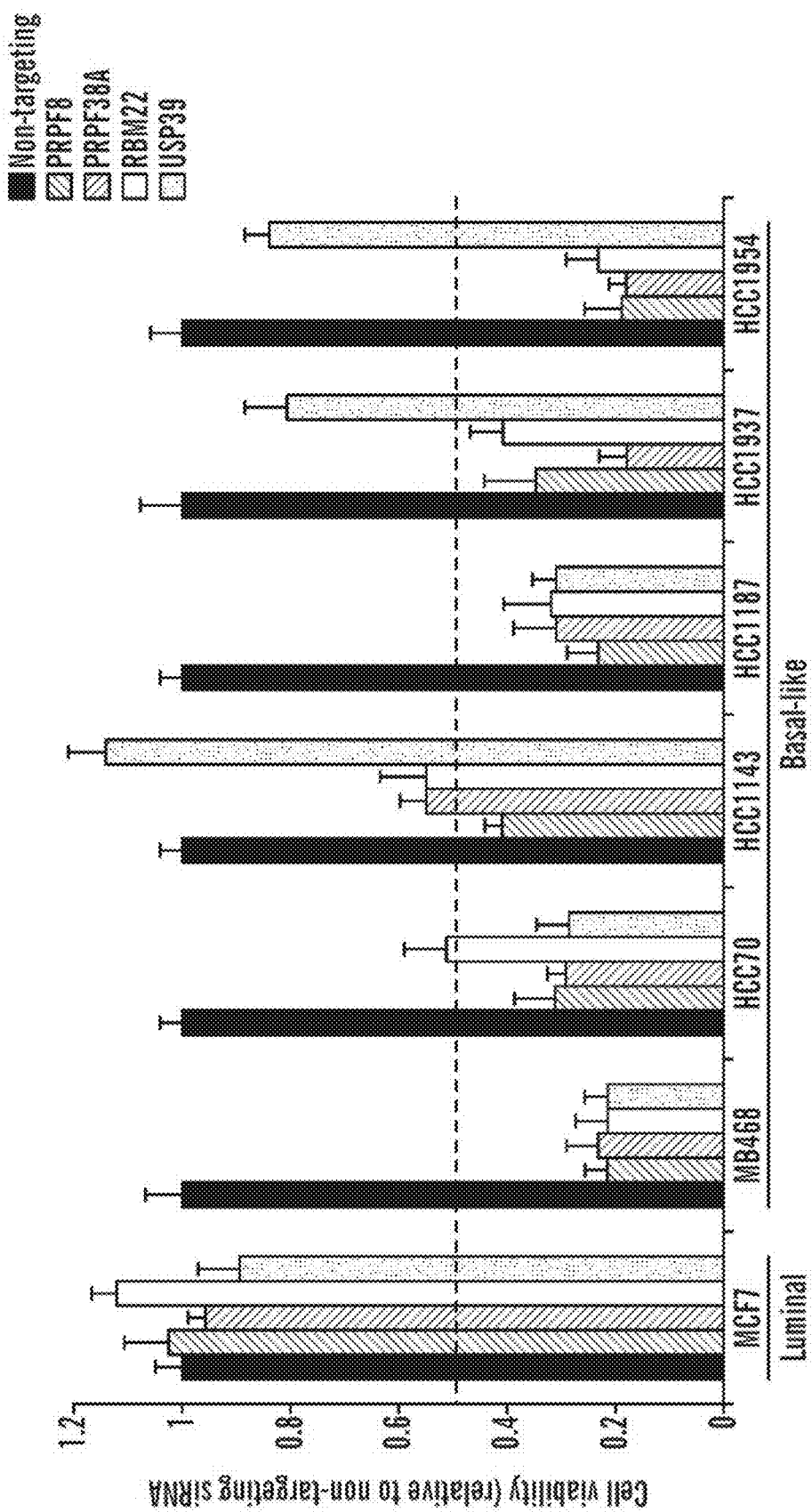
FIGS. 19A-19C demonstrate that basal dependency genes include 4 tri-snRNP spliceosome complex genes (PFPF8, PRPF38A, RBM22, USP39), 2 nuclear export genes (NUP205, RAN), and a kinetochore gene (NDC80).
Figure 19B:
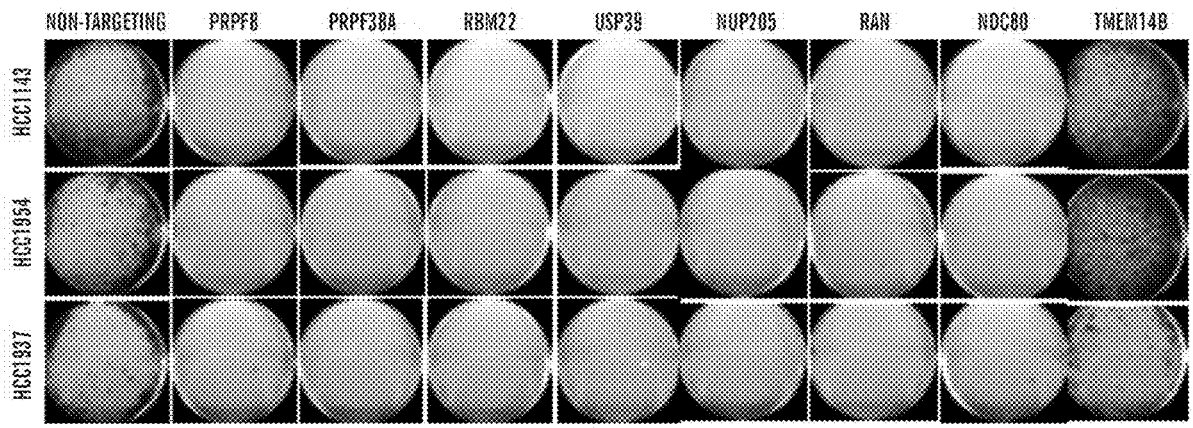
Figure 19C:
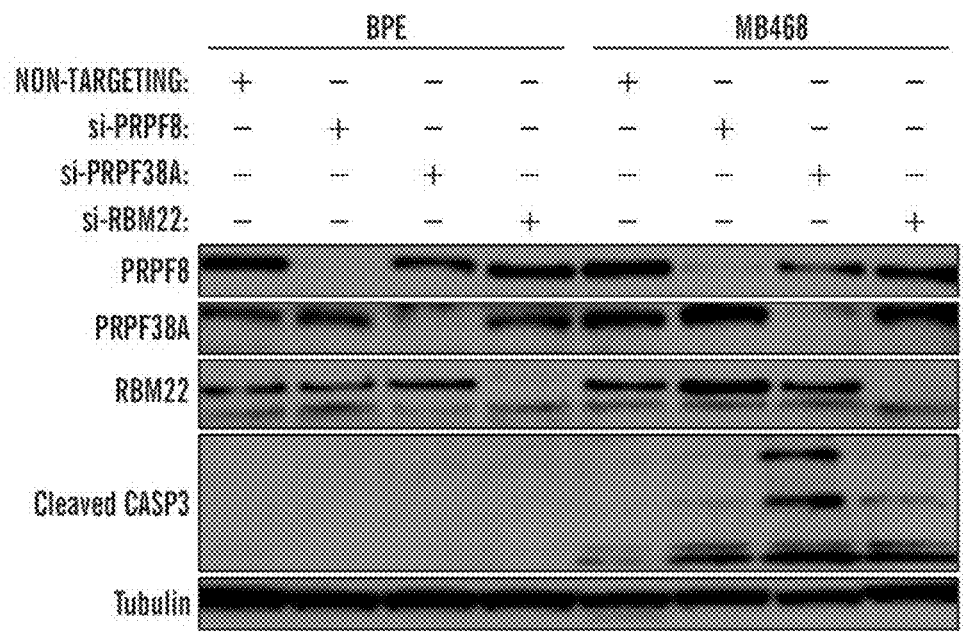

It is demonstrated herein that (1) the EpCAM aptamer on its own does not affect cell growth or viability of EpCAM+ breast tumor cell lines (not shown); (2) when normal breast biopsies are mixed with EpCAM+ TNBC human breast tumor tissues in vitro, fluorescent EpCAM-AsiCs only concentrate in the tumor (FIG. 14); (3) treatment of EpCAM+ luminal and basal-A TNBC cells, but not mesenchymal TNBCs, with PLK1 EpCAM-AsiCs blocks in vitro assays of tumor-initiating cells (T-IC, colony and mammosphere formation) and in vivo tumor initiation (FIGS. 15A-15C and 16); (4) subcutaneously (sc) injected EpCAM– AsiCs concentrate in EpCAM+ tumors in mice bearing EpCAM+ and EpCAM– TNBCs on either flank, distantly located from the injection site (FIG. 17A-18B); and (5) most importantly, sc injection of PLK1 EpCAM-AsiCs leads to complete regression of palpable basal-A TNBC xenografts (FIG. 18A-18B). In addition (6) a new siRNA screen identified novel shared genetic dependencies of basal-A TNBCs for EpCAM-AsiC knockdown (FIG. 19).

Without wishing to be bound by theory, T-ICs are heterogeneous and plastic in epithelial/mesenchymal gene expression. Although mesenchymal traits may facilitate initial tissue invasion, formation of clinically significant metastases (colonization) may require epithelial properties. EpCAM-mediated delivery of siRNA effectively blocks tumor initiation, but only for epithelial (basal-A TNBC, luminal) breast cancers.

The high affinity of the EpCAM aptamer and our uptake, gene knockdown, and proliferation experiments in uniform and mixed populations of cells show specific targeting to EpCAM+ cells. Normal epithelial cells and fibroblasts are not targeted. New data showing that EpCAM-AsiCs are not taken up by normal human breast biopsies are compelling.

Triple negative breast cancer (TNBC), a diverse group of highly malignant cancers that don't express the estrogen, progesterone and Her2 receptors, has the worst breast cancer prognosis. There is no targeted therapy for TNBCs, which often relapse after cytotoxic therapy. Described herein is a platform for gene knockdown therapeutics for basal-like TNBC, using specifically targeted RNA interference (RNAi). RNAi can selectively knockdown disease-causing genes. Realizing the therapeutic potential of gene knockdown for treating cancer, however, requires a robust method to deliver RNAs into disseminated cancer cells. There are 2 bottlenecks—getting RNAs across the cell membrane and from endosomes to the target cell cytoplasm where the RNAi machinery sits. An ideal=therapy would selectively knockdown genes in cancer cells, while sparing most normal cells to minimize toxicity.

Described herein is the knockdown of genes in basal-like TNBCs (the majority of TNBCs) with chimeric RNAs that use an aptamer (a structured nucleic acid selected for high affinity binding to a target molecule against EpCAM (also known as CD326 or ESA)" +, the first described tumor antigen. EpCAM is highly expressed on epithelial breast cancers (including basal-like TNBC)—on average 400-fold more than on normal breast tissue. It is also highly expressed on other epithelial cancers and is a marker of "cancer stem cells" (also called tumor-initiating cells (T-IC)). Aptamer-siRNA chimeras (AsiC) covalently link a targeting aptamer to an siRNA (FIG. 10B). Dicer cleaves the siRNA from the aptamer inside cells.

Epithelial breast cancer cells, but not mesenchymal or normal epithelial cells, selectively take up EpCAM-AsiCs and undergo gene knockdown in vitro. Moreover, knockdown strongly correlates with EpCAM levels. Knockdown of PLK1, a gene needed for mitosis, using EpCAM-AsiCs eliminates colony and mammosphere formation (in vitro assays that correlate with self renewal and tumor initiation) and tumor initiation in vivo, suggesting that EpCAM-AsiCs might be used to target T-ICs. Sc injection of PLK1 EpCAM-AsiCs caused complete regression of EpCAM+ TNBC xenografts, but had no effect on EpCAM– mesenchymal TNBCs.

It is described herein that EpCAM-AsiCs can be used for targeted gene knockdown to treat basallike TNBC cancers, sparing normal cells, and eliminate the T-ICs within them. Aside from their selective delivery to target cells, AsiCs have important advantages for cancer treatment compared to RNA delivery by nanoparticles, liposomes or RNA-binding proteins—(1) they bypass liver and lung trapping and concentrate in tumors; (2) as a single RNA molecule they are simpler and cheaper to manufacture than multicomponent drugs; (3) they have virtually no toxicity and do not stimulate innate immunity or inflammation or cause significant off-target effects; (4) because they do not elicit antibodies, they can be used repeatedly; (5) they are stable in serum and other body fluids.

It can be defined which breast cancer subtypes can be targeted by EpCAM-AsiCs and determine how EpCAM level affects uptake and gene silencing. The relative uptake/knockdown in cancer tissues vs normal epithelium can be evaluated. It can also be determined whether EpCAM-AsiCs can target breast T-ICs to inhibit tumor initiation. An important aim is to optimize EpCAM-AsiCs for uptake, endosomal release, systemic delivery and in vivo knockdown. Pharmacokinetics (PK) and pharmacodynamics (PD) of EpCAM-AsiC uptake, gene silencing and tumor suppression will be evaluated by live animal imaging in TNBC orthotopic xenografts. As proof of principle, the antitumor effect of knockdown of PLK1, which is needed for cell proliferation can be evaluated. Knockdown of other genes we identified in a genome-wide RNAi screen as genetic dependencies of basal-like TNBC can be evaluated. Described herein is the development of optimized EpCAM-AsiC and knowledge of its PK, PD and possible toxicity and identification of novel basallike TNBC dependency genes to target Described herein is: the verification of selective EpCAM-AsiC activity in epithelial breast cancers compared with normal epithelia and evaluate the potential of EpCAM-AsiCs to transfect and eliminate breast T-ICs (i.e., cancer stem cells); optimization of EpCAM-AsiCs to transfect and knockdown genes in epithelial TNBC cells in vitro and for systemic delivery and tumor concentration in vivo, and define PK and PD and maximally tolerated dose; evaluation of the antitumor effect of optimized EpCAM-AsiCs targeting PLK1 and novel dependency genes of basal-like TNBC in human epithelial TNBC models of primary and metastatic cancer in mice Although most TNBC patients respond to chemotherapy, within 3 yr about a third develop metastases and eventually die. Thus we need new approaches. TNBCs are heterogeneous, poorly differentiated tumors that may need to be treated by subtype or with individualized therapy. 1,3,4,72 Most TNBCs are basal-like or belong to the basal-A subtype. Described herein is a flexible, targeted platform for treating basal-like TNBCs that is suitable for personalized therapy. Not only will the drug be targeted to the tumor, but the drug targets can also be chosen to attack the tumor's Achilles' heels by knocking down tumor dependency genes. This present approach delivers small interfering RNAs (siRNA) into epithelial cancer cells by linking them to an RNA aptamer that binds to EpCAM (FIG. 10B), a cell surface receptor over-expressed on epithelial cancers, including basal-like TNBCs. EpCAM is highly expressed on epithelial cancers and their T-Ics.

EpCAM targeting can cause selective gene knockdown in basal-like TNBCs, but not normal epithelia. Selective knockdown will both reduce the drug dose and reduce tissue toxicity.

As described herein, 9 of 9 basal-A TNBC and luminal breast cancer lines were strongly EpCAM+, while a normal breast epithelial cell line, fibroblasts and mesenchymal TNBCs had close to background EpCAM (FIG. 1B). Thus virtually all basal-like TNBCs (and probably luminal breast cancers) will be targeted by EpCAM-AsiCs. Moreover, since ~100% of epithelial cancers, including lung, colon, pancreas and prostate, stain brightly for EpCAM, this platform could also be used for RNAi-based therapy of common cancers.

When RNAi was found in mammals, small RNAs were hailed as the next new drug class. Soon investigators realized that getting RNAi to work as a drug was not simple., However, after addressing the main obstacle to RNA therapy (cellular uptake), there is now optimism about RNAi-based drugs. Recent phase I/II studies have shown 80-95% gene knockdown in hypercholesterolemia, transthyretin-related amyloidosis, hepatitis C, hemophilia and liver metastasis, caused by aberrant liver gene expression. However, applying RNAi for cancer therapy is still a dream. The major obstacle to harnessing RNAi for cancer is delivering small RNAs into disseminated cells. Described herein are methods and compositions that overcome this problem, e.g., by the use of AsiCs.

AsiCs are a flexible platform that can target different cell surface receptors and knockdown any gene or combination of genes. By changing the aptamer, the AsiC platform can tackle the delivery roadblock that has thwarted the application of RNAi-based therapy to most diseases. This approach is ideal for personalized cancer therapy, since the choice of genes to target can be adjusted depending on a tumor's molecular characteristics. Moreover RNA cocktails can knockdown multiple genes at once to anticipate and overcome drug resistance.

Described herein is the development of an optimized EpCAM-AsiC with well defined PK/PD.

An important cancer research goal is to eliminate T-ICs (cancer stem cells). T-ICs are relatively resistant to chemotherapy and are thought responsible for tumor relapse and metastasis The AsiCs described herein are designed to target (epithelial) T-ICs with high efficiency. As such they can eliminate this aggressive subpopulation within tumors at risk for progressive disease (see FIG. 16).

In addition to their potential therapeutic use, EpCAM-AsiCs can also be a powerful in vivo research tool for identifying the dependency genes of tumors and T-ICs to define novel drug targets.

Described herein is a novel targeted therapy for epithelial cancers, and the T-ICs within them by targeting EpCAM, a tumor antigen widely over-expressed in epithelial cancers and their T-ICs. Targeted therapy so far has relied on using tumor-specific antibodies or inhibitors to oncogenic kinases. No one before has shown that an unconjugated AsiC can have potent antitumor effects or that AsiCs could be administered sc. There is currently no targeted therapy for TNBC or for T-ICs. Developing targeted therapy for TNBC and developing ways of eliminating T-ICs are important unmet goals of cancer research.

The methods described herein are targeted in 2 ways—the aptamer specifically delivers the therapeutic RNA to tumor cells, while the genes chosen for knockdown can be selected based on the specific molecular dependencies of the targeted tumor. By testing in vivo knockdown, it can be demonstrated that basal-like TNBCs and their T-ICs are selectively dependent on the proteasome, MCL1 and the U4/U6-U5 tri-snRNP splicing complex. This work can identify a new set of drug targets, suitable for both conventional and RNAi-based drugs.

The trafficking of siRNAs in transfected cells can be examined and each step of RNA processing in cells be systematically optimized to improve the drug features of an siRNA.

CD4-AsiCs durably knockdown gene expression in CD4+T lymphocytes and macrophages and inhibit HIV transmission to humanized mice. CD4-AsiCs specifically suppressed gene expression in CD4+ T cells and macrophages in polarized human cervicovaginal tissue explants and in the female genital tract of humanized mice. Because they are monomeric and don't cross-link the receptor, CD4-AsiCs did not activate the targeted cells. They also did not stimulate innate immunity. Intravaginal application of only 80 pmol of CD4-AsiCs directed against HIV genes and/or CCR5 to humanized mice completely blocked HIV sexual transmission. RNAi-mediated gene knockdown in vivo lasted several weeks. Transmission was blocked by CCR5 CD4-AsiCs applied 2 d before challenge. Significant, but incomplete, protection also occurred when exposure was delayed for 4 or 6 d. CD4-AsiCs targeting gag/vif provided protection when administered post-exposure. Thus CD4-AsiCs are promising for use in an HIV microbicide.

Protection against HIV transmission requires local knockdown in the genital tract. However, systemic delivery is more challenging and is needed for cancer. Because AsiCs are small enough to be filtered by the kidney, they are rapidly eliminated and do not efficiently cause gene silencing. In some embodiments, polyethylene glycol (PEG) can be attached to the 5'-end of the inactive (passenger) strand of the siRNA. .iv injected PEG-AsiCs concentrated in sc tumors. PEGylation extended the circulating T1/2 of ip injected AsiC from <35 min to >>30 hr, increased the durability of gene silencing to ~5 d and reduced the needed dose 8-fold. sc injection of unmodified CD4-AsiCs caused ~80% gene knockdown specifically in CD4+ cells in the spleen, proximal and distal lymph nodes of humanized mice (not shown). Sc injection of EpCAM-AsiCs similarly led to specific concentration/knockdown in EpCAM+ tumors (see below).

EpCAM-AsiCs selectively knockdown gene expression in EpCAM+ cancer cells The EpCAM-AsiCs have a ~42-44 nt long strand (19 nt aptamer+linker+20-22 nt siRNA strand)

annealed to a 20-22 nt complementary siRNA strand (FIG. 10B). Commercially synthesized with 2'-fluoropyrimidines, they are RNase resistant (T1/2>3 d in serum, data not shown) and do not trigger innate immunity. 37,91-93

Figure 13A:
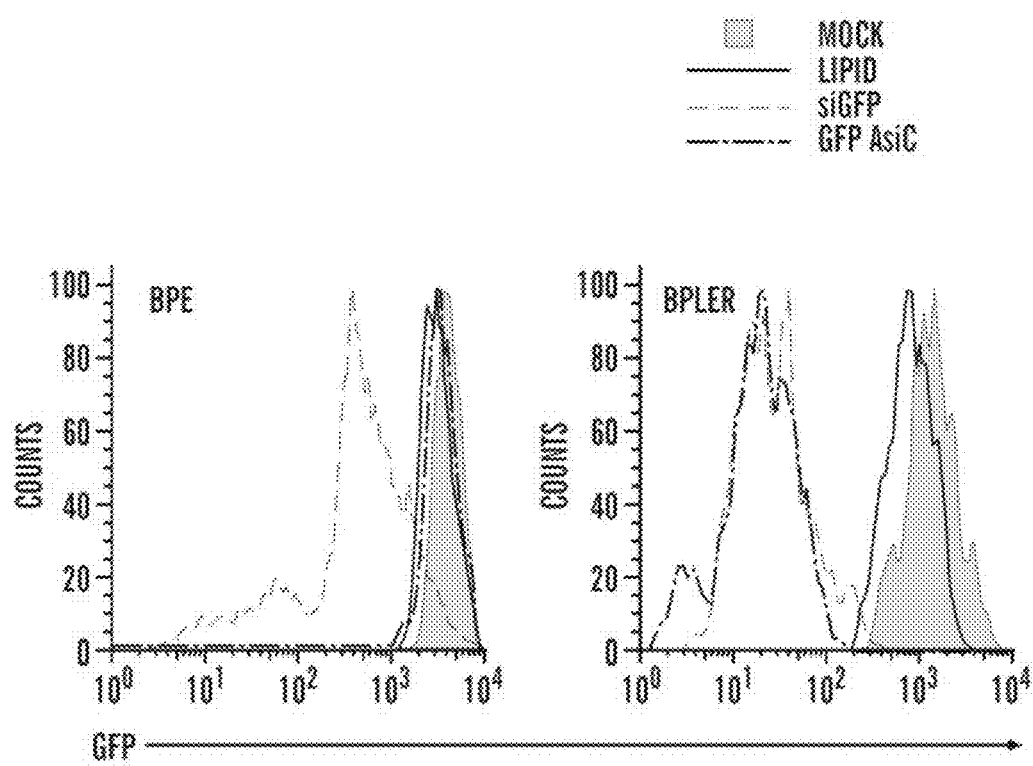
FIGS. 13A-13C EpCAM-AsiCs knockdown GFP protein (FIG. 13A) and AKT1 mRNA (FIGS. 13B-13C) only in EpCAM+ cell lines, but not in immortalized breast epithelial cell line (BPE) or mesenchymal basal B TNBC or human fibroblasts. A transfected siRNA is nonspecific in its knockdown. *, P<0.05
Figure 13B:
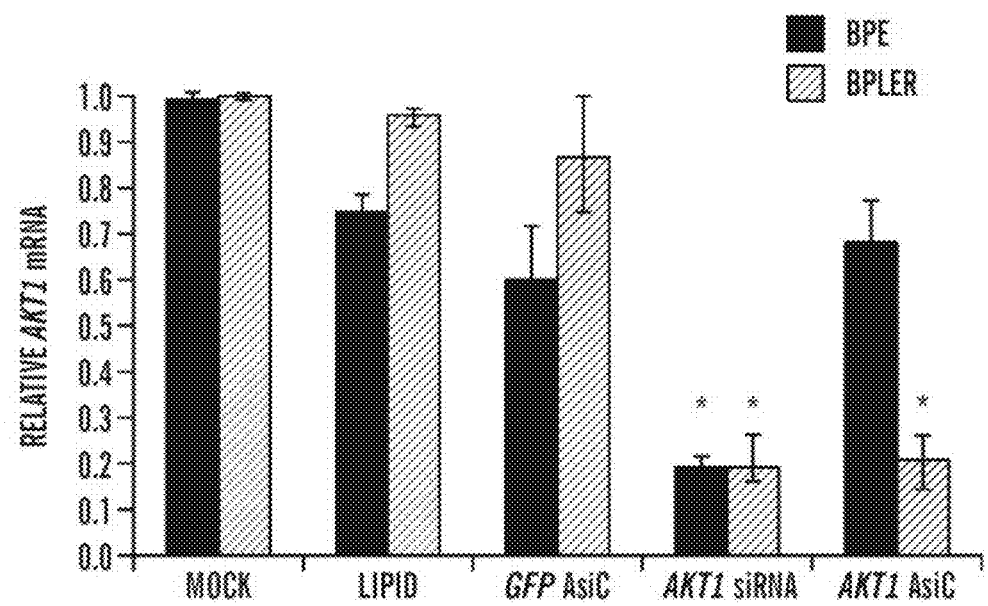
Figure 13C:
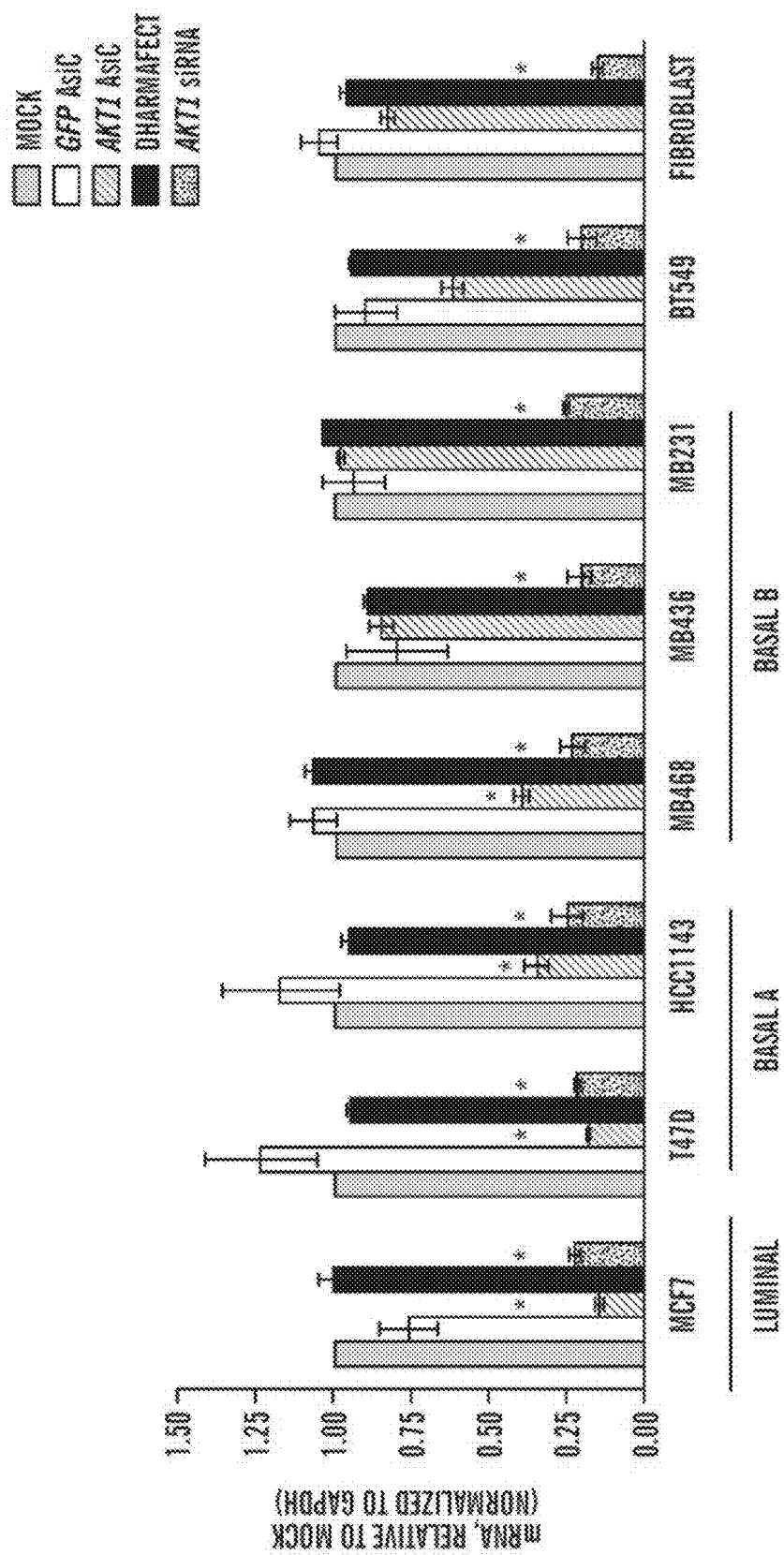

Surface EpCAM was high in all luminal and basal-like cell lines tested, but close to background in normal epithelia immortalized with hTERT (BPE) 94, fibroblasts and mesenchymal TNBCs (FIG. 1B). Several of a handful of designs tested (with the sense and antisense strands exchanged and several linkers) knocked down gene expression specifically in EpCAM+ cell lines, but the most effective design is shown in FIG. 10B. Gene knockdown of eGFP and AKT1 by EpCAM-AsiCs was uniform and selective for EpCAM+ cells and as effective as siRNA lipid transfection, which was not selective (FIG. 13A-13C). In 8 breast cancer cell lines, AKT1 knockdown and inhibition of cell proliferation by PLK1 EpCAM-AsiCs strongly correlated with EpCAM levels (FIG. 11B-11C). The EpCAM aptamer on its own had no effect on cell proliferation (not shown). When EpCAM–BPE cells were mixed with epithelial TNBC cell lines, EpCAM-AsiCs knocked down AKT1 and caused PLK1-sensitive cell death only in tumor cells, sparing the normal epithelial cells (not shown). The proportion of surviving tumor cells decreased 7-fold after 3 d. When we added fluorescent AsiCs, cholesterol-conjugated siRNAs (chol-siRNA, taken up by normal epithelia) or naked siRNAs to normal breast and tumor biopsy samples, EpCAM-AsiCs concentrated only in the tumors (FIG. 14). Thus EpCAM-AsiCs are specific for epithelial tumor cells.

Figure 15A:
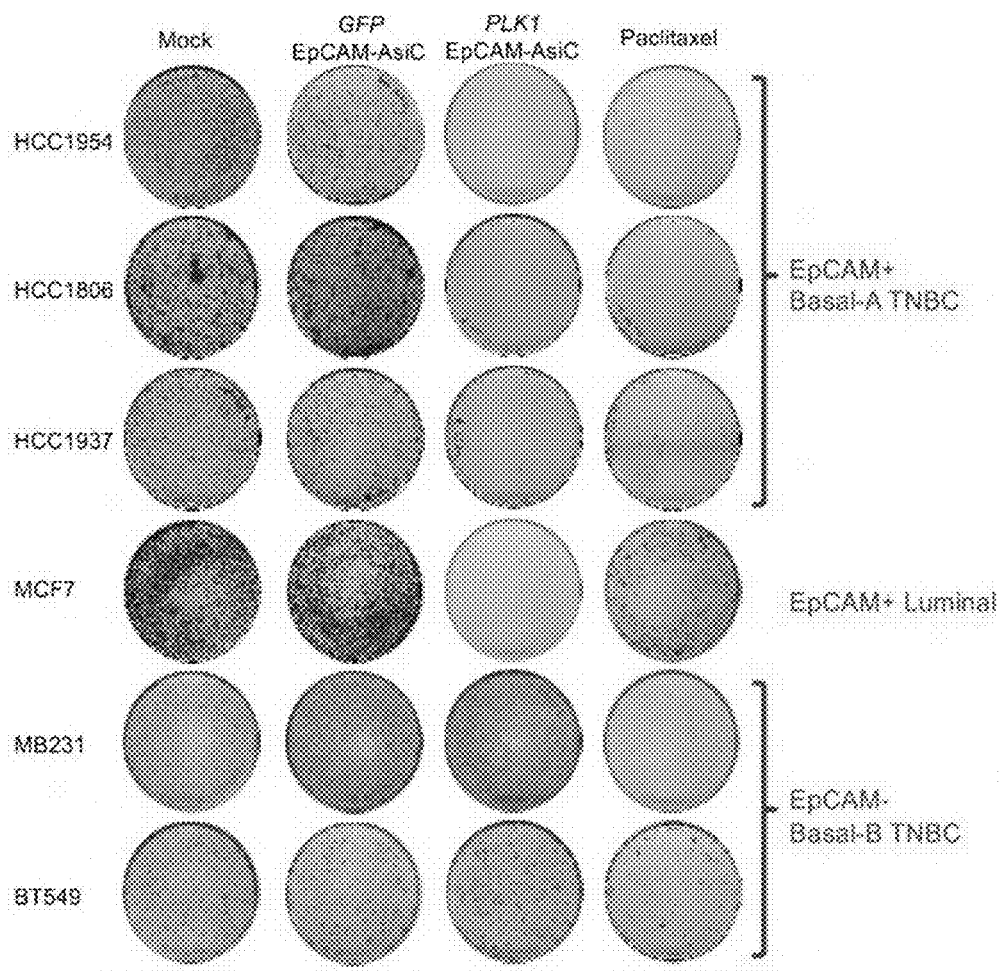
FIGS. 15A-15C. Treatment of EpCAM+, but with not EpCAM−, breast cancer lines with PLK1 EpCAM-AsiCs inhibits colony (FIGS. 15A, 15B) and mammosphere (FIG. 15C) function, in vitro assays of T-IC function.
Figure 15B:
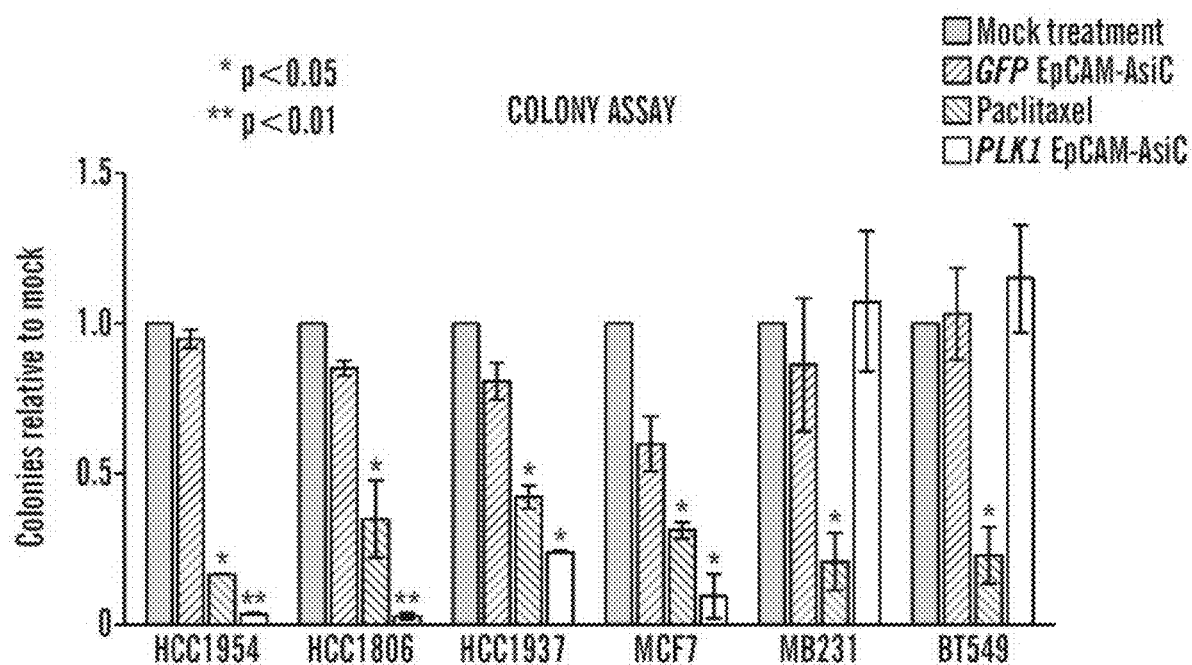
Figure 15C:
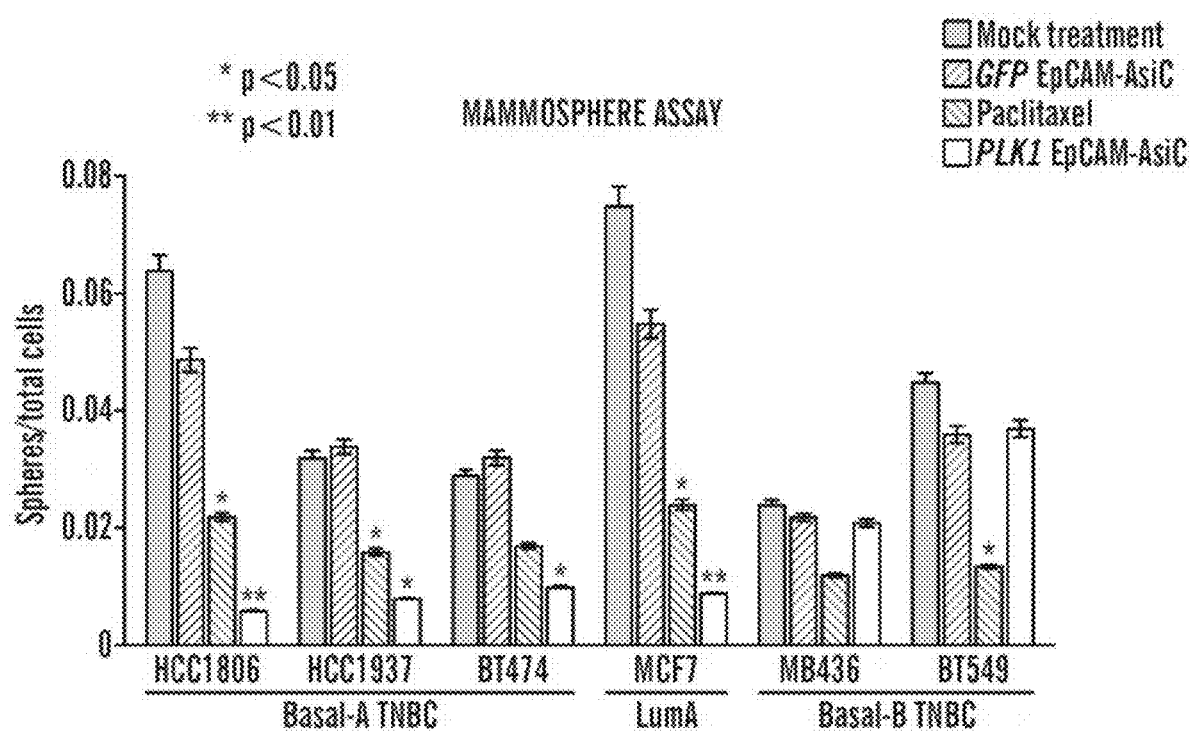
Figure 16:
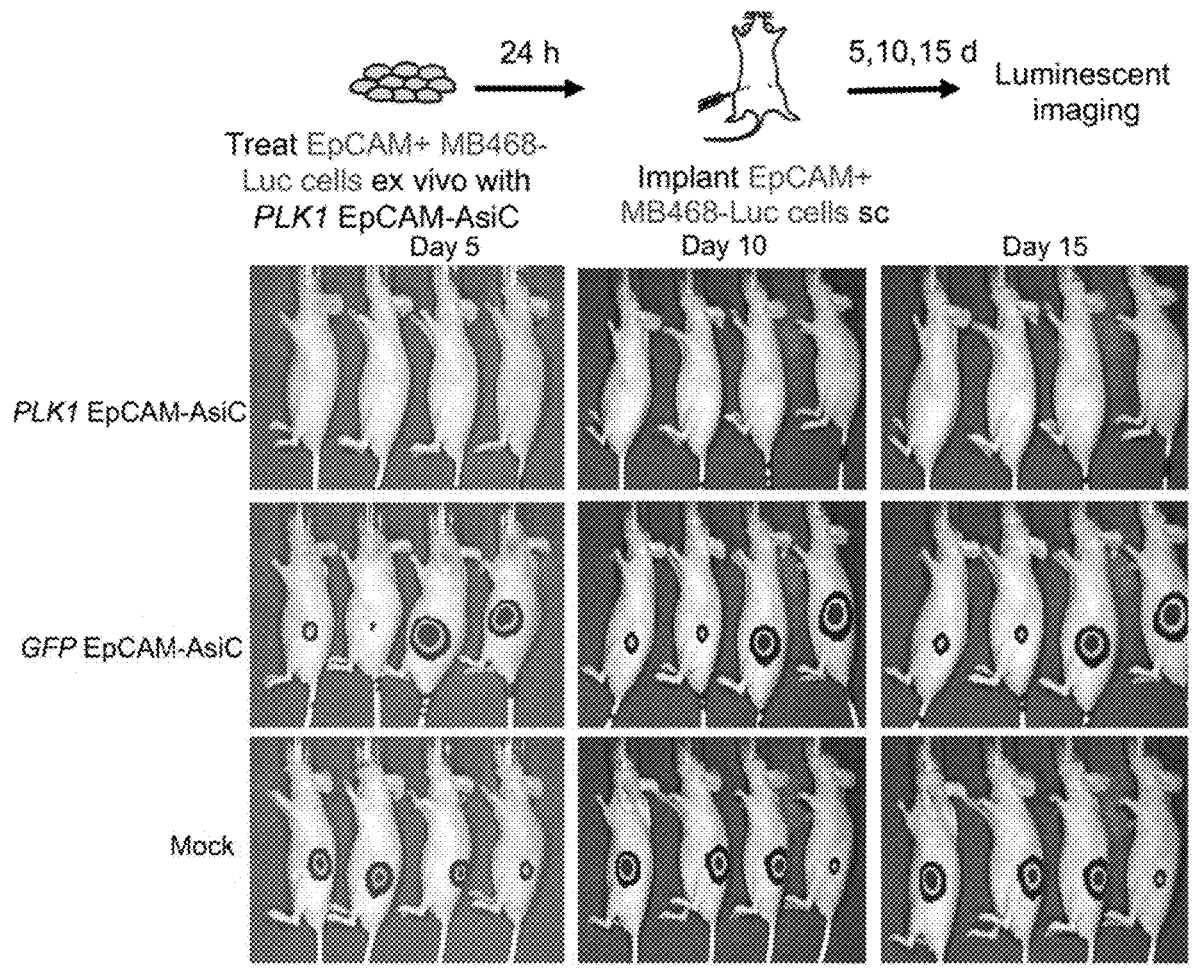
FIG. 16 demonstrates that ex vivo treatment of MB468 cells with PLK1 EpCAM-AsiCs eliminated their ability to form tumors in nude mice. An equal number of viable cells were implanted the day after treatment.

EpCAM-AsiCs inhibit T-ICs of EpCAM+ tumors. EpCAM was chosen for targeting partly because EpCAM marks T-ICs and metastasis-initiating cells (M-IC). To investigate whether EpCAM-AsiCs inhibit T-ICs, we compared colony and mammosphere formation (T-IC functional surrogates) after mock treatment, treatment with paclitaxel or with EpCAM-AsiCs against eGFP or PLK1. PLK1 EpCAM-AsiCs more strongly inhibited colony and mammosphere formation of multiple EpCAM+ basal-like TNBCs and a luminal cell line than paclitaxel, but was inactive against EpCAM– basal-B TNBCs (FIG. 15A-15C). To evaluate EpCAM-AsiC's effect on tumor initiation, viable luc+ EpCAM+ MB468 and EpCAM– MB231 cells, treated overnight with medium or PLK1 or GFP EpCAM-AsiCs, were implanted sc in nude mice. PLK1 EpCAM-AsiCs blocked tumor formation, but only in EpCAM+ tumors (FIG. 16 and data not shown). Thus EpCAM-AsiCs inhibit tumor initiation in EpCAM+ breast cancers.

Figure 17A:
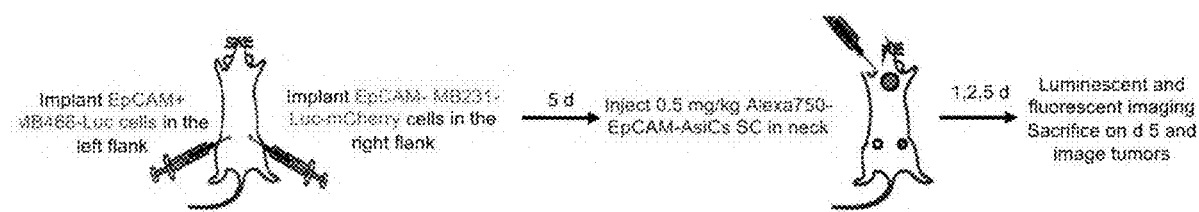
FIGS. 17A-17B demonstrate that EpCAM-AsiCs are selectively taken up into EpCAM+, but not EpCAM−, TNBC tumors.
Figure 17B:
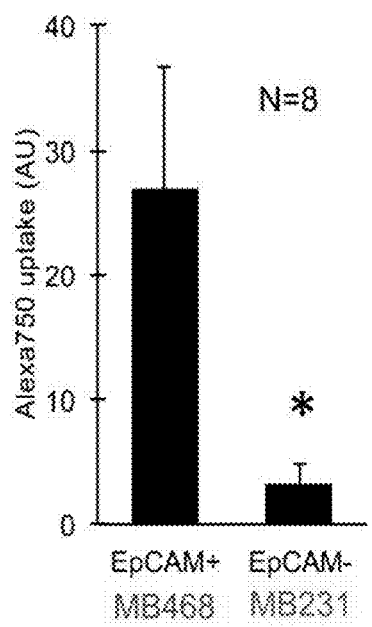

EpCAM-AsiCs are selectively taken up by EpCAM+ TNBCs and cause tumor regression To investigate the potential clinical usefulness of EpCAM-AsiCs, we first examined delivery of Alexa750-labeled EpCAM-AsiCs injected sc in the scruff of the neck of mice bearing EpCAM+ and EpCAM– TNBCs in each flank (FIG. 17A-17B). EpCAM-AsiCs concentrated only in the EpCAM+ tumor. Mice bearing bilateral tumors were mock treated or injected biweekly with PLK1 or GFP EpCAM-AsiCs and tumor growth was followed by luminescence. The EpCAM+ tumors rapidly completely regressed only in mice that received the PLK1-targeting AsiCs (FIG. 18A-18B). This experiment was repeated with additional control groups, the EpCAM aptamer on its own or PLK1 siRNA, neither of which had any anti-tumor activity (data not shown). Thus sc injected EpCAM-AsiCs show specific antitumor activity against basal-A TNBCs.

Live cell imaging of siRNA uptake, endosomal release and gene silencing An optimized spinning disk confocal microscope capable of single molecule detection was used to detect the weak cytosolic signal of released fluorescent RNAs, which was not before possible. HeLa cells incubated with Alexa647-siRNA lipoplexes were imaged every 3 s. RNA-containing late endosomes released a small fraction of their cargo RNA, which diffused rapidly to fill the cytosol (data not shown). Release occurred during a narrow time frame, ~15-20 min after endocytosis. ~104 siRNAs were released in a typical event. In HeLa cells, stably expressing eGFP-dl, GFP siRNAs caused GFP expression to decrease rapidly after endosomal release with a T1/2 of ~2.5 h. Only ~1000 cytosolic siRNAs were needed for efficient gene silencing. Release triggered autophagy, which sequestered the RNA-containing endosome within a double autophagic membrane. No release occurred after that.

We applied this method to study uptake/release of Cy3-labeled EpCAM-AsiCs, comparing EpCAM+ MB468 TNBCs with EpCAM– BPE cells. Uptake and release were negligible in BPE, but clear cut in MB468. This imaging method and our understanding of siRNA trafficking can be used to optimize EpCAM-AsiC design to improve endosomal release and knockdown.

Identification of basal-like TNBC dependency genes (BDGs). To identify genetic dependencies of basal-like TNBCs that EpCAM-AsiCs could target, a genomewide siRNA lethality screen was performed comparing basal-like BPLER and myoepithelial HMLER cells, human primary breast epithelial cells transformed with the same oncogenes in different media. Although essentially isogenic, BPLER are highly malignant and enriched for T-ICs, forming tumors in nude mice with only 50 cells, while HMLER require >105 cells to initiate tumors. The screen identified 154 genes on which BPLER, but not HMLER, depended. Proteasome genes were highly enriched (P<10-14). Expression of BPLER dependency genes correlated with poor prognosis in breast, but not lung or colon, cancer. Proteasome inhibitor sensitivity was a shared feature of basal-A TNBCs and correlated with MCL1 dependency. Normal breast epithelial cells, luminal breast cancer lines and mesenchymal TNBC lines did not depend on the proteasome or MCL1. Proteasome inhibition not only killed basal-A TNBCs, it also blocked T-IC function by colony and mammosphere assays, again mostly selectively in basal-like TNBCs. Brief exposure to bortezomib also inhibited tumor initiation of a mouse basallike TNBC line.

We next tested whether proteasome inhibition inhibited the growth of basal-like TNBC tumors in mice. Bortezomib does not penetrate well into solid tumors, which has limited its clinical use. The maximum tolerated iv dose (MTD) was needed to inhibit proteasome activity in sc tumors. Treatment with the MTD strongly inhibited tumor growth of 3 human and 1 mouse basal-A TNBC cell lines and 10 TNBCs that arose spontaneously in Tp53+/– mice, but was not active against basal-B or luminal cell lines. Similar results were obtained with carfilzomib. Bortezomib also blocked lung colonization of iv-injected mouse TNBC cells. Thus the proteasome is selectively required for epithelial TNBC growth, tumor initiation and metastasis. Although tumor penetration and PD may improve with newer proteasome inhibitors, proteasome gene knockdown might provide more effective proteasome inhibition.

Because TNBCs are heterogeneous1,3,4,72, we rescreened the 154 BPLER dependency genes in 4 basal-A TNBC and 3 luminal human cancer lines. Our goal was to identify additional shared dependencies of basal-like TNBC cell lines as potential EpCAM-AsiC targets. Only 21 of the 154 BPLER dependency genes reduced viability by at least 2-fold in 3 of 4 basal-A cell lines tested. These putative BDGs clustered in 4 functional groups—4 proteasome genes and MCL1 (previously validated), 10 genes implicated in RNA splicing, 2 genes implicated in mitosis and 2 genes required for nuclear export. 20 of the 21 BDGs were retested using a new set of siRNAs and 14 genes reconfirmed (the other "hits" may have been secondary to off-target effects or their knockdown could have been insufficient to cause lethality). Of note, 9 of 10 splicing genes reconfirmed. They included 4 members of the U4/U6-U5 tri-snRNP complex, PRPF8, PFPF38A, RBM22, USP39. Other interesting shared hits were the RAN nuclear export G protein and the nucleoporin NUP205, and NDC80, a kinetochore component that anchors the kinetochore to the mitotic spindle. (USP39 is also required for the mitotic spindle checkpoint).

TNBCs are known to be particularly susceptible to antimitotic agents. USP39 is overexpressed in breast cancer cells vs normal breast tissue and USP39 knockdown inhibited proliferation and colony formation of luminal MCF7 cells. Moreover in zebrafish, USP39 mutation leads to splicing defects of tumor suppressor genes like rb1 and p21. To explore the therapeutic effect of inhibiting splicing in basal-like TNBCs, we silenced the 4 spliceosome tri-snRNP complex BDGs (PRPF8, PRPF38A, RBM22, USP39) in 6 basallike cell lines and in luminal MCF7 cells (FIG. 19). Knock down of PRPF8, PRPF38A or RBM22 activated caspase-3 and was lethal for 6 of 6 basal-like cell lines, but not for MCF7; USP39 knockdown killed 3 of 6 basal-like cell lines. Spliceosome proteins were frequently up regulated in breast cancer cell lines of all subtypes. The viability of all 6 basal-like cells lines, but not MCF7 cells, was reduced at least 2-fold by knockdown of the mitotic kinetochore gene NDC80 or of nuclear export genes RAN or NUP205. Moreover, knockdown of each of the tri-snRNP complex genes, RAN, NUP205 or NDC80 blocked colony formation (a surrogate of T-IC potential) in 3 of 3 basal-like TNBC cell lines EpCAM-AsiCs can cause targeted gene knockdown in EpCAM+ tumors and the T-ICs within them. Although there may be some uptake in normal epithelial cells that weakly express EpCAM, gene knockdown will be concentrated in EpCAMbright tumor cells, especially in T-ICs. EpCAM-AsiCs can be optimized, as described herein, for favorable PK/PD to suppress tumor growth and metastasis of basal-like TNBCs with acceptable toxicity in mouse models.

EpCAM-AsiCs targeting eGFP, AKT1 and PLK1 are used herein as models for assessing gene knockdown and optimizing AsiC design. Cell lines stably expressing destabilized (dl)EGFP, with a protein T1/2 of ~1 hr, can be generated using lentiviruses. GFP expression can be readily quantified by flow and imaging, and its knockdown has no biological consequences. The short T1/2 allows for rapid and sensitive detection of knockdown. AKT1, which is expressed in all the cells we test, is a good endogenous gene to study, since its knockdown in TNBCs doesn't affect cell viability much. PLK1 is used as proof-of-concept for its antitumor effect because its knockdown is cytotoxic to all dividing cells. We previously showed that PLK1 knockdown using a different delivery strategy dramatically suppressed Her2+ breast cancer in mice. In a recent screen, PLK1 was unique amongst kinase genes because its knockdown eliminated breast T-ICs. We have achieved robust and reproducible gene knockdown with EpCAM-AsiCs targeting each of these genes.

EpCAM-AsiCs can be be purchased, e.g., as non-GMP RNAs from TriLink or NITTO Avecia. Each strand of the EpCAM-AsiC was synthesized with 2'-fluoropyrimidines and dT residues at their 3'-ends to protect against exonuclease digestion and then annealed to generate the final RNA (FIG. 10B). As we optimize the AsiC, other chemical modifications can be substituted and tested to determine if they confer improved activity. The aptamer alone and AsiCs bearing a nontargeting siRNA can serve as controls. Some of the eGFP EpCAM-AsiCs can also be annealed to an antisense strand modified at the 3'-end with a fluorophore (which doesn't affect AsiC activity (not shown)) to quantify AsiC uptake and trafficking within cells and in vivo.

Specific EpCAM-AsiC knockdown in epithelial breast cancers and breast cancer T-ICs vs normal epithelial cells. It can be determined which breast cancer subtypes are transfected with EpCAM-AsiCs and evaluate whether tumor knockdown is specific to cancer cells, first in cell lines and then in 10 tumor tissues to verify that the results for cell lines translate to tissues in situ. Because EpCAM-AsiCs might also transfect normal tissue stem cells, knockdown and toxicity to these rare basal cells will be assessed in the tissue experiments. We can also evaluate the potential of EpCAM-AsiCs to transfect and target breast T-ICs.

Types of breast cancer responsive to EpCAM-AsiCs We first need to know which types of breast cancer can be transfected with EpCAM-AsiCs and how specific gene knockdown is in tumors relative to normal epithelial cells. We extend our prelim. studies (FIGS. 13A-13C and 11B-11C) by evaluating in vitro knockdown in a panel of 20 human breast cancer cell lines that represent the common breast cancer subtypes, but are weighted towards TNBC (14 TNBC lines, plus a sampling of luminal and Her2+ cell lines). 95 EpCAM expression, uptake of Cy3-labeled AsiC and gene silencing in tumor lines can be compared to that in BPE94 and fibroblasts. This large tumor panel will enable us to evaluate how cell surface EpCAM levels influence gene silencing and whether there is an EpCAM expression threshold for efficient knockdown. We can also verify in a dose response experiment using a few EpCAM+ cell lines that the reported high binding affinity of the EpCAM aptamer is preserved in the AsiC. Specificity of uptake (versus nonspecific "sticking") can be verified by using acid washing to remove loosely adhered aptamers and showing that binding is competed by unlabeled aptamers and eliminated when cells are trypsinized before treatment. EpCAM-AsiC-mediated transfection can be compared to lipid transfection and naked siRNAs as controls. Knockdown will be assessed by flow cytometry and qRT-PCR after 5 d, the optimal time for AsiC-mediated knockdown. We expect that uptake and gene silencing will correlate with EpCAM levels. To verify that specificity for EpCAM+ cells is maintained in mixtures of EpCAM+ and EpCAMdim untransformed breast epithelial cells, we can compare fluorescent EpCAM-AsiC uptake, gene knockdown and survival when PLK1 is the gene target in mixtures of tumor cells expressing different levels of EpCAM (MFI ranging between 100-1000) with different numbers of GFP+ BPE cells.

Do epithelial breast cancer cells preferentially take up EpCAM-AsiCs and show knockdown relative to normal epithelial cells in tissue explants? To assess primary tumor knockdown and anticipate potential toxicity to normal tissue cells, we can assess in situ transfection and gene knockdown in explants of 10 luminal, Her2+ and TNBC breast cancers and surrounding normal tissue from mastectomy specimens. Samples from ~25 tumors can be analyzed to provide a comprehensive look at tumor subtypes. Tumor typing can be confirmed by histology and IHC staining for ER, PR, Her2, E-cadherin. We can compare normal tissues that have no large competing source of EpCAM+ cells to tissues that contain tumor cells. This might be important for anticipating toxicity in situations where AsiCs are given to patients with low/undetectable tumor burden following therapy or surgery. These experiments can permit the assessment of whether knockdown by 10 tumors is comparable to that in cell lines, whether tissue architecture affects uptake/knockdown in tumor cells and how well different tumor subtypes are transfected.

Based on the data presented herein, e.g., FIG. 14, it is contemplated herein that epithelial breast cancers, but not normal epithelial cells, can undergo efficient gene knockdown. Tissues cut into ~3×3×3 mm3 samples can be transfected in Optimem solution in microtiter wells. Lipoplexed siRNA and chol-siRNAs both knockdown genes in normal columnar and squamous genital tract epithelia, while naked siRNAs are not taken up. We can first verify these controls using siRNAs to target epithelial genes, which we have previously knocked down (such as E-cadherin, claudin3, cytokeratin (CK)-5 (a good marker of basal cells), and nectin-1), whose expression can be readily followed by IHC, fluorescence microscopy (FM) or flow cytometry of separated cells. Staining of the target gene product can be correlated with staining for phenotypic markers and fluorescent siRNAs to determine which cell types within the tissue are targeted. Pan-CK antibody can be used to distinguish epithelial cells (normal and tumor) from stroma. We can also compare knockdown of collagenase-digested 10 cells to tissue knockdown. Without wishing to be bound by theory, delivery and CK5 knockdown in rare basal tissue stem cells can be assessed, since EpCAM-AsiCs may target these cells and potentially lead to toxicity. Because toxicity to the GI tract is often dose limiting for cancer drugs, we can repeat these studies using colon tumor specimens to determine whether colon cancer cells, normal gut epithelia and crypt stem cells are transfected. These experiments can provide useful data regarding clinical toxicity and the choice of genes to knockdown, i.e. we might knockdown cancer dependency genes that are not essential for normal stem cells, if tissue stem cells are efficiently transfected. (Hematopoietic cells don't express EpCAM, so hematological toxicity is not expected.)

Can EpCAM-AsiCs be used to target breast tumor-initiating cells? One reason we chose EpCAM as aptamer target is its potential to transfect T-ICs ("cancer stem cells"). T-ICs are drug resistant and thought responsible for tumor initiation, relapse and metastasis. Breast T-ICs are not uniquely defined by phenotype, making experiments challenging, since T-ICs are defined functionally by their ability to initiate tumors that can be serially transplanted. Staining for CD44, CD24, EpCAM, CD133, CD49f or ALDH1 in different combinations enriches for T-ICs. 49,61,67,107-111

Different protocols define overlapping, but not identical, subsets of potential T-ICs. T-ICs are heterogeneous and show plasticity in their epithelial vs mesenchymal features (and in fact may have some features of both states). 28,95, 112-118 Some breast T-ICs are mesenchymal and don't express EpCAM. However, there is increasing evidence that the ability of basal-like TNBCs to colonize distant tissues and form macroscopic metastases—arguably the most clinically important function of T-ICs—depends on epithelial properties. Moreover our new data (FIGS. 15A-15C and 16) on the effect of EpCAM-AsiCs on T-IC function and tumor initiation indicate that EpCAM-AsiCs have anti-T-IC activity for basal-A TNBCs. We hypothesize that EpCAM-AsiCs are taken up by basal-like TNBC T-ICs and can be used for targeted therapy to cripple T-IC capability within them.

To analyze EpCAM-AsiC uptake and gene silencing in T-ICs, we can first stain a panel of breast cancer lines with EpCAM, CD44 and CD24 to identify breast cell lines whose putative T-IC populations contain cells that stain brightly for EpCAM. We can also examine EpCAM staining of mammospheres and Aldefluor+ cells 111,123,124 generated from these cell lines. We can select ~4-5 lines with the most uniform EpCAM expression within T-ICs as the most attractive cell lines to study in this subaim (and as controls, 1-2 basal-B cell lines whose T-ICs might lack EpCAM staining) and can produce stable eGFP-expressing variants. These cell lines, and their mammospheres and Aldefluor+ subpopulation, can be incubated with fluorescent eGFP EpCAM-AsiCs (and as control, nontargeting PSMA-AsiCs). AsiC uptake can be assessed together with EpCAM, CD44 and CD24 and Aldefluor staining. AsiCs should be taken up by EpCAM+ CD44+CD24−/dim Aldefluor+ cells. To assess gene knockdown in T-IC phenotype cells, we can monitor GFP in the T-IC population and remaining cells after treatment with eGFP or control siRNA-bearing AsiCs by flow cytometry and qRT-PCR (of Aldefluor+ or mammosphere populations). We can also assess knockdown of endogenous PLK1 and AKT1. These experiments can tell us whether T-ICs in different subtypes of breast cancer are targeted by EpCAM-AsiCs. Next we assess whether AsiCs inhibit mammosphere and colony formation, reduce phenotypic T-IC subpopulations, or the side population.

We can also design and evaluate AsiCs against additional genes needed for self-renewal or multipotency. Because basal-like TNBC T-ICs are sensitive to proteasome inhibition, we can evaluate knockdown of a proteasome component (PSMA2). Other potential T-IC dependency genes we will evaluate are MSI1, a gene highly expressed in breast T-ICs that regulates Wnt and Notch signaling 125-129, BMI1, a polycomb component needed for self-renewal 130-133, and possibly a few novel BDGs identified in our recent siRNA screen (FIG. 19). MSI1 knockdown decreases stem cell markers and mammosphere formation in MCF7 and T47D cells. 129

After verifying that these genes are expressed and knocked down in mammosphere cells, we can treat both adherent cells and mammospheres with AsiCs targeting these genes or eGFP as a negative control and measure the size of T-IC subpopulations after 5-7 d by staining for CD44, CD24, EpCAM, CD133, CD49f and ALDH1. We can also measure the proportion of cells that efflux small molecule dyes (the "side population"). These experiments can be complemented by functional assays quantifying colony forming cells and mammospheres. Serial replating can investigate whether propagation of T-ICs as spheres is inhibited.

Knocking down PLK1, MSI1, BMI1 or PSMA2 can reduce T-IC numbers, proliferation and function in some breast cancer subtypes, but different genes may be more active for different breast cell lines (i.e. proteasome inhibition eliminated T-ICs in basal-like TNBCs, but not non-TNBC tumors and in only 1 of 3 basal-B TNBCs95). The knockdown approaches that suppress T-IC can be further investigated by experiments using available chemical inhibitors and/or by knocking down other genes in the same pathway (such as NOTCH1, β-catenin or WNT1 for MSI1). The effect on T-ICs of EpCAM-AsiCs can be compared with the EpCAM aptamer on its own and the EpCAM antibody, adecatumumab (Amgen).

Next we determine whether short-term ex vivo exposure of basal-like TNBC lines to EpCAM-AsiCs inhibits tumor initiation as the ultimate measure of T-IC inhibition. The most promising AsiCs can be tested in vivo. Cell lines, treated overnight with AsiCs (and as negative controls AsiCs that use PSMA aptamer or contain eGFP siRNA), can be assessed for viability. After verifying that short-term siRNA exposure does not affect viability, ex vivo treated cells will be injected in a range of cell numbers orthotopically into NOD/scid/!c−/− (NSG) mice (these mice have the highest take for tumor implantation). Pretreatment with bortezomib, which reduced tumor initiation in basal-like TNBC"), or adecatumumab will be controls.

Optimize EpCAM-AsiCs To improve EpCAM-AsiC drug features, we can optimize each step of in vitro gene knockdown and in vivo delivery. We can also modify the chemistry of EpCAM-AsiCs (if needed) to minimize off-target effects.

In prelim. studies and published work, the AsiC concentration needed for optimal knockdown in vitro is ~1-4 µM, many fold higher than the −100 nM (or lower) concentrations used for lipid transfection. For knockdown, EpCAM-AsiCs follow the following steps: (1) cell receptor binding, (2) endocytosis, (3) endosomal release, (4) Dicer processing, (5) incorporation into the RNA-induced silencing complex (RISC), and (6) target mRNA cleavage. We can systematically optimize each step, focusing on steps (2) and (3), where we expect we can obtain the largest gains in efficacy. The AsiC design variables are the EpCAM aptamer, whose affinity affects steps 1 and 2; the linker sequence between the aptamer and the siRNA, which controls step 4; the siRNA sequence, which controls step 6. In addition each residue used for chemical synthesis from phosphoramidite building blocks can be chemically modified to reduce nuclease digestion, off-target suppression of partially complementary sequences, binding and stimulation of innate immune RNA sensors and improve cell uptake and in vivo PK. The most common chemical modifications are substituting S for O in the phosphate backbone (to produce RNase-resistant phosphorothioate (PS) linkages and substituting 2'-F, 2'-O-methyl (2'OMe), or 2'-O-methyoxyethyl (2'MOE) for the 2'-OH in the ribose. PS, 2'-F and 2'-OMe modifications are well tolerated in clinical trials and therefore we concentrate on them. 2'-OMe occurs naturally in rRNA and tRNA and is therefore safe, and 2'-F is also well tolerated; heavily Psmodified nucleotides are sticky (and cause binding to serum proteins, which can improve circulating T1/2) and can cause unwanted side effects; lightly modified PS-RNAs are not toxic. Chemical modifications can both inhibit and enhance gene silencing in steps 5 and 6 This can be an iterative process; as modifications are made at one step, the most attractive modified candidates can be optimized for other steps, drawing on lessons learned from previous candidates. We can verify that the modified AsiCs chosen for further development do not stimulate innate immunity or result in cellular toxicity. If they do, we can further modify our designs to avoid these problems.

Optimize In Vitro Knockdown (1) EpCAM binding The EpCAM aptamer has 12 nM affinity, It can be verified that that this affinity is preserved in the EpCAM-AsiC. If the AsiC has lower affinity than the aptamer, we can use bio-layer interferometry (OctetRED System, ICCB-Longwood Core) with recombinant EpCAM to compare the affinity of the aptamer and AsiC. If the AsiC has lower binding affinity, it may not fold properly. To enhance folding into the desired conformation we can try changing the type and length of the linker between the aptamer and the AsiC sense strand (i.e. we can incorporate more 3C linkers or triethylene or hexaethylene glycol spacers).

Figure 20:
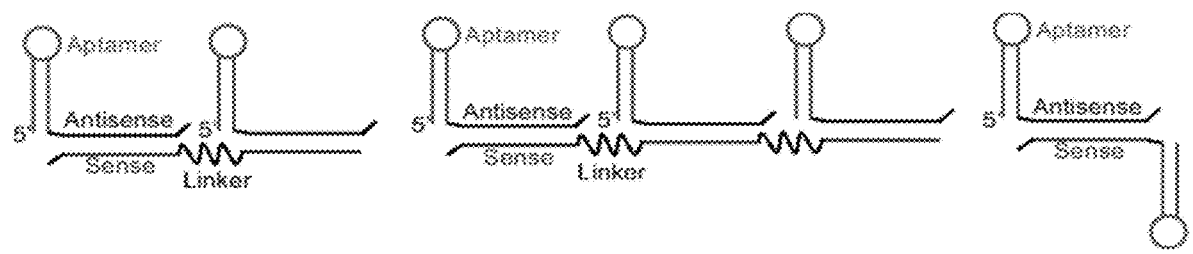
FIG. 20 depicts some possible designs for multimerized EpCAM-AsiCs to improve endocytosis. In these designs the sense and antisense strands could be exchanged and the linkers could be varied.

(2) Endocytosis The monomeric AsiC is slowly taken up by constitutive receptor recycling. This step can be optimized by receptor crosslinking to trigger active endocytosis, which requires aptamer multimerization. Multimerization of aptamers (with or without linked siRNAs) can increase binding avidity (by increasing valency) or convert an aptamer that does not cause signaling into an agonistic reagent. Aptamers can be multimerized by using streptavidin (SA) to bind biotinylated (Bi) aptamers and siRNAs; extending the aptamer with an adapter that binds to an organizing oligonucleotide that contains multiple complementary sequences connected by a flexible linker; or extending the aptamer with complementary adapter sequences to produce a dimer. We focus on all-RNA designs, which don't induce antibodies. Some of the designs we can test are shown in FIG. 20 (we can also test constructs with sense and antisense strands exchanged).

Time course and dose response experiments will compare fluorescently tagged multimeric constructs with the monomeric AsiC to assess the extent and rapidity of uptake and GFP knockdown by flow cytometry and live cell imaging (data not shown). If endocytosis is enhanced by multimerization, but knockdown does not improve, we can use Northern blotting to follow Dicer cleavage and determine whether the expected antisense strand is produced (see below). If not, we can alter the design of the linkers, for example by lengthening the duplex region from 21 to 27 nt, so the multimerized AsiC is a good Dicer substrate(&) and verify that the 5' end of the Dicer product originates at the intended base. Multimerization should reduce the AsiC concentration needed for knockdown many fold. However, multimerization could cause unwanted EpCAM signaling and promote tumor cell proliferation. We can verify that this is not the case using multimerized constructs targeting eGFP. An attractive feature of multimerization is that it could link multiple different siRNAs into a single RNA molecule for combinatorial gene knockdown to produce a cancer "cocktail".

If none of these multimers work, we can test monomeric AsiCs containing complementary sequences that enable RNAs to selfassemble into small nanoparticles or the SA-Bi strategy, using less immunostimulatory SA mutants.

(3) Endosomal release Although fewer than 1000 cytosolic siRNA molecules are estimated to be needed for knockdown (not shown), only a few percent of siRNAs in endocytosed liposomes are released into thecytosol. EpCAM-AsiC endosomal release can be assessed by live cell imaging to measure the efficiency of cytosolic release of endocytosed AsiCs. If this indicates less than desired endosomal release, then improving release should reduce the drug dose substantially. Preincubation and endocytosis of an amphipathic cationic peptide (mellitin) or polymer (butyl vinyl ether) that is reversibly masked, can enhance siRNA escape to the cytosol. Masking means that at neutral pH the peptide or polymer is uncharged and does not interact with the plasma membrane and damage it, but at the negative endosomal pH, a cationic molecule is generated that damages the endosomal membrane and releases coendocytosed oligonucleotides. Iv injection of these masked polymers within 2 hr of siRNA delivery potentiated hepatocyte knockdown by chol-siRNAs as much as 500 fold in mice and nonhuman primates.

We can first determine by live cell videomicroscopy whether prior transfection of masked cationic polymers facilitates EpCAM-AsiC (and lipoplexed siRNA) cytosolic delivery and eGFP knockdown in vitro. We can also investigate whether incubating EpCAM-AsiCs with basic peptides/polymers can also determine whether inhibition of endosomal acidification using bafilomycin A or concanamycin alters EpCAM-AsiC cytoplasmic release and knockdown, as the proton sponge theory predicts. If these experiments confirm the proton sponge theory, we can investigate strategies for altering EpCAM-AsiCs. These include covalent conjugation (via disulfide bonds spontaneously reversed in the cytosol's reducing environment) of the sense or antisense strand to cell penetrating peptides, including polyarginines of different sizes, protamine152, mellitin, transportan or penetratin and conjugation of the AsiC sense strand to butyl and amino vinyl ester or linkage of the sense strand to phosphospermines of different lengths. We can verify that these modifications do not alter solubility, result in cytotoxicity or innate immune stimulation or interfere with specific EpCAM targeting.

Dicer processing, RISC incorporation, target mRNA cleavage We next take the top 2-3 EpCAM-AsiCs, with the initial design as control, and examine whether siRNA function can be optimized. Northern blots, probed for the sense, antisense and aptamer parts of the EpCAM-AsiC, can analyze EpCAM-AsiC products within cells. Their migration can be compared to that of synthesized sense and antisense strands, aptamer and full length EpCAM-AsiC. If Dicer cleaves the AsiC as expected, we can recover RNAs that migrate like the sense and antisense strands (as well as unprocessed EpCAM-AsiCs from endosomes and a band the size of the aptamer joined to its linker). (Dicer dependence can be verified using HCT116 cells expressing hypomorphic Dicer). If the intracellular RNAs are not the expected size, we can clone them to determine where Dicer cuts. If the bands are not cut or are not where we want, we can redesign the linker and double stranded region to produce the desired cleavage. We can also investigate replacing the UUU linker with alternative linkers or combinations of linkers, by substituting or adding one or more 3C linkers or triethylene or hexaethylene glycol spacers, to enhance intracellular processing to the siRNA. We can also investigate whether a Dicer-independent design in which the aptamer is covalently joined to the sense or antisense strand of the siRNA by a disulfide bond, spontaneously reduced in the cytosol, leads to more efficient knockdown.

Once we have shown that the appropriate antisense strand is produced, we can next compare antisense strand incorporation into the RISC. Northern blotting and Taqman PCR will quantify how much of the input active strand in whole cell lysates is pulled down with pan-Ago antibody (2A8). Ago binding, the T1/2 of the siRNA in the RISC, and target gene knockdown are influenced by chemical modifications of the sense and antisense strands. Specific 2'-F and 2'-OMe chemical modifications on both strands arranged in proprietary positions and sequences can increase knockdown by 50-fold and PS linkages at the ends greatly increase gene knockdown duration. We can design a small set of AsiCs bearing different covalent modifications of the siRNA portions of the AsiC and analyze their effect on knockdown of eGFP, AKT1 and PLK1

EpCAM-AsiCs targeting additional genes that we evaluate in vivo can be designed with the most active siRNA sequences and best chemical modifications. A small group of siRNA sequences to test for knockdown (without aptamers, by transfection) can be identified by web algorithms. The most efficient siRNAs (pM activity), which also have low predicted melting temperatures (Tm), can be used, since these are processed better. If we need to use sequences with higher Tms, we can add a mismatch at the 3'-end of the sense strand to promote siRNA unwinding and incorporation of the active strand in the RISC.

Eliminate off target effects and toxicity These experiments can be performed with the original and the best optimized AsiCs. The lack of toxicity of the various AsiCs encoding eGFP siRNA (whose knockdown should not affect viability) can be formally assessed by Cell Titer-Glo assay of AsiC-incubated TNBC lines. Based on prior work, we do not expect significantly reduced viability. Lipid transfection will be used as a control for cytotoxic RNA delivery. Finally we can verify that each of the AsiCs is not immunostimulatory by qRT-PCR, performed 6 and 24 hr post AsiC incubation, to amplify a panel of inflammatory and innate immune response genes (IFNB, IFNG, IL1, IL8, IL10, OAS1, STAT1, IP10). qRT-PCR is the most sensitive assay for immunostimulation and we chose times that capture the peak response. Cells treated with poly(I:C) can serve as positive controls and mock-treated cells will be negative controls. If any AsiC is immunostimulatory (a sequence and concentration dependent property), we can evaluate whether additional chemical modifications, which reduce innate immune sensor binding, eliminate immune stimulation without compromising gene knockdown. A 2'-F or 2'-OMe modification of the second residue of either the full AsiC or the Dicer cleavage product can accomplish this goal.

Since the CD4-AsiC is not immunostimulatory in our prelim. studies and the optimized AsiCs are active at greatly reduced concentrations (and off-target effects are concentration dependent), innate immune stimulation is unlikely, but if detected, can be easily suppressed by chemical modification. In conjunction with the tissue explant studies we can also examine tissue histology carefully for disruption of epithelial tissue architecture and cell necrosis.

Optimize tumor concentration and define PK/PD, Next we evaluate and improve systemic T1/2 and tumor targeting in tumor-bearing mice. We can focus on the original AsiC design and a few of the in vitro optimized constructs (as they are identified). We can use qRT-PCR to measure circulating T1/2 and tissue distribution, in vivo imaging of the fluorescent AsiC to look at tumor localization and silencing of tumor cell mCherry (GFP is not used because of background autofluorescence) as a readout of gene silencing. Studies of EpCAM-AsiC PK/PD can be facilitated by our recent experience with in vivo imaging (FIGS. 16, 17A-17B, and 18A-18B, data not shown). These experiments can use nude mice bearing mammary fatpad xenografts of Luciferase-mCherry stable transfectants we have generated of EpCAM+ basal-A TNBC lines, such as MB468 or HCC1187, compared to an EpCAM– mesenchymal basal-B TNBC cell line, such as MB231. We have an expression plasmid for these tags and use lentivirus infection to produce stable transfectants. ~5-8 mice/gp will be used to obtain statistical significance based on our prelim. data in these models. We can first compare the blood and tumor concentration after iv and sc administration of the original AsiC construct and the constructs optimized for in vitro knockdown. Mice can be examined frequently for clinical signs of toxicity. Samples can be analyzed over 5d with frequent sample collection the first day. At each timepoint, blood and urine can be harvested and analyzed by Taqman assay for the antisense strand. Tumor and sample organs can be harvested at fewer timepoints from euthanized animals. Blood can be analyzed for hematological, liver and kidney toxicity by blood counts and serum chemistries. The circulating T1/2 and proportion of the injected drug that localizes to the EpCAM+ tumor can be calculated. Without wishing to be bound by theory, based on our preliminary experiments with sc and iv administration of the CD4-AsiCs and in vivo experience with the PSMA-AsiC, we expect that most of these EpCAM-AsiCs will be rapidly excreted after iv administration, but that sc injected EpCAM-AsiCs will concentrate in tumor xenografts. The larger multimerized constructs (FIG. 20) might resist kidney filtration and have better tumor concentration when given iv. The sc and iv PK results will be compared with mCherry knockdown following a single EpCAM-AsiC injection in a range of concentrations, assessed both by in vivo imaging (using the IVIS Spectrum) and by flow cytometry, FM, and qRT-PCR of tumor specimens harvested 4, 7 and 12 d post-treatment. These experiments can provide estimates of the effective dose required for peak tumor gene knockdown of 50, 75 and 90% (ED50, ED75, ED90) and for the durability of knockdown in the tumor (quantified as T-KD50=time for tumor expression to return halfway to control from the peak knockdown). These parameters can be determined for each chosen construct.

Next we assess ways to improve the circulating T1/2. These include increasing the size of the AsiC (i.e. by PEG conjugation comparing a few sizes, such as 10, 20 and 30 kD, avoiding polymers known to be toxic, such as PEI) and increasing binding to serum proteins to reduce renal filtration (i.e. by conjugation with cholesterol, which binds to serum LDL158,159 or by adding a diacyl tail to promote binding to serum albumin. We avoid strategies that produce particles or aggregates since these will have poorer tumor penetration and may be trapped in the liver. Linking PEG to the 5'-end of the aptamer, the 3'-end of the inactive siRNA or the 3'-end of the active strand should not interfere with RNAi. In vivo PK/PD/toxicity evaluation can be performed as above, using the unconjugated AsiC as a positive control (and benchmark) and the conjugated siRNA (without the aptamer) as a negative control. Two or three of the constructs that have the lowest ED75 or ED90 and longest T-KD50 for GFP will be retested using a PLK1 EpCAM-AsiC to determine the corresponding PK/PD parameters, to aid in designing the dosing regimen for antitumor efficacy experiments. We can also determine the maximally tolerated dose (MTD) for these PLK1 constructs.

Antitumor Effect of EpCAM AsiCs against basal-like TNBCs Our final goal is to test the EpCAM-AsiCs against orthotopic mammary fat pad tumors and metastases. We can use nude mice unless tumors do not grow or grow slowly, in which case we will switch to NSG mice. Live animal imaging can be performed using an IVIS Spectrum, sensitive for multicolor fluorescence and bioluminescence. These experiments can evaluate 2-3 of the best EpCAM-AsiCs identified.

Activity of PLK1 EpCAM-AsiCs against orthotopic xenografts We can begin by targeting PLK1/A few PLK1 EpCAM-AsiC designs, optimized as described above, can be injected sc and/or iv in groups of 5-8 mice (size chosen from power calculations based on previous experiments in which this group size gave statistically significant results) using doses and dosing schedules/injection route chosen based on the PK/PD results above. For example if the ED90 is well below the MTD, an initial experiment might investigate administering 2ED90 every T-KD50/2 d. Mice can initially be treated as soon as their tumors become palpable, but in later experiments we can investigate whether larger tumors of fixed diameters regress after multiple administrations. Mice bearing representative EpCAM+ basal-A (MB468, HC1187, BPLER) and EpCAM− basal-B (MB231) tumors will be compared. For some experiments, we can treat mice bearing these tumors in each flank, but these may require more mice because of intra-animal variations in tumor sizes. Control mice can be treated with PBS or naked siRNAs, the EpCAM aptamer on its own, EpCAM-AsiCs bearing scrambled siRNA sequences and PLK1 PSMA-AsiCs. In some experiments we can compare EpCAM-AsiC treatment with adecatumumab or paclitaxel. Tumor size will be quantified by luminescence and caliper measurements q3d. Treated mice can also be weighed and observed for clinical signs of toxicity and at time of sacrifice can be carefully examined for gut and bone marrow toxicity by blood counts and pathological examination of gut, bone marrow and spleen. Differences between groups can be assessed by one way ANOVA with corrections for multiple comparisons as needed. For AsiCs that are effective, we can also examine the immediate effect of treatment to evaluate the mechanism of antitumor activity and verify that the AsiCs are not activating innate immune responses. Tumor-bearing mice can be sacrificed 1-3 d after a single therapeutic or control injection and the tumors stained for activated caspases to determine if death is by apoptosis and by H&E to look for mitotic spindles to follow the expected effect of PLK1 knockdown. Serum interferons and pro-inflammatory cytokines can be assessed by multiplexed ELISA, and spleen and tumor cells analyzed by qRT-PCR for the corresponding mRNAs. If there is no antitumor effect or the antitumor effect is suboptimal, the dosing regimen can be adjusted to the MTD. If the antitumor effect is complete (complete tumor regression), then we can evaluate decreased doses and/or larger tumors at start of therapy. When control mice are sacrificed because untreated tumors have reached the allowed size, the treated mice can be sacrificed and mammary fatpads inspected for residual microscopic or macroscopic tumor by FM, H&E and IHC. Residual tumor cells can also be assessed for EpCAM expression to determine whether tumor resistance, if it occurs, may have developed as a consequence of down-regulating EpCAM. If no residual tumor cells are noted, we can perform an additional experiment to determine whether tumors are eradicated—mice will be treated for 1-2 weeks after the luciferase measurement has returned to background levels, and then mice can be observed for 1-2 months off treatment to see if tumors regrow or metastases appear. The most effective regimen(s) for basal-A TNBCs can also be evaluated against other breast cancer subtypes (luminal, Her2+) that we expect EpCAM to target.

PLK1 EpCAM-AsiC activity against metastatic tumors To evaluate the effectiveness of EpCAM-AsiCs against metastatic cancer cells, we can evaluate the PLK1 EpCAM-AsiCs against basal-A TNBC cell lines injected intravenously in NSG mice, which have the best tumor take. We can begin to treat mice as soon as lungs become luciferase+ after tail vein injection of basal-A (or basal-B as control) TNBCs. The treatment dosing can use the effective schedule and mode of administration determined above for primary tumors. Mice can be imaged q3d. The controls can be reduced to a mock-treated group and groups treated with paclitaxel or an EpCAM-AsiC containing a non-targeting siRNA. When the control mice need to be sacrificed, all groups can be imaged. Lungs, livers and brains can be dissected, weighed, imaged to quantify tumor burden, sections can be analyzed by H&E and staining for EpCAM, and one lung from each animal will be analyzed by qRT-PCR for relative expression of human/mouse Gapdh to quantify tumor burden independently. If mice treated with PLK1 EpCAM-AsiCs are completely protected from metastases or show a significant advantage compared to control groups, we can determine if mice with greater metastatic burdens are also protected by delaying the beginning of treatment until the tumor burden is greater.

We can also compare the most effective iv regimen with the most effective sc regimen identified above for treating orthotopic tumors, since RNA delivery/knockdown at metastatic sites could differ from primary tumor sites. We can also use this metastasis model to evaluate in vivo knockdown of our screen's BDG genes and genes identified above herein as necessary for tumor initiation ex vivo, since M-IC capability is thought to correlate with T-IC function.

Activity of EpCAM-AsiCs targeting BDF genes We can next compare PLK1 knockdown with knockdown of TNBC dependency genes identified in our siRNA screens or in the literature (such as XBP1). These in vivo experiments for each gene target chosen can involve (1) identifying active siRNAs for each gene and evaluating the effect of knockdown on cell proliferation and T-IC function in vitro; (2) designing and in vitro testing of AsiCs to knockdown the specific gene; (3) evaluating the effect of gene knockdown on in vitro proliferation and T-IC function in a variety of breast cancer cell lines; and (4) verifying the lack of off-target immune stimulation of the individual AsiC. The genes that behave best in vitro can be advanced to in vivo testing in orthotopic and metastatic models as described above for PLK1. In these experiments we can compare untreated mice with mice treated with EpCAM-AsiCs targeting the specific gene or PLK1. If there is a specific inhibitor drug for a particular gene target (i.e. bortezomib/carfilzomib for the proteasome), a group of control mice can also be treated with the drug for comparison. Exemplary genes for such experiments are proteasome genes and MCL1, U4/U6-U5 tri-snRNP complex genes96,97, XBP1 and the kinetochore gene NDC80. AsiCs that have the best in vivo activity on their own will also be evaluated in combinations with PLK1 AsiCs and each other. Since proteasome inhibitor sensitivity correlates strongly with MCL1 dependency in vitro (not shown), we hypothesize that proteasome gene and MCL1 knockdown will be synergistic. The synergy of different AsiC and AsiC/drug combinations can be formally tested by the isobologram method using different RNA dose combinations or combinations with relevant inhibitor drugs. In particular we will determine whether combining EpCAM-AsiCs with standard of care drugs, such as paclitaxel, is synergistic with the original construct.

LITERATURE CITED

1. Foulkes W D, Smith I E and Reis-Filho J S. 2010. Triple-negative breast cancer. N Engl J Med 363: 1938-1948.
2. Gusterson B. 2009. Do 'basal-like' breast cancers really exist? Nat Rev Cancer 9: 128-134.
3. Metzger-Filho O, Tutt A, de Azambuja E, Saini K S, Viale G, Loi S, Bradbury I, Bliss J M, Azim H A, Jr., Ellis P, Di Leo A, Baselga J, Sotiriou C and Piccart-Gebhart M. 2012. Dissecting the heterogeneity of triple-negative breast cancer. J Clin Oncol 30: 1879-1887.
4. Shah S P, Roth A, Goya R, Oloumi A, Ha G, Zhao Y, Turashvili G, Ding J, Tse K, Haffari G, Bashashati A, Prentice L M, Khattra J, Burleigh A, Yap D, Bernard V, McPherson A, Shumansky K, Crisan A, Giuliany R, Heravi-Moussavi A, Rosner J, Lai D, Birol I, Varhol R, Tam A, Dhalla N, Zeng T, Ma K, Chan S K, Griffith M, Moradian A, Cheng S W, Morin G B, Watson P, Gelmon K, Chia S, Chin S F, Curtis C, Rueda O M, Pharoah P D, Damaraju S, Mackey J, Hoon K, Harkins T, Tadigotla V, Sigaroudinia M, Gascard P, Tlsty T, Costello J F, Meyer I M, Eaves C J, Wasserman W W, Jones S, Huntsman D, Hirst M, Caldas C, Marra M A and Aparicio S. 2012. The clonal and mutational evolution spectrum of primary triple-negative breast cancers. Nature 486:395-399.
5. Dykxhoorn D M and Lieberman J. 2006. Knocking down disease with siRNAs. Cell 126: 231-235.
6. de Fougerolles A, Vomlocher H P, Maraganore J and Lieberman J. 2007. Interfering with disease: a progress report on siRNA-based therapeutics. Nat Rev Drug Discov 6: 443-453.
7. Petrocca F and Lieberman J. 2011. Promise and challenge of RNA interference-based therapy for cancer. J Clin Oncol 29: 747-754.
8. Watts J K and Corey D R. 2012. Silencing disease genes in the laboratory and the clinic. J Pathol 226: 365-379.
9. Burnett J C and Rossi J J. 2012. RNA-based therapeutics: current progress and future prospects. Chem Biol 19: 60-71.
10. Tabernero J, Shapiro G I, LoRusso P M, Cervantes A, Schwartz G K, Weiss G J, Paz-Ares L, Cho D C, Infante J R, Alsina M, Gounder M M, Falzone R, Harrop J, White A C, Toudjarska I, Bumcrot D, Meyers R E, Hinkle G, Svrzikapa N, Hutabarat R M, Clausen V A, Cehelsky J, Nochur S V, Gamba-Vitalo C, Vaishnaw A K, Sah D W, Gollob J A and Burris H A, 3rd. 2013. First-in-humans trial of an RNA interference therapeutic targeting VEGF and KSP in cancer patients with liver involvement. Cancer Discov 3: 406-417.
11. Janssen H L, Reesink H W, Lawitz E J, Zeuzem S, Rodriguez-Torres M, Patel K, van der Meer A J, Patick A K, Chen A, Zhou Y, Persson R, King B D, Kaupinen S, Levin A A and Hodges M R. 2013. Treatment of HCV infection by targeting microRNA. N Engl J Med 368: 1685-1694.
12. Alnylam. 2013. Interim Results for Phase II Trial of ALN-TTR02: A Novel RNAi Therapeutic for the Treatment of Familial Amyloidotic Polyneuropathy. Biennial Meeting of the Peripheral Nerve Society, St Malo, France
13. Fitzgerald K, Frank-Kamenetsky M, Shulga-Morskaya S, Liebow A, Bettencourt B R, Sutherland J E, Hutabarat R M, Clausen V A, Karsten V, Cehelsky J, Nochur S V, Kotelianski V, Horton J, Mant T, Chiesa J, Ritter J, Munisamy M, Vaishnaw A K, Gollob J A and Simon A. 2014. Effect of an RNA interference drug on the synthesis of proprotein convertase subtilisin/kexin type 9 (PCSK9) and the concentration of serum LDL cholesterol in healthy volunteers: a randomised, single-blind, placebo-controlled, phase 1 trial. Lancet 383: 60-68.
14. Akin A. 2014. ALN-AT3: An investigational RNAi Therapeutic targeting antithrombin for the treatment of helophilia. presentation at the World Federation of Hemophilia World Congress, Melbourne Australia
15. Peer D and Lieberman J. 2011. Special delivery: targeted therapy with small RNAs. Gene Ther 18: 1127-1133.
16. Daniels D A, Chen H, Hicke B J, Swiderek K M and Gold L. 2003. A tenascin-C aptamer identified by tumor cell SELEX: systematic evolution of ligands by exponential enrichment. Proc Natl Acad Sci USA 100: 15416-15421.
17. Huang Z and Szostak J W. 2003. Evolution of aptamers with a new specificity and new secondary structures from an ATP aptamer. RNA 9: 1456-1463.
18. Shigdar S, Lin J, Yu Y, Pastuovic M, Wei M and Duan W. 2011. RNA aptamer against a cancer stem cell marker epithelial cell adhesion molecule. Cancer Sci 102: 991-998.
19. Stingl J, Eaves C J, Zandieh I and Emerman J T. 2001. Characterization of bipotent mammary epithelial progenitor cells in normal adult human breast tissue. Breast Cancer Res Treat 67: 93-109.
20. Trzpis M, Popa E R, McLaughlin P M, van Goor H, Timmer A, Bosman G W, de Leij L M and Harmsen M C. 2007. Spatial and temporal expression patterns of the epithelial cell adhesion molecule (EpCAM/EGP-2) in developing and adult kidneys. Nephron Exp Nephrol 107: e 119-131.
21. Marhaba R, Klingbeil P, Nuebel T, Nazarenko I, Buechler M W and Zoeller M. 2008. CD44 and EpCAM: cancer-initiating cell markers. Curr Mol Med 8: 784-804.
22. Gonzalez B, Denzel S, Mack B, Conrad M and Gires O. 2009. EpCAM is involved in maintenance of the murine embryonic stem cell phenotype. Stem Cells 27: 1782-1791.
23. Lu T Y, Lu R M, Liao M Y, Yu J, Chung C H, Kao C F and Wu H C. 2010. Epithelial cell adhesion molecule regulation is associated with the maintenance of the undifferentiated phenotype of human embryonic stem cells. J Biol Chem 285: 8719-8732.
24. Martin-Killias P, Stefan N, Rothschild S, Pluckthun A and Zangemeister-Wittke U. 2011. A novel fusion toxin derived from an EpCAM-specific designed ankyrin repeat protein has potent antitumor activity. Clin Cancer Res 17: 100-110.
25. Spizzo G, Fong D, Wurm M, Ensinger C, Obrist P, Hofer C, Mazzoleni G, Gastl G and Went P. 2011. EpCAM expression in primary tumour tissues and metastases: an immunohistochemical analysis. J Clin Pathol 64: 415-420.
26. Keller P J, Arendt L M, Skibinski A, Logvinenko T, Klebba I, Dong S, Smith A E, Prat A, Perou C M, Gilmore H, Schnitt S, Naber S P, Garlick J A and Kuperwasser C. 2012. Defining the cellular precursors to human breast cancer. Proc Natl Acad Sci USA 109: 2772-2777.
27. Osta W A, Chen Y, Mikhitarian K, Mitas M, Salem M, Hannun Y A, Cole D J and Gillanders W E. 2004. EpCAM is overexpressed in breast cancer and is a potential target for breast cancer gene therapy. Cancer Res 64: 5818-5824.
28. Sarrio D, Franklin C K, Mackay A, Reis-Filho J S and Isacke C M. 2012. Epithelial and mesenchymal subpopulations within normal basal breast cell lines exhibit distinct stem cell/progenitor properties. Stem Cells 30: 292-303.
29. McNamara J O, 2nd, Andrechek E R, Wang Y, Viles K D, Rempel R E, Gilboa E, Sullenger B A and Giangrande P H. 2006. Cell type-specific delivery of siRNAs with aptamer-siRNA chimeras. Nat Biotechnol 24:1005-1015.
30. Dassie J P, Liu X Y, Thomas G S, Whitaker R M, Thiel K W, Stockdale K R, Meyerholz D K, McCaffrey A P, McNamara J O, 2nd and Giangrande P H. 2009. Systemic administration of optimized aptamer-siRNA chimeras promotes regression of PSMA-expressing tumors. Nat Biotechnol 27: 839-849.
31. Zhou J, Li H, Li S, Zaia J and Rossi J J. 2008. Novel dual inhibitory function aptamer-siRNA delivery system for HIV-1 therapy. Mol Ther 16: 1481-1489.
32. Zhou J and Rossi J J. 2010. Aptamer-targeted cell-specific RNA interference. Silence 1: 4.
33. Zhou J, Swiderski P, Li H, Zhang J, Neff C P, Akkina R and Rossi J J. 2009. Selection, characterization and application of new RNA HIV gp 120 aptamers for facile delivery of Dicer substrate siRNAs into HIV infected cells. Nucleic Acids Res 37: 3094-3109.
34. Neff C P, Zhou J, Remling L, Kuruvilla J, Zhang J, Li H, Smith D D, Swiderski P, Rossi J J and Akkina R. 2011. An aptamer-siRNA chimera suppresses HIV-1 viral loads and protects from helper CD4(+) T cell decline in humanized mice. Sci Transl Med 3: 66ra66.
35. McNamara J O, Kolonias D, Pastor F, Mittler R S, Chen L, Giangrande P H, Sullenger B and Gilboa E. 2008. Multivalent 4-1B B binding aptamers costimulate CD8+ T cells and inhibit tumor growth in mice. J Clin Invest 118: 376-386.
36. Kim M Y and Jeong S. 2011. In vitro selection of RNA aptamer and specific targeting of ErbB2 in breast cancer cells. Nucleic Acid Ther 21: 173-178.
37. Wheeler L A, Trifonova R, Vrbanac V, Basar E, McKernan S, Xu Z, Seung E, Deruaz M, Dudek T, Einarsson J I, Yang L, Allen™, Luster A D, Tager A M, Dykxhoorn D M and Lieberman J. 2011. Inhibition of HIV transmission in human cervicovaginal explants and humanized mice using CD4 aptamer-siRNA chimeras. J Clin Invest 121: 2401-2412.
38. Rockey W M, Hernandez F J, Huang S Y, Cao S, Howell C A, Thomas G S, Liu X Y, Lapteva N, Spencer D M, McNamara J O, Zou X, Chen S J and Giangrande P H. 2011. Rational truncation of an RNA aptamer to prostatespecific membrane antigen using computational structural modeling. Nucleic Acid Ther 21: 299-314.
39. Thiel K W, Hernandez L I, Dassie J P, Thiel W H, Liu X, Stockdale K R, Rothman A M, Hernandez F J, McNamara J O, 2nd and Giangrande P H. 2012. Delivery of chemo-sensitizing siRNAs to HER2+-breast cancer cells using RNA aptamers. Nucleic Acids Res 40: 6319-6337.
40. Pastor F, Kolonias D, Giangrande P H and Gilboa E. 2010. Induction of tumour immunity by targeted inhibition of nonsense-mediated mRNA decay. Nature 465: 227-230.
41. Zhou J and Rossi J J. 2011. Cell-specific aptamer-mediated targeted drug delivery. Oligonucleotides 21:1-10.
42. Pastor F, Kolonias D, McNamara J O, 2nd and Gilboa E. 2011. Targeting 4-1B B costimulation to disseminated tumor lesions with bi-specific oligonucleotide aptamers. Mol Ther 19: 1878-1886.
43. Wheeler L A, Vrbanac V, Trifonova R, Brehm M A, Gilboa-Geffen A, Tanno S, Greiner D L, Luster A D, Tager A M and Lieberman J. 2013. Durable knockdown and protection from HIV transmission in humanized mice treated with gel-formulated CD4 aptamer-siRNA chimeras. Mol Ther 21: 1378-1389.
44. Hussain A F, Tur M K and Barth S. 2013. An aptamer-siRNA chimera silences the eukaryotic elongation factor 2 gene and induces apoptosis in cancers expressing alphavbeta3 integrin. Nucleic Acid Ther 23: 203-212.
45. Wang C W, Chung W H, Cheng Y F, Ying N W, Peck K, Chen Y T and Hung S I. 2013. A new nucleic acid based agent inhibits cytotoxic T lymphocyte-mediated immune disorders. J Allergy Clin Immunol 132: 713-722 e711.
46. Dassie J P and Giangrande P H. 2013. Current progress on aptamer-targeted oligonucleotide therapeutics. Ther Deliv 4: 1527-1546.
47. Lai W Y, Wang W Y, Chang Y C, Chang C J, Yang P C and Peck K. 2014. Synergistic inhibition of lung cancer cell invasion, tumor growth and angiogenesis using aptamer-siRNA chimeras. Biomaterials 35: 2905-2914.
48. Yoo H, Jung H, Kim S A and Mok H. 2014. Multivalent comb-type aptamer-siRNA conjugates for efficient and selective intracellular delivery. Chem Commun (Camb) 50: 6765-6767.

49. Al-Hajj M, Wicha M S, Benito-Hernandez A, Morrison S J and Clarke M F. 2003. Prospective identification of tumorigenic breast cancer cells. Proc Natl Acad Sci USA 100: 3983-3988.
50. Dick J E. 2003. Breast cancer stem cells revealed. Proc Natl Acad Sci USA 100: 3547-3549.
51. Hirschmann-Jax C, Foster A E, Wulf G G, Nuchtern J G, Jax T W, Gobel U, Goodell M A and Brenner M K 2004. A distinct "side population" of cells with high drug efflux capacity in human tumor cells. Proc Natl Acad Sci USA 101: 14228-14233.
52. Dean M, Fojo T and Bates S. 2005. Tumour stem cells and drug resistance. Nat Rev Cancer 5: 275-284.
53. Bao S, Wu Q, McLendon R E, Hao Y, Shi Q, Hjelmeland A B, Dewhirst M W, Bigner D D and Rich J N. 2006. Glioma stem cells promote radioresistance by preferential activation of the DNA damage response. Nature 444: 756-760.
54. Jordan C T, Guzman M L and Noble M. 2006. Cancer stem cells. N Engl J Med 355: 1253-1261.
55. Phillips™, McBride W H and Pajonk F. 2006. The response of CD24(−/low)/CD44+ breast cancer-initiating cells to radiation. J Natl Cancer Inst 98: 1777-1785.
56. Polyak K and Hahn W C. 2006. Roots and stems: stem cells in cancer. Nat Med 12: 296-300.
57. Sheridan C, Kishimoto H, Fuchs R K, Mehrotra S, Bhat-Nakshatri P, Turner C H, Goulet R, Jr., Badve S and Nakshatri H. 2006. CD44+/CD24− breast cancer cells exhibit enhanced invasive properties: an early step necessary for metastasis. Breast Cancer Res 8: R59.
58. Wicha M S. 2006. Cancer stem cells and metastasis: lethal seeds. Clin Cancer Res 12: 5606-5607.
59. Cho R W, Wang X, Diehn M, Shedden K, Chen G Y, Sherlock G, Gurney A, Lewicki J and Clarke M F. 2008. Isolation and Molecular Characterization of Cancer Stem Cells in MMTV-Wnt-1Murine Breast Tumors. Stem cells (Dayton, Ohio) 26: 364-371.
60. Dalerba P and Clarke M. 2007. Cancer Stem Cells and Tumor Metastasis: First Steps into Uncharted Territory. Cell Stem Cell 1: 241-242.
61. Fillmore C and Kuperwasser C. 2007. Human breast cancer stem cell markers CD44 and CD24: enriching for cells with functional properties in mice or in man? Breast Cancer Res 9: 303.
62. Kelly P N, Dakic A, Adams J M, Nutt S L and Strasser A. 2007. Tumor growth need not be driven by rare cancer stem cells. Science 317: 337.
63. O'Brien C A, Pollett A, Gallinger S and Dick J E. 2007. A human colon cancer cell capable of initiating tumour growth in immunodeficient mice. Nature 445: 106-110.
64. Shafee N, Smith C R, Wei S, Kim Y, Mills G B, Hortobagyi G N, Stanbridge E J and Lee E Y-H P. 2008. Cancer stem cells contribute to cisplatin resistance in Brca1/p53-mediated mouse mammary tumors. Cancer Res 68: 3243-3250.
65. Charafe-Jauffret E, Ginestier C, Iovino F, Wicinski J, Cervera N, Finetti P, Hur M-H, Diebel M E, Monville F, Dutcher J, Brown M, Viens P, Xerri L, Bertucci F, Stassi G, Dontu G, Birnbaum D and Wicha M S. 2009. Breast Cancer Cell Lines Contain Functional Cancer Stem Cells with Metastatic Capacity and a Distinct Molecular Signature. Cancer Res 69: 1302-1313.
66. Rosen J M and Jordan C T. 2009. The Increasing Complexity of the Cancer Stem Cell Paradigm. Science (New York, N.Y.) 324: 1670-1673.
67. Liu H, Patel M R, Prescher J A, Patsialou A, Qian D, Lin J, Wen S, Chang Y F, Bachmann M H, Shimono Y, Dalerba P, Adorno M, Lobo N, Bueno J, Dirbas F M, Goswami S, Somlo G, Condeelis J, Contag C H, Gambhir S S and Clarke M F. 2010. Cancer stem cells from human breast tumors are involved in spontaneous metastases in orthotopic mouse models. Proc Natl Acad Sci USA 107: 18115-18120.
68. McDermott S P and Wicha M S. 2010. Targeting breast cancer stem cells. Mol Oncol 4: 404-419.
69. Federici G, Espina V, Liotta L and Edmiston K H. 2011. Breast cancer stem cells: a new target for therapy. Oncology 25: 25-28, 30.
70. Castano Z, Fillmore C M, Kim C F and McAllister S S. 2012. The bed and the bugs: interactions between the tumor microenvironment and cancer stem cells. Semin Cancer Biol 22: 462-470.
71. Valent P, Bonnet D, De Maria R, Lapidot T, Copland M, Melo J V, Chomienne C, Ishikawa F, Schuringa J J, Stassi G, Huntly B, Herrmann H, Soulier J, Roesch A, Schuurhuis G J, Wohrer S, Arock M, Zuber J, Cerny-Reiterer S, Johnsen H E, Andreeff M and Eaves C. 2012. Cancer stem cell definitions and terminology: the devil is in the details. Nat Rev Cancer 12: 767-775.
72. Lehmann B D, Bauer J A, Chen X, Sanders M E, Chakravarthy A B, Shyr Y and Pietenpol J A. 2011. Identification of human triple-negative breast cancer subtypes and preclinical models for selection of targeted therapies. J Clin Invest 121: 2750-2767.
73. Soysal S D, Muenst S, Barbie T, Fleming T, Gao F, Spizzo G, Oertli D, Viehl C T, Obermann E C and Gillanders W E. 2013. EpCAM expression varies significantly and is differentially associated with prognosis in the luminal B HER2(+), basal-like, and HER2 intrinsic subtypes of breast cancer. Br J Cancer 108: 1480-1487.
74. Imrich S, Hachmeister M and Gires O. 2012. EpCAM and its potential role in tumor-initiating cells. Cell Adh Migr 6: 30-38.
75. Munz M, Baeuerle P A and Gires O. 2009. The emerging role of EpCAM in cancer and stem cell signaling. Cancer Res 69: 5627-5629.
76. Ladwein M, Pape U F, Schmidt D S, Schnolzer M, Fiedler S, Langbein L, Franke W W, Moldenhauer G and Zoller M. 2005. The cell-cell adhesion molecule EpCAM interacts directly with the tight junction protein claudin7. Exp Cell Res 309: 345-357.
77. Schulze K, Gasch C, Staufer K, Nashan B, Lohse A W, Pantel K, Riethdorf S and Wege H. 2013. Presence of EpCAM-positive circulating tumor cells as biomarker for systemic disease strongly correlates to survival in patients with hepatocellular carcinoma. Int J Cancer 78. Konigsberg R, Obermayr E, Bises G, Pfeiler G, Gneist M, Wrba F, de Santis M, Zeillinger R, Hudec M and Dittrich C. 2011. Detection of EpCAM positive and negative circulating tumor cells in metastatic breast cancer patients. Acta Oncol 50: 700-710.
79. Weissenstein U, Schumann A, ReifM, Link S, Toffol-Schmidt U D and Heusser P. 2012. Detection of circulating tumor cells in blood of metastatic breast cancer patients using a combination of cytokeratin and EpCAM antibodies. BMC Cancer 12: 206.
80. Zhao S, Yang H, Zhang M, Zhang D, Liu Y, Song Y, Zhang X, Li H, Ma W and Zhang Q. 2013. Circulating tumor cells (CTCs) detected by triple-marker EpCAM, CK19, and hMAM R T-PCR and their relation to clinical outcome in metastatic breast cancer patients. Cell Biochem Biophys 65: 263-273.
81. Chen Q, Ge F, Cui W, Wang F, Yang Z, Guo Y, Li L, Bremner R M and Lin P P. 2013. Lung cancer circulating 81. (continued) tumor cells isolated by the EpCAM-independent enrichment strategy correlate with Cytokeratin 19-derived CYFRA21-1 and pathological staging. Clin Chim Acta 419: 57-61.
82. Oberneder R, Weckermann D, Ebner B, Quadt C, Kirchinger P, Raum T, Locher M, Prang N, Baeuerle P A and Leo E. 2006. A phase I study with adecatumumab, a human antibody directed against epithelial cell adhesion molecule, in hormone refractory prostate cancer patients. Eur J Cancer 42: 2530-2538.
83. Schmidt M, Scheulen M E, Dittrich C, Obrist P, Marschner N, Dirix L, Ruttinger D, Schuler M, Reinhardt C and Awada A. 2010. An open-label, randomized phase II study of adecatumumab, a fully human anti-EpCAM antibody, as monotherapy in patients with metastatic breast cancer. Annals of oncology: official journal of the European Society for Medical Oncology/ESMO 21: 275-282.
84. Kurtz J E and Dufour P. 2010. Adecatumumab: an anti-EpCAM monoclonal antibody, from the bench to the bedside. Expert Opin Biol Ther 10: 951-958.
85. Marschner N, Ruttinger D, Zugmaier G, Nemere G, Lehmann J, Obrist P, Baeuerle P A, Wolf A, Schmidt M, Abrahamsson P A, Reinhardt C and Heidenreich A. 2010. Phase II study of the human anti-epithelial cell adhesion molecule antibody adecatumumab in prostate cancer patients with increasing serum levels of prostate-specific antigen after radical prostatectomy. Urol Int 85: 386-395.
86. Schmidt M, Ruttinger D, Sebastian M, Hanusch C A, Marschner N, Baeuerle P A, Wolf A, Goppel G, Oruzio D, Schlimok G, Steger G G, Wolf C, Eiermann W, Lang A and Schuler M. 2012. Phase I B study of the EpCAM antibody adecatumumab combined with docetaxel in patients with EpCAM-positive relapsed or refractory advanced-stage breast cancer. Annals of oncology: official journal of the European Society for Medical Oncology/ESMO 23: 2306-2313.
87. Munz M, Murr A, Kvesic M, Rau D, Mangold S, Pflanz S, Lumsden J, Volkland J, Fagerberg J, Riethmuller G, Ruttinger D, Kufer P, Baeuerle P A and Raum T. 2010. Side-by-side analysis of five clinically tested anti-EpCAM monoclonal antibodies. Cancer cell international 10: 44.
88. Thiel K W and Giangrande P H. 2010. Intracellular delivery of RNA-based therapeutics using aptamers. Ther Deliv 1: 849-861.
89. Keefe A D, Pai S and Ellington A. 2010. Aptamers as therapeutics. Nat Rev Drug Discov 9: 537-550.
90. Sundaram P, Kurniawan H, Byrne M E and Wower J. 2013. Therapeutic RNA aptamers in clinical trials. Eur J Pharm Sci 48: 259-271.
91. Jackson A L, Bartz S R, Schelter J, Kobayashi S V, Burchard J, Mao M, Li B, Cavet G and Linsley P S. 2003. Expression profiling reveals off-target gene regulation by RNAi. Nat Biotechnol 21: 635-637.
92. Scacheri P C, Rozenblatt-Rosen O, Caplen N J, Wolfsberg T G, Umayam L, Lee J C, Hughes C M, Shanmugam K S, Bhattacharjee A, Meyerson M and Collins F S. 2004. Short interfering RNAs can induce unexpected and divergent changes in the levels of untargeted proteins in mammalian cells. Proc Natl Acad Sci USA 101: 1892-1897.
93. Jackson A L, Burchard J, Leake D, Reynolds A, Schelter J, Guo J, Johnson J M, Lim L, Karpilow J, Nichols K, Marshall W, Khvorova A and Linsley P S. 2006. Position-specific chemical modification of siRNAs reduces "off-target" transcript silencing. RNA 12: 1197-1205.
94. Ince T A, Richardson A L, Bell G W, Saitoh M, Godar S, Karnoub A E, Iglehart J D and Weinberg R A. 2007. Transformation of different human breast epithelial cell types leads to distinct tumor phenotypes. Cancer Cell 12: 160-170.
95. Petrocca F, Altschuler G, Tan S M, Mendillo M L, Yan H, Jerry D J, Kung A L, Hide W, Ince T A and Lieberman J. 2013. A Genome-wide siRNA Screen Identifies Proteasome Addiction as a Vulnerability of Basallike Triple-Negative Breast Cancer Cells. Cancer Cell 24: 182-196.
96. Behrens S E and Luhrmann R. 1991. Immunoaffinity purification of a [U4/U6. U5] tri-snRNP from human cells. Genes Dev 5: 1439-1452.
97. Huang Y H, Chung C S, Kao D I, Kao T C and Cheng S C. 2014. Sad1 counteracts Brr2-mediated dissociation of U4/U6. U5 in tri-snRNP homeostasis. Mol Cell Biol 34: 210-220.
98. van Leuken R J, Luna-Vargas M P, Sixma T K, Wolthuis R M and Medema R H. 2008. Usp39 is essential for mitotic spindle checkpoint integrity and controls mRNA-levels of aurora B. Cell Cycle 7: 2710-2719.
99. Cheng Y, Holloway M P, Nguyen K, McCauley D, Landesman Y, Kauffman M G, Shacham S and Altura R A. 2014. XPO1 (CRM1) inhibition represses STAT3 activation to drive a survivin-dependent oncogenic switch in triple-negative breast cancer. Mol Cancer Ther 13: 675-686.
100. Wang H, Ji X, Liu X, Yao R, Chi J, Liu S, Wang Y, Cao W and Zhou Q. 2013. Lentivirus-mediated inhibition of USP39 suppresses the growth of breast cancer cells in vitro. Oncol Rep 30: 2871-2877.
101. Rios Y, Melmed S, Lin S and Liu N A. 2011. Zebrafish usp39 mutation leads to rb1 mRNA splicing defect and pituitary lineage expansion. PLoS Genet 7: e1001271.
102. Adler A S, McCleland M L, Yee S, Yaylaoglu M, Hussain S, Cosino E, Quinones G, Modrusan Z, Seshagiri S, Torres E, Chopra V S, Haley B, Zhang Z, Blackwood E M, Singh M, Junttila M, Stephan J P, Liu J, Pau G, Fearon E R, Jiang Z and Firestein R. 2014. An integrative analysis of colon cancer identifies an essential function for PRPF6 in tumor growth. Genes Dev 28: 1068-1084.
103. Yao Y D, Sun T M, Huang S Y, Dou S, Lin L, Chen J N, Ruan J B, Mao C Q, Yu F Y, Zeng M S, Zang J Y, Liu Q, Su F X, Zhang P, Lieberman J, Wang J and Song E. 2012. Targeted delivery of PLK1-siRNA by ScFv suppresses Her2+ breast cancer growth and metastasis. Sci Transl Med 4: 130ra148.
104. Hu K, Law J H, Fotovati A and Dunn S E. 2012. Small interfering RNA library screen identified polo-like kinase-1 (PLK1) as a potential therapeutic target for breast cancer that uniquely eliminates tumor-initiating cells. Breast Cancer Res 14: R22.
105. Palliser D, Chowdhury D, Wang Q Y, Lee S J, Bronson R T, Knipe D M and Lieberman J. 2006. An siRNAbased microbicide protects mice from lethal herpes simplex virus 2 infection. Nature 439: 89-94.
106. Wu Y, Navarro F, Lal A, Basar E, Pandey R K, Manoharan M, Feng Y, Lee S J, Lieberman J and Palliser D. 2009. Durable protection from Herpes Simplex Virus-2 transmission following intravaginal application of siRNAs targeting both a viral and host gene. Cell Host Microbe 5: 84-94.
107. Dontu G, Abdallah W M, Foley J M, Jackson K W, Clarke M F, Kawamura M J and Wicha M S. 2003. In vitro propagation and transcriptional profiling of human mammary stem/progenitor cells. Genes Dev 17: 1253-1270.

108. Ponti D, Costa A, Zaffaroni N, Pratesi G, Petrangolini G, Coradini D, Pilotti S, Pierotti M A and Daidone M G. 2005. Isolation and in vitro propagation of tumorigenic breast cancer cells with stem/progenitor cell properties. Cancer Res 65: 5506-5511.
109. Park S Y, Lee H E, Li H, Shipitsin M, Gelman R and Polyak K. 2010. Heterogeneity for stem cell-related markers according to tumor subtype and histologic stage in breast cancer. Clin Cancer Res 16: 876-887.
110. Leth-Larsen R, Terp M G, Christensen A G, Elias D, Kuhlwein T, Jensen O N, Petersen O W and Ditzel H J. 2012. Functional heterogeneity within the CD44 high human breast cancer stem cell-like compartment reveals a gene signature predictive of distant metastasis. Mol Med 18: 1109-1121.
111. Ricardo S, Vieira A F, Gerhard R, Leitao D, Pinto R, Cameselle-Teijeiro J F, Milanezi F, Schmitt F and Paredes J. 2011. Breast cancer stem cell markers CD44, CD24 and ALDH1: expression distribution within intrinsic molecular subtype. J Clin Pathol 64: 937-946.
112. Polyak K and Weinberg R A. 2009. Transitions between epithelial and mesenchymal states: acquisition of malignant and stem cell traits. Nat Rev Cancer 9: 265-273.
113. Biddle A, Liang X, Gammon L, Fazil B, Harper L J, Emich H, Costea D E and Mackenzie I C. 2011. Cancer Stem Cells in Squamous Cell Carcinoma Switch between Two Distinct Phenotypes That Are Preferentially Migratory or Proliferative. Cancer Res 71: 5317-5326.
114. Scheel C, Eaton E N, Li S H-J, Chaffer C L, Reinhardt F, Kah K-J, Bell G, Guo W, Rubin J, Richardson A L and Weinberg R A. 2011. Paracrine and Autocrine Signals Induce and Maintain Mesenchymal and Stem Cell States in the Breast. Cell 145: 926-940.
115. Visvader J E and Stingl J. 2014. Mammary stem cells and the differentiation hierarchy: current status and perspectives. Genes Dev 28: 1143-1158.
116. Smalley M, Piggott L and Clarkson R. 2013. Breast cancer stem cells: Obstacles to therapy. Cancer Lett 338: 57-62.
117. Chaffer C L, Marjanovic N D, Lee T, Bell G, Kleer C G, Reinhardt F, D'Alessio A C, Young R A and Weinberg R A. 2013. Poised chromatin at the ZEB 1 promoter enables breast cancer cell plasticity and enhances tumorigenicity. Cell 154: 61-74.
118. Liu S, Cong Y, Wang D, Sun Y, Deng L, Liu Y, Martin-Trevino R, Shang L, McDermott S P, Landis M D, Hong S, Adams A, D'Angelo R, Ginestier C, Charafe-Jauffret E, Clouthier S G, Bimbaum D, Wong S T, Zhan M, Chang J C and Wicha M S. 2014. Breast Cancer Stem Cells Transition between Epithelial and Mesenchymal States Reflective of their Normal Counterparts. Stem Cell Reports 2: 78-91.
119. Dykxhoorn D M, Wu Y, Xie H, Yu F, Lal A, Petrocca F, Martinvalet D, Song E, Lim B and Lieberman J. 2009. miR-200 enhances mouse breast cancer cell colonization to form distant metastases. PLoS One 4:e7181.
120. Korpal M, Ell B J, Buffa F M, Ibrahim T, Blanco M A, Celia-Terrassa T, Mercatali L, Khan Z, Goodarzi H, Hua Y, Wei Y, Hu G, Garcia B A, Ragoussis J, Amadori D, Harris A L and Kang Y. 2011. Direct targeting of Sec23a by miR-200s influences cancer cell secretome and promotes metastatic colonization. Nat Med 17: 1101-1108.
121. Stankic M, Pavlovic S, Chin Y, Brogi E, Padua D, Norton L, Massague J and Benezra R. 2013. TGF-beta-Id1 signaling opposes Twist1 and promotes metastatic colonization via a mesenchymal-to-epithelial transition. Cell Rep 5: 1228-1242.
122. Yu F, Yao H, Zhu P, Zhang X, Pan Q, Gong C, Huang Y, Hu X, Su F, Lieberman J and Song E. 2007. let7 Regulates Self Renewal and Tumorigenicity of Breast Cancer Cells. Cell 131: 1109-1123.
123. Douville J, Beaulieu R and Balicki D. 2009. ALDH1 as a functional marker of cancer stem and progenitor cells. Stem cells and development 18: 17-25.
124. Seigel G M, Campbell L M, Narayan M and Gonzalez-Fernandez F. 2005. Cancer stem cell characteristics in retinoblastoma. Mol Vis 11: 729-737.
125. Clarke R B. 2005. Isolation and characterization of human mammary stem cells. Cell Prolif 38: 375-386.
126. Clarke R B, Anderson E, Howell A and Potten C S. 2003. Regulation of human breast epithelial stem cells. Cell Prolif 36 Suppl 1: 45-58.
127. Clarke R B, Spence K, Anderson E, Howell A, Okano H and Potten C S. 2005. A putative human breast stem cell population is enriched for steroid receptor-positive cells. Dev Biol 277: 443-456.
128. Kagara N, Huynh K T, Kuo C, Okano H, Sim M S, Elashoff D, Chong K, Giuliano A E and Hoon D S. 2012. Epigenetic regulation of cancer stem cell genes in triple-negative breast cancer. Am J Pathol 181: 257-267.
129. Wang X Y, Penalva L O, Yuan H, Linnoila R I, Lu J, Okano H and Glazer R I. 2010. Musashi1 regulates breast tumor cell proliferation and is a prognostic indicator of poor survival. Mol Cancer 9: 221.
130. Liu G, Yuan X, Zeng Z, Tunici P, Ng H, Abdulkadir I R, Lu L, Irvin D, Black K L and Yu J S. 2006. Analysis of gene expression and chemoresistance of C D 133+ cancer stem cells in glioblastoma. Mol Cancer 5: 67.
131. Polytarchou C, Iliopoulos D and Struhl K. 2012. An integrated transcriptional regulatory circuit that reinforces the breast cancer stem cell state. Proc Natl Acad Sci USA 109: 14470-14475.
132. Pietersen A, Evers B, Prasad A, Tanger E, Cornelissensteijger P, Jonkers J and Vanlohuizen M. 2008. Bmi1 Regulates Stem Cells and Proliferation and Differentiation of Committed Cells in Mammary Epithelium. Curr Biol 18: 1094-1099.
133. Hoenerhoff M J, Chu I, Barkan D, Liu Z-y, Datta S, Dimri G P and Green J E. 2009. BMI1 cooperates with H-RAS to induce an aggressive breast cancer phenotype with brain metastases. Oncogene 28: 3022-3032.
134. Ge Q, Dallas A, Ilves H, Shorenstein J, Behlke M A and Johnston B H. 2010. Effects of chemical modification on the potency, serum stability, and immunostimulatory properties of short shRNAs. RNA 16: 118-130.
135. Behlke M A. 2008. Chemical modification of siRNAs for in vivo use. Oligonucleotides 18: 305-319.
136. Collingwood M A, Rose S D, Huang L, Hillier C, Amarzguioui M, Wiiger M T, Soifer H S, Rossi J J and Behlke M A. 2008. Chemical modification patterns compatible with high potency dicer-substrate small interfering RNAs. Oligonucleotides 18: 187-200.
137. Chu T C, Twu K Y, Ellington A D and Levy M. 2006. Aptamer mediated siRNA delivery. Nucleic Acids Res 34: e73.
138. Santulli-Marotto S, Nair S K, Rusconi C, Sullenger B and Gilboa E. 2003. Multivalent RNA aptamers that inhibit CTLA-4 and enhance tumor immunity. Cancer Res 63: 7483-7489.
139. Dollins C M, Nair S, Boczkowski D, Lee J, Layzer J M, Gilboa E and Sullenger B A. 2008. Assembling OX40 aptamers on a molecular scaffold to create a receptor-activating aptamer. Chem Biol 15: 675-682.

140. Kim Y, Cao Z and Tan W. 2008. Molecular assembly for high-performance bivalent nucleic acid inhibitor. Proc Natl Acad Sci USA 105: 5664-5669.

141. Tian L and Heyduk T. 2009. Bivalent ligands with long nanometer-scale flexible linkers. Biochemistry 48: 264-275.

142. Wullner U, Neefl, Eller A, Kleines M, Tur M K and Barth S. 2008. Cell-specific induction of apoptosis by rationally designed bivalent aptamer-siRNA transcripts silencing eukaryotic elongation factor 2. Curr Cancer Drug Targets 8: 554-565.

143. Zhou J, Neff C P, Swiderski P, Li H, Smith D D, Aboellail T, Remling-Mulder L, Akkina R and Rossi J J. 2013. Functional in vivo delivery of multiplexed anti-HIV-1 siRNAs via a chemically synthesized aptamer with a sticky bridge. Mol Ther 21: 192-200.

144. Zhou J, Tiemann K, Chomchan P, Alluin J, Swiderski P, Burnett J, Zhang X, Forman S, Chen R and Rossi J. 2013. Dual functional BAFF receptor aptamers inhibit ligand-induced proliferation and deliver siRNAs to NHL cells. Nucleic Acids Res 41: 4266-4283.

145. Kim D H, Behlke M A, Rose S D, Chang M S, Choi S and Rossi J J. 2005. Synthetic dsRNA Dicer substrates enhance RNAi potency and efficacy. Nat Biotechnol 23: 222-226.

146. Shu Y, Haque F, Shu D, Li W, Zhu Z, Kotb M, Lyubchenko Y and Guo P. 2013. Fabrication of 14 different RNA nanoparticles for specific tumor targeting without accumulation in normal organs. RNA 19: 767-777.

147. Guo P. 2011. RNA Nanotechnology: methods for synthesis, conjugation, assembly and application of RNA nanoparticles. Methods 54: 201-203.

148. Meyer D L, Schultz J, Lin Y, Henry A, Sanderson J, Jackson J M, Goshorn S, Rees A R and Graves S S. 2001. Reduced antibody response to streptavidin through site-directed mutagenesis. Protein Sci 10: 491-503.

149. Stalder L, Heusermann W, Sokol L, Trojer D, Wirz J, Hean J, Fritzsche A, Aeschimann F, Pfanzagl V, Basselet P, Weiler J, Hintersteiner M, Morrissey D V and Meisner-Kober N C. 2013. The rough endoplasmatic reticulum is a central nucleation site of siRNA-mediated RNA silencing. Embo J 32: 1115-1127.

150. Rehman Z U, Hoekstra D and Zuhorn I S. 2013. Mechanism of Polyplex- and Lipoplex-Mediated Delivery of Nucleic Acids: Real-Time Visualization of Transient Membrane Destabilization without Endosomal Lysis. ACS Nano 7: 3767-3777.

151. Cho Y W, Kim J D and Park K. 2003. Polycation gene delivery systems: escape from endosomes to cytosol. J Pharm Pharmacol 55: 721-734.

152. Song E, Zhu P, Lee S K, Chowdhury D, Kussman S, Dykxhoorn D M, Feng Y, Palliser D, Weiner D B, Shankar P, Marasco W A and Lieberman J. 2005. Antibody mediated in vivo delivery of small interfering RNAs via cell-surface receptors. Nat Biotechnol 23: 709-717.

153. Wooddell C I, Rozema D B, Hossbach M, John M, Hamilton H L, Chu Q, Hegge J O, Klein J J, Wakefield D H, Oropeza C E, Deckert J, Roehl I, Jahn-Hofmann K, Hadwiger P, Vornlocher H P, McLachlan A and Lewis D L. 2013. Hepatocyte-targeted RNAi Therapeutics for the Treatment of Chronic Hepatitis B Virus Infection. Mol Ther 21: 973-985.

154. Wong S C, Klein J J, Hamilton H L, Chu Q, Frey C L, Trubetskoy V S, Hegge J, Wakefield D, Rozema D B and Lewis D L. 2012. Co-injection of a targeted, reversibly masked endosomolytic polymer dramatically improves the efficacy of cholesterol-conjugated small interfering RNAs in vivo. Nucleic Acid Ther 22: 380-390.

155. Shim M S and Kwon Y J. 2011. Dual mode polyspermine with tunable degradability for plasmid DNA and siRNA delivery. Biomaterials 32: 4009-4020.

156. Novina C D, Murray M F, Dykxhoorn D M, Beresford P J, Riess J, Lee S K, Collman R G, Lieberman J, Shankar P and Sharp P A. 2002. siRNA-directed inhibition of HIV-1 infection. Nat Med 8: 681-686.

157. Berezhnoy A, Brenneman R, Bajgelman M, Seales D and Gilboa E. 2012. Thermal Stability of siRNA Modulates Aptamer-conjugated siRNA Inhibition. Mol Ther Nucleic Acids 1: e51.

158. Krutzfeldt J, Rajewsky N, Braich R, Rajeev K G, Tuschl T, Manoharan M and Stoffel M. 2005. Silencing of microRNAs in vivo with 'antagomirs'. Nature 438: 685-689.

159. Wolfrum C, Shi S, Jayaprakash K N, Jayaraman M, Wang G, Pandey R K, Rajeev K G, Nakayama T, Charrise K, Ndungo E M, Zimmermann T, Koteliansky V, Manoharan M and Stoffel M. 2007. Mechanisms and optimization of in vivo delivery of lipophilic siRNAs. Nat Biotechnol 25: 1149-1157.

160. Liu H, Moynihan K D, Zheng Y, Szeto G L, Li A V, Huang B, Van Egeren D S, Park C and Irvine D J. 2014. Structure-based programming of lymph-node targeting in molecular vaccines. Nature 507: 519-522.

161. Chen X, Iliopoulos D, Zhang Q, Tang Q, Greenblatt M B, Hatziapostolou M, Lim E, Tam W L, Ni M, Chen Y, Mai J, Shen H, Hu D Z, Adoro S, Hu B, Song M, Tan C, Landis M D, Ferrari M, Shin S J, Brown M, Chang J C, Liu X S and Glimcher L H. 2014. XBP1 promotes triple-negative breast cancer by controlling the HIF1alpha pathway. Nature 508: 103-107.

162. Tallarida R J. 2010. Combination analysis. Adv Exp Med Biol 678: 133-137.

Example 6

Material and Methods
Cell Culture

Human BPE and BPLER cells were grown in WIT medium (Stemgent). MB468 were transduced with a luciferase reporter. All other human cell lines were obtained from ATCC and grown in MEM (MCF7, BT474), McCoy's 5A (SKBR3), RPMI1640 (HCC1806, HCC1143, HCC1937, HCC1954, HCC1187, MB468, T47D) or DMEM (MB231, BT549, MB436) all supplemented with 10% FBS, 1 mM L-glutamine and penicillin/streptomycin (Gibco) unless otherwise indicated. 4T1 mouse breast cancer cells, were grown in 10% FBS DMEM. For in vivo imaging, MB468 cells stably expressing Firefly luciferase (MB468-luc) were used and MB231 cells stably expressing Firefly luciferase and mCherry (MB231-luc-mCherry) were selected after infection with pLV-Fluc-mCherry-Puro lentivirus. MB231 Cells were selected with puromycin.

For uptake and silencing treatment, cells were plated at low density (10,000 cells/well in 96-well plates) and treated immediately. All AsiC and siRNA treatments were performed in either OptiMEM or WIT medium. Cell viability was assessed by CellTiter-Glo (Promega) or by Trypan-Blue staining in 96-well plates.

For colony formation assay, 1,000 viable cells were treated for 6 h in round bottom 96-well plates and then transferred to 10-cm plates in serum-containing medium. Medium was replaced every 3 d. After 8-14 d, cells were fixed in methanol (~20C) and stained with crystal violet. For sphere formation assay, 1,000/ml viable cells were treated for 6 h in round bottom 96-well plates and then cultured in suspension in serum-free DMEM/F121:1 (Invitrogen), supplemented with EGF (20 ng/ml, BD Biosciences), B27 (1:50, Invitrogen), 0.4% bovine serum albumin (Sigma) and 4 μg/ml insulin (Sigma). Spheres were counted after 1 or 2 weeks.

siRNA Transfection

Cells were transfected with Dharmafect I per the manufacturer's protocol. See below herein for all siRNA sequences.

Flow Cytometry.

For flow cytometry, cells were stained as previously described (Yu, F. et al (2007). let-7 Regulates Self Renewal and Tumorigenicity of Breast Cancer Cells. Cell 131, 1109-1123. ), briefly, direct immunostaining of EpCAM and AKT1 was performed using 1:50 dilutions of hAb for 30-60 minutes at 4° C. (BioLegend/BD). Cells were stained in PBS containing 0.5% FCS, 1 mM EDTA, and 25 mM HEPES. Samples were washed twice in the same buffer. Data was acquired using FACS-Canto II (BD Biosciences). Analyses were performed in triplicate and 10,000 gated events/sample were counted. All data analysis was performed using FlowJo (Treestar Inc.).

RNA Analysis.

qRT-PCR analysis was performed as described (Petrocca, F., et al. (2008). E2F1-regulated microRNAs impair TGF-beta-dependent cell-cycle arrest and apoptosis in gastric cancer. Cancer Cell 13, 272-286). Briefly, total RNA was extracted with Trizol (Invitrogen) and cDNA prepared from 1000 ng total RNA using Thermoscript RT kit (Invitrogen) as per the manufacturer's SYBR Green Master Mix (Applied Biosystems) and a BioRad C1000 Thermal Cycler (Biorad). Relative CT values were normalized to GAPDH and converted to a linear scale.

Collagenase Digestion of Human Breast Tissue.

Fresh breast or colon cancer and control biopsies were received from the UMASS Tissue Bank, samples were cut into 3×3×3 mm samples and placed in a 96well plate with 100 ul RPMI. Samples were treated with either Alexa647-siRNA-GFP, Alexa647-chol-siRNA-GFP or Cy3-AsiC-GFP for 24 hr. Samples were photographed and digested. Three samples from each treatment were pooled and put in 10 ml RPMI containing 1 mg/ml collagenase II (Sigma-Aldrich) for 30 minutes at 37° C. with shaking. Samples were disrupted in a gentleMACS dissociator (Miltenyi) using the spleen program for 30 minutes at 37° C. both before and after collagenase digestion. Cell suspensions were passed through a 70-Gm cell strainer (BD Falcon), washed with 30 ml RPMI, and stained for flow cytometry.

Animal Experiments

All animal procedures were performed with Harvard Medical School and Boston Children's Hospital Animal Care and Use Committee approval. Nude mice were purchased from the Jackson Laboratory.

In Vivo Experiments.

For tumor initiation studies 8-week old female Nu/J mice (Stock #002019, Jackson Laboratories) were injected subcutaneously with MB468-luc ($5\times10^6$) cells pretreated for 24 h with EpCAM-AsiC-GFP, EpCAM-AsiC-PLK1 or untreated. Cells were trypsinized with Tryple Express (Invitrogen), resuspended in WIT media and injected subcutaneously in the flank. Following intraperitoneal injection of 150 mg/kg D-luciferin (Caliper Life Sciences) luminescent images of the whole body were taken every 5 days for a total of 20 days using the IVIS Spectra system (Caliper Life Sciences).

For AsiC uptake experiments MB468-luc ($5\times10^6$) and MB231-luc-mCherry ($5\times10^5$) cells trypsinized with Tryple Express (Invitrogen), were resuspended in a 1:1 WIT-Matrigel solution and injected subcutaneously in the flank of 8-week old female Nu/J mice (Stock #002019, Jackson Laboratories). Tumors size was analyzed daily using the IVIS Spectra system (Caliper Life Sciences). After 5 days tumors were clearly visible and mice were injected subcutaneously in the neck area with Alexa750-EpCAM-AsiC-GFP (0.5 mg/kg). Localization of the AsiC compared to the tumor was tested every 48 h for 7 days.

For tumor inhibition studies, MB468-luc ($5\times10^6$) and MB231-luc-mCherry ($5\times10^5$) cells trypsinized with Tryple Express (Invitrogen), resuspended in a 1:1 WIT-Matrigel solution and injected subcutaneously in the flank of 8-week old female Nu/J mice (Stock #002019, Jackson Laboratories). Tumors size was analyzed daily using the IVIS Spectra, after 5 days tumors were clearly visible. Mice bearing tumors of comparable size were randomized into 5 groups and treated with 5 mg/kg of EpCAM-AsiC-PLK1, EpCAM-AsiC-GFP, EpCAM-Aptamer, siRNA-PLK1 or untreated. Mice were treated every 72 h for 14 days.

All Images were analyzed using Living Image® software (Caliper Life Sciences).

Statistical Analysis

Student's t-tests, computed using Microsoft Excel, were used to analyze the significance between the treated samples and the controls where the test type was set to one-tail distribution and two-sample equal variance.

Results:

EpCAM-AsiC Specifically Targets Basal a Breast Cancer Cells

Figure 21A:
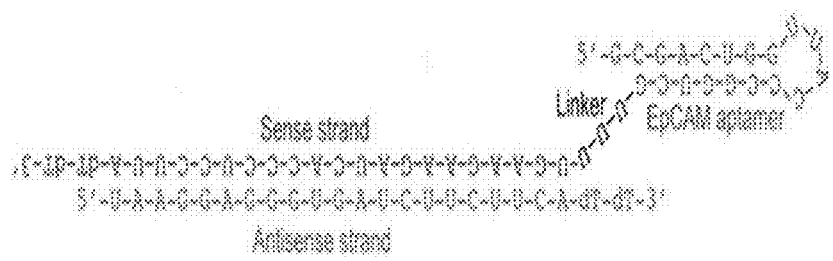
FIGS. 21A-21D demonstrate that EpCAM aptamer specifically targets Basal A breast cancer cells.
Figures 21B, 21C:
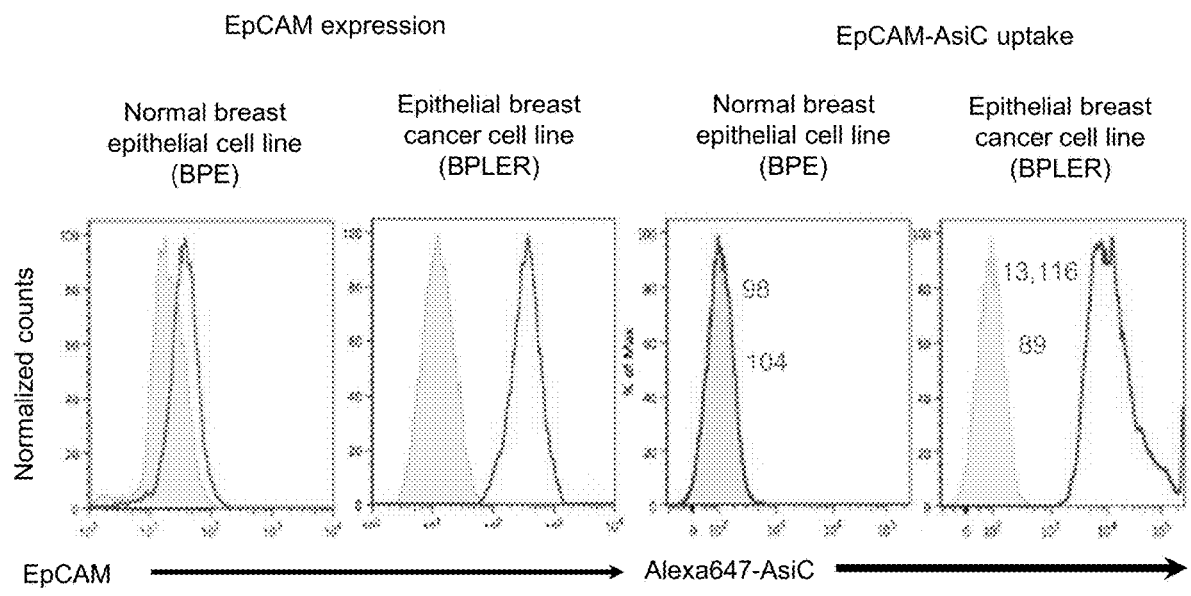
Figure 21D:
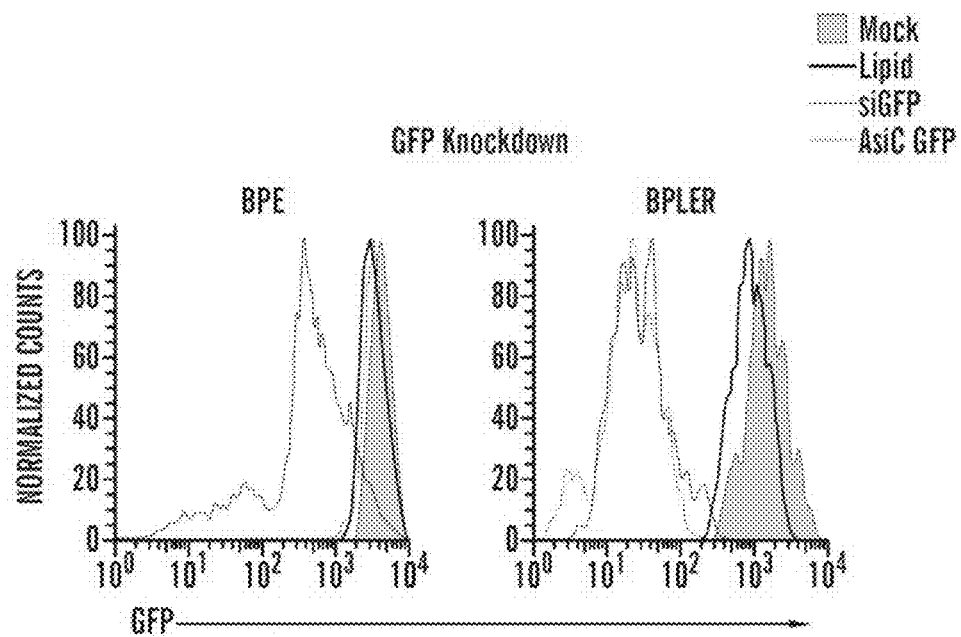
Figure 22:
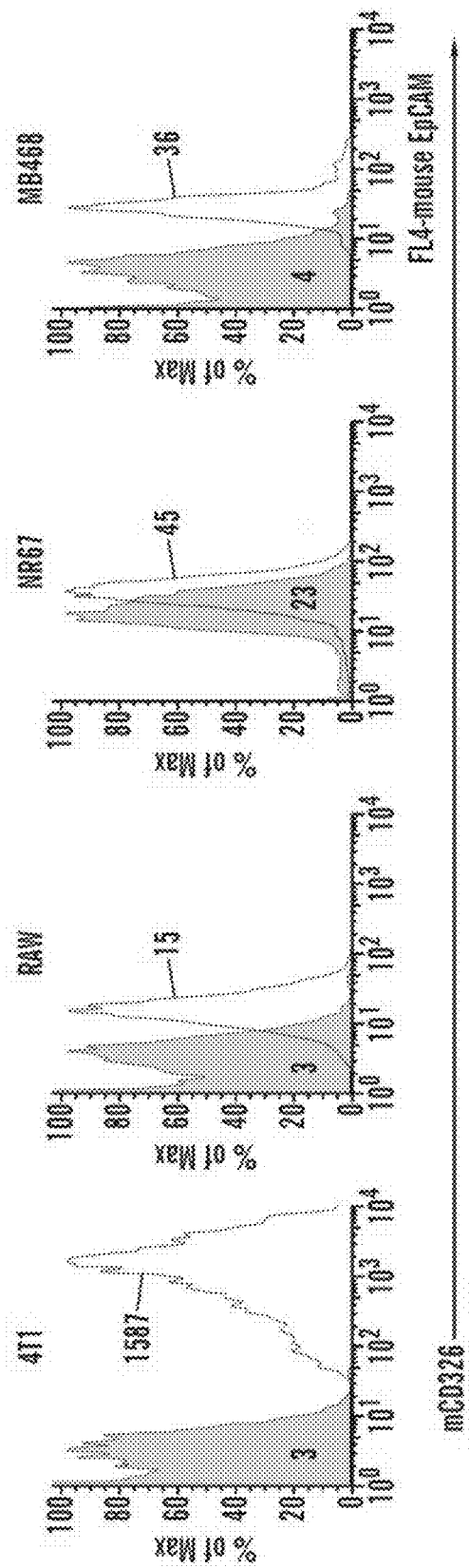
FIG. 22 depicts graphs demonstrating that EpCAM aptamers do not bind mouse EpCAM. Mouse ESA (EpCAM) levels were determined using flow cytometry with a mCD326 antibody. 4T1 cell an epithelial mouse breast cancer cell line displayed high expression levels of EpCAM. Both RAW (mouse monocyte cell line) and MB468 (human basal A cell line) displayed an increase in EpCAM expression but much smaller than 4T1 cells. A mouse mesanchymal cancer cell line (67NR) displayed a minimal increase in EpCAM expression. Uptake experiments demonstrated that EpCAM-Aptamer was not taken up by neither 4T1 nor 67NR cells.
Figure 22:
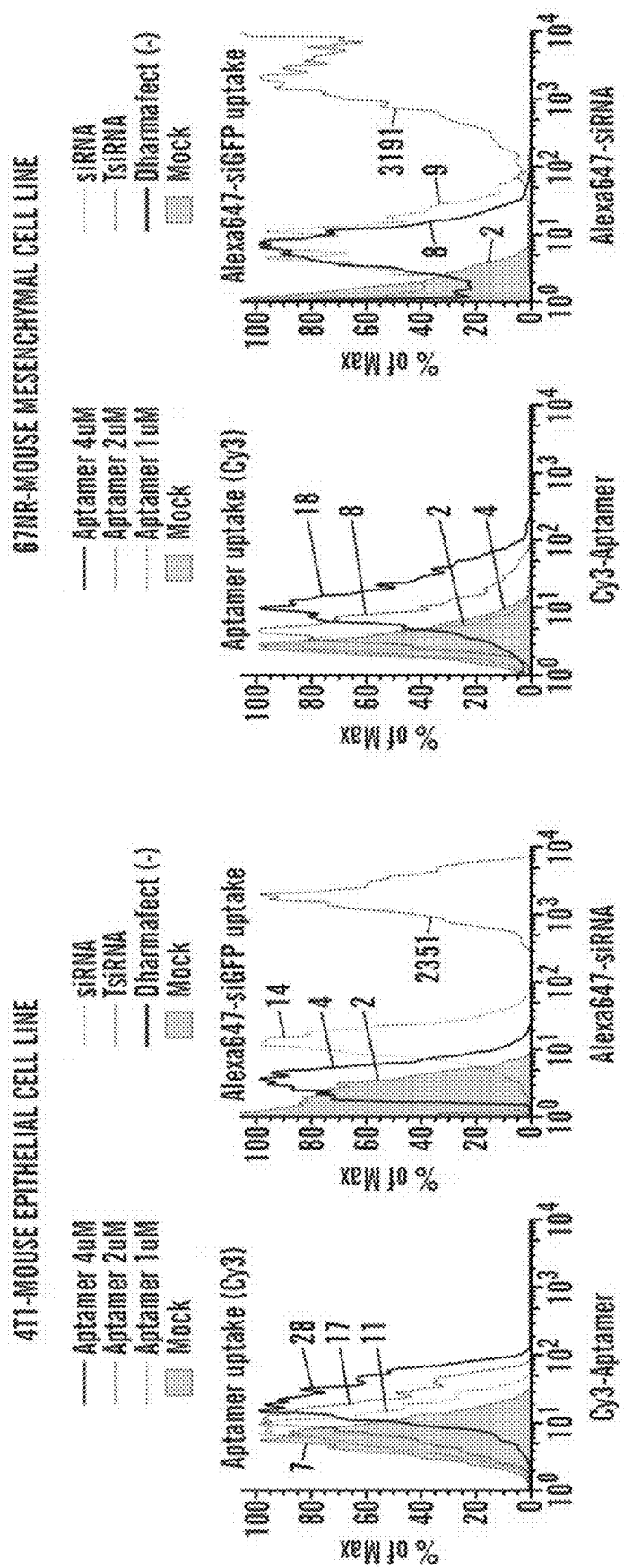
Figure 23:
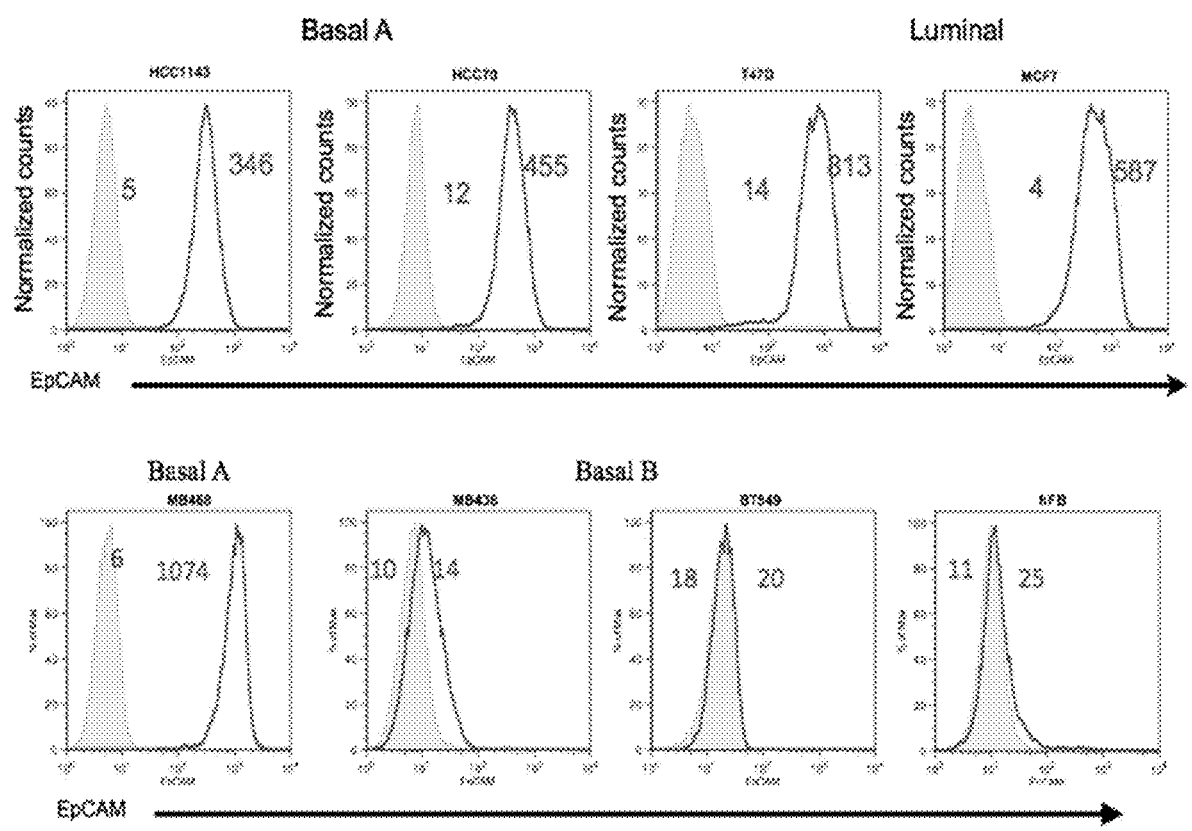
FIG. 23 depicts graphs demonstrating that EpCAM is over expressed in basal A and luminal but not basal B breast cancer cell lines. Representative FACS plots of 8 different breast cancer cell lines, testing EpCAM expression levels by flow cytometery using a hEpCAM Antibody. EpCAM is over expressed in all basal A and luminal cells lines and not in basal B. (mock, shaded gray EpCAM, black)

An EpCAM aptamer was selected by Systematic Evolution of Ligands by Exponential Enrichment (SELEX) for binding to human EpCAM. The optimized aptamer is only 19 nucleotides (nt) long and binds to human EpCAM with 12 nM affinity (Shigdar S. et. al. RNA aptamer against a cancer stem cell marker epithelial cell adhesion molecule affinity Cancer Sci. 2011 May; 102(5):991-8). It does not bind to mouse EpCAM (FIG. 22). Its short length is ideal for an AsiC drug, since RNAs of ~60 nt or less in length can be cheaply and efficiently chemically synthesized. The EpCAM-AsiCs we designed consist of a longer strand of 42-44 nt (19 nt aptamer+3 nt linker+20-22 nt sense (inactive) strand of the siRNA), which is annealed to a 20-22 nt antisense (active) siRNA strand (FIG. 21A). Both strands were commercially synthesized with 2'-fluoropyrimidine substitutions, which confer enhanced stability in serum and other bodily fluids (T1/2>>3 d) and prevent stimulation of innate immune RNA sensors. We first assessed EpCAM cell surface levels by flow cytometry in a panel of human breast cell lines (Table 2, FIG. 23). EpCAM was highly expressed by all basal A and luminal cancer cell lines tested, but not by basal B cancer cell lines. EpCAM staining of normal human epithelial cells (BPE) was close to background, while its transformed derivative BPLER had bright EpCAM staining (FIG. 21B). Several of a handful of designs tested (with the sense and antisense strands exchanged and several linkers) knocked down gene expression in EpCAM+, but not EpCAM−, cell lines, but the design that worked best in dose response experiments is shown in FIG. 21A. To test whether EpCAM-AsiC will be specifically taken up by EpCAM+ cell lines we labeled the 3' end of the antisense strand of the AsiC with Alexa647. BPLER basal A TNBC cell line overexpresses EpCAM, while BPE a control epithelial breast cell line do not (FIG. 21B). Both BPLER and BPE cell were treated with the Alexa647-EpCAM-AsiC targeting GFP, only BPLER displayed uptake of the AsiC (FIG. 21C). We further validated the selective uptake of EpCAM-AsiC, by treating EpCAM+ MDA-MB-468 cells and BPE controls with Cy3 labeled EpCAM-Aptamer (the 19 nt aptamer was labeled with Cy3 at the 5' end). After 22 and 43 hours we clearly saw selective AsiC uptake in EpCAM+ cells (data not shown). To understand the ability of EpCAM AsiC to selectively trigger gene knockdown we chose BPLER and BPE cell lines which stably overexpress GFP. Cells were treated with either EpCAM-AsiCs targeting GFP or transfected with GFP-siRNA as a positive control (FIG. 21D). Although transfection with GFP-siRNAs knocked down gene expression equivalently in BPE and BPLER, EpCAM-AsiCs selectively knocked down expression in BPLER without any lipid; knockdown was uniform and comparable to that achieved with lipid transfection.

These results clearly indicate that EpCAM-AsiC is selectively taken-up by EpCAM+ cell and can induce gene knockdown specifically in these EpCAM+ cells. Also we show that using different fluorophores (Alexa647 or Cy3) at different locations (5' of aptamer or 3' of anti-sense strand) did not impact the specific uptake.

Figure 24A:
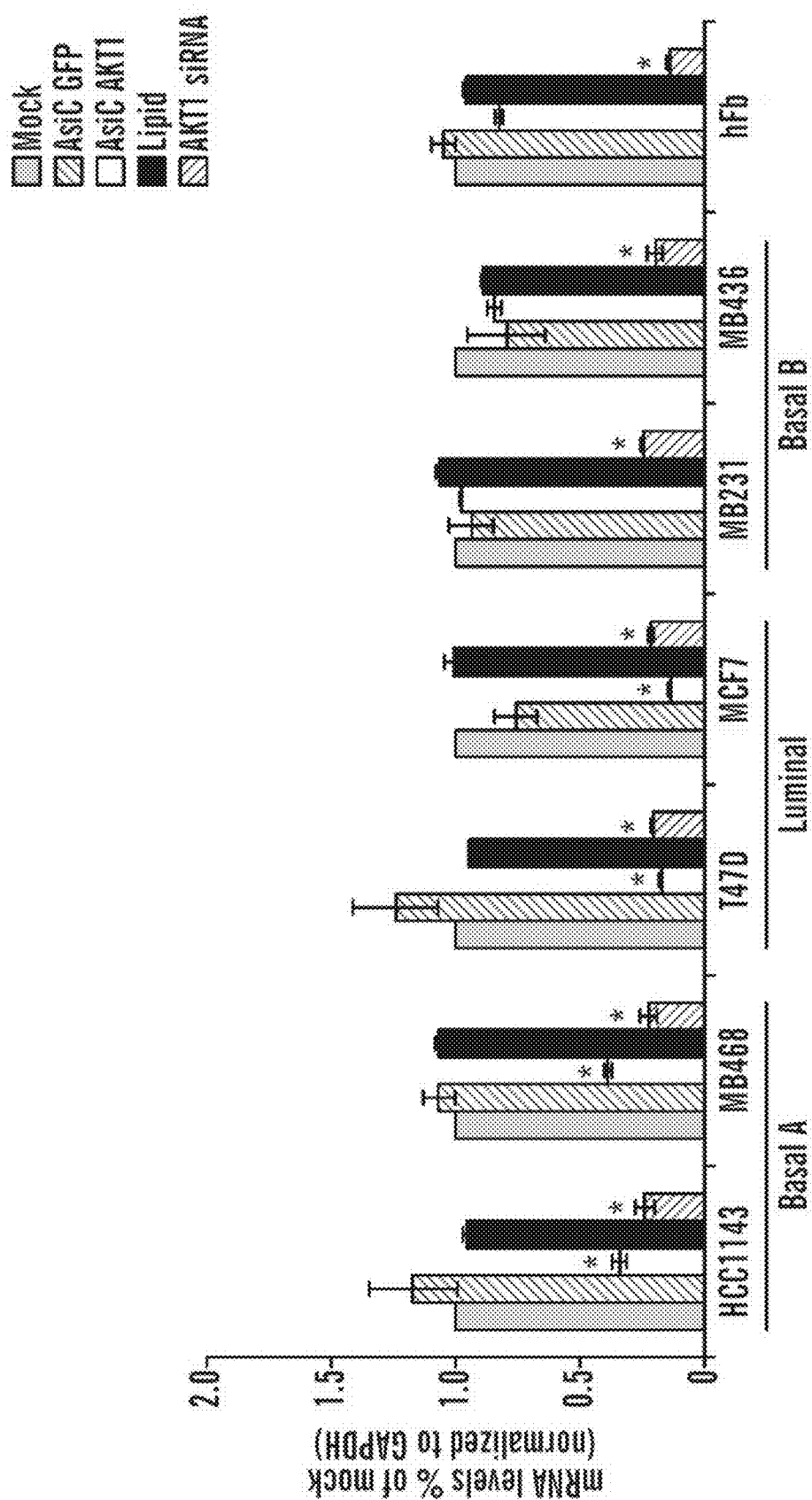
FIGS. 24A-24F demonstrate that EpCAM AsiC specifically silences gene expression in Basal A breast cancer cells. EpCAM-AsiC targeting AKT1 selectively knocks-down AKT1 mRNA (FIG. 24A) and protein (FIGS. 24B, 24C) expression in basal A and luminal breast cancer cell lines and not in basal B or human fibroblasts (hFb). Transfection with siRNA targeting AKT1 induces gene knockdown in all cell lines, while treatment with EpCAM-AsiC targeting GFP doesn't effect AKT1 mRNA and protein levels (* p<0.05, p<0.01). Plots of AKT1 Protein and gene Knockdown comparing the effect of EpCAM-AsiC to siRNA transfection. EpCAM-AsiC induced knockdown correlates with EpCAM expression (FIG. 24D, 24E). (n=3; mean±SEM normalized to mock; *P<0.05, **P<0.01, 2-tailed t test).
Figure 24B:
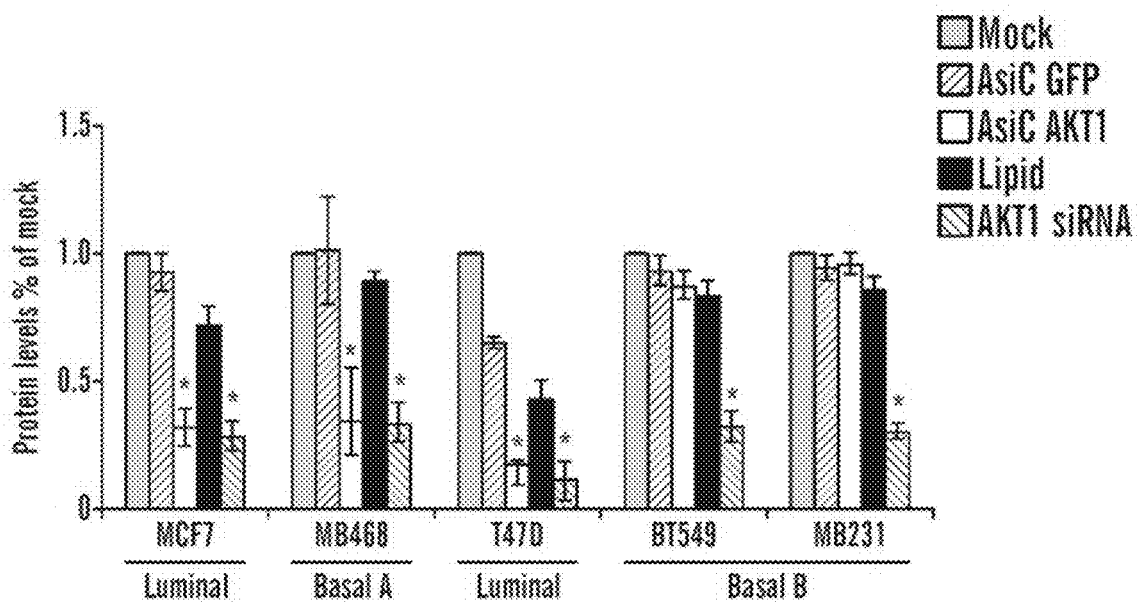
Figure 24C:
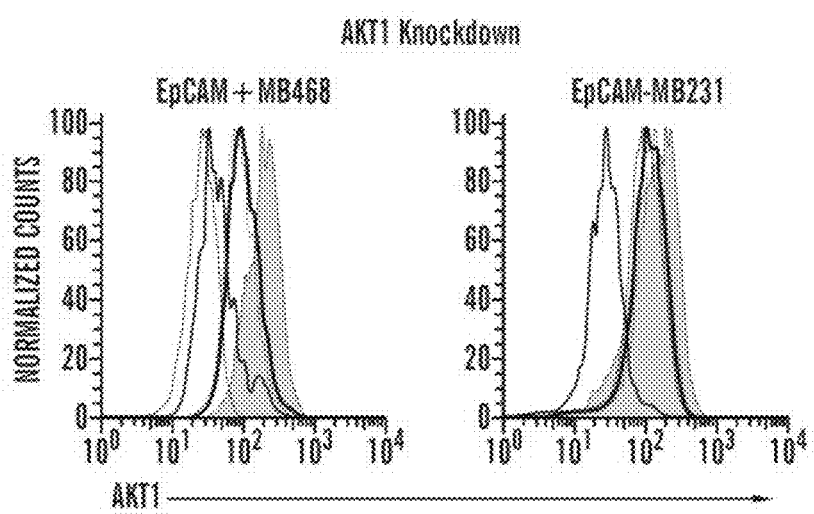
Figure 24D:
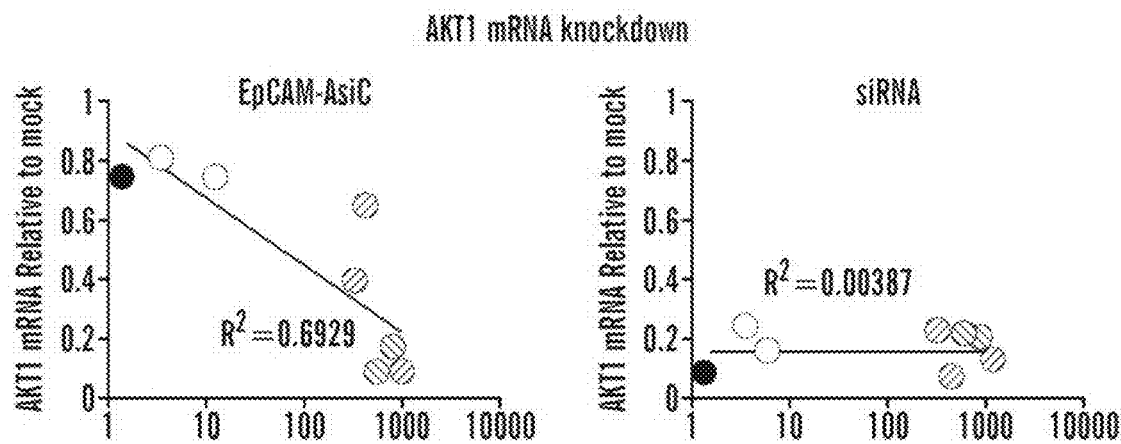
Figure 24E:
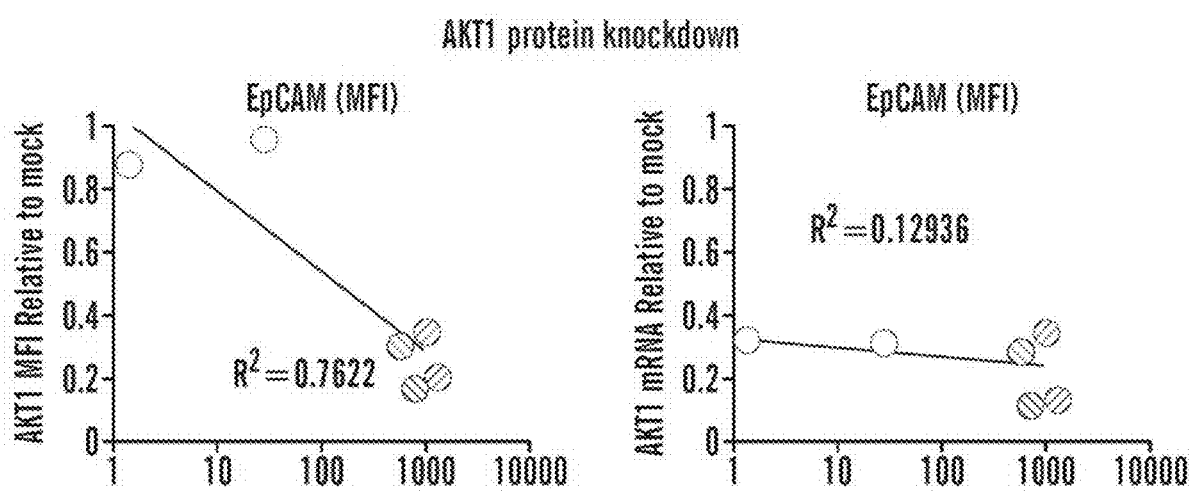

Specific mRNA and protein knockdown was further analyzed on 8 different breast cancer cells lines. Here we show that basal A and luminal cell lines which overexpress EpCAM displayed decreased AKT1 mRNA and protein levels following treatment with EpCAM-AsiC targeting AKT1. Transfection with AKT1-siRNA had a similar knockdown effect on all cell lines, while using EpCAM-AsiC targeting GFP as a control did not effect any of the cell lines (FIG. 24A, 24B). There was a clear correlation between EpCAM expression level and the knockdown effect both at an mRNA and protein level (FIG. 24D, 24E).

Figure 25A:
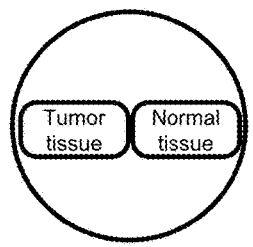
FIGS. 25A-25E demonstrate that human TNBC tissue specifically takes up Cy3-EpCAM aptamers.
Figure 25B:
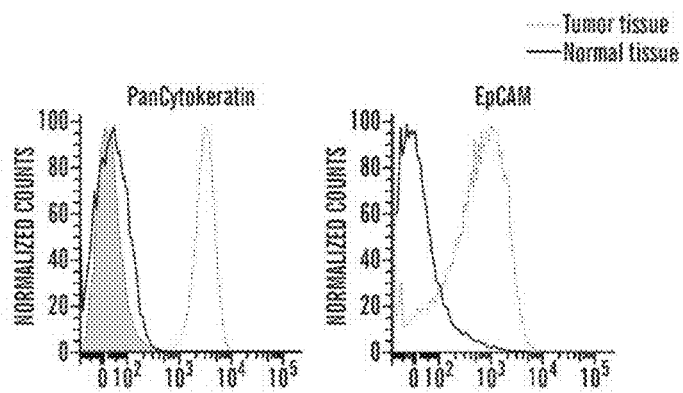
Figure 25C:
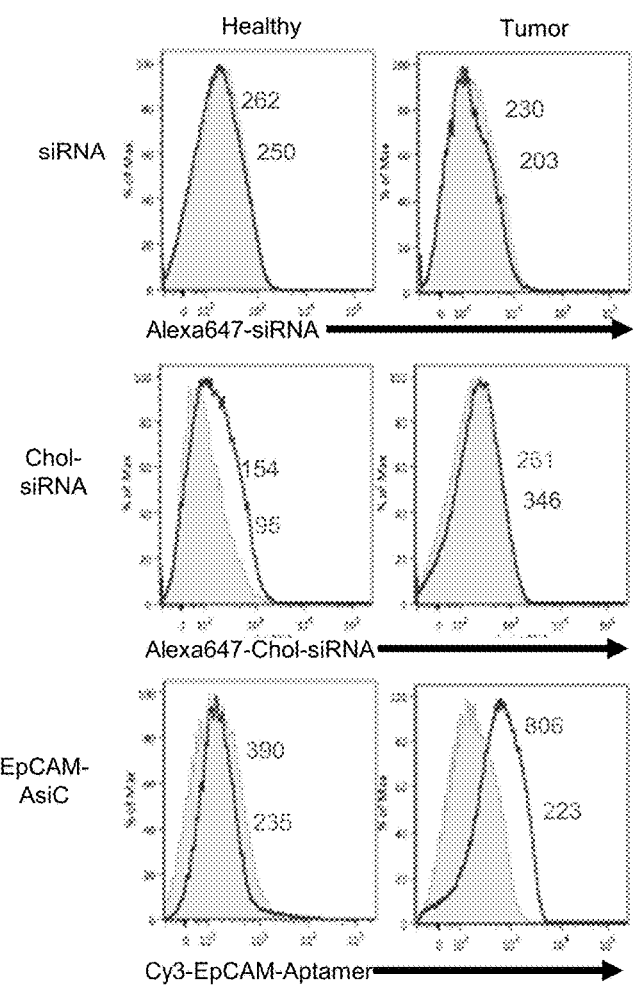
Figure 25D:
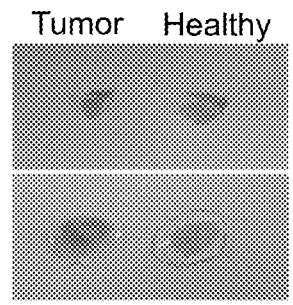
Figure 25E:
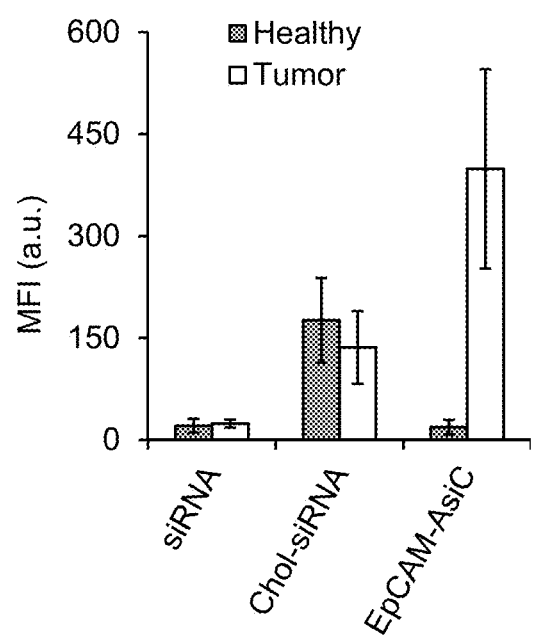
Figure 26:
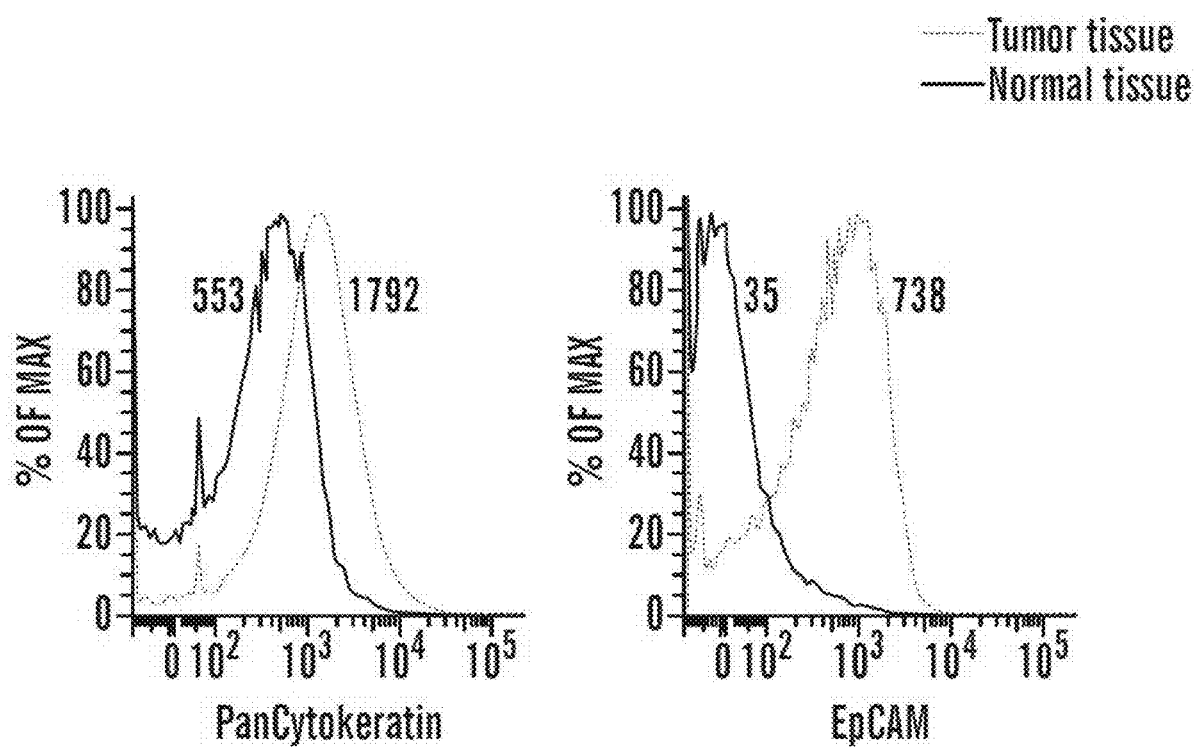
FIG. 26 depicts graphs demonstrating that EpCAM-AsiC is taken up by both healthy and colon cancer biopsies. Cy3-EpCAM-AsiC targeting GFP, Alexa647-siRNA-GFP or Alexa647-chol-siRNA-GFP (2 µM of each) were added to colon cancer and control explants and incubated for 24 h before tissues were digested with collagenase to a single cell suspension and analyzed by flow cytometry. Representative histograms show that EpCAM-AsiC, siRNA and chol-siRNA penetrated both tumor and healthy tissue with similar efficacy.
Figure 26:
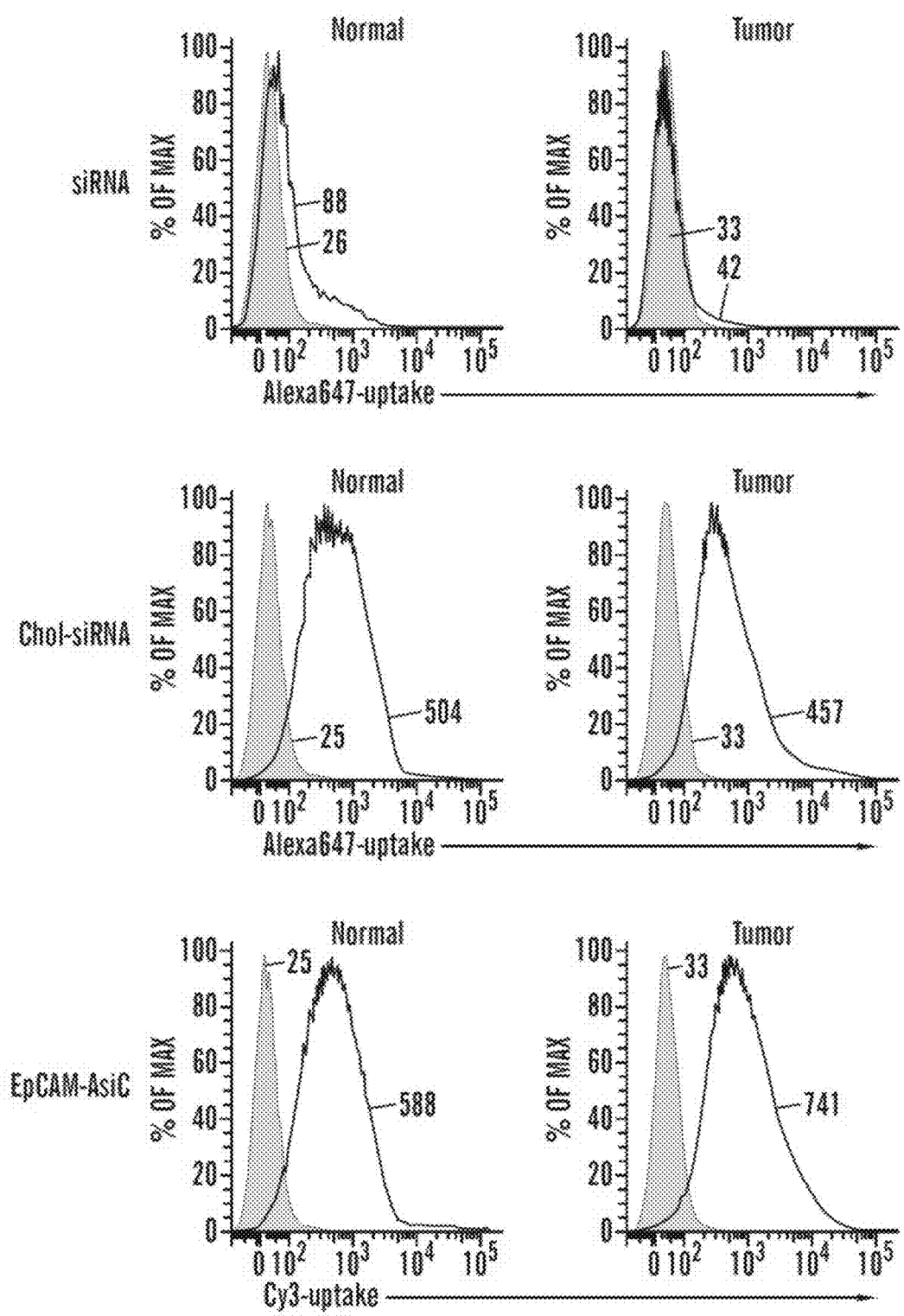

To determine if human epithelial breast cancer tissue can specifically take up EpCAM-AsiC compared to healthy human tissue. We tested human epithelial breast cancer biopsies and healthy control tissue from the same patient. Samples were treated for 24 h with Alexa647-siRNA-GFP, Alexa647-chol-siRNA-GFP or Cy3-EpCAM-AsiC-GFP (FIG. 25A). Human tumor samples display higher EpCAM level as well as higher cytokeratin levels, an epithelial cell marker (FIG. 25B). Labeled siRNA and chol-siRNA penetrated both tumor and healthy tissue with similar efficacy while EpCAM-AsiC was selectively uptaken by the tumor tissue and not by the healthy control tissue sample (FIG. 25C, 25D). The uptake experiment was repeated in tumors from three different patients, each biopsy received was tested 3 times for each treatment. A summary of all three patients (FIG. 25E). Colon cancer biopsies were tested and compared to matched healthy samples, both healthy and tumor colon samples were able to take up Cy3-EpCAM-AsiC-GFP (FIG. 26)

Figure 27A:
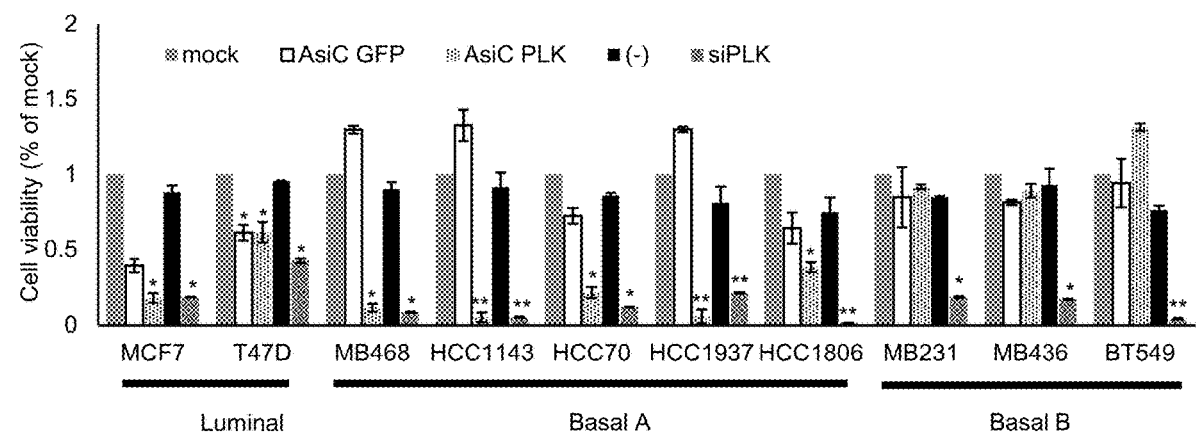
FIGS. 27A-27D demonstrate that EpCAM AsiC targeting PLK1 specifically inhibits cell proliferation in Basal A breast cancer cells. The effect of EpCAM-AsiC targeting PLK1 on cell proliferation was tested on 10 breast cancer cell lines representative of basal A, B and luminal cell lines using cell-titer-glo assay (CTG). EpCAM-AsiC targeting PLK1 decreased cell proliferation in both basal A and luminal cell lines while having no effect on basal B cells (FIG. 27A). A correlation was seen between EpCAM expression levels and cell viability (FIG. 27B). Basal A (EpCAM+GFP−) cell were co-cultured with BPE (EpCAM-GFP+) cells and treated with EpCAM-AsiC targeting PLK1 or untreated. Untreated co-culture displayed a similar ration of cells following EpCAM-AsiC targeting PLK1 treatment the ratio of EpCAM+ cells decreased and EpCAM− cells increased.
Figure 27B:
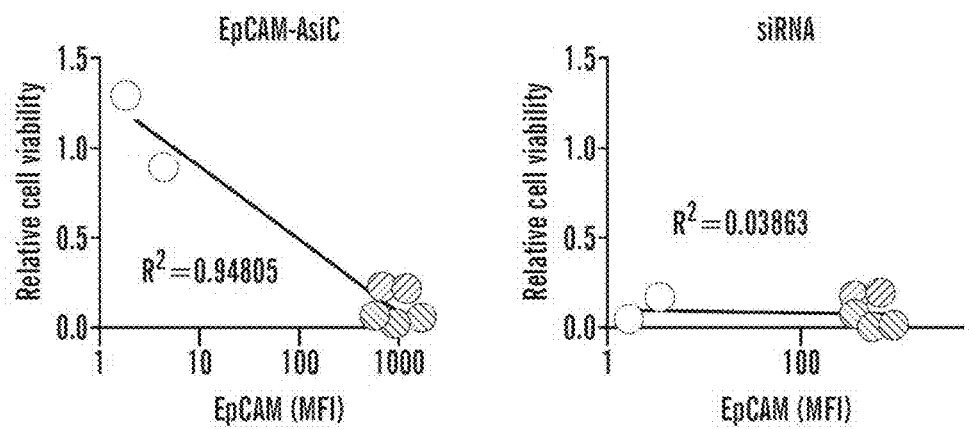
Figure 27C:
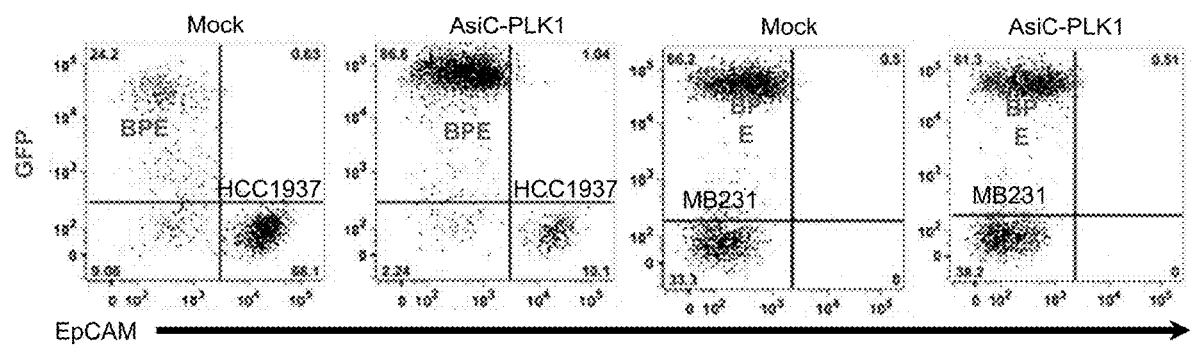
Figure 27D:
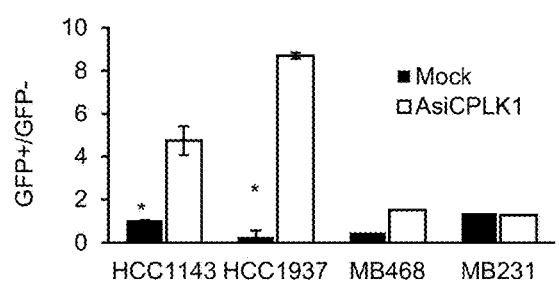

EpCAM AsiC Targeting PLK1 Specifically Inhibits Cell Proliferation in Basal a Breast Cancer Cells To understand whether EpCAM-AsiC can specifically target basal A and luminal breast cancer cells and inhibit proliferation we designed an EpCAM-AsiC targeting PLK1. PLK1 is a known trigger for G2/NI transition. The effect of EpCAM-AsiC targeting PLK1 on cell proliferation was tested on 10 breast cancer cells representative of basal A, B and luminal cell lines. EpCAM-AsiC targeting PLK1 decreased cell proliferation in both basal A and luminal cell lines while having no effect on basal B cells (FIG. 27A). A correlation was seen between EpCAM expression levels and cell viability (FIG. 27B). To understand if EpCAM-AsiC will specifically target EpCAM+ cells in a mix cell population HCC1937 (EpCAM+GFP−) cell were co-cultured with BPE (EpCAM-GFP+) cells and treated with EpCAM-AsiC targeting PLK1 or untreated. Untreated co-culture displayed a similar ration of cells (41% BPE and 59% HCC1937). Following EpCAM-AsiC targeting PLK1 treatment the ratio of EpCAM+ cells decreased to 17% and EpCAM− cells increased to 83% indicating that the EpCAM-AsiC specifically suppresses proliferation in EpCAM+ cells. The co-culture was repeated with other basal A cell lines (MB468 and HCC1143) similar reults were obtained. When BPE cells were grown in a co-culture with basal B cell (MB231) the ratio between BPE and MB231 cells stayed the same regardless of the EpCAM-AsiC treatment (66% BPE and 33% MB231 in untreated co-culture and 61% BPE and 38% MB231 following EpCAM-AsiC treatment) (FIG. 27C, 27D).

Figure 28:
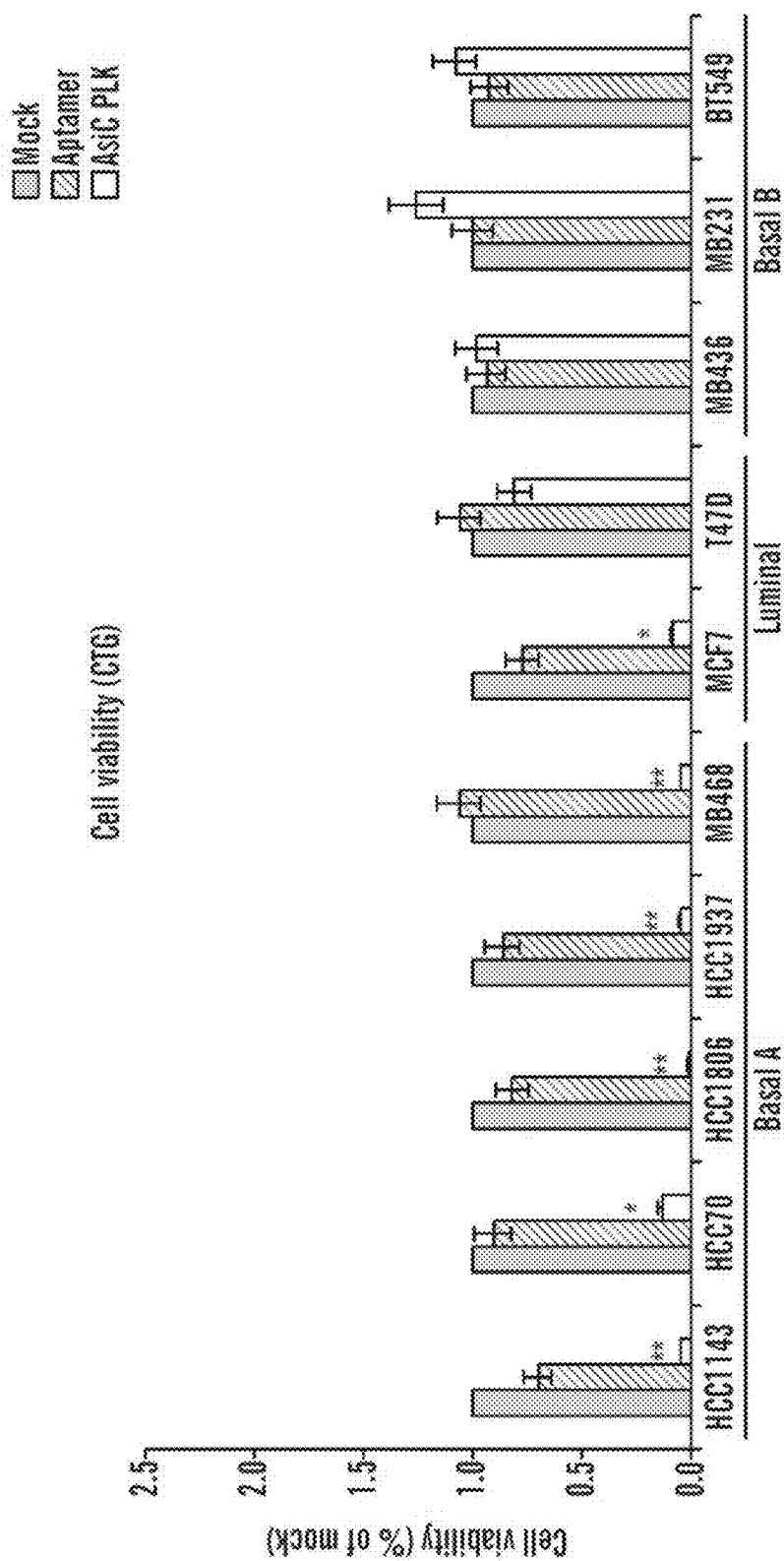
FIG. 28 depicts a graph demonstrating specific decrease in cell viability in Basal A breast cancer cell lines is PLK1 dependent. Ten different breast cancer cell lines representing basal A, B and luminal cells were treated with either EpCAM-AsiC targeting PLK1 or just the EpCAM-aptamer and compared to untreated controls. None of the cell lines treated with EpCAM-aptamer displayed decrease in cell viability, while basal A and luminal cell lines displayed a decrease in cell viability following treatment with EpCAM-AsiC targeting PLK1.

To determine if the suppression effect of EpCAM-AsiC targeting PLK1 on cell viability in basal A cells is triggered by EpCAM-aptamer binding to the EpCAM receptor or by silencing of PLK1 we treated cell with the EpCAM-aptamer and compared to EpCAM-AsiC targeting PLK1. EpCAM-AsiC targeting PLK1 suppressed cell viability in basal A and luminal cell lines while EpCAM-aptamer didn't effect cell viability in any of the cell lines (FIG. 28).

One of our goals was to understand if EpCAM-AsiC targeting PLK1 could be utilized to target T-ICs within a tumor. To examine whether it might be active not only against the bulk of cells within basal-A and luminal cells, but also against the T-ICs within them, we treated basal A,B and luminal cell lines with EpCAM-AsiC targeting PLK1 for 24 hr and tested the effect on in vitro colony and sphere formation. Basal A and luminal cell lines that form colonies when plated at clonal density (HCC1937, HCC1954, HCC1806 and MCF7) lost the ability to form colonies after EpCAM-AsiC targeting PLK1 treatment, whereas resistant clones emerged after paclitaxel treatment (FIG. FIG. 29A-29B). In contrast, exposure to EpCAM-AsiC targeting PLK1 did not effect colony formation of basal B (MB231 and BT549) cells, while paclitaxel had a similar effect to basal A and luminal cells, reducing colony formation but still resistant clones invariably emerged. Likewise, among breast cancer cell lines that form spheres under non-adherent conditions, paclitaxel, reduced sphere-formation in all (FIG. 29C), while EpCAM-AsiC targeting PLK1 specifically inhibited sphere formation in basal A and luminal. To examine whether pretreatment with EpCAM-AsiC targeting PLK1 will inhibit or delay tumor initiation in-vivo we treat MB-468-luc cell with EpCAM-AsiC targeting PLK1, GFP or untreated for 24 h and injected the cells into the flank of nude mice. Using the IVIS Spectra imaging system we followed tumor growth every 5 days for 20 days. Cells pretreated with EpCAM-AsiC targeting PLK1 did not show any sign of a tumor after 20 days while untreated cells or cells pretreated with EpCAM-AsiC targeting GFP displayed tumors after 5 days and the tumor size grew during the 20 days (FIG. 29D).

Figure 30A:
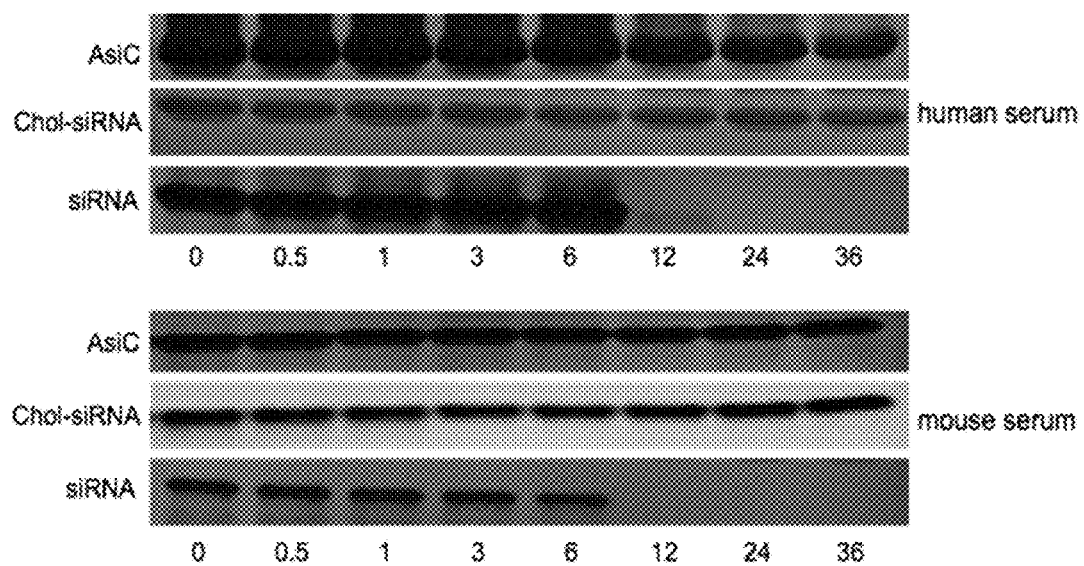
FIGS. 30A-30B demonstrate that EpCAM AsiC is stable in human and mouse serum for 36 hours. EpCAM-AsiC targeting GFP synthesized using 2'-fluoro-pyrimidines, chemically-stabilized 21-mer cholesterol-conjugated GFP-siRNAs (chol-siRNA), and unmodified 21-mer GFP-siRNA, each in 100 ul PBS, which were added to 100 µl of of human or mouse serum. At regular intervals, 20 µL was removed, and resuspended in gel loading buffer and frozen at −80° C. before being electrophoresed on a denaturing PAGE gel.
Figure 30B:
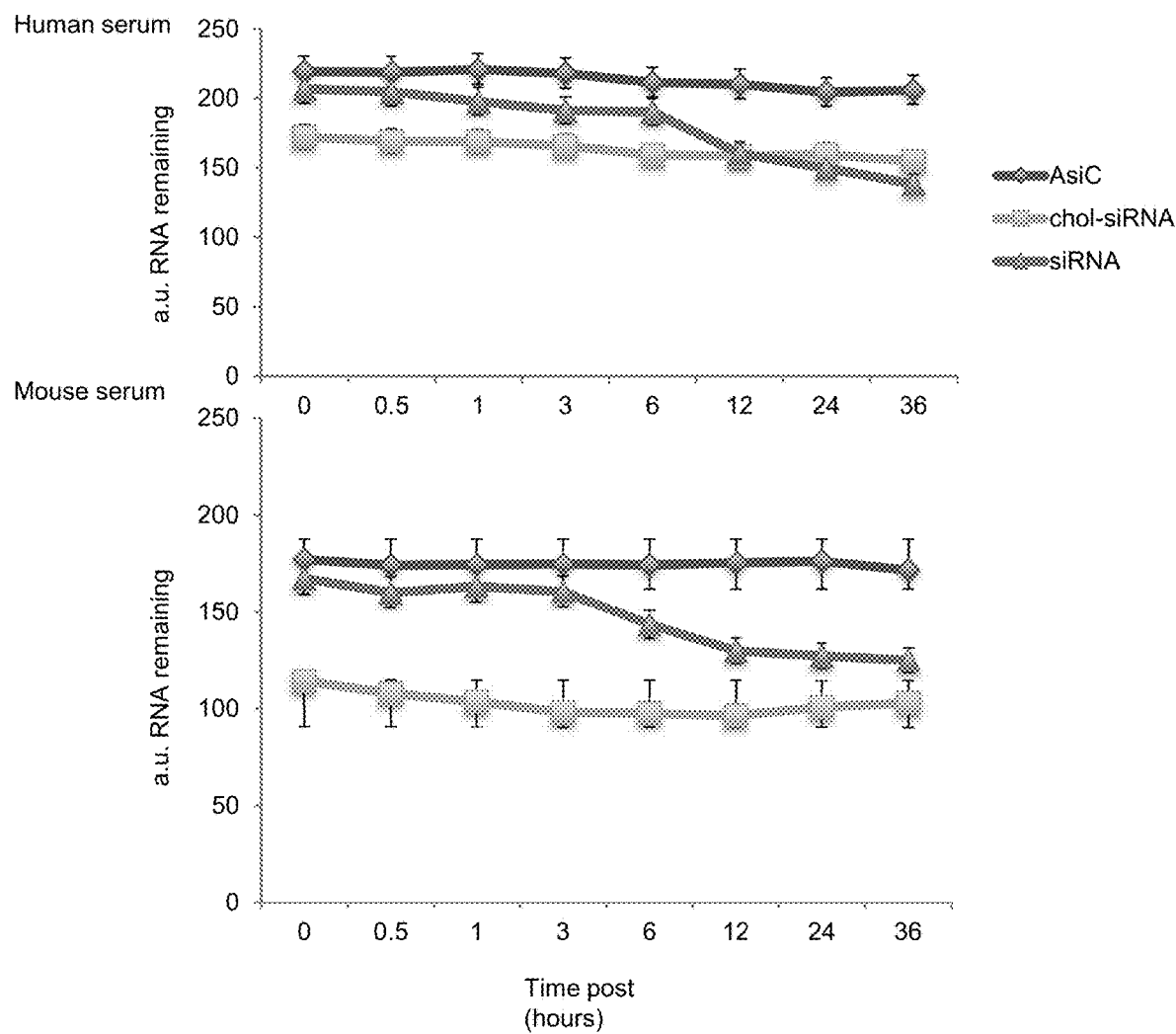
Figure 31A:
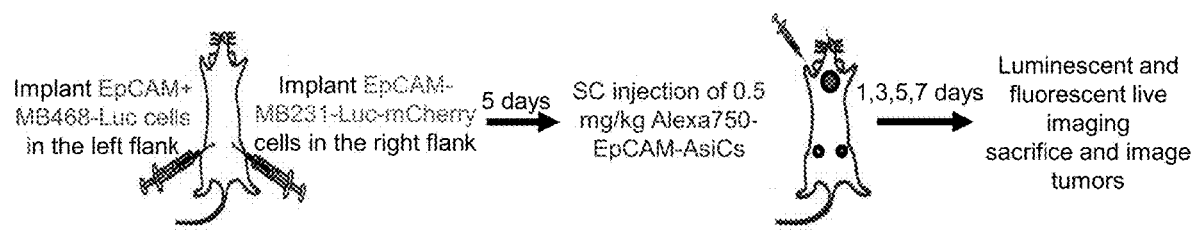
FIGS. 31A-31B demonstrate selective uptake of Alexa750-EpCAM-AsiCs into EpCAM+ tumors.
Figure 31B:
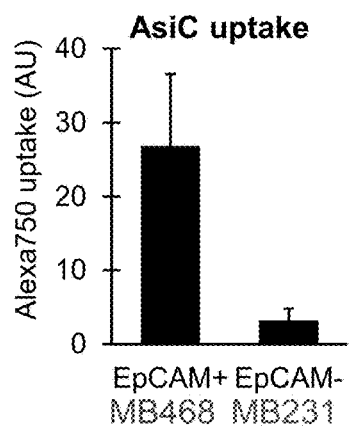

EpCAM AsiC Targeting PLK1 Specifically Inhibits Tumor Initiation and Growth in Basal a Breast Cancer Cells We were able to show that EpCAM-AsiC can specifically target EpCAM+ cell in-vitro, to understand whether this ability is retained in-vivo we first tested the stability of EpCAM-AsiC in mouse and human serum over time. We saw that EpCAM-AsiC is stable for at least 36 h in both mouse and human serum (FIG. 30A-30B). We injected nude mice with both MB468-luc and MB231-luc-mCherry cells on opposite flanks. After 5 days when tumors were clearly visible using the IVIS Spectra imaging system, we injected mice s.c. (in the neck area, as far away as possible from the tumor cells injection sight) with 0.5 mg/kg of Alexa750 labeled EpCAM-AsiC targeting GFP. The mice were imaged immediately after injection and again after 24, 48 hr and 5 days to follow the AsiC localization. The Alexa750 labeled EpCAM-AsiC targeting GFP was clearly localized to the MB468-luc tumor (EpCAM+) and not the MB231-luc-mCherry (EpCAM−) tumor (FIG. 31A). Analysis of 7 mice indicates a significant increase of Alexa750 in MB468 (EpCAM+) tumors (FIG. 31B). At day 5 the tumors were removed and visualized to validate that the Alexa750 labeled EpCAM-AsiC targeting GFP indeed entered the tumors. Increased level of Alexa750 was negatively correlated with mCherry levels (data not shown)

Figure 32A:
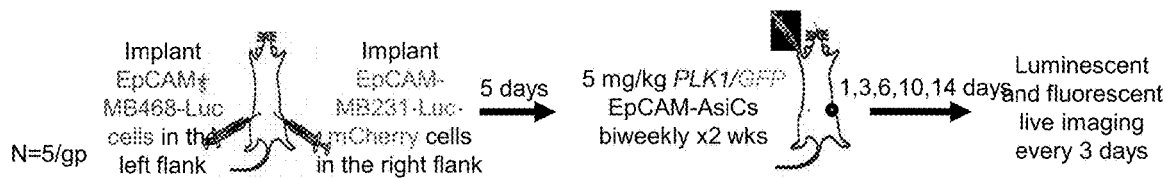
FIGS. 32A-32B demonstrate that EpCAM AsiC targeting PLK1 specifically inhibits tumor growth in Basal A breast cancer cells.
Figure 32B:
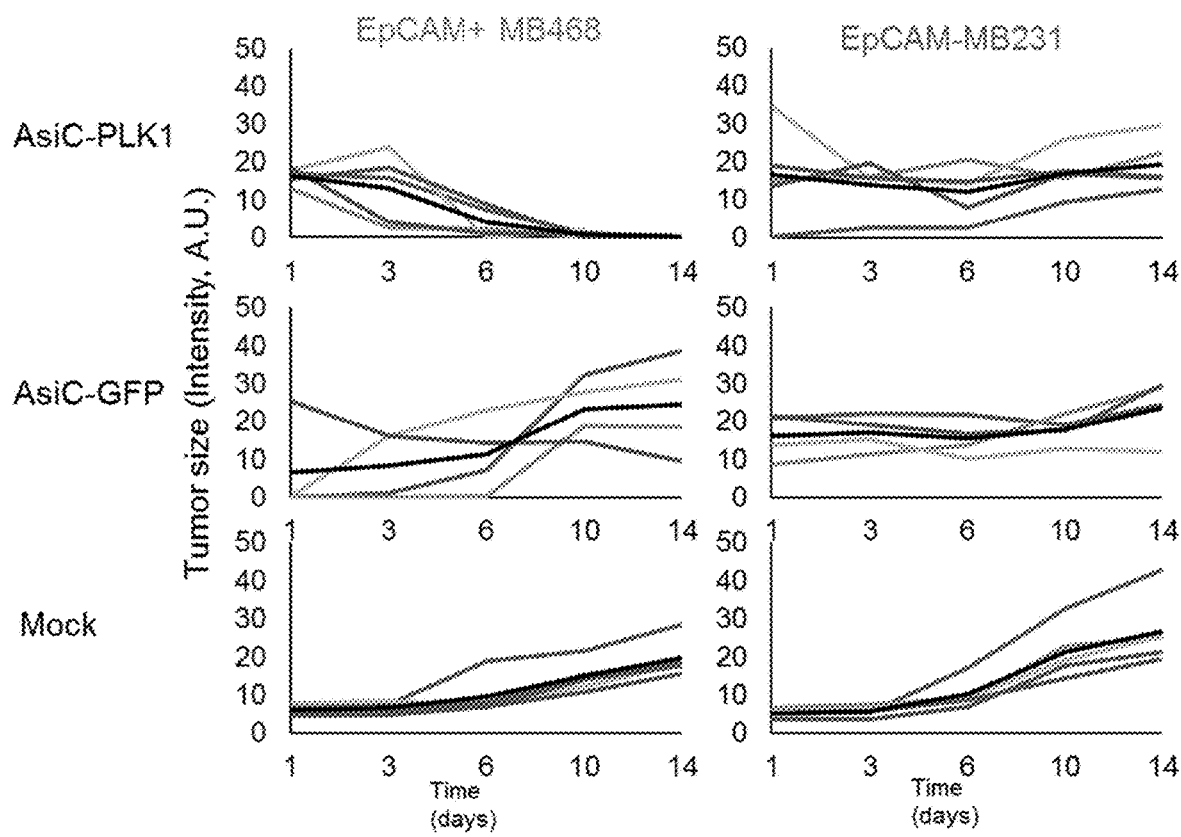

Our cell viability and tumor initiation data indicates that EpCAM AsiC targeting PLK1 specifically inhibits tumor growth in Basal A breast cancer cells. To test this hypothesis we injected nude mice with ether EpCAM− basal B cells (MB231-luc-mCherry cells) or EpCAM+ basal A cells (MB468-luc cells). Once tumors were clearly visible by the IVIS imaging system mice were treated with 5 mg/Kg of either EpCAM AsiC targeting PLK1 or GFP every 72 h for 14 days or left untreated. Mice were imaged using the IVIS Spectra imaging system every 72 h for 14 days. MB468-luc tumors treated with EpCAM-AsiC targeting PLK1 shrunk in size as early as 6 days post treatment and in many mice completely disappeared after 14 days, while MB231-luc-mCherry tumors remained unchanged. We believe that EpCAM-AsiC did have some effect even though it was targeting GFP since basal A tumor treated with GFP AsiC did not increase in size as much as control untreated mice. Treatment with EpCAM-Asic targeting GFP suppress tumor growth in both EpCAM+ and EpCAM-tumors but didn't eliminate tumors. Untreated tumors both EpCAM+ and EpCAM− increased in size over the 14 days (FIG. 32A-32B).

TABLE 1

EpCAM-AsiC Sequences

| AsiC construct | Sequence | SEQ ID NO |
|---|---|---|
| EpCAM PLK1 sense | GCG ACU GGU UAC CCG GUC GUU UUG AAG AAG AUC ACC CUC CUU AdTdT | 1 |
| EpCAM PLK1 anti-sense | UAA GGA GGG UGA UCU UCU UCA dTdT | 2 |
| EpCAM AKT1 sense | GCG ACU GGU UAC CCG GUC GUU GCU GGA GAA CCU CAU GCU GdTdT | 23 |
| EpCAM AKT1 anti-sense | CAG CAU GAG GUU CUC CAG CdTdT | 24 |
| EpCAM GFP sense | GCG ACU GGU UAC CCG GUC GUU UGG CUA CGU CCA GGA GCG CAdTdT | 25 |
| EpCAM GFP anti-sense | UGC GCU CCU GGA CGU AGC CdTdT | 26 |
| siGFP sense | UGG CUA CGU CCA GGA GCG | 27 |
| siGFP antisense | UGC GCU CCU GGA CGU AGC | 28 |
| siAKT1 sense | GCU GGA GAA CCU CAU GCU G | 29 |
| siAKT1 antisense | CAG CAU GAG GUU CUC CAG C | 30 |
| siPLK1 sense | UGA AGA AGA UCA CCC UCC UUA | 31 |
| siPLK1 antisense | UAA GGA GGG UGA UCU UCU UCA | 32 |

TABLE 2

EpCAM mean fluorescence intensity (MFI) of human breast cell lines

| Cell line | Subtype | EpCAM MFI |
|---|---|---|
| BPE | immortalized normal epithelium | 2 |
| BPLER | basal-A TNBC | 109 |
| HMLER | unclassified TNBC (myoepithelial) | 72 |
| HCC1143 | basal-A TNBC | 1068 |
| HCC1937 | basal-A TNBC | 806 |
| HCC1187 | basal-A TNBC | 289 |
| HCC1806 | basal-A TNBC | 558 |
| HCC70 | basal-A TNBC | 443 |
| MB468 | basal-A TNBC | 340 |
| MCF7 | luminal | 583 |
| T47D | luminal | 799 |
| BT549 | basal-B TNBC | 2 |
| MB231 | basal-B TNBC | 31 |
| MB436 | basal-B TNBC | 4 |
| Human fibroblast | Normal tissue | 14 |

Example 7

Triple negative breast cancers have the worst prognosis of any breast cancer subtype and there is no targeted TNBC therapy. TNBCs have the phenotype associated with tumor initiating cells (T-IC), also known as cancer stem cells. T-IC are resistant to chemotherapy and thought to be responsible for tumor relapse and metastasis.

EpCAM is expressed at gap junctions at low levels on normal epithelial cells, but much more highly expressed (100-1000-fold greater) throughout the membrane of virtually all epithelial cancers and is a known TI-C marker.

Described herein is a strategy for gene knockdown therapeutics for basal-like TNBCs. As described herein, the aptamer-siRNA chimera (AsiC) platform is adapted to transfect epithelial breast cancer cells while also targeting breast tumor-initiating cells (T-IC). The aptamer binds to EpCAM, highly expressed on cancer cells and cancer stem cells. As proof-of-concept, the siRNA is directed at a kinase required for mitosis in all cells (PLK1).

As demonstrated herein, the EpCAM-AsiC's are stable in human and mouse. The EpCAM AsiCs can be chemically synthesized with 2'-F pyrimidines and dTdT at the 3'-ends, which makes them resistant to RNases and unlikely to stimulate innate immunity.

Figure 24F:
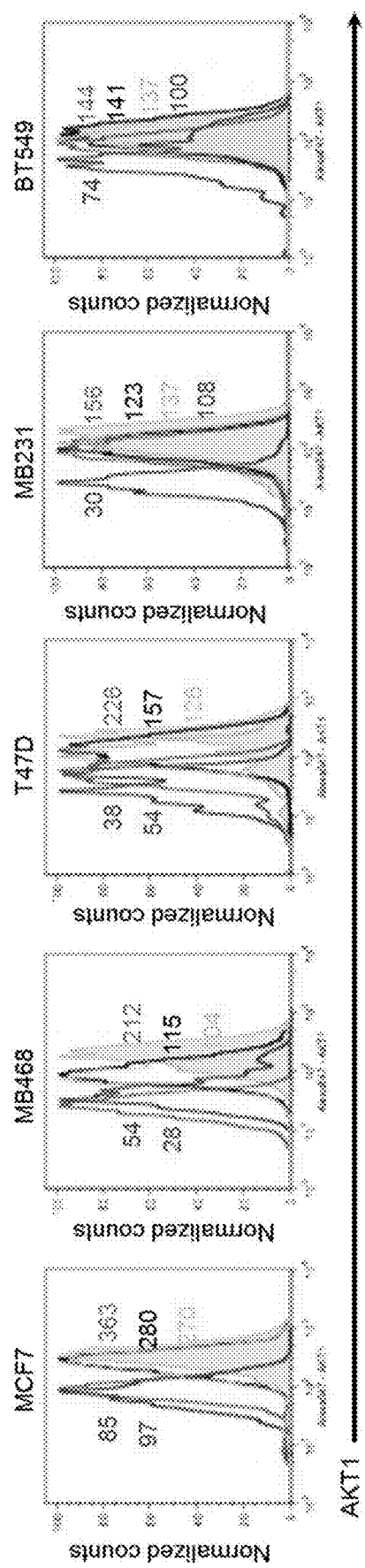

Cells were treated with 4 mM EpCAM-AsiC for 5 days and specific AKT1 protein silencing by AKT1-AsiC was detected by flow cytometry (FIG. 24F).

MB468 tumors regress only after treatment with PLK1 EpCAM-AsiC. Mice with sc MB468 tumors were treated with 5 mg/kg RNA 2x/wk beginning when tumors became palpable. PLK1 EpCAM-AsiC, GFP SpCAM-AsiC, EpCAM aptamer, PLK1 siRNA, and mock treated samples were analyzed (FIG. 33)

What is claimed herein is:

1. An aptamer-siRNA chimera (AsiC) chimeric molecule comprising an Epithelial Cell Adhesion Molecule (EpCAM) binding aptamer domain and an inhibitory nucleic acid domain that inhibits Polo-like Kinase 1 (Plk1) wherein the chimeric molecule comprises the sequence of SEQ ID NO: 1 or 3.

2. The molecule of claim 1, wherein the 3' end of the molecule comprises dTdT.

3. The molecule of claim 1, wherein the molecule comprises at least one 2'-F pyrimidine.

4. A pharmaceutical composition comprising the molecule of claim 1 and a pharmaceutically acceptable carrier.

5. The composition of claim 4, comprising at least two chimeric molecules, wherein the chimeric molecules have different aptamer domains or inhibitory nucleic acid domains.

6. The composition of claim 5, wherein different apatmer or inhibitory nucleic acid domains recognize different targets.

7. The composition of claim 5, wherein different apatmer or inhibitory nucleic acid domains have different sequences and recognize the same target.

8. The composition of claim 4, further comprising an additional cancer treatment.

9. The composition of claim 8, wherein the cancer treatment is paclitaxel.

* * * * *